US012807657B2

(12) United States Patent
Asakura et al.

(10) Patent No.: US 12,807,657 B2
(45) Date of Patent: Nov. 24, 2026

(54) PROTEIN COMPOSITION PRODUCTION METHOD

(71) Applicant: CRANE Inc., Tsuruoka (JP)

(72) Inventors: Tetsuo Asakura, Fuchu (JP); Yunosuke Abe, Tsuruoka (JP); Hideto Ishii, Tsuruoka (JP)

(73) Assignee: CRANE Inc., Tsuruoka (JP)

( * ) Notice: Subject to any disclaimer, the term of this patent is extended or adjusted under 35 U.S.C. 154(b) by 593 days.

(21) Appl. No.: 17/280,125

(22) PCT Filed: Sep. 30, 2019

(86) PCT No.: PCT/JP2019/038614
§ 371 (c)(1),
(2) Date: Mar. 25, 2021

(87) PCT Pub. No.: WO2020/067572
PCT Pub. Date: Apr. 2, 2020

(65) Prior Publication Data

US 2021/0340193 A1 Nov. 4, 2021

(30) Foreign Application Priority Data

Sep. 28, 2018 (JP) ................................ 2018-185614
Sep. 27, 2019 (JP) ................................ 2019-177553

(51) Int. Cl.
*C07K 14/435* (2006.01)
*D01F 4/02* (2006.01)

(52) U.S. Cl.
CPC .......... *C07K 14/43518* (2013.01); *D01F 4/02* (2013.01)

(58) Field of Classification Search
CPC ....... C07K 14/43518; D01F 4/02; D01F 4/00; D01F 11/02; D01D 5/06
See application file for complete search history.

(56) References Cited

U.S. PATENT DOCUMENTS

| | | | | |
|---|---|---|---|---|
| 7,186,806 | B2 * | 3/2007 | Ueda | D06M 11/17 424/443 |
| 2004/0073010 | A1 | 4/2004 | Ueda et al. | |
| 2014/0058066 | A1 | 2/2014 | Sekiyama et al. | |
| 2014/0264985 | A1 * | 9/2014 | Sutti | D01D 5/40 264/11 |
| 2015/0183841 | A1 * | 7/2015 | Lo | A61L 27/52 264/164 |
| 2020/0031886 | A1 | 1/2020 | Morinaga et al. | |
| 2022/0324923 | A1 * | 10/2022 | Takahashi | D01F 4/02 |

FOREIGN PATENT DOCUMENTS

| | | | |
|---|---|---|---|
| CN | 103146297 | A | 6/2013 |
| CN | 103320886 | A | 9/2013 |
| EP | 0488687 | A2 | 6/1992 |
| JP | H04-263614 | A | 9/1992 |
| JP | 10298201 | A * | 11/1998 |
| JP | H10-298201 | A | 11/1998 |
| JP | 2004-503204 | A | 2/2004 |
| JP | 2005-515309 | A | 5/2005 |
| JP | 2007-177370 | A | 7/2007 |
| JP | 2010-236149 | A | 10/2010 |
| WO | 01/53333 | A1 | 7/2001 |
| WO | 02/052099 | A1 | 7/2002 |
| WO | 03/060207 | A1 | 7/2003 |
| WO | 2012/165476 | A1 | 12/2012 |
| WO | 2018/164020 | A1 | 9/2018 |

OTHER PUBLICATIONS

Rice et al. (Nature, 1959, 184(4704):2015-2016 (Year: 1959).*
Hu et al. (Biomacromolecules, 2011, 12(5):1686-1696) (Year: 2011).*
Brand et al. (Textile Res J, 1962, 32(1):39-49) (Year: 1962).*
Rippon (Friction in Textile Materials, 2008, p. 253-291) (Year: 2008).*
Lee et al. (Phys Chem Chem Phys, 2016, 18:4814-4821) (Year: 2016).*
Shoulders et al. (Ann Rev Biochem, 2009, 78:929-958) (Year: 2009).*
Zeeman et al. (Biomaterials, 1999, 20:921-931) (Year: 1999).*
Machine Translation of Yamashita JPH1029201A, obtained from Google Patents, 2023 (Year: 2023).*
Zheng et al. (Proteomics Sys Biol, 2016, 16:1059) (Year: 2016).*
Cavallaro et al. (Biotechnol Bioeng, 1994, 43:781) (Year: 1994).*
Hormann et al. (Biochem, 1971, 10:932) (Year: 1971).*
Guinea et al. (J Exp Biol, 2005, 208:25) (Year: 2005).*
Laidler et al. (J Chem Ed, 1984, 61:494) (Year: 1984).*
Stefanidis et al. (JACS, 1993, 115:6045) (Year: 1993).*
International Search Report issued in corresponding International Patent Application No. PCT/JP2019/038614 dated Dec. 17, 2019.
International Preliminary Report on Patentability and Written Opinion issued in corresponding International Patent Application No. PCT/JP2019/038614 dated Apr. 8, 2021.
Extended European Search Report issued in corresponding European Patent Application No. 19867810.4 dated Jun. 7, 2022.

* cited by examiner

*Primary Examiner* — David Steadman
*Assistant Examiner* — Joseph R Spangler
(74) *Attorney, Agent, or Firm* — Studebaker Brackett PLLC

(57) ABSTRACT

A production method of a protein composition, the method comprising a step of hydrolyzing an ester group by bringing a raw material composition containing an esterified protein into contact with an acidic or basic medium.

19 Claims, 11 Drawing Sheets

Specification includes a Sequence Listing.

(A)
BEFORE CRIMPING (B)
AFTER CRIMPING (C)
BEFORE CRIMPING: 300mm (D)
AFTER CRIMPING: 200mm

SEQUENCE LISTING

```
<160> NUMBER OF SEQ ID NOS: 44

<210> SEQ ID NO 1
<211> LENGTH: 50
<212> TYPE: PRT
<213> ORGANISM: Araneus diadematus

<400> SEQUENCE: 1

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn Tyr Gly
            20                  25                  30

Ala Ser Ala Gln Tyr Thr Gln Met Val Gly Gln Ser Val Ala Gln Ala
        35                  40                  45

Leu Ala
    50


<210> SEQ ID NO 2
<211> LENGTH: 30
<212> TYPE: PRT
<213> ORGANISM: Araneus diadematus

<400> SEQUENCE: 2

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn
            20                  25                  30


<210> SEQ ID NO 3
<211> LENGTH: 21
<212> TYPE: PRT
<213> ORGANISM: Araneus diadematus

<400> SEQUENCE: 3

Ser Gly Cys Asp Val Leu Val Gln Ala Leu Leu Glu Val Val Ser Ala
1               5                   10                  15

Leu Val Ser Ile Leu
            20


<210> SEQ ID NO 4
<211> LENGTH: 1154
<212> TYPE: PRT
<213> ORGANISM: Artificial Sequence
<220> FEATURE:
<223> OTHER INFORMATION: recombinant spider silk protein
      ADF3KaiLargeNRSH1

<400> SEQUENCE: 4

Met His His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45
```

```
Pro Tyr Gly Pro Gly Ala Ser Ala Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
        115                 120                 125

Ala Gly Gly Asn Gly Pro Gly Ser Gly Gln Gln Gly Ala Gly Gln Gln
    130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gly Gln Gly Pro Tyr Gly
                245                 250                 255

Pro Gly Ala Ser Ala Ala Ala Ala Ala Ala Gly Gly Tyr Gly Pro Gly
            260                 265                 270

Tyr Gly Gln Gln Gly Pro Gly Gln Gln Gly Pro Gly Gly Gln Gly Pro
        275                 280                 285

Tyr Gly Pro Gly Ala Ser Ala Ala Ser Ala Ala Ser Gly Gly Tyr Gly
    290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Ala Gly Gly
                325                 330                 335

Tyr Gly Pro Gly Ser Gly Gln Gln Gly Pro Gly Gln Gln Gly Pro Gly
            340                 345                 350

Gln Gln Gly Pro Gly Gln Gln Gly Pro Gly Gly Gln Gly Pro Tyr Gly
        355                 360                 365

Pro Gly Ala Ser Ala Ala Ala Ala Ala Ala Gly Gly Tyr Gly Pro Gly
    370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Ala Gly Ala Ala Gly
        435                 440                 445

Gly Tyr Gly Pro Gly Ser Gly Gln Gln Gly Pro Gly Gln Gln Gly Pro
    450                 455                 460
```

```
Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
                485                 490                 495

Pro Gly Ala Ser Ala Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
        515                 520                 525

Gly Gly Gln Gly Pro Tyr Gly Pro Gly Ala Ala Ser Ala Ala Val Ser
    530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
                565                 570                 575

Ala Ser Ala Ala Ala Ala Ala Ala Gly Gly Tyr Gly Pro Gly Ser Gly
            580                 585                 590

Gln Gln Gly Pro Ser Gln Gln Gly Pro Gly Gln Gln Gly Pro Gly Gly
        595                 600                 605

Gln Gly Pro Tyr Gly Pro Gly Ala Ser Ala Ala Ala Ala Ala Ala Gly
    610                 615                 620

Gly Tyr Gly Pro Gly Ser Gly Gln Gln Gly Pro Gly Gly Gln Gly Pro
625                 630                 635                 640

Tyr Gly Pro Gly Ser Ser Ala Ala Ala Ala Ala Ala Gly Gly Asn Gly
                645                 650                 655

Pro Gly Ser Gly Gln Gln Gly Ala Gly Gln Gln Gly Pro Gly Gln Gln
            660                 665                 670

Gly Pro Gly Ala Ser Ala Ala Ala Ala Ala Ala Gly Gly Tyr Gly Pro
        675                 680                 685

Gly Ser Gly Gln Gln Gly Pro Gly Gln Gln Gly Pro Gly Gly Gln Gly
    690                 695                 700

Pro Tyr Gly Pro Gly Ala Ser Ala Ala Ala Ala Ala Ala Gly Gly Tyr
705                 710                 715                 720

Gly Pro Gly Ser Gly Gln Gly Pro Gly Gln Gln Gly Pro Gly Gly Gln
                725                 730                 735

Gly Pro Tyr Gly Pro Gly Ala Ser Ala Ala Ala Ala Ala Ala Gly Gly
            740                 745                 750

Tyr Gly Pro Gly Ser Gly Gln Gln Gly Pro Gly Gln Gln Gly Pro Gly
        755                 760                 765

Gln Gln Gly Pro Gly Gly Gln Gly Pro Tyr Gly Pro Gly Ala Ser Ala
    770                 775                 780

Ala Ala Ala Ala Ala Gly Gly Tyr Gly Pro Gly Tyr Gly Gln Gln Gly
785                 790                 795                 800

Pro Gly Gln Gln Gly Pro Gly Gly Gln Gly Pro Tyr Gly Pro Gly Ala
                805                 810                 815

Ser Ala Ala Ser Ala Ala Ser Gly Gly Tyr Gly Pro Gly Ser Gly Gln
            820                 825                 830

Gln Gly Pro Gly Gln Gln Gly Pro Gly Gly Gln Gly Pro Tyr Gly Pro
        835                 840                 845

Gly Ala Ser Ala Ala Ala Ala Ala Ala Gly Gly Tyr Gly Pro Gly Ser
    850                 855                 860

Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
```

```
            885                 890                 895

Ala Ala Ala Ala Ala Gly Gly Tyr Gly Pro Gly Ser Gly Gln Gln Gly
            900                 905                 910

Pro Gly Gln Gln Gly Pro Gly Gln Gln Gly Pro Gly Gln Gln Gly Pro
        915                 920                 925

Gly Gln Gln Gly Pro Gly Gln Gln Gly Pro Gly Gln Gln Gly Pro Gly
    930                 935                 940

Gln Gln Gly Pro Gly Gln Gln Gly Pro Gly Gly Gln Gly Ala Tyr Gly
945                 950                 955                 960

Pro Gly Ala Ser Ala Ala Ala Gly Ala Ala Gly Gly Tyr Gly Pro Gly
                965                 970                 975

Ser Gly Gln Gln Gly Pro Gly Gln Gln Gly Pro Gly Gln Gln Gly Pro
            980                 985                 990

Gly Gln Gln Gly Pro Gly Gln Gln  Gly Pro Gly Gln Gln  Gly Pro Gly
        995                 1000                1005

Gln Gln  Gly Pro Gly Gln Gln  Gly Pro Tyr Gly Pro  Gly Ala Ser
    1010                1015                1020

Ala Ala  Ala Ala Ala Ala Gly  Gly Tyr Gly Pro Gly  Ser Gly Gln
    1025                1030                1035

Gln Gly  Pro Gly Gln Gln Gly  Pro Gly Gln Gln Gly  Pro Gly Gly
    1040                1045                1050

Gln Gly  Pro Tyr Gly Pro Gly  Ala Ala Ser Ala Ala  Val Ser Val
    1055                1060                1065

Gly Gly  Tyr Gly Pro Gln Ser  Ser Ser Val Pro Val  Ala Ser Ala
    1070                1075                1080

Val Ala  Ser Arg Leu Ser Ser  Pro Ala Ala Ser Ser  Arg Val Ser
    1085                1090                1095

Ser Ala  Val Ser Ser Leu Val  Ser Ser Gly Pro Thr  Lys His Ala
    1100                1105                1110

Ala Leu  Ser Asn Thr Ile Ser  Ser Val Val Ser Gln  Val Ser Ala
    1115                1120                1125

Ser Asn  Pro Gly Leu Ser Gly  Cys Asp Val Leu Val  Gln Ala Leu
    1130                1135                1140

Leu Glu  Val Val Ser Ala Leu  Val Ser Ile Leu
    1145                1150


<210> SEQ ID NO 5
<211> LENGTH: 24
<212> TYPE: PRT
<213> ORGANISM: Artificial Sequence
<220> FEATURE:
<223> OTHER INFORMATION: His tag and start codon

<400> SEQUENCE: 5

Met His His His His His His His His His His Ser Ser Gly Ser Ser
1               5                   10                  15

Leu Glu Val Leu Phe Gln Gly Pro
            20


<210> SEQ ID NO 6
<211> LENGTH: 597
<212> TYPE: PRT
<213> ORGANISM: Artificial Sequence
<220> FEATURE:
<223> OTHER INFORMATION: Met-PRT380

<400> SEQUENCE: 6
```

```
Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Ala Ala Ala Ala Ala Gly Gln Tyr Gly Pro Gly Gln Gln Gly
        35                  40                  45

Pro Gly Gln Gln Gly Pro Gly Ser Ser Ala Ala Ala Ala Ala Gly Pro
    50                  55                  60

Gly Gln Tyr Gly Pro Gly Gln Gln Gly Pro Ser Ala Ser Ala Ala Ala
65                  70                  75                  80

Ala Ala Gly Pro Gly Ser Gly Gln Gln Gly Pro Gly Ala Ser Ala Ala
                85                  90                  95

Ala Ala Ala Gly Gln Tyr Gly Pro Gly Gln Gln Gly Pro Gly Gln Gln
            100                 105                 110

Gly Pro Gly Ser Ser Ala Ala Ala Ala Ala Gly Gln Tyr Gly Ser Gly
        115                 120                 125

Pro Gly Gln Gln Gly Pro Tyr Gly Ser Ala Ala Ala Ala Ala Gly Pro
    130                 135                 140

Gly Ser Gly Gln Tyr Gly Gln Gly Pro Tyr Gly Pro Gly Ala Ser Ala
145                 150                 155                 160

Ala Ala Ala Ala Gly Pro Gly Gln Tyr Gly Pro Gly Gln Gln Gly Pro
                165                 170                 175

Ser Ala Ser Ala Ala Ala Ala Ala Gly Ser Gly Gln Gln Gly Pro Gly
            180                 185                 190

Gln Tyr Gly Pro Tyr Ala Ser Ala Ala Ala Ala Ala Gly Gln Tyr Gly
        195                 200                 205

Ser Gly Pro Gly Gln Gln Gly Pro Tyr Gly Pro Gly Gln Ser Ala Ala
    210                 215                 220

Ala Ala Ala Gly Ser Gly Gln Gln Gly Pro Gly Gln Gln Gly Pro Tyr
225                 230                 235                 240

Ala Ser Ala Ala Ala Ala Ala Gly Pro Gly Gln Gln Gly Pro Tyr Gly
                245                 250                 255

Pro Gly Ser Ser Ala Ala Ala Ala Ala Gly Gln Tyr Gly Tyr Gly Pro
            260                 265                 270

Gly Gln Gln Gly Pro Tyr Gly Pro Gly Ala Ser Ala Ala Ala Ala Ala
        275                 280                 285

Gly Gln Asn Gly Pro Gly Ser Gly Gln Tyr Gly Pro Gly Gln Gln Gly
    290                 295                 300

Pro Gly Gln Ser Ala Ala Ala Ala Ala Gly Pro Gly Gln Gln Gly Pro
305                 310                 315                 320

Tyr Gly Pro Gly Ala Ser Ala Ala Ala Ala Ala Gly Gln Tyr Gly Pro
                325                 330                 335

Gly Gln Gln Gly Pro Gly Gln Tyr Gly Pro Gly Ser Ser Ala Ala Ala
            340                 345                 350

Ala Ala Gly Pro Gly Gln Gln Gly Pro Tyr Gly Pro Gly Ser Ser Ala
        355                 360                 365

Ala Ala Ala Ala Gly Gln Tyr Gly Pro Gly Gln Gln Gly Pro Tyr Gly
    370                 375                 380

Pro Gly Gln Ser Ala Ala Ala Ala Ala Gly Gln Tyr Gln Gln Gly Pro
385                 390                 395                 400

Gly Gln Gln Gly Pro Tyr Gly Pro Gly Ala Ser Ala Ala Ala Ala Ala
                405                 410                 415

Gly Pro Gly Gln Gln Gly Pro Tyr Gly Pro Gly Ala Ser Ala Ala Ala
```

```
            420                 425                 430

Ala Ala Gly Pro Gly Gln Tyr Gly Pro Gly Gln Gln Gly Pro Ser Ala
        435                 440                 445

Ser Ala Ala Ala Ala Ala Gly Gln Tyr Gly Ser Gly Pro Gly Gln Tyr
    450                 455                 460

Gly Pro Tyr Gly Pro Gly Gln Ser Ala Ala Ala Ala Ala Gly Pro Gly
465                 470                 475                 480

Ser Gly Gln Gln Gly Gln Gly Pro Tyr Gly Pro Gly Ala Ser Ala Ala
                485                 490                 495

Ala Ala Ala Gly Gln Tyr Gly Pro Gly Gln Gln Gly Pro Tyr Gly Pro
            500                 505                 510

Gly Gln Ser Ala Ala Ala Ala Ala Gly Pro Gly Ser Gly Gln Tyr Gly
        515                 520                 525

Pro Gly Ala Ser Ala Ala Ala Ala Ala Gly Gln Asn Gly Pro Gly Ser
    530                 535                 540

Gly Gln Tyr Gly Pro Gly Gln Gln Gly Pro Gly Gln Ser Ala Ala Ala
545                 550                 555                 560

Ala Ala Gly Gln Tyr Gln Gln Gly Pro Gly Gln Gln Gly Pro Tyr Gly
                565                 570                 575

Pro Gly Ala Ser Ala Ala Ala Ala Ala Gly Pro Gly Ser Gly Gln Gln
            580                 585                 590

Gly Pro Gly Ala Ser
        595


<210> SEQ ID NO 7
<211> LENGTH: 590
<212> TYPE: PRT
<213> ORGANISM: Artificial Sequence
<220> FEATURE:
<223> OTHER INFORMATION: Met-PRT410

<400> SEQUENCE: 7

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Ala Gly Pro Gly Gln Tyr Gly Pro
    50                  55                  60

Gly Gln Gln Gly Pro Ser Ala Ser Ala Ala Ala Ala Ala Gly Pro Gly
65                  70                  75                  80

Ser Gly Gln Gln Gly Pro Gly Ala Ser Gly Gln Tyr Gly Pro Gly Gln
                85                  90                  95

Gln Gly Pro Gly Gln Gln Gly Pro Gly Ser Ser Ala Ala Ala Ala Ala
            100                 105                 110

Gly Gln Tyr Gly Ser Gly Pro Gly Gln Gln Gly Pro Tyr Gly Ser Ala
        115                 120                 125

Ala Ala Ala Ala Gly Pro Gly Ser Gly Gln Tyr Gly Gln Gly Pro Tyr
    130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Ala Gly Ser Gly Gln Gln Gly Pro
                165                 170                 175

Gly Gln Tyr Gly Pro Tyr Ala Ser Ala Ala Ala Ala Ala Gly Gln Tyr
```

-continued

```
            180                 185                 190

Gly Ser Gly Pro Gly Gln Gln Gly Pro Tyr Gly Pro Gly Gln Ser Gly
        195                 200                 205

Ser Gly Gln Gln Gly Pro Gly Gln Gln Gly Pro Tyr Ala Ser Ala Ala
    210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
                245                 250                 255

Pro Tyr Gly Pro Gly Ala Ser Gly Gln Asn Gly Pro Gly Ser Gly Gln
            260                 265                 270

Tyr Gly Pro Gly Gln Gln Gly Pro Gly Gln Ser Ala Ala Ala Ala Ala
        275                 280                 285

Gly Pro Gly Gln Gln Gly Pro Tyr Gly Pro Gly Ala Ser Ala Ala Ala
    290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gly Gln Gln Gly Pro Tyr Gly Pro Gly Ser
                325                 330                 335

Ser Ala Ala Ala Ala Ala Gly Gln Tyr Gly Pro Gly Gln Gln Gly Pro
            340                 345                 350

Tyr Gly Pro Gly Gln Ser Ala Ala Ala Ala Ala Gly Gln Tyr Gln Gln
        355                 360                 365

Gly Pro Gly Gln Gln Gly Pro Tyr Gly Pro Gly Ala Ser Gly Pro Gly
    370                 375                 380

Gln Gln Gly Pro Tyr Gly Pro Gly Ala Ser Ala Ala Ala Ala Ala Gly
385                 390                 395                 400

Pro Gly Gln Tyr Gly Pro Gly Gln Gln Gly Pro Ser Ala Ser Ala Ala
                405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
        435                 440                 445

Tyr Gly Pro Gly Ala Ser Ala Ala Ala Ala Ala Gly Gln Tyr Gly Pro
    450                 455                 460

Gly Gln Gln Gly Pro Tyr Gly Pro Gly Gln Ser Ala Ala Ala Ala Ala
465                 470                 475                 480

Gly Pro Gly Ser Gly Gln Tyr Gly Pro Gly Ala Ser Gly Gln Asn Gly
                485                 490                 495

Pro Gly Ser Gly Gln Tyr Gly Pro Gly Gln Gln Gly Pro Gly Gln Ser
            500                 505                 510

Ala Ala Ala Ala Ala Gly Gln Tyr Gln Gln Gly Pro Gly Gln Gln Gly
        515                 520                 525

Pro Tyr Gly Pro Gly Ala Ser Ala Ala Ala Ala Ala Gly Gln Tyr Gly
    530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gln Gly Pro Tyr Ala Ser Ala Ala Ala
                565                 570                 575

Ala Ala Gly Pro Gly Ser Gly Gln Gln Gly Pro Gly Ala Ser
            580                 585                 590
```

<210> SEQ ID NO 8

<211> LENGTH: 565
<212> TYPE: PRT
<213> ORGANISM: Artificial Sequence
<220> FEATURE:
<223> OTHER INFORMATION: Met-PRT525

<400> SEQUENCE: 8

```
Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Ala Ala Gly Pro Gly
    50                  55                  60

Gln Tyr Gly Pro Gly Gln Gln Gly Pro Ser Ala Ser Ala Ala Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
            100                 105                 110

Ser Ala Ala Ala Ala Ala Ala Ala Gly Ser Tyr Gly Ser Gly Pro Gly
        115                 120                 125

Gln Gln Gly Pro Tyr Gly Ser Ala Ala Ala Ala Ala Ala Ala Gly Pro
    130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Gln Gln Gly Pro Ser Ala Ser Ala Ala
                165                 170                 175

Ala Ala Ala Ala Ala Gly Ser Gly Gln Gln Gly Pro Gly Gln Tyr Gly
            180                 185                 190

Pro Tyr Ala Ser Ala Ala Ala Ala Ala Ala Ala Gly Ser Tyr Gly Ser
        195                 200                 205

Gly Pro Gly Gln Gln Gly Pro Tyr Gly Pro Gly Gln Ser Gly Ser Gly
    210                 215                 220

Gln Gln Gly Pro Gly Gln Gln Gly Pro Tyr Ala Ser Ala Ala Ala Ala
225                 230                 235                 240

Ala Ala Ala Gly Pro Gly Gln Gln Gly Pro Tyr Gly Pro Gly Ser Ser
                245                 250                 255

Ala Ala Ala Ala Ala Ala Ala Gly Ser Tyr Gly Tyr Gly Pro Gly Gln
            260                 265                 270

Gln Gly Pro Tyr Gly Pro Gly Ala Ser Gly Gln Asn Gly Pro Gly Ser
        275                 280                 285

Gly Gln Tyr Gly Pro Gly Gln Gln Gly Pro Gly Pro Ser Ala Ala Ala
    290                 295                 300

Ala Ala Ala Ala Gly Pro Gly Gln Gln Gly Pro Tyr Gly Pro Gly Ala
305                 310                 315                 320

Ser Ala Ala Ala Ala Ala Ala Ala Gly Ser Tyr Gly Pro Gly Gln Gln
                325                 330                 335

Gly Pro Gly Gln Tyr Gly Pro Gly Ser Ser Gly Pro Gly Gln Gln Gly
            340                 345                 350

Pro Tyr Gly Pro Gly Ser Ser Ala Ala Ala Ala Ala Ala Ala Gly Ser
        355                 360                 365

Tyr Gly Pro Gly Gln Gln Gly Pro Tyr Gly Pro Gly Pro Ser Ala Ala
    370                 375                 380
```

```
Ala Ala Ala Ala Ala Gly Ser Tyr Gln Gln Gly Pro Gly Gln Gln Gly
385                 390                 395                 400

Pro Tyr Gly Pro Gly Ala Ser Gly Pro Gly Gln Gln Gly Pro Tyr Gly
                405                 410                 415

Pro Gly Ala Ser Ala Ala Ala Ala Ala Ala Ala Gly Pro Gly Gln Tyr
            420                 425                 430

Gly Pro Gly Gln Gln Gly Pro Ser Ala Ser Ala Ala Ala Ala Ala Ala
        435                 440                 445

Ala Gly Ser Tyr Gly Ser Gly Pro Gly Gln Tyr Gly Pro Tyr Gly Pro
    450                 455                 460

Gly Gln Ser Gly Pro Gly Ser Gly Gln Gln Gly Gln Gly Pro Tyr Gly
465                 470                 475                 480

Pro Gly Ala Ser Ala Ala Ala Ala Ala Ala Ala Gly Ser Tyr Gly Pro
                485                 490                 495

Gly Gln Gln Gly Pro Tyr Gly Pro Gly Pro Ser Ala Ala Ala Ala Ala
            500                 505                 510

Ala Ala Gly Pro Gly Ser Gly Gln Tyr Gly Pro Gly Ala Ser Gly Gln
        515                 520                 525

Asn Gly Pro Gly Ser Gly Gln Tyr Gly Pro Gly Gln Gln Gly Pro Gly
    530                 535                 540

Pro Ser Ala Ala Ala Ala Ala Ala Ala Gly Pro Gly Ser Gly Gln Gln
545                 550                 555                 560

Gly Pro Gly Ala Ser
                565
```

<210> SEQ ID NO 9
<211> LENGTH: 2364
<212> TYPE: PRT
<213> ORGANISM: Artificial Sequence
<220> FEATURE:
<223> OTHER INFORMATION: Met-PRT799

<400> SEQUENCE: 9

```
Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Ala Gly Pro Gly Gln Tyr Gly Pro
    50                  55                  60

Gly Gln Gln Gly Pro Ser Ala Ser Ala Ala Ala Ala Ala Gly Pro Gly
65                  70                  75                  80

Ser Gly Gln Gln Gly Pro Gly Ala Ser Gly Gln Tyr Gly Pro Gly Gln
                85                  90                  95

Gln Gly Pro Gly Gln Gln Gly Pro Gly Ser Ser Ala Ala Ala Ala Ala
            100                 105                 110

Gly Gln Tyr Gly Ser Gly Pro Gly Gln Gln Gly Pro Tyr Gly Ser Ala
        115                 120                 125

Ala Ala Ala Ala Gly Pro Gly Ser Gly Gln Tyr Gly Gln Gly Pro Tyr
    130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Ala Gly Ser Gly Gln Gln Gly Pro
                165                 170                 175
```

```
Gly Gln Tyr Gly Pro Tyr Ala Ser Ala Ala Ala Ala Ala Gly Gln Tyr
            180                 185                 190

Gly Ser Gly Pro Gly Gln Gln Gly Pro Tyr Gly Pro Gly Gln Ser Gly
        195                 200                 205

Ser Gly Gln Gln Gly Pro Gly Gln Gln Gly Pro Tyr Ala Ser Ala Ala
    210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
                245                 250                 255

Pro Tyr Gly Pro Gly Ala Ser Gly Gln Asn Gly Pro Gly Ser Gly Gln
            260                 265                 270

Tyr Gly Pro Gly Gln Gln Gly Pro Gly Gln Ser Ala Ala Ala Ala Ala
        275                 280                 285

Gly Pro Gly Gln Gln Gly Pro Tyr Gly Pro Gly Ala Ser Ala Ala Ala
    290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gly Gln Gln Gly Pro Tyr Gly Pro Gly Ser
                325                 330                 335

Ser Ala Ala Ala Ala Ala Gly Gln Tyr Gly Pro Gly Gln Gln Gly Pro
            340                 345                 350

Tyr Gly Pro Gly Gln Ser Ala Ala Ala Ala Ala Gly Gln Tyr Gln Gln
        355                 360                 365

Gly Pro Gly Gln Gln Gly Pro Tyr Gly Pro Gly Ala Ser Gly Pro Gly
    370                 375                 380

Gln Gln Gly Pro Tyr Gly Pro Gly Ala Ser Ala Ala Ala Ala Ala Gly
385                 390                 395                 400

Pro Gly Gln Tyr Gly Pro Gly Gln Gln Gly Pro Ser Ala Ser Ala Ala
                405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
        435                 440                 445

Tyr Gly Pro Gly Ala Ser Ala Ala Ala Ala Ala Gly Gln Tyr Gly Pro
    450                 455                 460

Gly Gln Gln Gly Pro Tyr Gly Pro Gly Gln Ser Ala Ala Ala Ala Ala
465                 470                 475                 480

Gly Pro Gly Ser Gly Gln Tyr Gly Pro Gly Ala Ser Gly Gln Asn Gly
                485                 490                 495

Pro Gly Ser Gly Gln Tyr Gly Pro Gly Gln Gln Gly Pro Gly Gln Ser
            500                 505                 510

Ala Ala Ala Ala Ala Gly Gln Tyr Gln Gln Gly Pro Gly Gln Gln Gly
        515                 520                 525

Pro Tyr Gly Pro Gly Ala Ser Ala Ala Ala Ala Ala Gly Gln Tyr Gly
    530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gln Gly Pro Tyr Ala Ser Ala Ala Ala
                565                 570                 575

Ala Ala Gly Pro Gly Ser Gly Gln Gln Gly Pro Gly Ala Ser Gly Gln
            580                 585                 590
```

```
Gln Gly Pro Tyr Gly Pro Gly Ala Ser Ala Ala Ala Ala Ala Gly Gln
        595                 600                 605

Asn Gly Pro Gly Ser Gly Gln Gln Gly Pro Gly Gln Ser Gly Gln Tyr
    610                 615                 620

Gly Pro Gly Gln Gln Gly Pro Gly Gln Gln Gly Pro Gly Ser Ser Ala
625                 630                 635                 640

Ala Ala Ala Ala Gly Pro Gly Gln Tyr Gly Pro Gly Gln Gln Gly Pro
                645                 650                 655

Ser Ala Ser Ala Ala Ala Ala Ala Gly Pro Gly Ser Gly Gln Gln Gly
            660                 665                 670

Pro Gly Ala Ser Gly Gln Tyr Gly Pro Gly Gln Gln Gly Pro Gly Gln
        675                 680                 685

Gln Gly Pro Gly Ser Ser Ala Ala Ala Ala Ala Gly Gln Tyr Gly Ser
    690                 695                 700

Gly Pro Gly Gln Gln Gly Pro Tyr Gly Ser Ala Ala Ala Ala Ala Gly
705                 710                 715                 720

Pro Gly Ser Gly Gln Tyr Gly Gln Gly Pro Tyr Gly Pro Gly Ala Ser
                725                 730                 735

Gly Pro Gly Gln Tyr Gly Pro Gly Gln Gln Gly Pro Ser Ala Ser Ala
            740                 745                 750

Ala Ala Ala Ala Gly Ser Gly Gln Gln Gly Pro Gly Gln Tyr Gly Pro
        755                 760                 765

Tyr Ala Ser Ala Ala Ala Ala Ala Gly Gln Tyr Gly Ser Gly Pro Gly
    770                 775                 780

Gln Gln Gly Pro Tyr Gly Pro Gly Gln Ser Gly Ser Gly Gln Gln Gly
785                 790                 795                 800

Pro Gly Gln Gln Gly Pro Tyr Ala Ser Ala Ala Ala Ala Ala Gly Pro
                805                 810                 815

Gly Gln Gln Gly Pro Tyr Gly Pro Gly Ser Ser Ala Ala Ala Ala Ala
            820                 825                 830

Gly Gln Tyr Gly Tyr Gly Pro Gly Gln Gln Gly Pro Tyr Gly Pro Gly
        835                 840                 845

Ala Ser Gly Gln Asn Gly Pro Gly Ser Gly Gln Tyr Gly Pro Gly Gln
    850                 855                 860

Gln Gly Pro Gly Gln Ser Ala Ala Ala Ala Ala Gly Pro Gly Gln Gln
865                 870                 875                 880

Gly Pro Tyr Gly Pro Gly Ala Ser Ala Ala Ala Ala Ala Gly Gln Tyr
                885                 890                 895

Gly Pro Gly Gln Gln Gly Pro Gly Gln Tyr Gly Pro Gly Ser Ser Gly
            900                 905                 910

Pro Gly Gln Gln Gly Pro Tyr Gly Pro Gly Ser Ser Ala Ala Ala Ala
        915                 920                 925

Ala Gly Gln Tyr Gly Pro Gly Gln Gln Gly Pro Tyr Gly Pro Gly Gln
    930                 935                 940

Ser Ala Ala Ala Ala Ala Gly Gln Tyr Gln Gln Gly Pro Gly Gln Gln
945                 950                 955                 960

Gly Pro Tyr Gly Pro Gly Ala Ser Gly Pro Gly Gln Gln Gly Pro Tyr
                965                 970                 975

Gly Pro Gly Ala Ser Ala Ala Ala Ala Ala Gly Pro Gly Gln Tyr Gly
            980                 985                 990

Pro Gly Gln Gln Gly Pro Ser Ala  Ser Ala Ala Ala Ala  Ala Gly Gln
        995                 1000                 1005

Tyr Gly  Ser Gly Pro Gly Gln  Tyr Gly Pro Tyr Gly  Pro Gly Gln
```

```
    1010                1015                1020

Ser Gly  Pro Gly Ser Gly Gln  Gln Gly Gln Gly Pro  Tyr Gly Pro
    1025                1030                1035

Gly Ala  Ser Ala Ala Ala Ala  Ala Gly Gln Tyr Gly  Pro Gly Gln
    1040                1045                1050

Gln Gly  Pro Tyr Gly Pro Gly  Gln Ser Ala Ala Ala  Ala Ala Gly
    1055                1060                1065

Pro Gly  Ser Gly Gln Tyr Gly  Pro Gly Ala Ser Gly  Gln Asn Gly
    1070                1075                1080

Pro Gly  Ser Gly Gln Tyr Gly  Pro Gly Gln Gln Gly  Pro Gly Gln
    1085                1090                1095

Ser Ala  Ala Ala Ala Ala Gly  Gln Tyr Gln Gln Gly  Pro Gly Gln
    1100                1105                1110

Gln Gly  Pro Tyr Gly Pro Gly  Ala Ser Ala Ala Ala  Ala Ala Gly
    1115                1120                1125

Gln Tyr  Gly Ser Gly Pro Gly  Gln Gln Gly Pro Tyr  Gly Pro Gly
    1130                1135                1140

Gln Ser  Gly Ser Gly Gln Gln  Gly Pro Gly Gln Gln  Gly Pro Tyr
    1145                1150                1155

Ala Ser  Ala Ala Ala Ala Ala  Gly Pro Gly Ser Gly  Gln Gln Gly
    1160                1165                1170

Pro Gly  Ala Ser Gly Gln Gln  Gly Pro Tyr Gly Pro  Gly Ala Ser
    1175                1180                1185

Ala Ala  Ala Ala Ala Gly Gln  Asn Gly Pro Gly Ser  Gly Gln Gln
    1190                1195                1200

Gly Pro  Gly Gln Ser Gly Gln  Tyr Gly Pro Gly Gln  Gln Gly Pro
    1205                1210                1215

Gly Gln  Gln Gly Pro Gly Ser  Ser Ala Ala Ala Ala  Ala Gly Pro
    1220                1225                1230

Gly Gln  Tyr Gly Pro Gly Gln  Gln Gly Pro Ser Ala  Ser Ala Ala
    1235                1240                1245

Ala Ala  Ala Gly Pro Gly Ser  Gly Gln Gln Gly Pro  Gly Ala Ser
    1250                1255                1260

Gly Gln  Tyr Gly Pro Gly Gln  Gln Gly Pro Gly Gln  Gln Gly Pro
    1265                1270                1275

Gly Ser  Ser Ala Ala Ala Ala  Ala Gly Gln Tyr Gly  Ser Gly Pro
    1280                1285                1290

Gly Gln  Gln Gly Pro Tyr Gly  Ser Ala Ala Ala Ala  Ala Gly Pro
    1295                1300                1305

Gly Ser  Gly Gln Tyr Gly Gln  Gly Pro Tyr Gly Pro  Gly Ala Ser
    1310                1315                1320

Gly Pro  Gly Gln Tyr Gly Pro  Gly Gln Gln Gly Pro  Ser Ala Ser
    1325                1330                1335

Ala Ala  Ala Ala Ala Gly Ser  Gly Gln Gln Gly Pro  Gly Gln Tyr
    1340                1345                1350

Gly Pro  Tyr Ala Ser Ala Ala  Ala Ala Ala Gly Gln  Tyr Gly Ser
    1355                1360                1365

Gly Pro  Gly Gln Gln Gly Pro  Tyr Gly Pro Gly Gln  Ser Gly Ser
    1370                1375                1380

Gly Gln  Gln Gly Pro Gly Gln  Gln Gly Pro Tyr Ala  Ser Ala Ala
    1385                1390                1395

Ala Ala  Ala Gly Pro Gly Gln  Gln Gly Pro Tyr Gly  Pro Gly Ser
    1400                1405                1410
```

```
Ser Ala Ala Ala Ala Ala Gly Gln Tyr Gly Tyr Gly Pro Gly Gln
    1415                1420                1425

Gln Gly Pro Tyr Gly Pro Gly Ala Ser Gly Gln Asn Gly Pro Gly
    1430                1435                1440

Ser Gly Gln Tyr Gly Pro Gly Gln Gln Gly Pro Gly Gln Ser Ala
    1445                1450                1455

Ala Ala Ala Ala Gly Pro Gly Gln Gln Gly Pro Tyr Gly Pro Gly
    1460                1465                1470

Ala Ser Ala Ala Ala Ala Ala Gly Gln Tyr Gly Pro Gly Gln Gln
    1475                1480                1485

Gly Pro Gly Gln Tyr Gly Pro Gly Ser Ser Gly Pro Gly Gln Gln
    1490                1495                1500

Gly Pro Tyr Gly Pro Gly Ser Ser Ala Ala Ala Ala Ala Gly Gln
    1505                1510                1515

Tyr Gly Pro Gly Gln Gln Gly Pro Tyr Gly Pro Gly Gln Ser Ala
    1520                1525                1530

Ala Ala Ala Ala Gly Gln Tyr Gln Gln Gly Pro Gly Gln Gln Gly
    1535                1540                1545

Pro Tyr Gly Pro Gly Ala Ser Gly Pro Gly Gln Gln Gly Pro Tyr
    1550                1555                1560

Gly Pro Gly Ala Ser Ala Ala Ala Ala Ala Gly Pro Gly Gln Tyr
    1565                1570                1575

Gly Pro Gly Gln Gln Gly Pro Ser Ala Ser Ala Ala Ala Ala Ala
    1580                1585                1590

Gly Gln Tyr Gly Ser Gly Pro Gly Gln Tyr Gly Pro Tyr Gly Pro
    1595                1600                1605

Gly Gln Ser Gly Pro Gly Ser Gly Gln Gln Gly Gln Gly Pro Tyr
    1610                1615                1620

Gly Pro Gly Ala Ser Ala Ala Ala Ala Ala Gly Gln Tyr Gly Pro
    1625                1630                1635

Gly Gln Gln Gly Pro Tyr Gly Pro Gly Gln Ser Ala Ala Ala Ala
    1640                1645                1650

Ala Gly Pro Gly Ser Gly Gln Tyr Gly Pro Gly Ala Ser Gly Gln
    1655                1660                1665

Asn Gly Pro Gly Ser Gly Gln Tyr Gly Pro Gly Gln Gln Gly Pro
    1670                1675                1680

Gly Gln Ser Ala Ala Ala Ala Ala Gly Gln Tyr Gln Gln Gly Pro
    1685                1690                1695

Gly Gln Gln Gly Pro Tyr Gly Pro Gly Ala Ser Ala Ala Ala Ala
    1700                1705                1710

Ala Gly Gln Tyr Gly Ser Gly Pro Gly Gln Gln Gly Pro Tyr Gly
    1715                1720                1725

Pro Gly Gln Ser Gly Ser Gly Gln Gln Gly Pro Gly Gln Gln Gly
    1730                1735                1740

Pro Tyr Ala Ser Ala Ala Ala Ala Ala Gly Pro Gly Ser Gly Gln
    1745                1750                1755

Gln Gly Pro Gly Ala Ser Gly Gln Gln Gly Pro Tyr Gly Pro Gly
    1760                1765                1770

Ala Ser Ala Ala Ala Ala Ala Gly Gln Asn Gly Pro Gly Ser Gly
    1775                1780                1785

Gln Gln Gly Pro Gly Gln Ser Gly Gln Tyr Gly Pro Gly Gln Gln
    1790                1795                1800
```

```
Gly Pro Gly Gln Gln Gly Pro Gly Ser Ser Ala Ala Ala Ala Ala
    1805                1810                1815

Gly Pro Gly Gln Tyr Gly Pro Gly Gln Gln Gly Pro Ser Ala Ser
    1820                1825                1830

Ala Ala Ala Ala Ala Gly Pro Gly Ser Gly Gln Gln Gly Pro Gly
    1835                1840                1845

Ala Ser Gly Gln Tyr Gly Pro Gly Gln Gln Gly Pro Gly Gln Gln
    1850                1855                1860

Gly Pro Gly Ser Ser Ala Ala Ala Ala Ala Gly Gln Tyr Gly Ser
    1865                1870                1875

Gly Pro Gly Gln Gln Gly Pro Tyr Gly Ser Ala Ala Ala Ala Ala
    1880                1885                1890

Gly Pro Gly Ser Gly Gln Tyr Gly Gln Gly Pro Tyr Gly Pro Gly
    1895                1900                1905

Ala Ser Gly Pro Gly Gln Tyr Gly Pro Gly Gln Gln Gly Pro Ser
    1910                1915                1920

Ala Ser Ala Ala Ala Ala Ala Gly Ser Gly Gln Gln Gly Pro Gly
    1925                1930                1935

Gln Tyr Gly Pro Tyr Ala Ser Ala Ala Ala Ala Ala Gly Gln Tyr
    1940                1945                1950

Gly Ser Gly Pro Gly Gln Gln Gly Pro Tyr Gly Pro Gly Gln Ser
    1955                1960                1965

Gly Ser Gly Gln Gln Gly Pro Gly Gln Gln Gly Pro Tyr Ala Ser
    1970                1975                1980

Ala Ala Ala Ala Ala Gly Pro Gly Gln Gln Gly Pro Tyr Gly Pro
    1985                1990                1995

Gly Ser Ser Ala Ala Ala Ala Ala Gly Gln Tyr Gly Tyr Gly Pro
    2000                2005                2010

Gly Gln Gln Gly Pro Tyr Gly Pro Gly Ala Ser Gly Gln Asn Gly
    2015                2020                2025

Pro Gly Ser Gly Gln Tyr Gly Pro Gly Gln Gln Gly Pro Gly Gln
    2030                2035                2040

Ser Ala Ala Ala Ala Ala Gly Pro Gly Gln Gln Gly Pro Tyr Gly
    2045                2050                2055

Pro Gly Ala Ser Ala Ala Ala Ala Ala Gly Gln Tyr Gly Pro Gly
    2060                2065                2070

Gln Gln Gly Pro Gly Gln Tyr Gly Pro Gly Ser Ser Gly Pro Gly
    2075                2080                2085

Gln Gln Gly Pro Tyr Gly Pro Gly Ser Ser Ala Ala Ala Ala Ala
    2090                2095                2100

Gly Gln Tyr Gly Pro Gly Gln Gln Gly Pro Tyr Gly Pro Gly Gln
    2105                2110                2115

Ser Ala Ala Ala Ala Ala Gly Gln Tyr Gln Gln Gly Pro Gly Gln
    2120                2125                2130

Gln Gly Pro Tyr Gly Pro Gly Ala Ser Gly Pro Gly Gln Gln Gly
    2135                2140                2145

Pro Tyr Gly Pro Gly Ala Ser Ala Ala Ala Ala Ala Gly Pro Gly
    2150                2155                2160

Gln Tyr Gly Pro Gly Gln Gln Gly Pro Ser Ala Ser Ala Ala Ala
    2165                2170                2175

Ala Ala Gly Gln Tyr Gly Ser Gly Pro Gly Gln Tyr Gly Pro Tyr
    2180                2185                2190

Gly Pro Gly Gln Ser Gly Pro Gly Ser Gly Gln Gln Gly Gln Gly
```

```
    2195                2200                2205

Pro Tyr  Gly Pro Gly Ala Ser  Ala Ala Ala Ala Ala  Gly Gln Tyr
    2210                2215                2220

Gly Pro  Gly Gln Gln Gly Pro  Tyr Gly Pro Gly Gln  Ser Ala Ala
    2225                2230                2235

Ala Ala  Ala Gly Pro Gly Ser  Gly Gln Tyr Gly Pro  Gly Ala Ser
    2240                2245                2250

Gly Gln  Asn Gly Pro Gly Ser  Gly Gln Tyr Gly Pro  Gly Gln Gln
    2255                2260                2265

Gly Pro  Gly Gln Ser Ala Ala  Ala Ala Ala Gly Gln  Tyr Gln Gln
    2270                2275                2280

Gly Pro  Gly Gln Gln Gly Pro  Tyr Gly Pro Gly Ala  Ser Ala Ala
    2285                2290                2295

Ala Ala  Ala Gly Gln Tyr Gly  Ser Gly Pro Gly Gln  Gln Gly Pro
    2300                2305                2310

Tyr Gly  Pro Gly Gln Ser Gly  Ser Gly Gln Gln Gly  Pro Gly Gln
    2315                2320                2325

Gln Gly  Pro Tyr Ala Ser Ala  Ala Ala Ala Ala Gly  Pro Gly Ser
    2330                2335                2340

Gly Gln  Gln Gly Ser Ser Val  Asp Lys Leu Ala Ala  Ala Leu Glu
    2345                2350                2355

His His  His His His His
    2360


<210> SEQ ID NO 10
<211> LENGTH: 597
<212> TYPE: PRT
<213> ORGANISM: Artificial Sequence
<220> FEATURE:
<223> OTHER INFORMATION: Met-PRT313

<400> SEQUENCE: 10

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
            20                  25                  30

Gly Ser Ala Ala Ala Ala Ala Gly Gly Tyr Gly Pro Gly Gly Gln Gly
        35                  40                  45

Pro Gly Gln Gln Gly Pro Gly Ser Ser Ala Ala Ala Ala Ala Gly Pro
    50                  55                  60

Gly Gly Tyr Gly Pro Gly Gly Gln Gly Pro Ser Ala Ser Ala Ala Ala
65                  70                  75                  80

Ala Ala Gly Pro Gly Ser Gly Gln Gln Gly Pro Gly Ala Ser Ala Ala
                85                  90                  95

Ala Ala Ala Gly Gly Tyr Gly Pro Gly Gly Gln Gly Pro Gly Gln Gln
            100                 105                 110

Gly Pro Gly Ser Ser Ala Ala Ala Ala Ala Gly Gly Tyr Gly Ser Gly
        115                 120                 125

Pro Gly Gln Gln Gly Pro Tyr Gly Ser Ala Ala Ala Ala Ala Gly Pro
    130                 135                 140

Gly Ser Gly Gly Tyr Gly Gln Gly Pro Tyr Gly Pro Gly Ala Ser Ala
145                 150                 155                 160

Ala Ala Ala Ala Gly Pro Gly Gly Tyr Gly Pro Gly Gly Gln Gly Pro
                165                 170                 175

Ser Ala Ser Ala Ala Ala Ala Ala Gly Ser Gly Gln Gln Gly Pro Gly
```

-continued

```
            180                 185                 190

Gly Tyr Gly Pro Tyr Ala Ser Ala Ala Ala Ala Ala Gly Gly Tyr Gly
        195                 200                 205

Ser Gly Pro Gly Gln Gln Gly Pro Tyr Gly Pro Gly Gly Ser Ala Ala
    210                 215                 220

Ala Ala Ala Gly Ser Gly Gln Gln Gly Pro Gly Gln Gln Gly Pro Tyr
225                 230                 235                 240

Ala Ser Ala Ala Ala Ala Ala Gly Pro Gly Gly Gln Gly Pro Tyr Gly
                245                 250                 255

Pro Gly Ser Ser Ala Ala Ala Ala Ala Gly Gly Tyr Gly Tyr Gly Pro
            260                 265                 270

Gly Gly Gln Gly Pro Tyr Gly Pro Gly Ala Ser Ala Ala Ala Ala Ala
        275                 280                 285

Gly Gly Asn Gly Pro Gly Ser Gly Gly Tyr Gly Pro Gly Gln Gln Gly
    290                 295                 300

Pro Gly Gly Ser Ala Ala Ala Ala Ala Gly Pro Gly Gly Gln Gly Pro
305                 310                 315                 320

Tyr Gly Pro Gly Ala Ser Ala Ala Ala Ala Ala Gly Gly Tyr Gly Pro
                325                 330                 335

Gly Gly Gln Gly Pro Gly Gly Tyr Gly Pro Gly Ser Ser Ala Ala Ala
            340                 345                 350

Ala Ala Gly Pro Gly Gly Gln Gly Pro Tyr Gly Pro Gly Ser Ser Ala
        355                 360                 365

Ala Ala Ala Ala Gly Gly Tyr Gly Pro Gly Gln Gln Gly Pro Tyr Gly
    370                 375                 380

Pro Gly Gly Ser Ala Ala Ala Ala Ala Gly Gly Tyr Gln Gln Gly Pro
385                 390                 395                 400

Gly Gly Gln Gly Pro Tyr Gly Pro Gly Ala Ser Ala Ala Ala Ala Ala
                405                 410                 415

Gly Pro Gly Gly Gln Gly Pro Tyr Gly Pro Gly Ala Ser Ala Ala Ala
            420                 425                 430

Ala Ala Gly Pro Gly Gly Tyr Gly Pro Gly Gly Gln Gly Pro Ser Ala
        435                 440                 445

Ser Ala Ala Ala Ala Ala Gly Gly Tyr Gly Ser Gly Pro Gly Gly Tyr
    450                 455                 460

Gly Pro Tyr Gly Pro Gly Gly Ser Ala Ala Ala Ala Ala Gly Pro Gly
465                 470                 475                 480

Ser Gly Gln Gln Gly Gln Gly Pro Tyr Gly Pro Gly Ala Ser Ala Ala
                485                 490                 495

Ala Ala Ala Gly Gly Tyr Gly Pro Gly Gln Gln Gly Pro Tyr Gly Pro
            500                 505                 510

Gly Gly Ser Ala Ala Ala Ala Ala Gly Pro Gly Ser Gly Gly Tyr Gly
        515                 520                 525

Pro Gly Ala Ser Ala Ala Ala Ala Ala Gly Gly Asn Gly Pro Gly Ser
    530                 535                 540

Gly Gly Tyr Gly Pro Gly Gln Gln Gly Pro Gly Gly Ser Ala Ala Ala
545                 550                 555                 560

Ala Ala Gly Gly Tyr Gln Gln Gly Pro Gly Gly Gln Gly Pro Tyr Gly
                565                 570                 575

Pro Gly Ala Ser Ala Ala Ala Ala Ala Gly Pro Gly Ser Gly Gln Gln
            580                 585                 590

Gly Pro Gly Ala Ser
        595
```

<210> SEQ ID NO 11
<211> LENGTH: 12
<212> TYPE: PRT
<213> ORGANISM: Artificial Sequence
<220> FEATURE:
<223> OTHER INFORMATION: HisTag

<400> SEQUENCE: 11

Met His His His His His His Ser Ser Gly Ser Ser
1 5 10

<210> SEQ ID NO 12
<211> LENGTH: 608
<212> TYPE: PRT
<213> ORGANISM: Artificial Sequence
<220> FEATURE:
<223> OTHER INFORMATION: PRT380

<400> SEQUENCE: 12

Met His His His His His His Ser Ser Gly Ser Ser Gly Pro Gly Gln
1 5 10 15

Gln Gly Pro Tyr Gly Pro Gly Ala Ser Ala Ala Ala Ala Ala Gly Gln
20 25 30

Asn Gly Pro Gly Ser Gly Gln Gln Gly Pro Gly Gln Ser Ala Ala Ala
35 40 45

Ala Ala Gly Gln Tyr Gly Pro Gly Gln Gln Gly Pro Gly Gln Gln Gly
50 55 60

Pro Gly Ser Ser Ala Ala Ala Ala Ala Gly Pro Gly Gln Tyr Gly Pro
65 70 75 80

Gly Gln Gln Gly Pro Ser Ala Ser Ala Ala Ala Ala Ala Gly Pro Gly
85 90 95

Ser Gly Gln Gln Gly Pro Gly Ala Ser Ala Ala Ala Ala Ala Gly Gln
100 105 110

Tyr Gly Pro Gly Gln Gln Gly Pro Gly Gln Gln Gly Pro Gly Ser Ser
115 120 125

Ala Ala Ala Ala Ala Gly Gln Tyr Gly Ser Gly Pro Gly Gln Gln Gly
130 135 140

Pro Tyr Gly Ser Ala Ala Ala Ala Ala Gly Pro Gly Ser Gly Gln Tyr
145 150 155 160

Gly Gln Gly Pro Tyr Gly Pro Gly Ala Ser Ala Ala Ala Ala Ala Gly
165 170 175

Pro Gly Gln Tyr Gly Pro Gly Gln Gln Gly Pro Ser Ala Ser Ala Ala
180 185 190

Ala Ala Ala Gly Ser Gly Gln Gln Gly Pro Gly Gln Tyr Gly Pro Tyr
195 200 205

Ala Ser Ala Ala Ala Ala Ala Gly Gln Tyr Gly Ser Gly Pro Gly Gln
210 215 220

Gln Gly Pro Tyr Gly Pro Gly Gln Ser Ala Ala Ala Ala Ala Gly Ser
225 230 235 240

Gly Gln Gln Gly Pro Gly Gln Gln Gly Pro Tyr Ala Ser Ala Ala Ala
245 250 255

Ala Ala Gly Pro Gly Gln Gln Gly Pro Tyr Gly Pro Gly Ser Ser Ala
260 265 270

Ala Ala Ala Ala Gly Gln Tyr Gly Tyr Gly Pro Gly Gln Gln Gly Pro
275 280 285

Tyr Gly Pro Gly Ala Ser Ala Ala Ala Ala Ala Gly Gln Asn Gly Pro

```
    290                 295                 300

Gly Ser Gly Gln Tyr Gly Pro Gly Gln Gln Gly Pro Gly Gln Ser Ala
305                 310                 315                 320

Ala Ala Ala Ala Gly Pro Gly Gln Gln Gly Pro Tyr Gly Pro Gly Ala
                325                 330                 335

Ser Ala Ala Ala Ala Ala Gly Gln Tyr Gly Pro Gly Gln Gln Gly Pro
            340                 345                 350

Gly Gln Tyr Gly Pro Gly Ser Ser Ala Ala Ala Ala Ala Gly Pro Gly
        355                 360                 365

Gln Gln Gly Pro Tyr Gly Pro Gly Ser Ser Ala Ala Ala Ala Ala Gly
    370                 375                 380

Gln Tyr Gly Pro Gly Gln Gln Gly Pro Tyr Gly Pro Gly Gln Ser Ala
385                 390                 395                 400

Ala Ala Ala Ala Gly Gln Tyr Gln Gln Gly Pro Gly Gln Gln Gly Pro
                405                 410                 415

Tyr Gly Pro Gly Ala Ser Ala Ala Ala Ala Ala Gly Pro Gly Gln Gln
            420                 425                 430

Gly Pro Tyr Gly Pro Gly Ala Ser Ala Ala Ala Ala Ala Gly Pro Gly
        435                 440                 445

Gln Tyr Gly Pro Gly Gln Gln Gly Pro Ser Ala Ser Ala Ala Ala Ala
    450                 455                 460

Ala Gly Gln Tyr Gly Ser Gly Pro Gly Gln Tyr Gly Pro Tyr Gly Pro
465                 470                 475                 480

Gly Gln Ser Ala Ala Ala Ala Ala Gly Pro Gly Ser Gly Gln Gln Gly
                485                 490                 495

Gln Gly Pro Tyr Gly Pro Gly Ala Ser Ala Ala Ala Ala Ala Gly Gln
            500                 505                 510

Tyr Gly Pro Gly Gln Gln Gly Pro Tyr Gly Pro Gly Gln Ser Ala Ala
        515                 520                 525

Ala Ala Ala Gly Pro Gly Ser Gly Gln Tyr Gly Pro Gly Ala Ser Ala
    530                 535                 540

Ala Ala Ala Ala Gly Gln Asn Gly Pro Gly Ser Gly Gln Tyr Gly Pro
545                 550                 555                 560

Gly Gln Gln Gly Pro Gly Gln Ser Ala Ala Ala Ala Ala Gly Gln Tyr
                565                 570                 575

Gln Gln Gly Pro Gly Gln Gln Gly Pro Tyr Gly Pro Gly Ala Ser Ala
            580                 585                 590

Ala Ala Ala Ala Gly Pro Gly Ser Gly Gln Gln Gly Pro Gly Ala Ser
        595                 600                 605


<210> SEQ ID NO 13
<211> LENGTH: 601
<212> TYPE: PRT
<213> ORGANISM: Artificial Sequence
<220> FEATURE:
<223> OTHER INFORMATION: PRT410

<400> SEQUENCE: 13

Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Gly Gln
            20                  25                  30

Asn Gly Pro Gly Ser Gly Gln Gln Gly Pro Gly Gln Ser Gly Gln Tyr
        35                  40                  45

Gly Pro Gly Gln Gln Gly Pro Gly Gln Gln Gly Pro Gly Ser Ser Ala
```

-continued

```
    50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Ala Gly Gln Tyr Gly Ser
        115                 120                 125

Gly Pro Gly Gln Gln Gly Pro Tyr Gly Ser Ala Ala Ala Ala Ala Gly
    130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Ala Gly Ser Gly Gln Gln Gly Pro Gly Gln Tyr Gly Pro
            180                 185                 190

Tyr Ala Ser Ala Ala Ala Ala Ala Gly Gln Tyr Gly Ser Gly Pro Gly
        195                 200                 205

Gln Gln Gly Pro Tyr Gly Pro Gly Gln Ser Gly Ser Gly Gln Gln Gly
    210                 215                 220

Pro Gly Gln Gln Gly Pro Tyr Ala Ser Ala Ala Ala Ala Ala Gly Pro
225                 230                 235                 240

Gly Gln Gln Gly Pro Tyr Gly Pro Gly Ser Ser Ala Ala Ala Ala Ala
                245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
        275                 280                 285

Gln Gly Pro Gly Gln Ser Ala Ala Ala Ala Ala Gly Pro Gly Gln Gln
    290                 295                 300

Gly Pro Tyr Gly Pro Gly Ala Ser Ala Ala Ala Ala Ala Gly Gln Tyr
305                 310                 315                 320

Gly Pro Gly Gln Gln Gly Pro Gly Gln Tyr Gly Pro Gly Ser Ser Gly
                325                 330                 335

Pro Gly Gln Gln Gly Pro Tyr Gly Pro Gly Ser Ser Ala Ala Ala Ala
            340                 345                 350

Ala Gly Gln Tyr Gly Pro Gly Gln Gln Gly Pro Tyr Gly Pro Gly Gln
        355                 360                 365

Ser Ala Ala Ala Ala Ala Gly Gln Tyr Gln Gln Gly Pro Gly Gln Gln
    370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Ala Gly Pro Gly Gln Tyr Gly
                405                 410                 415

Pro Gly Gln Gln Gly Pro Ser Ala Ser Ala Ala Ala Ala Ala Gly Gln
            420                 425                 430

Tyr Gly Ser Gly Pro Gly Gln Tyr Gly Pro Tyr Gly Pro Gly Gln Ser
        435                 440                 445

Gly Pro Gly Ser Gly Gln Gln Gly Gln Gly Pro Tyr Gly Pro Gly Ala
    450                 455                 460

Ser Ala Ala Ala Ala Ala Gly Gln Tyr Gly Pro Gly Gln Gln Gly Pro
465                 470                 475                 480
```

```
Tyr Gly Pro Gly Gln Ser Ala Ala Ala Ala Ala Gly Pro Gly Ser Gly
                485                 490                 495

Gln Tyr Gly Pro Gly Ala Ser Gly Gln Asn Gly Pro Gly Ser Gly Gln
            500                 505                 510

Tyr Gly Pro Gly Gln Gln Gly Pro Gly Gln Ser Ala Ala Ala Ala Ala
        515                 520                 525

Gly Gln Tyr Gln Gln Gly Pro Gly Gln Gln Gly Pro Tyr Gly Pro Gly
    530                 535                 540

Ala Ser Ala Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Ala Gly Pro Gly
            580                 585                 590

Ser Gly Gln Gln Gly Pro Gly Ala Ser
        595                 600


<210> SEQ ID NO 14
<211> LENGTH: 576
<212> TYPE: PRT
<213> ORGANISM: Artificial Sequence
<220> FEATURE:
<223> OTHER INFORMATION: PRT525

<400> SEQUENCE: 14

Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Ala Ala
            20                  25                  30

Gly Ser Asn Gly Pro Gly Ser Gly Gln Gln Gly Pro Gly Gln Ser Gly
        35                  40                  45

Gln Tyr Gly Pro Gly Gln Gln Gly Pro Gly Gln Gln Gly Pro Gly Ser
    50                  55                  60

Ser Ala Ala Ala Ala Ala Ala Ala Gly Pro Gly Gln Tyr Gly Pro Gly
65                  70                  75                  80

Gln Gln Gly Pro Ser Ala Ser Ala Ala Ala Ala Ala Ala Ala Gly Pro
                85                  90                  95

Gly Ser Gly Gln Gln Gly Pro Gly Ala Ser Gly Gln Tyr Gly Pro Gly
            100                 105                 110

Gln Gln Gly Pro Gly Gln Gln Gly Pro Gly Ser Ser Ala Ala Ala Ala
        115                 120                 125

Ala Ala Ala Gly Ser Tyr Gly Ser Gly Pro Gly Gln Gln Gly Pro Tyr
    130                 135                 140

Gly Ser Ala Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Gln Gln Gly Pro Ser Ala Ser Ala Ala Ala Ala Ala Ala Ala
            180                 185                 190

Gly Ser Gly Gln Gln Gly Pro Gly Gln Tyr Gly Pro Tyr Ala Ser Ala
        195                 200                 205

Ala Ala Ala Ala Ala Ala Gly Ser Tyr Gly Ser Gly Pro Gly Gln Gln
    210                 215                 220

Gly Pro Tyr Gly Pro Gly Gln Ser Gly Ser Gly Gln Gln Gly Pro Gly
225                 230                 235                 240
```

```
Gln Gln Gly Pro Tyr Ala Ser Ala Ala Ala Ala Ala Ala Ala Gly Pro
                245                 250                 255

Gly Gln Gln Gly Pro Tyr Gly Pro Gly Ser Ser Ala Ala Ala Ala Ala
            260                 265                 270

Ala Ala Gly Ser Tyr Gly Tyr Gly Pro Gly Gln Gln Gly Pro Tyr Gly
        275                 280                 285

Pro Gly Ala Ser Gly Gln Asn Gly Pro Gly Ser Gly Gln Tyr Gly Pro
    290                 295                 300

Gly Gln Gln Gly Pro Gly Pro Ser Ala Ala Ala Ala Ala Ala Ala Gly
305                 310                 315                 320

Pro Gly Gln Gln Gly Pro Tyr Gly Pro Gly Ala Ser Ala Ala Ala Ala
                325                 330                 335

Ala Ala Ala Gly Ser Tyr Gly Pro Gly Gln Gln Gly Pro Gly Gln Tyr
            340                 345                 350

Gly Pro Gly Ser Ser Gly Pro Gly Gln Gln Gly Pro Tyr Gly Pro Gly
        355                 360                 365

Ser Ser Ala Ala Ala Ala Ala Ala Ala Gly Ser Tyr Gly Pro Gly Gln
    370                 375                 380

Gln Gly Pro Tyr Gly Pro Gly Pro Ser Ala Ala Ala Ala Ala Ala Ala
385                 390                 395                 400

Gly Ser Tyr Gln Gln Gly Pro Gly Gln Gln Gly Pro Tyr Gly Pro Gly
                405                 410                 415

Ala Ser Gly Pro Gly Gln Gln Gly Pro Tyr Gly Pro Gly Ala Ser Ala
            420                 425                 430

Ala Ala Ala Ala Ala Ala Gly Pro Gly Gln Tyr Gly Pro Gly Gln Gln
        435                 440                 445

Gly Pro Ser Ala Ser Ala Ala Ala Ala Ala Ala Ala Gly Ser Tyr Gly
    450                 455                 460

Ser Gly Pro Gly Gln Tyr Gly Pro Tyr Gly Pro Gly Gln Ser Gly Pro
465                 470                 475                 480

Gly Ser Gly Gln Gln Gly Gln Gly Pro Tyr Gly Pro Gly Ala Ser Ala
                485                 490                 495

Ala Ala Ala Ala Ala Ala Gly Ser Tyr Gly Pro Gly Gln Gln Gly Pro
            500                 505                 510

Tyr Gly Pro Gly Pro Ser Ala Ala Ala Ala Ala Ala Ala Gly Pro Gly
        515                 520                 525

Ser Gly Gln Tyr Gly Pro Gly Ala Ser Gly Gln Asn Gly Pro Gly Ser
    530                 535                 540

Gly Gln Tyr Gly Pro Gly Gln Gln Gly Pro Gly Pro Ser Ala Ala Ala
545                 550                 555                 560

Ala Ala Ala Ala Gly Pro Gly Ser Gly Gln Gln Gly Pro Gly Ala Ser
                565                 570                 575
```

<210> SEQ ID NO 15
<211> LENGTH: 2375
<212> TYPE: PRT
<213> ORGANISM: Artificial Sequence
<220> FEATURE:
<223> OTHER INFORMATION: PRT799

<400> SEQUENCE: 15

```
Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Gly Gln
            20                  25                  30
```

-continued

```
Asn Gly Pro Gly Ser Gly Gln Gln Gly Pro Gly Gln Ser Gly Gln Tyr
        35                  40                  45

Gly Pro Gly Gln Gln Gly Pro Gly Gln Gln Gly Pro Gly Ser Ser Ala
    50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Ala Gly Gln Tyr Gly Ser
        115                 120                 125

Gly Pro Gly Gln Gln Gly Pro Tyr Gly Ser Ala Ala Ala Ala Ala Gly
    130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Ala Gly Ser Gly Gln Gln Gly Pro Gly Gln Tyr Gly Pro
            180                 185                 190

Tyr Ala Ser Ala Ala Ala Ala Ala Gly Gln Tyr Gly Ser Gly Pro Gly
        195                 200                 205

Gln Gln Gly Pro Tyr Gly Pro Gly Gln Ser Gly Ser Gly Gln Gln Gly
    210                 215                 220

Pro Gly Gln Gln Gly Pro Tyr Ala Ser Ala Ala Ala Ala Ala Gly Pro
225                 230                 235                 240

Gly Gln Gln Gly Pro Tyr Gly Pro Gly Ser Ser Ala Ala Ala Ala Ala
                245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
        275                 280                 285

Gln Gly Pro Gly Gln Ser Ala Ala Ala Ala Ala Gly Pro Gly Gln Gln
    290                 295                 300

Gly Pro Tyr Gly Pro Gly Ala Ser Ala Ala Ala Ala Ala Gly Gln Tyr
305                 310                 315                 320

Gly Pro Gly Gln Gln Gly Pro Gly Gln Tyr Gly Pro Gly Ser Ser Gly
                325                 330                 335

Pro Gly Gln Gln Gly Pro Tyr Gly Pro Gly Ser Ser Ala Ala Ala Ala
            340                 345                 350

Ala Gly Gln Tyr Gly Pro Gly Gln Gln Gly Pro Tyr Gly Pro Gly Gln
        355                 360                 365

Ser Ala Ala Ala Ala Ala Gly Gln Tyr Gln Gln Gly Pro Gly Gln Gln
    370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Ala Gly Pro Gly Gln Tyr Gly
                405                 410                 415

Pro Gly Gln Gln Gly Pro Ser Ala Ser Ala Ala Ala Ala Ala Gly Gln
            420                 425                 430

Tyr Gly Ser Gly Pro Gly Gln Tyr Gly Pro Tyr Gly Pro Gly Gln Ser
        435                 440                 445
```

```
Gly Pro Gly Ser Gly Gln Gln Gly Gln Gly Pro Tyr Gly Pro Gly Ala
    450                 455                 460

Ser Ala Ala Ala Ala Ala Gly Gln Tyr Gly Pro Gly Gln Gln Gly Pro
465                 470                 475                 480

Tyr Gly Pro Gly Gln Ser Ala Ala Ala Ala Ala Gly Pro Gly Ser Gly
                485                 490                 495

Gln Tyr Gly Pro Gly Ala Ser Gly Gln Asn Gly Pro Gly Ser Gly Gln
            500                 505                 510

Tyr Gly Pro Gly Gln Gln Gly Pro Gly Gln Ser Ala Ala Ala Ala Ala
        515                 520                 525

Gly Gln Tyr Gln Gln Gly Pro Gly Gln Gln Gly Pro Tyr Gly Pro Gly
    530                 535                 540

Ala Ser Ala Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Ala Gly Pro Gly
            580                 585                 590

Ser Gly Gln Gln Gly Pro Gly Ala Ser Gly Gln Gln Gly Pro Tyr Gly
        595                 600                 605

Pro Gly Ala Ser Ala Ala Ala Ala Ala Gly Gln Asn Gly Pro Gly Ser
    610                 615                 620

Gly Gln Gln Gly Pro Gly Gln Ser Gly Gln Tyr Gly Pro Gly Gln Gln
625                 630                 635                 640

Gly Pro Gly Gln Gln Gly Pro Gly Ser Ser Ala Ala Ala Ala Ala Gly
                645                 650                 655

Pro Gly Gln Tyr Gly Pro Gly Gln Gln Gly Pro Ser Ala Ser Ala Ala
            660                 665                 670

Ala Ala Ala Gly Pro Gly Ser Gly Gln Gln Gly Pro Gly Ala Ser Gly
        675                 680                 685

Gln Tyr Gly Pro Gly Gln Gln Gly Pro Gly Gln Gln Gly Pro Gly Ser
    690                 695                 700

Ser Ala Ala Ala Ala Ala Gly Gln Tyr Gly Ser Gly Pro Gly Gln Gln
705                 710                 715                 720

Gly Pro Tyr Gly Ser Ala Ala Ala Ala Ala Gly Pro Gly Ser Gly Gln
                725                 730                 735

Tyr Gly Gln Gly Pro Tyr Gly Pro Gly Ala Ser Gly Pro Gly Gln Tyr
            740                 745                 750

Gly Pro Gly Gln Gln Gly Pro Ser Ala Ser Ala Ala Ala Ala Ala Gly
        755                 760                 765

Ser Gly Gln Gln Gly Pro Gly Gln Tyr Gly Pro Tyr Ala Ser Ala Ala
    770                 775                 780

Ala Ala Ala Gly Gln Tyr Gly Ser Gly Pro Gly Gln Gln Gly Pro Tyr
785                 790                 795                 800

Gly Pro Gly Gln Ser Gly Ser Gly Gln Gln Gly Pro Gly Gln Gln Gly
                805                 810                 815

Pro Tyr Ala Ser Ala Ala Ala Ala Ala Gly Pro Gly Gln Gln Gly Pro
            820                 825                 830

Tyr Gly Pro Gly Ser Ser Ala Ala Ala Ala Ala Gly Gln Tyr Gly Tyr
        835                 840                 845

Gly Pro Gly Gln Gln Gly Pro Tyr Gly Pro Gly Ala Ser Gly Gln Asn
    850                 855                 860

Gly Pro Gly Ser Gly Gln Tyr Gly Pro Gly Gln Gln Gly Pro Gly Gln
```

-continued

```
865                 870                 875                 880

Ser Ala Ala Ala Ala Ala Gly Pro Gly Gln Gln Gly Pro Tyr Gly Pro
                885                 890                 895

Gly Ala Ser Ala Ala Ala Ala Ala Gly Gln Tyr Gly Pro Gly Gln Gln
            900                 905                 910

Gly Pro Gly Gln Tyr Gly Pro Gly Ser Ser Gly Pro Gly Gln Gln Gly
        915                 920                 925

Pro Tyr Gly Pro Gly Ser Ser Ala Ala Ala Ala Ala Gly Gln Tyr Gly
    930                 935                 940

Pro Gly Gln Gln Gly Pro Tyr Gly Pro Gly Gln Ser Ala Ala Ala Ala
945                 950                 955                 960

Ala Gly Gln Tyr Gln Gln Gly Pro Gly Gln Gln Gly Pro Tyr Gly Pro
                965                 970                 975

Gly Ala Ser Gly Pro Gly Gln Gln Gly Pro Tyr Gly Pro Gly Ala Ser
            980                 985                 990

Ala Ala Ala Ala Ala Gly Pro Gly  Gln Tyr Gly Pro Gly  Gln Gln Gly
        995                 1000                1005

Pro Ser  Ala Ser Ala Ala Ala  Ala Ala Gly Gln Tyr  Gly Ser Gly
    1010                1015                1020

Pro Gly  Gln Tyr Gly Pro Tyr  Gly Pro Gly Gln Ser  Gly Pro Gly
    1025                1030                1035

Ser Gly  Gln Gln Gly Gln Gly  Pro Tyr Gly Pro Gly  Ala Ser Ala
    1040                1045                1050

Ala Ala  Ala Ala Gly Gln Tyr  Gly Pro Gly Gln Gln  Gly Pro Tyr
    1055                1060                1065

Gly Pro  Gly Gln Ser Ala Ala  Ala Ala Ala Gly Pro  Gly Ser Gly
    1070                1075                1080

Gln Tyr  Gly Pro Gly Ala Ser  Gly Gln Asn Gly Pro  Gly Ser Gly
    1085                1090                1095

Gln Tyr  Gly Pro Gly Gln Gln  Gly Pro Gly Gln Ser  Ala Ala Ala
    1100                1105                1110

Ala Ala  Gly Gln Tyr Gln Gln  Gly Pro Gly Gln Gln  Gly Pro Tyr
    1115                1120                1125

Gly Pro  Gly Ala Ser Ala Ala  Ala Ala Ala Gly Gln  Tyr Gly Ser
    1130                1135                1140

Gly Pro  Gly Gln Gln Gly Pro  Tyr Gly Pro Gly Gln  Ser Gly Ser
    1145                1150                1155

Gly Gln  Gln Gly Pro Gly Gln  Gln Gly Pro Tyr Ala  Ser Ala Ala
    1160                1165                1170

Ala Ala  Ala Gly Pro Gly Ser  Gly Gln Gln Gly Pro  Gly Ala Ser
    1175                1180                1185

Gly Gln  Gln Gly Pro Tyr Gly  Pro Gly Ala Ser Ala  Ala Ala Ala
    1190                1195                1200

Ala Gly  Gln Asn Gly Pro Gly  Ser Gly Gln Gln Gly  Pro Gly Gln
    1205                1210                1215

Ser Gly  Gln Tyr Gly Pro Gly  Gln Gln Gly Pro Gly  Gln Gln Gly
    1220                1225                1230

Pro Gly  Ser Ser Ala Ala Ala  Ala Ala Gly Pro Gly  Gln Tyr Gly
    1235                1240                1245

Pro Gly  Gln Gln Gly Pro Ser  Ala Ser Ala Ala Ala  Ala Ala Gly
    1250                1255                1260

Pro Gly  Ser Gly Gln Gln Gly  Pro Gly Ala Ser Gly  Gln Tyr Gly
    1265                1270                1275
```

```
Pro Gly Gln Gln Gly Pro Gly Gln Gln Gly Pro Gly Ser Ser Ala
    1280                1285                1290

Ala Ala Ala Ala Gly Gln Tyr Gly Ser Gly Pro Gly Gln Gln Gly
    1295                1300                1305

Pro Tyr Gly Ser Ala Ala Ala Ala Ala Gly Pro Gly Ser Gly Gln
    1310                1315                1320

Tyr Gly Gln Gly Pro Tyr Gly Pro Gly Ala Ser Gly Pro Gly Gln
    1325                1330                1335

Tyr Gly Pro Gly Gln Gln Gly Pro Ser Ala Ser Ala Ala Ala Ala
    1340                1345                1350

Ala Gly Ser Gly Gln Gln Gly Pro Gly Gln Tyr Gly Pro Tyr Ala
    1355                1360                1365

Ser Ala Ala Ala Ala Ala Gly Gln Tyr Gly Ser Gly Pro Gly Gln
    1370                1375                1380

Gln Gly Pro Tyr Gly Pro Gly Gln Ser Gly Ser Gly Gln Gln Gly
    1385                1390                1395

Pro Gly Gln Gln Gly Pro Tyr Ala Ser Ala Ala Ala Ala Ala Gly
    1400                1405                1410

Pro Gly Gln Gln Gly Pro Tyr Gly Pro Gly Ser Ser Ala Ala Ala
    1415                1420                1425

Ala Ala Gly Gln Tyr Gly Tyr Gly Pro Gly Gln Gln Gly Pro Tyr
    1430                1435                1440

Gly Pro Gly Ala Ser Gly Gln Asn Gly Pro Gly Ser Gly Gln Tyr
    1445                1450                1455

Gly Pro Gly Gln Gln Gly Pro Gly Gln Ser Ala Ala Ala Ala Ala
    1460                1465                1470

Gly Pro Gly Gln Gln Gly Pro Tyr Gly Pro Gly Ala Ser Ala Ala
    1475                1480                1485

Ala Ala Ala Gly Gln Tyr Gly Pro Gly Gln Gln Gly Pro Gly Gln
    1490                1495                1500

Tyr Gly Pro Gly Ser Ser Gly Pro Gly Gln Gln Gly Pro Tyr Gly
    1505                1510                1515

Pro Gly Ser Ser Ala Ala Ala Ala Ala Gly Gln Tyr Gly Pro Gly
    1520                1525                1530

Gln Gln Gly Pro Tyr Gly Pro Gly Gln Ser Ala Ala Ala Ala Ala
    1535                1540                1545

Gly Gln Tyr Gln Gln Gly Pro Gly Gln Gln Gly Pro Tyr Gly Pro
    1550                1555                1560

Gly Ala Ser Gly Pro Gly Gln Gln Gly Pro Tyr Gly Pro Gly Ala
    1565                1570                1575

Ser Ala Ala Ala Ala Ala Gly Pro Gly Gln Tyr Gly Pro Gly Gln
    1580                1585                1590

Gln Gly Pro Ser Ala Ser Ala Ala Ala Ala Ala Gly Gln Tyr Gly
    1595                1600                1605

Ser Gly Pro Gly Gln Tyr Gly Pro Tyr Gly Pro Gly Gln Ser Gly
    1610                1615                1620

Pro Gly Ser Gly Gln Gln Gly Gln Gly Pro Tyr Gly Pro Gly Ala
    1625                1630                1635

Ser Ala Ala Ala Ala Ala Gly Gln Tyr Gly Pro Gly Gln Gln Gly
    1640                1645                1650

Pro Tyr Gly Pro Gly Gln Ser Ala Ala Ala Ala Ala Gly Pro Gly
    1655                1660                1665
```

```
Ser Gly  Gln Tyr Gly Pro Gly  Ala Ser Gly Gln Asn  Gly Pro Gly
    1670                 1675                 1680

Ser Gly  Gln Tyr Gly Pro Gly  Gln Gln Gly Pro Gly  Gln Ser Ala
    1685                 1690                 1695

Ala Ala  Ala Ala Gly Gln Tyr  Gln Gln Gly Pro Gly  Gln Gln Gly
    1700                 1705                 1710

Pro Tyr  Gly Pro Gly Ala Ser  Ala Ala Ala Ala Ala  Gly Gln Tyr
    1715                 1720                 1725

Gly Ser  Gly Pro Gly Gln Gln  Gly Pro Tyr Gly Pro  Gly Gln Ser
    1730                 1735                 1740

Gly Ser  Gly Gln Gln Gly Pro  Gly Gln Gln Gly Pro  Tyr Ala Ser
    1745                 1750                 1755

Ala Ala  Ala Ala Ala Gly Pro  Gly Ser Gly Gln Gln  Gly Pro Gly
    1760                 1765                 1770

Ala Ser  Gly Gln Gln Gly Pro  Tyr Gly Pro Gly Ala  Ser Ala Ala
    1775                 1780                 1785

Ala Ala  Ala Gly Gln Asn Gly  Pro Gly Ser Gly Gln  Gln Gly Pro
    1790                 1795                 1800

Gly Gln  Ser Gly Gln Tyr Gly  Pro Gly Gln Gln Gly  Pro Gly Gln
    1805                 1810                 1815

Gln Gly  Pro Gly Ser Ser Ala  Ala Ala Ala Ala Gly  Pro Gly Gln
    1820                 1825                 1830

Tyr Gly  Pro Gly Gln Gln Gly  Pro Ser Ala Ser Ala  Ala Ala Ala
    1835                 1840                 1845

Ala Gly  Pro Gly Ser Gly Gln  Gln Gly Pro Gly Ala  Ser Gly Gln
    1850                 1855                 1860

Tyr Gly  Pro Gly Gln Gln Gly  Pro Gly Gln Gln Gly  Pro Gly Ser
    1865                 1870                 1875

Ser Ala  Ala Ala Ala Ala Gly  Gln Tyr Gly Ser Gly  Pro Gly Gln
    1880                 1885                 1890

Gln Gly  Pro Tyr Gly Ser Ala  Ala Ala Ala Ala Gly  Pro Gly Ser
    1895                 1900                 1905

Gly Gln  Tyr Gly Gln Gly Pro  Tyr Gly Pro Gly Ala  Ser Gly Pro
    1910                 1915                 1920

Gly Gln  Tyr Gly Pro Gly Gln  Gln Gly Pro Ser Ala  Ser Ala Ala
    1925                 1930                 1935

Ala Ala  Ala Gly Ser Gly Gln  Gln Gly Pro Gly Gln  Tyr Gly Pro
    1940                 1945                 1950

Tyr Ala  Ser Ala Ala Ala Ala  Ala Gly Gln Tyr Gly  Ser Gly Pro
    1955                 1960                 1965

Gly Gln  Gln Gly Pro Tyr Gly  Pro Gly Gln Ser Gly  Ser Gly Gln
    1970                 1975                 1980

Gln Gly  Pro Gly Gln Gln Gly  Pro Tyr Ala Ser Ala  Ala Ala Ala
    1985                 1990                 1995

Ala Gly  Pro Gly Gln Gln Gly  Pro Tyr Gly Pro Gly  Ser Ser Ala
    2000                 2005                 2010

Ala Ala  Ala Ala Gly Gln Tyr  Gly Tyr Gly Pro Gly  Gln Gln Gly
    2015                 2020                 2025

Pro Tyr  Gly Pro Gly Ala Ser  Gly Gln Asn Gly Pro  Gly Ser Gly
    2030                 2035                 2040

Gln Tyr  Gly Pro Gly Gln Gln  Gly Pro Gly Gln Ser  Ala Ala Ala
    2045                 2050                 2055

Ala Ala  Gly Pro Gly Gln Gln  Gly Pro Tyr Gly Pro  Gly Ala Ser
```

```
    2060                2065                2070

Ala Ala  Ala Ala Ala Gly Gln  Tyr Gly Pro Gly Gln  Gln Gly Pro
    2075                2080                2085

Gly Gln  Tyr Gly Pro Gly Ser  Ser Gly Pro Gly Gln  Gln Gly Pro
    2090                2095                2100

Tyr Gly  Pro Gly Ser Ser Ala  Ala Ala Ala Ala Gly  Gln Tyr Gly
    2105                2110                2115

Pro Gly  Gln Gln Gly Pro Tyr  Gly Pro Gly Gln Ser  Ala Ala Ala
    2120                2125                2130

Ala Ala  Gly Gln Tyr Gln Gln  Gly Pro Gly Gln Gln  Gly Pro Tyr
    2135                2140                2145

Gly Pro  Gly Ala Ser Gly Pro  Gly Gln Gln Gly Pro  Tyr Gly Pro
    2150                2155                2160

Gly Ala  Ser Ala Ala Ala Ala  Ala Gly Pro Gly Gln  Tyr Gly Pro
    2165                2170                2175

Gly Gln  Gln Gly Pro Ser Ala  Ser Ala Ala Ala Ala  Ala Gly Gln
    2180                2185                2190

Tyr Gly  Ser Gly Pro Gly Gln  Tyr Gly Pro Tyr Gly  Pro Gly Gln
    2195                2200                2205

Ser Gly  Pro Gly Ser Gly Gln  Gln Gly Gln Gly Pro  Tyr Gly Pro
    2210                2215                2220

Gly Ala  Ser Ala Ala Ala Ala  Ala Gly Gln Tyr Gly  Pro Gly Gln
    2225                2230                2235

Gln Gly  Pro Tyr Gly Pro Gly  Gln Ser Ala Ala Ala  Ala Ala Gly
    2240                2245                2250

Pro Gly  Ser Gly Gln Tyr Gly  Pro Gly Ala Ser Gly  Gln Asn Gly
    2255                2260                2265

Pro Gly  Ser Gly Gln Tyr Gly  Pro Gly Gln Gln Gly  Pro Gly Gln
    2270                2275                2280

Ser Ala  Ala Ala Ala Ala Gly  Gln Tyr Gln Gln Gly  Pro Gly Gln
    2285                2290                2295

Gln Gly  Pro Tyr Gly Pro Gly  Ala Ser Ala Ala Ala  Ala Ala Gly
    2300                2305                2310

Gln Tyr  Gly Ser Gly Pro Gly  Gln Gln Gly Pro Tyr  Gly Pro Gly
    2315                2320                2325

Gln Ser  Gly Ser Gly Gln Gln  Gly Pro Gly Gln Gln  Gly Pro Tyr
    2330                2335                2340

Ala Ser  Ala Ala Ala Ala Ala  Gly Pro Gly Ser Gly  Gln Gln Gly
    2345                2350                2355

Ser Ser  Val Asp Lys Leu Ala  Ala Ala Leu Glu His  His His His
    2360                2365                2370

His His
    2375


<210> SEQ ID NO 16
<211> LENGTH: 608
<212> TYPE: PRT
<213> ORGANISM: Artificial Sequence
<220> FEATURE:
<223> OTHER INFORMATION: PRT313

<400> SEQUENCE: 16

Met His His His His His His Ser Ser Gly Ser Ser Gly Pro Gly Gly
1               5                   10                  15

Gln Gly Pro Tyr Gly Pro Gly Ala Ser Ala Ala Ala Ala Ala Gly Gly
```

```
            20                  25                  30

Asn Gly Pro Gly Ser Gly Gln Gln Gly Pro Gly Gly Ser Ala Ala Ala
        35                  40                  45

Ala Ala Gly Gly Tyr Gly Pro Gly Gly Gln Gly Pro Gly Gln Gln Gly
    50                  55                  60

Pro Gly Ser Ser Ala Ala Ala Ala Ala Gly Pro Gly Gly Tyr Gly Pro
65                  70                  75                  80

Gly Gly Gln Gly Pro Ser Ala Ser Ala Ala Ala Ala Ala Gly Pro Gly
                85                  90                  95

Ser Gly Gln Gln Gly Pro Gly Ala Ser Ala Ala Ala Ala Ala Gly Gly
            100                 105                 110

Tyr Gly Pro Gly Gly Gln Gly Pro Gly Gln Gln Gly Pro Gly Ser Ser
        115                 120                 125

Ala Ala Ala Ala Ala Gly Gly Tyr Gly Ser Gly Pro Gly Gln Gln Gly
    130                 135                 140

Pro Tyr Gly Ser Ala Ala Ala Ala Ala Gly Pro Gly Ser Gly Gly Tyr
145                 150                 155                 160

Gly Gln Gly Pro Tyr Gly Pro Gly Ala Ser Ala Ala Ala Ala Ala Gly
                165                 170                 175

Pro Gly Gly Tyr Gly Pro Gly Gly Gln Gly Pro Ser Ala Ser Ala Ala
            180                 185                 190

Ala Ala Ala Gly Ser Gly Gln Gln Gly Pro Gly Gly Tyr Gly Pro Tyr
        195                 200                 205

Ala Ser Ala Ala Ala Ala Ala Gly Gly Tyr Gly Ser Gly Pro Gly Gln
    210                 215                 220

Gln Gly Pro Tyr Gly Pro Gly Gly Ser Ala Ala Ala Ala Ala Gly Ser
225                 230                 235                 240

Gly Gln Gln Gly Pro Gly Gln Gln Gly Pro Tyr Ala Ser Ala Ala Ala
                245                 250                 255

Ala Ala Gly Pro Gly Gly Gln Gly Pro Tyr Gly Pro Gly Ser Ser Ala
            260                 265                 270

Ala Ala Ala Ala Gly Gly Tyr Gly Tyr Gly Pro Gly Gly Gln Gly Pro
        275                 280                 285

Tyr Gly Pro Gly Ala Ser Ala Ala Ala Ala Ala Gly Gly Asn Gly Pro
    290                 295                 300

Gly Ser Gly Gly Tyr Gly Pro Gly Gln Gln Gly Pro Gly Gly Ser Ala
305                 310                 315                 320

Ala Ala Ala Ala Gly Pro Gly Gly Gln Gly Pro Tyr Gly Pro Gly Ala
                325                 330                 335

Ser Ala Ala Ala Ala Ala Gly Gly Tyr Gly Pro Gly Gly Gln Gly Pro
            340                 345                 350

Gly Gly Tyr Gly Pro Gly Ser Ser Ala Ala Ala Ala Ala Gly Pro Gly
        355                 360                 365

Gly Gln Gly Pro Tyr Gly Pro Gly Ser Ser Ala Ala Ala Ala Ala Gly
    370                 375                 380

Gly Tyr Gly Pro Gly Gln Gln Gly Pro Tyr Gly Pro Gly Gly Ser Ala
385                 390                 395                 400

Ala Ala Ala Ala Gly Gly Tyr Gln Gln Gly Pro Gly Gly Gln Gly Pro
                405                 410                 415

Tyr Gly Pro Gly Ala Ser Ala Ala Ala Ala Ala Gly Pro Gly Gly Gln
            420                 425                 430

Gly Pro Tyr Gly Pro Gly Ala Ser Ala Ala Ala Ala Ala Gly Pro Gly
        435                 440                 445
```

Gly Tyr Gly Pro Gly Gly Gln Gly Pro Ser Ala Ser Ala Ala Ala Ala
    450                 455                 460

Ala Gly Gly Tyr Gly Ser Gly Pro Gly Gly Tyr Gly Pro Tyr Gly Pro
465                 470                 475                 480

Gly Gly Ser Ala Ala Ala Ala Ala Gly Pro Gly Ser Gly Gln Gln Gly
                485                 490                 495

Gln Gly Pro Tyr Gly Pro Gly Ala Ser Ala Ala Ala Ala Ala Gly Gly
            500                 505                 510

Tyr Gly Pro Gly Gln Gln Gly Pro Tyr Gly Pro Gly Gly Ser Ala Ala
        515                 520                 525

Ala Ala Ala Gly Pro Gly Ser Gly Gly Tyr Gly Pro Gly Ala Ser Ala
    530                 535                 540

Ala Ala Ala Ala Gly Gly Asn Gly Pro Gly Ser Gly Gly Tyr Gly Pro
545                 550                 555                 560

Gly Gln Gln Gly Pro Gly Gly Ser Ala Ala Ala Ala Ala Gly Gly Tyr
                565                 570                 575

Gln Gln Gly Pro Gly Gly Gln Gly Pro Tyr Gly Pro Gly Ala Ser Ala
            580                 585                 590

Ala Ala Ala Ala Gly Pro Gly Ser Gly Gln Gln Gly Pro Gly Ala Ser
        595                 600                 605

<210> SEQ ID NO 17
<211> LENGTH: 590
<212> TYPE: PRT
<213> ORGANISM: Artificial Sequence
<220> FEATURE:
<223> OTHER INFORMATION: Met-PRT399

<400> SEQUENCE: 17

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
            20                  25                  30

Gly Ser Gly Gly Tyr Gly Pro Gly Gly Gln Gly Pro Gly Gln Gln Gly
        35                  40                  45

Pro Gly Ser Ser Ala Ala Ala Ala Ala Gly Pro Gly Gly Tyr Gly Pro
    50                  55                  60

Gly Gly Gln Gly Pro Ser Ala Ser Ala Ala Ala Ala Ala Gly Pro Gly
65                  70                  75                  80

Ser Gly Gln Gln Gly Pro Gly Ala Ser Gly Gly Tyr Gly Pro Gly Gly
                85                  90                  95

Gln Gly Pro Gly Gln Gln Gly Pro Gly Ser Ser Ala Ala Ala Ala Ala
            100                 105                 110

Gly Gly Tyr Gly Ser Gly Pro Gly Gln Gln Gly Pro Tyr Gly Ser Ala
        115                 120                 125

Ala Ala Ala Ala Gly Pro Gly Ser Gly Gly Tyr Gly Gln Gly Pro Tyr
    130                 135                 140

Gly Pro Gly Ala Ser Gly Pro Gly Gly Tyr Gly Pro Gly Gly Gln Gly
145                 150                 155                 160

Pro Ser Ala Ser Ala Ala Ala Ala Ala Gly Ser Gly Gln Gln Gly Pro
                165                 170                 175

Gly Gly Tyr Gly Pro Tyr Ala Ser Ala Ala Ala Ala Ala Gly Gly Tyr
            180                 185                 190

Gly Ser Gly Pro Gly Gln Gln Gly Pro Tyr Gly Pro Gly Gly Ser Gly
        195                 200                 205

```
Ser Gly Gln Gln Gly Pro Gly Gln Gln Gly Pro Tyr Ala Ser Ala Ala
    210                 215                 220

Ala Ala Ala Gly Pro Gly Gly Gln Gly Pro Tyr Gly Pro Gly Ser Ser
225                 230                 235                 240

Ala Ala Ala Ala Ala Gly Gly Tyr Gly Tyr Gly Pro Gly Gly Gln Gly
                245                 250                 255

Pro Tyr Gly Pro Gly Ala Ser Gly Gly Asn Gly Pro Gly Ser Gly Gly
            260                 265                 270

Tyr Gly Pro Gly Gln Gln Gly Pro Gly Gly Ser Ala Ala Ala Ala Ala
        275                 280                 285

Gly Pro Gly Gly Gln Gly Pro Tyr Gly Pro Gly Ala Ser Ala Ala Ala
    290                 295                 300

Ala Ala Gly Gly Tyr Gly Pro Gly Gly Gln Gly Pro Gly Gly Tyr Gly
305                 310                 315                 320

Pro Gly Ser Ser Gly Pro Gly Gly Gln Gly Pro Tyr Gly Pro Gly Ser
                325                 330                 335

Ser Ala Ala Ala Ala Ala Gly Gly Tyr Gly Pro Gly Gln Gln Gly Pro
            340                 345                 350

Tyr Gly Pro Gly Gly Ser Ala Ala Ala Ala Ala Gly Gly Tyr Gln Gln
        355                 360                 365

Gly Pro Gly Gly Gln Gly Pro Tyr Gly Pro Gly Ala Ser Gly Pro Gly
    370                 375                 380

Gly Gln Gly Pro Tyr Gly Pro Gly Ala Ser Ala Ala Ala Ala Ala Gly
385                 390                 395                 400

Pro Gly Gly Tyr Gly Pro Gly Gly Gln Gly Pro Ser Ala Ser Ala Ala
                405                 410                 415

Ala Ala Ala Gly Gly Tyr Gly Ser Gly Pro Gly Gly Tyr Gly Pro Tyr
            420                 425                 430

Gly Pro Gly Gly Ser Gly Pro Gly Ser Gly Gln Gln Gly Gln Gly Pro
        435                 440                 445

Tyr Gly Pro Gly Ala Ser Ala Ala Ala Ala Ala Gly Gly Tyr Gly Pro
    450                 455                 460

Gly Gln Gln Gly Pro Tyr Gly Pro Gly Gly Ser Ala Ala Ala Ala Ala
465                 470                 475                 480

Gly Pro Gly Ser Gly Gly Tyr Gly Pro Gly Ala Ser Gly Gly Asn Gly
                485                 490                 495

Pro Gly Ser Gly Gly Tyr Gly Pro Gly Gln Gln Gly Pro Gly Gly Ser
            500                 505                 510

Ala Ala Ala Ala Ala Gly Gly Tyr Gln Gln Gly Pro Gly Gly Gln Gly
        515                 520                 525

Pro Tyr Gly Pro Gly Ala Ser Ala Ala Ala Ala Ala Gly Gly Tyr Gly
    530                 535                 540

Ser Gly Pro Gly Gln Gln Gly Pro Tyr Gly Pro Gly Gly Ser Gly Ser
545                 550                 555                 560

Gly Gln Gln Gly Pro Gly Gln Gln Gly Pro Tyr Ala Ser Ala Ala Ala
                565                 570                 575

Ala Ala Gly Pro Gly Ser Gly Gln Gln Gly Pro Gly Ala Ser
            580                 585                 590


<210> SEQ ID NO 18
<211> LENGTH: 601
<212> TYPE: PRT
<213> ORGANISM: Artificial Sequence
<220> FEATURE:
```

<223> OTHER INFORMATION: PRT399

<400> SEQUENCE: 18

```
Met His His His His His His Ser Ser Gly Ser Ser Gly Pro Gly Gly
1               5                   10                  15

Gln Gly Pro Tyr Gly Pro Gly Ala Ser Ala Ala Ala Ala Ala Gly Gly
            20                  25                  30

Asn Gly Pro Gly Ser Gly Gln Gln Gly Pro Gly Gly Ser Gly Gly Tyr
        35                  40                  45

Gly Pro Gly Gly Gln Gly Pro Gly Gln Gln Gly Pro Gly Ser Ser Ala
    50                  55                  60

Ala Ala Ala Ala Gly Pro Gly Gly Tyr Gly Pro Gly Gly Gln Gly Pro
65                  70                  75                  80

Ser Ala Ser Ala Ala Ala Ala Ala Gly Pro Gly Ser Gly Gln Gln Gly
                85                  90                  95

Pro Gly Ala Ser Gly Gly Tyr Gly Pro Gly Gly Gln Gly Pro Gly Gln
            100                 105                 110

Gln Gly Pro Gly Ser Ser Ala Ala Ala Ala Ala Gly Gly Tyr Gly Ser
        115                 120                 125

Gly Pro Gly Gln Gln Gly Pro Tyr Gly Ser Ala Ala Ala Ala Ala Gly
    130                 135                 140

Pro Gly Ser Gly Gly Tyr Gly Gln Gly Pro Tyr Gly Pro Gly Ala Ser
145                 150                 155                 160

Gly Pro Gly Gly Tyr Gly Pro Gly Gly Gln Gly Pro Ser Ala Ser Ala
                165                 170                 175

Ala Ala Ala Ala Gly Ser Gly Gln Gln Gly Pro Gly Gly Tyr Gly Pro
            180                 185                 190

Tyr Ala Ser Ala Ala Ala Ala Ala Gly Gly Tyr Gly Ser Gly Pro Gly
        195                 200                 205

Gln Gln Gly Pro Tyr Gly Pro Gly Gly Ser Gly Ser Gly Gln Gln Gly
    210                 215                 220

Pro Gly Gln Gln Gly Pro Tyr Ala Ser Ala Ala Ala Ala Ala Gly Pro
225                 230                 235                 240

Gly Gly Gln Gly Pro Tyr Gly Pro Gly Ser Ser Ala Ala Ala Ala Ala
                245                 250                 255

Gly Gly Tyr Gly Tyr Gly Pro Gly Gly Gln Gly Pro Tyr Gly Pro Gly
            260                 265                 270

Ala Ser Gly Gly Asn Gly Pro Gly Ser Gly Gly Tyr Gly Pro Gly Gln
        275                 280                 285

Gln Gly Pro Gly Gly Ser Ala Ala Ala Ala Ala Gly Pro Gly Gly Gln
    290                 295                 300

Gly Pro Tyr Gly Pro Gly Ala Ser Ala Ala Ala Ala Ala Gly Gly Tyr
305                 310                 315                 320

Gly Pro Gly Gly Gln Gly Pro Gly Gly Tyr Gly Pro Gly Ser Ser Gly
                325                 330                 335

Pro Gly Gly Gln Gly Pro Tyr Gly Pro Gly Ser Ser Ala Ala Ala Ala
            340                 345                 350

Ala Gly Gly Tyr Gly Pro Gly Gln Gln Gly Pro Tyr Gly Pro Gly Gly
        355                 360                 365

Ser Ala Ala Ala Ala Ala Gly Gly Tyr Gln Gln Gly Pro Gly Gly Gln
    370                 375                 380

Gly Pro Tyr Gly Pro Gly Ala Ser Gly Pro Gly Gly Gln Gly Pro Tyr
385                 390                 395                 400
```

```
Gly Pro Gly Ala Ser Ala Ala Ala Ala Ala Gly Pro Gly Gly Tyr Gly
                405                 410                 415

Pro Gly Gly Gln Gly Pro Ser Ala Ser Ala Ala Ala Ala Ala Gly Gly
            420                 425                 430

Tyr Gly Ser Gly Pro Gly Gly Tyr Gly Pro Tyr Gly Pro Gly Gly Ser
        435                 440                 445

Gly Pro Gly Ser Gly Gln Gln Gly Gln Gly Pro Tyr Gly Pro Gly Ala
    450                 455                 460

Ser Ala Ala Ala Ala Ala Gly Gly Tyr Gly Pro Gly Gln Gln Gly Pro
465                 470                 475                 480

Tyr Gly Pro Gly Gly Ser Ala Ala Ala Ala Ala Gly Pro Gly Ser Gly
                485                 490                 495

Gly Tyr Gly Pro Gly Ala Ser Gly Gly Asn Gly Pro Gly Ser Gly Gly
            500                 505                 510

Tyr Gly Pro Gly Gln Gln Gly Pro Gly Gly Ser Ala Ala Ala Ala Ala
        515                 520                 525

Gly Gly Tyr Gln Gln Gly Pro Gly Gly Gln Gly Pro Tyr Gly Pro Gly
    530                 535                 540

Ala Ser Ala Ala Ala Ala Ala Gly Gly Tyr Gly Ser Gly Pro Gly Gln
545                 550                 555                 560

Gln Gly Pro Tyr Gly Pro Gly Gly Ser Gly Ser Gly Gln Gln Gly Pro
                565                 570                 575

Gly Gln Gln Gly Pro Tyr Ala Ser Ala Ala Ala Ala Ala Gly Pro Gly
            580                 585                 590

Ser Gly Gln Gln Gly Pro Gly Ala Ser
        595                 600


<210> SEQ ID NO 19
<211> LENGTH: 612
<212> TYPE: PRT
<213> ORGANISM: Artificial Sequence
<220> FEATURE:
<223> OTHER INFORMATION: Met-PRT720

<400> SEQUENCE: 19

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Ala Gly Pro Gly Gln Tyr Val Leu
    50                  55                  60

Ile Gly Pro Gly Gln Gln Val Leu Ile Gly Pro Ser Ala Ser Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
            100                 105                 110

Ser Ala Ala Ala Ala Ala Gly Ser Tyr Gly Ser Val Leu Ile Gly Pro
        115                 120                 125

Gly Gln Gln Val Leu Ile Gly Pro Tyr Gly Ser Ala Ala Ala Ala Ala
    130                 135                 140

Gly Pro Gly Ser Gly Gln Tyr Gly Gln Gly Pro Tyr Gly Pro Gly Ala
145                 150                 155                 160
```

```
Ser Gly Pro Gly Gln Tyr Gly Pro Gly Gln Gln Gly Pro Ser Ala Ser
                165                 170                 175

Ala Ala Ala Ala Ala Gly Ser Gly Gln Gln Val Leu Ile Gly Pro Gly
            180                 185                 190

Gln Tyr Val Leu Ile Gly Pro Tyr Ala Ser Ala Ala Ala Ala Ala Gly
        195                 200                 205

Gln Tyr Gly Ser Gly Pro Gly Gln Gln Gly Pro Tyr Gly Pro Gly Gln
    210                 215                 220

Ser Gly Ser Gly Gln Gln Gly Pro Gly Gln Gln Gly Pro Tyr Ala Ser
225                 230                 235                 240

Ala Ala Ala Ala Ala Gly Pro Gly Gln Gln Val Leu Ile Gly Pro Tyr
                245                 250                 255

Val Leu Ile Gly Pro Gly Ser Ser Ala Ala Ala Ala Ala Gly Gln Tyr
            260                 265                 270

Gly Tyr Gly Pro Gly Gln Gln Gly Pro Tyr Gly Pro Gly Ala Ser Gly
        275                 280                 285

Gln Asn Gly Pro Gly Ser Gly Gln Tyr Gly Pro Gly Gln Gln Gly Pro
    290                 295                 300

Gly Gln Ser Ala Ala Ala Ala Ala Gly Pro Gly Gln Gln Val Leu Ile
305                 310                 315                 320

Gly Pro Tyr Val Leu Ile Gly Pro Gly Ala Ser Ala Ala Ala Ala Ala
                325                 330                 335

Gly Gln Tyr Gly Pro Gly Gln Gln Gly Pro Gly Gln Tyr Gly Pro Gly
            340                 345                 350

Ser Ser Gly Pro Gly Gln Gln Gly Pro Tyr Gly Pro Gly Ser Ser Ala
        355                 360                 365

Ala Ala Ala Ala Gly Ser Tyr Gly Pro Gly Gln Gln Val Leu Ile Gly
    370                 375                 380

Pro Tyr Val Leu Ile Gly Pro Gly Pro Ser Ala Ala Ala Ala Ala Gly
385                 390                 395                 400

Gln Tyr Gln Gln Gly Pro Gly Gln Gln Gly Pro Tyr Gly Pro Gly Ala
                405                 410                 415

Ser Gly Pro Gly Gln Gln Gly Pro Tyr Gly Pro Gly Ala Ser Ala Ala
            420                 425                 430

Ala Ala Ala Gly Pro Gly Gln Tyr Val Leu Ile Gly Pro Gly Gln Gln
        435                 440                 445

Val Leu Ile Gly Pro Ser Ala Ser Ala Ala Ala Ala Ala Gly Gln Tyr
    450                 455                 460

Gly Ser Gly Pro Gly Gln Tyr Gly Pro Tyr Gly Pro Gly Gln Ser Gly
465                 470                 475                 480

Pro Gly Ser Gly Gln Gln Gly Gln Gly Pro Tyr Gly Pro Gly Ala Ser
                485                 490                 495

Ala Ala Ala Ala Ala Gly Ser Tyr Gly Pro Gly Gln Gln Val Leu Ile
            500                 505                 510

Gly Pro Tyr Val Leu Ile Gly Pro Gly Pro Ser Ala Ala Ala Ala Ala
        515                 520                 525

Gly Pro Gly Ser Gly Gln Tyr Gly Pro Gly Ala Ser Gly Gln Asn Gly
    530                 535                 540

Pro Gly Ser Gly Gln Tyr Gly Pro Gly Gln Gln Gly Pro Gly Gln Ser
545                 550                 555                 560

Ala Ala Ala Ala Ala Gly Gln Tyr Gln Gln Val Leu Ile Gly Pro Gly
                565                 570                 575

Gln Gln Gly Pro Tyr Val Leu Ile Gly Pro Gly Ala Ser Ala Ala Ala
```

```
            580                 585                 590

Ala Ala Gly Pro Gly Ser Gly Gln Gln Val Leu Ile Gly Pro Gly Ala
        595                 600                 605

Ser Val Leu Ile
    610


<210> SEQ ID NO 20
<211> LENGTH: 592
<212> TYPE: PRT
<213> ORGANISM: Artificial Sequence
<220> FEATURE:
<223> OTHER INFORMATION: Met-PRT665

<400> SEQUENCE: 20

Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Ala Ala Gly Pro Gly
    50                  55                  60

Gln Tyr Val Leu Ile Gly Pro Gly Gln Gln Gly Pro Ser Ala Ser Ala
65                  70                  75                  80

Ala Ala Ala Ala Ala Ala Gly Pro Gly Ser Gly Gln Gln Gly Pro Gly
                85                  90                  95

Ala Ser Gly Gln Tyr Gly Pro Gly Gln Gln Gly Pro Gly Gln Gln Gly
            100                 105                 110

Pro Gly Ser Ser Ala Ala Ala Ala Ala Ala Ala Gly Ser Tyr Gly Ser
        115                 120                 125

Val Leu Ile Gly Pro Gly Gln Gln Gly Pro Tyr Gly Ser Ala Ala Ala
    130                 135                 140

Ala Ala Ala Ala Gly Pro Gly Ser Gly Gln Tyr Gly Gln Gly Pro Tyr
145                 150                 155                 160

Gly Pro Gly Ala Ser Gly Pro Gly Gln Tyr Gly Pro Gly Gln Gln Gly
                165                 170                 175

Pro Ser Ala Ser Ala Ala Ala Ala Ala Ala Ala Gly Ser Gly Gln Gln
            180                 185                 190

Val Leu Ile Gly Pro Gly Gln Tyr Gly Pro Tyr Ala Ser Ala Ala Ala
        195                 200                 205

Ala Ala Ala Ala Gly Ser Tyr Gly Ser Gly Pro Gly Gln Gln Gly Pro
    210                 215                 220

Tyr Gly Pro Gly Gln Ser Gly Ser Gly Gln Gln Gly Pro Gly Gln Gln
225                 230                 235                 240

Gly Pro Tyr Ala Ser Ala Ala Ala Ala Ala Ala Ala Gly Pro Gly Gln
                245                 250                 255

Gln Val Leu Ile Gly Pro Tyr Gly Pro Gly Ser Ser Ala Ala Ala Ala
            260                 265                 270

Ala Ala Ala Gly Ser Tyr Gly Tyr Gly Pro Gly Gln Gln Gly Pro Tyr
        275                 280                 285

Gly Pro Gly Ala Ser Gly Gln Asn Gly Pro Gly Ser Gly Gln Tyr Gly
    290                 295                 300

Pro Gly Gln Gln Gly Pro Gly Pro Ser Ala Ala Ala Ala Ala Ala Ala
305                 310                 315                 320

Gly Pro Gly Gln Gln Val Leu Ile Gly Pro Tyr Gly Pro Gly Ala Ser
```

```
                325                 330                 335

Ala Ala Ala Ala Ala Ala Ala Gly Ser Tyr Gly Pro Gly Gln Gln Gly
            340                 345                 350

Pro Gly Gln Tyr Gly Pro Gly Ser Ser Gly Pro Gly Gln Gln Gly Pro
        355                 360                 365

Tyr Gly Pro Gly Ser Ser Ala Ala Ala Ala Ala Ala Ala Gly Ser Tyr
    370                 375                 380

Gly Pro Gly Gln Gln Val Leu Ile Gly Pro Tyr Gly Pro Gly Pro Ser
385                 390                 395                 400

Ala Ala Ala Ala Ala Ala Ala Gly Ser Tyr Gln Gln Gly Pro Gly Gln
                405                 410                 415

Gln Gly Pro Tyr Gly Pro Gly Ala Ser Gly Pro Gly Gln Gln Gly Pro
            420                 425                 430

Tyr Gly Pro Gly Ala Ser Ala Ala Ala Ala Ala Ala Ala Gly Pro Gly
        435                 440                 445

Gln Tyr Val Leu Ile Gly Pro Gly Gln Gln Gly Pro Ser Ala Ser Ala
    450                 455                 460

Ala Ala Ala Ala Ala Ala Gly Ser Tyr Gly Ser Gly Pro Gly Gln Tyr
465                 470                 475                 480

Gly Pro Tyr Gly Pro Gly Gln Ser Gly Pro Gly Ser Gly Gln Gln Gly
                485                 490                 495

Gln Gly Pro Tyr Gly Pro Gly Ala Ser Ala Ala Ala Ala Ala Ala Ala
            500                 505                 510

Gly Ser Tyr Gly Pro Gly Gln Gln Val Leu Ile Gly Pro Tyr Gly Pro
        515                 520                 525

Gly Pro Ser Ala Ala Ala Ala Ala Ala Ala Gly Pro Gly Ser Gly Gln
    530                 535                 540

Tyr Gly Pro Gly Ala Ser Gly Gln Asn Gly Pro Gly Ser Gly Gln Tyr
545                 550                 555                 560

Gly Pro Gly Gln Gln Gly Pro Gly Pro Ser Ala Ala Ala Ala Ala Ala
                565                 570                 575

Ala Gly Pro Gly Ser Gly Gln Gln Gly Pro Gly Ala Ser Val Leu Ile
            580                 585                 590


<210> SEQ ID NO 21
<211> LENGTH: 619
<212> TYPE: PRT
<213> ORGANISM: Artificial Sequence
<220> FEATURE:
<223> OTHER INFORMATION: Met-PRT666

<400> SEQUENCE: 21

Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Ala Ala Gly Pro Gly
    50                  55                  60

Gln Tyr Val Leu Ile Gly Pro Gly Gln Gln Val Leu Ile Gly Pro Ser
65                  70                  75                  80

Ala Ser Ala Ala Ala Ala Ala Ala Ala Gly Pro Gly Ser Gly Gln Gln
                85                  90                  95

Gly Pro Gly Ala Ser Gly Gln Tyr Gly Pro Gly Gln Gln Gly Pro Gly
```

```
            100                 105                 110

Gln Gln Gly Pro Gly Ser Ser Ala Ala Ala Ala Ala Ala Ala Gly Ser
        115                 120                 125

Tyr Gly Ser Val Leu Ile Gly Pro Gly Gln Gln Val Leu Ile Gly Pro
    130                 135                 140

Tyr Gly Ser Ala Ala Ala Ala Ala Ala Ala Gly Pro Gly Ser Gly Gln
145                 150                 155                 160

Tyr Gly Gln Gly Pro Tyr Gly Pro Gly Ala Ser Gly Pro Gly Gln Tyr
                165                 170                 175

Gly Pro Gly Gln Gln Gly Pro Ser Ala Ser Ala Ala Ala Ala Ala Ala
            180                 185                 190

Ala Gly Ser Gly Gln Gln Val Leu Ile Gly Pro Gly Gln Tyr Val Leu
        195                 200                 205

Ile Gly Pro Tyr Ala Ser Ala Ala Ala Ala Ala Ala Ala Gly Ser Tyr
    210                 215                 220

Gly Ser Gly Pro Gly Gln Gln Gly Pro Tyr Gly Pro Gly Gln Ser Gly
225                 230                 235                 240

Ser Gly Gln Gln Gly Pro Gly Gln Gln Gly Pro Tyr Ala Ser Ala Ala
                245                 250                 255

Ala Ala Ala Ala Ala Gly Pro Gly Gln Gln Val Leu Ile Gly Pro Tyr
            260                 265                 270

Val Leu Ile Gly Pro Gly Ser Ser Ala Ala Ala Ala Ala Ala Ala Gly
        275                 280                 285

Ser Tyr Gly Tyr Gly Pro Gly Gln Gln Gly Pro Tyr Gly Pro Gly Ala
    290                 295                 300

Ser Gly Gln Asn Gly Pro Gly Ser Gly Gln Tyr Gly Pro Gly Gln Gln
305                 310                 315                 320

Gly Pro Gly Pro Ser Ala Ala Ala Ala Ala Ala Ala Gly Pro Gly Gln
                325                 330                 335

Gln Val Leu Ile Gly Pro Tyr Val Leu Ile Gly Pro Gly Ala Ser Ala
            340                 345                 350

Ala Ala Ala Ala Ala Ala Gly Ser Tyr Gly Pro Gly Gln Gln Gly Pro
        355                 360                 365

Gly Gln Tyr Gly Pro Gly Ser Ser Gly Pro Gly Gln Gln Gly Pro Tyr
    370                 375                 380

Gly Pro Gly Ser Ser Ala Ala Ala Ala Ala Ala Ala Gly Ser Tyr Gly
385                 390                 395                 400

Pro Gly Gln Gln Val Leu Ile Gly Pro Tyr Val Leu Ile Gly Pro Gly
                405                 410                 415

Pro Ser Ala Ala Ala Ala Ala Ala Ala Gly Ser Tyr Gln Gln Gly Pro
            420                 425                 430

Gly Gln Gln Gly Pro Tyr Gly Pro Gly Ala Ser Gly Pro Gly Gln Gln
        435                 440                 445

Gly Pro Tyr Gly Pro Gly Ala Ser Ala Ala Ala Ala Ala Ala Ala Gly
    450                 455                 460

Pro Gly Gln Tyr Val Leu Ile Gly Pro Gly Gln Gln Val Leu Ile Gly
465                 470                 475                 480

Pro Ser Ala Ser Ala Ala Ala Ala Ala Ala Ala Gly Ser Tyr Gly Ser
                485                 490                 495

Gly Pro Gly Gln Tyr Gly Pro Tyr Gly Pro Gly Gln Ser Gly Pro Gly
            500                 505                 510

Ser Gly Gln Gln Gly Gln Gly Pro Tyr Gly Pro Gly Ala Ser Ala Ala
        515                 520                 525
```

Ala Ala Ala Ala Ala Gly Ser Tyr Gly Pro Gly Gln Gln Val Leu Ile
    530                 535                 540

Gly Pro Tyr Val Leu Ile Gly Pro Gly Pro Ser Ala Ala Ala Ala Ala
545                 550                 555                 560

Ala Ala Gly Pro Gly Ser Gly Gln Tyr Gly Pro Gly Ala Ser Gly Gln
                565                 570                 575

Asn Gly Pro Gly Ser Gly Gln Tyr Gly Pro Gly Gln Gln Gly Pro Gly
            580                 585                 590

Pro Ser Ala Ala Ala Ala Ala Ala Ala Gly Pro Gly Ser Gly Gln Gln
        595                 600                 605

Val Leu Ile Gly Pro Gly Ala Ser Val Leu Ile
    610                 615

<210> SEQ ID NO 22
<211> LENGTH: 623
<212> TYPE: PRT
<213> ORGANISM: Artificial Sequence
<220> FEATURE:
<223> OTHER INFORMATION: PRT720

<400> SEQUENCE: 22

Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Gly Gln
            20                  25                  30

Asn Gly Pro Gly Ser Gly Gln Gln Gly Pro Gly Gln Ser Gly Gln Tyr
        35                  40                  45

Gly Pro Gly Gln Gln Gly Pro Gly Gln Gln Gly Pro Gly Ser Ser Ala
    50                  55                  60

Ala Ala Ala Ala Gly Pro Gly Gln Tyr Val Leu Ile Gly Pro Gly Gln
65                  70                  75                  80

Gln Val Leu Ile Gly Pro Ser Ala Ser Ala Ala Ala Ala Ala Gly Pro
                85                  90                  95

Gly Ser Gly Gln Gln Gly Pro Gly Ala Ser Gly Gln Tyr Gly Pro Gly
            100                 105                 110

Gln Gln Gly Pro Gly Gln Gln Gly Pro Gly Ser Ser Ala Ala Ala Ala
        115                 120                 125

Ala Gly Ser Tyr Gly Ser Val Leu Ile Gly Pro Gly Gln Gln Val Leu
    130                 135                 140

Ile Gly Pro Tyr Gly Ser Ala Ala Ala Ala Ala Gly Pro Gly Ser Gly
145                 150                 155                 160

Gln Tyr Gly Gln Gly Pro Tyr Gly Pro Gly Ala Ser Gly Pro Gly Gln
                165                 170                 175

Tyr Gly Pro Gly Gln Gln Gly Pro Ser Ala Ser Ala Ala Ala Ala Ala
            180                 185                 190

Gly Ser Gly Gln Gln Val Leu Ile Gly Pro Gly Gln Tyr Val Leu Ile
        195                 200                 205

Gly Pro Tyr Ala Ser Ala Ala Ala Ala Ala Gly Gln Tyr Gly Ser Gly
    210                 215                 220

Pro Gly Gln Gln Gly Pro Tyr Gly Pro Gly Gln Ser Gly Ser Gly Gln
225                 230                 235                 240

Gln Gly Pro Gly Gln Gln Gly Pro Tyr Ala Ser Ala Ala Ala Ala Ala
                245                 250                 255

Gly Pro Gly Gln Gln Val Leu Ile Gly Pro Tyr Val Leu Ile Gly Pro
            260                 265                 270

Gly Ser Ser Ala Ala Ala Ala Ala Gly Gln Tyr Gly Tyr Gly Pro Gly
275 280 285

Gln Gln Gly Pro Tyr Gly Pro Gly Ala Ser Gly Gln Asn Gly Pro Gly
290 295 300

Ser Gly Gln Tyr Gly Pro Gly Gln Gln Gly Pro Gly Gln Ser Ala Ala
305 310 315 320

Ala Ala Ala Gly Pro Gly Gln Gln Val Leu Ile Gly Pro Tyr Val Leu
325 330 335

Ile Gly Pro Gly Ala Ser Ala Ala Ala Ala Ala Gly Gln Tyr Gly Pro
340 345 350

Gly Gln Gln Gly Pro Gly Gln Tyr Gly Pro Gly Ser Ser Gly Pro Gly
355 360 365

Gln Gln Gly Pro Tyr Gly Pro Gly Ser Ser Ala Ala Ala Ala Ala Gly
370 375 380

Ser Tyr Gly Pro Gly Gln Gln Val Leu Ile Gly Pro Tyr Val Leu Ile
385 390 395 400

Gly Pro Gly Pro Ser Ala Ala Ala Ala Ala Gly Gln Tyr Gln Gln Gly
405 410 415

Pro Gly Gln Gln Gly Pro Tyr Gly Pro Gly Ala Ser Gly Pro Gly Gln
420 425 430

Gln Gly Pro Tyr Gly Pro Gly Ala Ser Ala Ala Ala Ala Ala Gly Pro
435 440 445

Gly Gln Tyr Val Leu Ile Gly Pro Gly Gln Gln Val Leu Ile Gly Pro
450 455 460

Ser Ala Ser Ala Ala Ala Ala Ala Gly Gln Tyr Gly Ser Gly Pro Gly
465 470 475 480

Gln Tyr Gly Pro Tyr Gly Pro Gly Gln Ser Gly Pro Gly Ser Gly Gln
485 490 495

Gln Gly Gln Gly Pro Tyr Gly Pro Gly Ala Ser Ala Ala Ala Ala Ala
500 505 510

Gly Ser Tyr Gly Pro Gly Gln Gln Val Leu Ile Gly Pro Tyr Val Leu
515 520 525

Ile Gly Pro Gly Pro Ser Ala Ala Ala Ala Ala Gly Pro Gly Ser Gly
530 535 540

Gln Tyr Gly Pro Gly Ala Ser Gly Gln Asn Gly Pro Gly Ser Gly Gln
545 550 555 560

Tyr Gly Pro Gly Gln Gln Gly Pro Gly Gln Ser Ala Ala Ala Ala Ala
565 570 575

Gly Gln Tyr Gln Gln Val Leu Ile Gly Pro Gly Gln Gln Gly Pro Tyr
580 585 590

Val Leu Ile Gly Pro Gly Ala Ser Ala Ala Ala Ala Ala Gly Pro Gly
595 600 605

Ser Gly Gln Gln Val Leu Ile Gly Pro Gly Ala Ser Val Leu Ile
610 615 620

<210> SEQ ID NO 23
<211> LENGTH: 603
<212> TYPE: PRT
<213> ORGANISM: Artificial Sequence
<220> FEATURE:
<223> OTHER INFORMATION: PRT665

<400> SEQUENCE: 23

Met His His His His His His Ser Ser Gly Ser Ser Gly Pro Gly Gln
1 5 10 15

```
Gln Gly Pro Tyr Gly Pro Gly Ala Ser Ala Ala Ala Ala Ala Ala Ala
            20                  25                  30

Gly Ser Asn Gly Pro Gly Ser Gly Gln Gln Gly Pro Gly Gln Ser Gly
        35                  40                  45

Gln Tyr Gly Pro Gly Gln Gln Gly Pro Gly Gln Gln Gly Pro Gly Ser
    50                  55                  60

Ser Ala Ala Ala Ala Ala Ala Ala Gly Pro Gly Gln Tyr Val Leu Ile
65                  70                  75                  80

Gly Pro Gly Gln Gln Gly Pro Ser Ala Ser Ala Ala Ala Ala Ala Ala
                85                  90                  95

Ala Gly Pro Gly Ser Gly Gln Gln Gly Pro Gly Ala Ser Gly Gln Tyr
            100                 105                 110

Gly Pro Gly Gln Gln Gly Pro Gly Gln Gln Gly Pro Gly Ser Ser Ala
        115                 120                 125

Ala Ala Ala Ala Ala Ala Gly Ser Tyr Gly Ser Val Leu Ile Gly Pro
    130                 135                 140

Gly Gln Gln Gly Pro Tyr Gly Ser Ala Ala Ala Ala Ala Ala Ala Gly
145                 150                 155                 160

Pro Gly Ser Gly Gln Tyr Gly Gln Gly Pro Tyr Gly Pro Gly Ala Ser
                165                 170                 175

Gly Pro Gly Gln Tyr Gly Pro Gly Gln Gln Gly Pro Ser Ala Ser Ala
            180                 185                 190

Ala Ala Ala Ala Ala Ala Gly Ser Gly Gln Gln Val Leu Ile Gly Pro
        195                 200                 205

Gly Gln Tyr Gly Pro Tyr Ala Ser Ala Ala Ala Ala Ala Ala Ala Gly
    210                 215                 220

Ser Tyr Gly Ser Gly Pro Gly Gln Gln Gly Pro Tyr Gly Pro Gly Gln
225                 230                 235                 240

Ser Gly Ser Gly Gln Gln Gly Pro Gly Gln Gln Gly Pro Tyr Ala Ser
                245                 250                 255

Ala Ala Ala Ala Ala Ala Ala Gly Pro Gly Gln Gln Val Leu Ile Gly
            260                 265                 270

Pro Tyr Gly Pro Gly Ser Ser Ala Ala Ala Ala Ala Ala Ala Gly Ser
        275                 280                 285

Tyr Gly Tyr Gly Pro Gly Gln Gln Gly Pro Tyr Gly Pro Gly Ala Ser
    290                 295                 300

Gly Gln Asn Gly Pro Gly Ser Gly Gln Tyr Gly Pro Gly Gln Gln Gly
305                 310                 315                 320

Pro Gly Pro Ser Ala Ala Ala Ala Ala Ala Ala Gly Pro Gly Gln Gln
                325                 330                 335

Val Leu Ile Gly Pro Tyr Gly Pro Gly Ala Ser Ala Ala Ala Ala Ala
            340                 345                 350

Ala Ala Gly Ser Tyr Gly Pro Gly Gln Gln Gly Pro Gly Gln Tyr Gly
        355                 360                 365

Pro Gly Ser Ser Gly Pro Gly Gln Gln Gly Pro Tyr Gly Pro Gly Ser
    370                 375                 380

Ser Ala Ala Ala Ala Ala Ala Ala Gly Ser Tyr Gly Pro Gly Gln Gln
385                 390                 395                 400

Val Leu Ile Gly Pro Tyr Gly Pro Gly Pro Ser Ala Ala Ala Ala Ala
                405                 410                 415

Ala Ala Gly Ser Tyr Gln Gln Gly Pro Gly Gln Gln Gly Pro Tyr Gly
            420                 425                 430
```

```
Pro Gly Ala Ser Gly Pro Gly Gln Gln Gly Pro Tyr Gly Pro Gly Ala
        435                 440                 445

Ser Ala Ala Ala Ala Ala Ala Ala Gly Pro Gly Gln Tyr Val Leu Ile
    450                 455                 460

Gly Pro Gly Gln Gln Gly Pro Ser Ala Ser Ala Ala Ala Ala Ala Ala
465                 470                 475                 480

Ala Gly Ser Tyr Gly Ser Gly Pro Gly Gln Tyr Gly Pro Tyr Gly Pro
                485                 490                 495

Gly Gln Ser Gly Pro Gly Ser Gly Gln Gln Gly Gln Gly Pro Tyr Gly
            500                 505                 510

Pro Gly Ala Ser Ala Ala Ala Ala Ala Ala Ala Gly Ser Tyr Gly Pro
        515                 520                 525

Gly Gln Gln Val Leu Ile Gly Pro Tyr Gly Pro Gly Pro Ser Ala Ala
    530                 535                 540

Ala Ala Ala Ala Ala Gly Pro Gly Ser Gly Gln Tyr Gly Pro Gly Ala
545                 550                 555                 560

Ser Gly Gln Asn Gly Pro Gly Ser Gly Gln Tyr Gly Pro Gly Gln Gln
                565                 570                 575

Gly Pro Gly Pro Ser Ala Ala Ala Ala Ala Ala Ala Gly Pro Gly Ser
            580                 585                 590

Gly Gln Gln Gly Pro Gly Ala Ser Val Leu Ile
        595                 600


<210> SEQ ID NO 24
<211> LENGTH: 630
<212> TYPE: PRT
<213> ORGANISM: Artificial Sequence
<220> FEATURE:
<223> OTHER INFORMATION: PRT666

<400> SEQUENCE: 24

Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Ala Ala
            20                  25                  30

Gly Ser Asn Gly Pro Gly Ser Gly Gln Gln Gly Pro Gly Gln Ser Gly
        35                  40                  45

Gln Tyr Gly Pro Gly Gln Gln Gly Pro Gly Gln Gln Gly Pro Gly Ser
    50                  55                  60

Ser Ala Ala Ala Ala Ala Ala Ala Gly Pro Gly Gln Tyr Val Leu Ile
65                  70                  75                  80

Gly Pro Gly Gln Gln Val Leu Ile Gly Pro Ser Ala Ser Ala Ala Ala
                85                  90                  95

Ala Ala Ala Ala Gly Pro Gly Ser Gly Gln Gln Gly Pro Gly Ala Ser
            100                 105                 110

Gly Gln Tyr Gly Pro Gly Gln Gln Gly Pro Gly Gln Gln Gly Pro Gly
        115                 120                 125

Ser Ser Ala Ala Ala Ala Ala Ala Ala Gly Ser Tyr Gly Ser Val Leu
    130                 135                 140

Ile Gly Pro Gly Gln Gln Val Leu Ile Gly Pro Tyr Gly Ser Ala Ala
145                 150                 155                 160

Ala Ala Ala Ala Ala Gly Pro Gly Ser Gly Gln Tyr Gly Gln Gly Pro
                165                 170                 175

Tyr Gly Pro Gly Ala Ser Gly Pro Gly Gln Tyr Gly Pro Gly Gln Gln
            180                 185                 190
```

```
Gly Pro Ser Ala Ser Ala Ala Ala Ala Ala Ala Ala Gly Ser Gly Gln
        195                 200                 205

Gln Val Leu Ile Gly Pro Gly Gln Tyr Val Leu Ile Gly Pro Tyr Ala
    210                 215                 220

Ser Ala Ala Ala Ala Ala Ala Ala Gly Ser Tyr Gly Ser Gly Pro Gly
225                 230                 235                 240

Gln Gln Gly Pro Tyr Gly Pro Gly Gln Ser Gly Ser Gly Gln Gln Gly
                245                 250                 255

Pro Gly Gln Gln Gly Pro Tyr Ala Ser Ala Ala Ala Ala Ala Ala Ala
            260                 265                 270

Gly Pro Gly Gln Gln Val Leu Ile Gly Pro Tyr Val Leu Ile Gly Pro
        275                 280                 285

Gly Ser Ser Ala Ala Ala Ala Ala Ala Ala Gly Ser Tyr Gly Tyr Gly
    290                 295                 300

Pro Gly Gln Gln Gly Pro Tyr Gly Pro Gly Ala Ser Gly Gln Asn Gly
305                 310                 315                 320

Pro Gly Ser Gly Gln Tyr Gly Pro Gly Gln Gln Gly Pro Gly Pro Ser
                325                 330                 335

Ala Ala Ala Ala Ala Ala Ala Gly Pro Gly Gln Gln Val Leu Ile Gly
            340                 345                 350

Pro Tyr Val Leu Ile Gly Pro Gly Ala Ser Ala Ala Ala Ala Ala Ala
        355                 360                 365

Ala Gly Ser Tyr Gly Pro Gly Gln Gln Gly Pro Gly Gln Tyr Gly Pro
    370                 375                 380

Gly Ser Ser Gly Pro Gly Gln Gln Gly Pro Tyr Gly Pro Gly Ser Ser
385                 390                 395                 400

Ala Ala Ala Ala Ala Ala Ala Gly Ser Tyr Gly Pro Gly Gln Gln Val
                405                 410                 415

Leu Ile Gly Pro Tyr Val Leu Ile Gly Pro Gly Pro Ser Ala Ala Ala
            420                 425                 430

Ala Ala Ala Ala Gly Ser Tyr Gln Gln Gly Pro Gly Gln Gln Gly Pro
        435                 440                 445

Tyr Gly Pro Gly Ala Ser Gly Pro Gly Gln Gln Gly Pro Tyr Gly Pro
    450                 455                 460

Gly Ala Ser Ala Ala Ala Ala Ala Ala Ala Gly Pro Gly Gln Tyr Val
465                 470                 475                 480

Leu Ile Gly Pro Gly Gln Gln Val Leu Ile Gly Pro Ser Ala Ser Ala
                485                 490                 495

Ala Ala Ala Ala Ala Ala Gly Ser Tyr Gly Ser Gly Pro Gly Gln Tyr
            500                 505                 510

Gly Pro Tyr Gly Pro Gly Gln Ser Gly Pro Gly Ser Gly Gln Gln Gly
        515                 520                 525

Gln Gly Pro Tyr Gly Pro Gly Ala Ser Ala Ala Ala Ala Ala Ala Ala
    530                 535                 540

Gly Ser Tyr Gly Pro Gly Gln Gln Val Leu Ile Gly Pro Tyr Val Leu
545                 550                 555                 560

Ile Gly Pro Gly Pro Ser Ala Ala Ala Ala Ala Ala Ala Gly Pro Gly
                565                 570                 575

Ser Gly Gln Tyr Gly Pro Gly Ala Ser Gly Gln Asn Gly Pro Gly Ser
            580                 585                 590

Gly Gln Tyr Gly Pro Gly Gln Gln Gly Pro Gly Pro Ser Ala Ala Ala
        595                 600                 605

Ala Ala Ala Ala Gly Pro Gly Ser Gly Gln Gln Val Leu Ile Gly Pro
```

```
    610                 615                 620

Gly Ala Ser Val Leu Ile
625                 630


<210> SEQ ID NO 25
<211> LENGTH: 593
<212> TYPE: PRT
<213> ORGANISM: Artificial Sequence
<220> FEATURE:
<223> OTHER INFORMATION: Met-PRT888

<400> SEQUENCE: 25

Met Gly Ser Ser Gly Pro Gly Val Leu Gly Pro Tyr Gly Pro Gly Ala
1               5                   10                  15

Ser Ala Ala Ala Ala Ala Gly Gln Asn Gly Pro Gly Ser Gly Val Leu
            20                  25                  30

Gly Pro Gly Gln Ser Gly Gln Tyr Gly Pro Gly Val Leu Gly Pro Gly
        35                  40                  45

Val Leu Gly Pro Gly Ser Ser Ala Ala Ala Ala Ala Gly Pro Gly Gln
    50                  55                  60

Tyr Gly Pro Gly Val Leu Gly Pro Ser Ala Ser Ala Ala Ala Ala Ala
65                  70                  75                  80

Gly Pro Gly Ser Gly Val Leu Gly Pro Gly Ala Ser Gly Gln Tyr Gly
                85                  90                  95

Pro Gly Val Leu Gly Pro Gly Val Leu Gly Pro Gly Ser Ser Ala Ala
            100                 105                 110

Ala Ala Ala Gly Gln Tyr Gly Ser Gly Pro Gly Val Leu Gly Pro Tyr
        115                 120                 125

Gly Ser Ala Ala Ala Ala Ala Gly Pro Gly Ser Gly Gln Tyr Gly Gln
    130                 135                 140

Gly Pro Tyr Gly Pro Gly Ala Ser Gly Pro Gly Gln Tyr Gly Pro Gly
145                 150                 155                 160

Val Leu Gly Pro Ser Ala Ser Ala Ala Ala Ala Ala Gly Ser Gly Val
                165                 170                 175

Leu Gly Pro Gly Gln Tyr Gly Pro Tyr Ala Ser Ala Ala Ala Ala Ala
            180                 185                 190

Gly Gln Tyr Gly Ser Gly Pro Gly Val Leu Gly Pro Tyr Gly Pro Gly
        195                 200                 205

Gln Ser Gly Ser Gly Val Leu Gly Pro Gly Val Leu Gly Pro Tyr Ala
    210                 215                 220

Ser Ala Ala Ala Ala Ala Gly Pro Gly Val Leu Gly Pro Tyr Gly Pro
225                 230                 235                 240

Gly Ser Ser Ala Ala Ala Ala Ala Gly Gln Tyr Gly Tyr Gly Pro Gly
                245                 250                 255

Val Leu Gly Pro Tyr Gly Pro Gly Ala Ser Gly Gln Asn Gly Pro Gly
            260                 265                 270

Ser Gly Gln Tyr Gly Pro Gly Val Leu Gly Pro Gly Gln Ser Ala Ala
        275                 280                 285

Ala Ala Ala Gly Pro Gly Val Leu Gly Pro Tyr Gly Pro Gly Ala Ser
    290                 295                 300

Ala Ala Ala Ala Ala Gly Gln Tyr Gly Pro Gly Val Leu Gly Pro Gly
305                 310                 315                 320

Gln Tyr Gly Pro Gly Ser Ser Gly Pro Gly Val Leu Gly Pro Tyr Gly
                325                 330                 335

Pro Gly Ser Ser Ala Ala Ala Ala Ala Gly Gln Tyr Gly Pro Gly Val
```

```
            340                 345                 350

Leu Gly Pro Tyr Gly Pro Gly Gln Ser Ala Ala Ala Ala Ala Gly Gln
        355                 360                 365

Tyr Val Leu Gly Pro Gly Val Leu Gly Pro Tyr Gly Pro Gly Ala Ser
    370                 375                 380

Gly Pro Gly Val Leu Gly Pro Tyr Gly Pro Gly Ala Ser Ala Ala Ala
385                 390                 395                 400

Ala Ala Gly Pro Gly Gln Tyr Gly Pro Gly Val Leu Gly Pro Ser Ala
                405                 410                 415

Ser Ala Ala Ala Ala Ala Gly Gln Tyr Gly Ser Gly Pro Gly Gln Tyr
            420                 425                 430

Gly Pro Tyr Gly Pro Gly Gln Ser Gly Pro Gly Ser Gly Val Leu Gly
        435                 440                 445

Gln Gly Pro Tyr Gly Pro Gly Ala Ser Ala Ala Ala Ala Ala Gly Gln
    450                 455                 460

Tyr Gly Pro Gly Val Leu Gly Pro Tyr Gly Pro Gly Gln Ser Ala Ala
465                 470                 475                 480

Ala Ala Ala Gly Pro Gly Ser Gly Gln Tyr Gly Pro Gly Ala Ser Gly
                485                 490                 495

Gln Asn Gly Pro Gly Ser Gly Gln Tyr Gly Pro Gly Val Leu Gly Pro
            500                 505                 510

Gly Gln Ser Ala Ala Ala Ala Ala Gly Gln Tyr Val Leu Gly Pro Gly
        515                 520                 525

Val Leu Gly Pro Tyr Gly Pro Gly Ala Ser Ala Ala Ala Ala Ala Gly
    530                 535                 540

Gln Tyr Gly Ser Gly Pro Gly Val Leu Gly Pro Tyr Gly Pro Gly Gln
545                 550                 555                 560

Ser Gly Ser Gly Val Leu Gly Pro Gly Val Leu Gly Pro Tyr Ala Ser
                565                 570                 575

Ala Ala Ala Ala Ala Gly Pro Gly Ser Gly Val Leu Gly Pro Gly Ala
            580                 585                 590

Ser


<210> SEQ ID NO 26
<211> LENGTH: 590
<212> TYPE: PRT
<213> ORGANISM: Artificial Sequence
<220> FEATURE:
<223> OTHER INFORMATION: Met-PRT965

<400> SEQUENCE: 26

Met Gly Pro Gly Thr Ser Gly Pro Tyr Gly Pro Gly Ala Ser Ala Ala
1               5                   10                  15

Ala Ala Ala Gly Ala Asn Gly Pro Gly Ser Gly Thr Ser Gly Pro Gly
            20                  25                  30

Ala Ser Gly Ala Tyr Gly Pro Gly Thr Ser Gly Pro Gly Thr Ser Gly
        35                  40                  45

Pro Gly Ser Ser Ala Ala Ala Ala Ala Gly Pro Gly Ala Tyr Gly Pro
    50                  55                  60

Gly Thr Ser Gly Pro Ser Ala Ser Ala Ala Ala Ala Ala Gly Pro Gly
65                  70                  75                  80

Ser Gly Thr Ser Gly Pro Gly Ala Ser Gly Ala Tyr Gly Pro Gly Thr
                85                  90                  95

Ser Gly Pro Gly Thr Ser Gly Pro Gly Ser Ser Ala Ala Ala Ala Ala
            100                 105                 110
```

```
Gly Ala Tyr Gly Ser Gly Pro Gly Thr Ser Gly Pro Tyr Gly Ser Ala
        115                 120                 125

Ala Ala Ala Ala Gly Pro Gly Ser Gly Ala Tyr Gly Ala Gly Pro Tyr
    130                 135                 140

Gly Pro Gly Ala Ser Gly Pro Gly Ala Tyr Gly Pro Gly Thr Ser Gly
145                 150                 155                 160

Pro Ser Ala Ser Ala Ala Ala Ala Ala Gly Ser Gly Thr Ser Gly Pro
                165                 170                 175

Gly Ala Tyr Gly Pro Tyr Ala Ser Ala Ala Ala Ala Ala Gly Ala Tyr
            180                 185                 190

Gly Ser Gly Pro Gly Thr Ser Gly Pro Tyr Gly Pro Gly Ala Ser Gly
        195                 200                 205

Ser Gly Thr Ser Gly Pro Gly Thr Ser Gly Pro Tyr Ala Ser Ala Ala
    210                 215                 220

Ala Ala Ala Gly Pro Gly Thr Ser Gly Pro Tyr Gly Pro Gly Ser Ser
225                 230                 235                 240

Ala Ala Ala Ala Ala Gly Ala Tyr Gly Tyr Gly Pro Gly Thr Ser Gly
                245                 250                 255

Pro Tyr Gly Pro Gly Ala Ser Gly Ala Asn Gly Pro Gly Ser Gly Ala
            260                 265                 270

Tyr Gly Pro Gly Thr Ser Gly Pro Gly Ala Ser Ala Ala Ala Ala Ala
        275                 280                 285

Gly Pro Gly Thr Ser Gly Pro Tyr Gly Pro Gly Ala Ser Ala Ala Ala
    290                 295                 300

Ala Ala Gly Ala Tyr Gly Pro Gly Thr Ser Gly Pro Gly Ala Tyr Gly
305                 310                 315                 320

Pro Gly Ser Ser Gly Pro Gly Thr Ser Gly Pro Tyr Gly Pro Gly Ser
                325                 330                 335

Ser Ala Ala Ala Ala Ala Gly Ala Tyr Gly Pro Gly Thr Ser Gly Pro
            340                 345                 350

Tyr Gly Pro Gly Ala Ser Ala Ala Ala Ala Ala Gly Ala Tyr Thr Ser
        355                 360                 365

Gly Pro Gly Thr Ser Gly Pro Tyr Gly Pro Gly Ala Ser Gly Pro Gly
    370                 375                 380

Thr Ser Gly Pro Tyr Gly Pro Gly Ala Ser Ala Ala Ala Ala Ala Gly
385                 390                 395                 400

Pro Gly Ala Tyr Gly Pro Gly Thr Ser Gly Pro Ser Ala Ser Ala Ala
                405                 410                 415

Ala Ala Ala Gly Ala Tyr Gly Ser Gly Pro Gly Ala Tyr Gly Pro Tyr
            420                 425                 430

Gly Pro Gly Ala Ser Gly Pro Gly Ser Gly Thr Ser Gly Ala Gly Pro
        435                 440                 445

Tyr Gly Pro Gly Ala Ser Ala Ala Ala Ala Ala Gly Ala Tyr Gly Pro
    450                 455                 460

Gly Thr Ser Gly Pro Tyr Gly Pro Gly Ala Ser Ala Ala Ala Ala Ala
465                 470                 475                 480

Gly Pro Gly Ser Gly Ala Tyr Gly Pro Gly Ala Ser Gly Ala Asn Gly
                485                 490                 495

Pro Gly Ser Gly Ala Tyr Gly Pro Gly Thr Ser Gly Pro Gly Ala Ser
            500                 505                 510

Ala Ala Ala Ala Ala Gly Ala Tyr Thr Ser Gly Pro Gly Thr Ser Gly
        515                 520                 525
```

```
Pro Tyr Gly Pro Gly Ala Ser Ala Ala Ala Ala Ala Gly Ala Tyr Gly
    530                 535                 540

Ser Gly Pro Gly Thr Ser Gly Pro Tyr Gly Pro Gly Ala Ser Gly Ser
545                 550                 555                 560

Gly Thr Ser Gly Pro Gly Thr Ser Gly Pro Tyr Ala Ser Ala Ala Ala
                565                 570                 575

Ala Ala Gly Pro Gly Ser Gly Thr Ser Gly Pro Gly Ala Ser
            580                 585                 590


<210> SEQ ID NO 27
<211> LENGTH: 593
<212> TYPE: PRT
<213> ORGANISM: Artificial Sequence
<220> FEATURE:
<223> OTHER INFORMATION: Met-PRT889

<400> SEQUENCE: 27

Met Gly Ser Ser Gly Pro Gly Val Leu Gly Pro Tyr Gly Pro Gly Ala
1               5                   10                  15

Ser Ala Ala Ala Ala Ala Gly Ile Asn Gly Pro Gly Ser Gly Val Leu
            20                  25                  30

Gly Pro Gly Ile Ser Gly Ile Tyr Gly Pro Gly Val Leu Gly Pro Gly
        35                  40                  45

Val Leu Gly Pro Gly Ser Ser Ala Ala Ala Ala Ala Gly Pro Gly Ile
    50                  55                  60

Tyr Gly Pro Gly Val Leu Gly Pro Ser Ala Ser Ala Ala Ala Ala Ala
65                  70                  75                  80

Gly Pro Gly Ser Gly Val Leu Gly Pro Gly Ala Ser Gly Ile Tyr Gly
                85                  90                  95

Pro Gly Val Leu Gly Pro Gly Val Leu Gly Pro Gly Ser Ser Ala Ala
            100                 105                 110

Ala Ala Ala Gly Ile Tyr Gly Ser Gly Pro Gly Val Leu Gly Pro Tyr
        115                 120                 125

Gly Ser Ala Ala Ala Ala Ala Gly Pro Gly Ser Gly Ile Tyr Gly Ile
    130                 135                 140

Gly Pro Tyr Gly Pro Gly Ala Ser Gly Pro Gly Ile Tyr Gly Pro Gly
145                 150                 155                 160

Val Leu Gly Pro Ser Ala Ser Ala Ala Ala Ala Ala Gly Ser Gly Val
                165                 170                 175

Leu Gly Pro Gly Ile Tyr Gly Pro Tyr Ala Ser Ala Ala Ala Ala Ala
            180                 185                 190

Gly Ile Tyr Gly Ser Gly Pro Gly Val Leu Gly Pro Tyr Gly Pro Gly
        195                 200                 205

Ile Ser Gly Ser Gly Val Leu Gly Pro Gly Val Leu Gly Pro Tyr Ala
    210                 215                 220

Ser Ala Ala Ala Ala Ala Gly Pro Gly Val Leu Gly Pro Tyr Gly Pro
225                 230                 235                 240

Gly Ser Ser Ala Ala Ala Ala Ala Gly Ile Tyr Gly Tyr Gly Pro Gly
                245                 250                 255

Val Leu Gly Pro Tyr Gly Pro Gly Ala Ser Gly Ile Asn Gly Pro Gly
            260                 265                 270

Ser Gly Ile Tyr Gly Pro Gly Val Leu Gly Pro Gly Ile Ser Ala Ala
        275                 280                 285

Ala Ala Ala Gly Pro Gly Val Leu Gly Pro Tyr Gly Pro Gly Ala Ser
    290                 295                 300
```

Ala Ala Ala Ala Ala Gly Ile Tyr Gly Pro Gly Val Leu Gly Pro Gly
305 310 315 320

Ile Tyr Gly Pro Gly Ser Ser Gly Pro Gly Val Leu Gly Pro Tyr Gly
325 330 335

Pro Gly Ser Ser Ala Ala Ala Ala Ala Gly Ile Tyr Gly Pro Gly Val
340 345 350

Leu Gly Pro Tyr Gly Pro Gly Ile Ser Ala Ala Ala Ala Ala Gly Ile
355 360 365

Tyr Val Leu Gly Pro Gly Val Leu Gly Pro Tyr Gly Pro Gly Ala Ser
370 375 380

Gly Pro Gly Val Leu Gly Pro Tyr Gly Pro Gly Ala Ser Ala Ala Ala
385 390 395 400

Ala Ala Gly Pro Gly Ile Tyr Gly Pro Gly Val Leu Gly Pro Ser Ala
405 410 415

Ser Ala Ala Ala Ala Ala Gly Ile Tyr Gly Ser Gly Pro Gly Ile Tyr
420 425 430

Gly Pro Tyr Gly Pro Gly Ile Ser Gly Pro Gly Ser Gly Val Leu Gly
435 440 445

Ile Gly Pro Tyr Gly Pro Gly Ala Ser Ala Ala Ala Ala Ala Gly Ile
450 455 460

Tyr Gly Pro Gly Val Leu Gly Pro Tyr Gly Pro Gly Ile Ser Ala Ala
465 470 475 480

Ala Ala Ala Gly Pro Gly Ser Gly Ile Tyr Gly Pro Gly Ala Ser Gly
485 490 495

Ile Asn Gly Pro Gly Ser Gly Ile Tyr Gly Pro Gly Val Leu Gly Pro
500 505 510

Gly Ile Ser Ala Ala Ala Ala Ala Gly Ile Tyr Val Leu Gly Pro Gly
515 520 525

Val Leu Gly Pro Tyr Gly Pro Gly Ala Ser Ala Ala Ala Ala Ala Gly
530 535 540

Ile Tyr Gly Ser Gly Pro Gly Val Leu Gly Pro Tyr Gly Pro Gly Ile
545 550 555 560

Ser Gly Ser Gly Val Leu Gly Pro Gly Val Leu Gly Pro Tyr Ala Ser
565 570 575

Ala Ala Ala Ala Ala Gly Pro Gly Ser Gly Val Leu Gly Pro Gly Ala
580 585 590

Ser

<210> SEQ ID NO 28
<211> LENGTH: 590
<212> TYPE: PRT
<213> ORGANISM: Artificial Sequence
<220> FEATURE:
<223> OTHER INFORMATION: Met-PRT916

<400> SEQUENCE: 28

Met Gly Pro Gly Val Ile Gly Pro Tyr Gly Pro Gly Ala Ser Ala Ala
1 5 10 15

Ala Ala Ala Gly Leu Asn Gly Pro Gly Ser Gly Val Ile Gly Pro Gly
20 25 30

Leu Ser Gly Leu Tyr Gly Pro Gly Val Ile Gly Pro Gly Val Ile Gly
35 40 45

Pro Gly Ser Ser Ala Ala Ala Ala Ala Gly Pro Gly Leu Tyr Gly Pro
50 55 60

Gly Val Ile Gly Pro Ser Ala Ser Ala Ala Ala Ala Ala Gly Pro Gly

-continued

```
65                  70                  75                  80

Ser Gly Val Ile Gly Pro Gly Ala Ser Gly Leu Tyr Gly Pro Gly Val
                85                  90                  95

Ile Gly Pro Gly Val Ile Gly Pro Gly Ser Ser Ala Ala Ala Ala Ala
            100                 105                 110

Gly Leu Tyr Gly Ser Gly Pro Gly Val Ile Gly Pro Tyr Gly Ser Ala
        115                 120                 125

Ala Ala Ala Ala Gly Pro Gly Ser Gly Leu Tyr Gly Leu Gly Pro Tyr
    130                 135                 140

Gly Pro Gly Ala Ser Gly Pro Gly Leu Tyr Gly Pro Gly Val Ile Gly
145                 150                 155                 160

Pro Ser Ala Ser Ala Ala Ala Ala Ala Gly Ser Gly Val Ile Gly Pro
                165                 170                 175

Gly Leu Tyr Gly Pro Tyr Ala Ser Ala Ala Ala Ala Ala Gly Leu Tyr
            180                 185                 190

Gly Ser Gly Pro Gly Val Ile Gly Pro Tyr Gly Pro Gly Leu Ser Gly
        195                 200                 205

Ser Gly Val Ile Gly Pro Gly Val Ile Gly Pro Tyr Ala Ser Ala Ala
    210                 215                 220

Ala Ala Ala Gly Pro Gly Val Ile Gly Pro Tyr Gly Pro Gly Ser Ser
225                 230                 235                 240

Ala Ala Ala Ala Ala Gly Leu Tyr Gly Tyr Gly Pro Gly Val Ile Gly
                245                 250                 255

Pro Tyr Gly Pro Gly Ala Ser Gly Leu Asn Gly Pro Gly Ser Gly Leu
            260                 265                 270

Tyr Gly Pro Gly Val Ile Gly Pro Gly Leu Ser Ala Ala Ala Ala Ala
        275                 280                 285

Gly Pro Gly Val Ile Gly Pro Tyr Gly Pro Gly Ala Ser Ala Ala Ala
    290                 295                 300

Ala Ala Gly Leu Tyr Gly Pro Gly Val Ile Gly Pro Gly Leu Tyr Gly
305                 310                 315                 320

Pro Gly Ser Ser Gly Pro Gly Val Ile Gly Pro Tyr Gly Pro Gly Ser
                325                 330                 335

Ser Ala Ala Ala Ala Ala Gly Leu Tyr Gly Pro Gly Val Ile Gly Pro
            340                 345                 350

Tyr Gly Pro Gly Leu Ser Ala Ala Ala Ala Ala Gly Leu Tyr Val Ile
        355                 360                 365

Gly Pro Gly Val Ile Gly Pro Tyr Gly Pro Gly Ala Ser Gly Pro Gly
    370                 375                 380

Val Ile Gly Pro Tyr Gly Pro Gly Ala Ser Ala Ala Ala Ala Ala Gly
385                 390                 395                 400

Pro Gly Leu Tyr Gly Pro Gly Val Ile Gly Pro Ser Ala Ser Ala Ala
                405                 410                 415

Ala Ala Ala Gly Leu Tyr Gly Ser Gly Pro Gly Leu Tyr Gly Pro Tyr
            420                 425                 430

Gly Pro Gly Leu Ser Gly Pro Gly Ser Gly Val Ile Gly Leu Gly Pro
        435                 440                 445

Tyr Gly Pro Gly Ala Ser Ala Ala Ala Ala Ala Gly Leu Tyr Gly Pro
    450                 455                 460

Gly Val Ile Gly Pro Tyr Gly Pro Gly Leu Ser Ala Ala Ala Ala Ala
465                 470                 475                 480

Gly Pro Gly Ser Gly Leu Tyr Gly Pro Gly Ala Ser Gly Leu Asn Gly
                485                 490                 495
```

```
Pro Gly Ser Gly Leu Tyr Gly Pro Gly Val Ile Gly Pro Gly Leu Ser
            500                 505                 510

Ala Ala Ala Ala Ala Gly Leu Tyr Val Ile Gly Pro Gly Val Ile Gly
        515                 520                 525

Pro Tyr Gly Pro Gly Ala Ser Ala Ala Ala Ala Ala Gly Leu Tyr Gly
    530                 535                 540

Ser Gly Pro Gly Val Ile Gly Pro Tyr Gly Pro Gly Leu Ser Gly Ser
545                 550                 555                 560

Gly Val Ile Gly Pro Gly Val Ile Gly Pro Tyr Ala Ser Ala Ala Ala
                565                 570                 575

Ala Ala Gly Pro Gly Ser Gly Val Ile Gly Pro Gly Ala Ser
            580                 585                 590


<210> SEQ ID NO 29
<211> LENGTH: 590
<212> TYPE: PRT
<213> ORGANISM: Artificial Sequence
<220> FEATURE:
<223> OTHER INFORMATION: Met-PRT918

<400> SEQUENCE: 29

Met Gly Pro Gly Val Phe Gly Pro Tyr Gly Pro Gly Ala Ser Ala Ala
1               5                   10                  15

Ala Ala Ala Gly Ile Asn Gly Pro Gly Ser Gly Val Phe Gly Pro Gly
            20                  25                  30

Ile Ser Gly Ile Tyr Gly Pro Gly Val Phe Gly Pro Gly Val Phe Gly
        35                  40                  45

Pro Gly Ser Ser Ala Ala Ala Ala Ala Gly Pro Gly Ile Tyr Gly Pro
    50                  55                  60

Gly Val Phe Gly Pro Ser Ala Ser Ala Ala Ala Ala Ala Gly Pro Gly
65                  70                  75                  80

Ser Gly Val Phe Gly Pro Gly Ala Ser Gly Ile Tyr Gly Pro Gly Val
                85                  90                  95

Phe Gly Pro Gly Val Phe Gly Pro Gly Ser Ser Ala Ala Ala Ala Ala
            100                 105                 110

Gly Ile Tyr Gly Ser Gly Pro Gly Val Phe Gly Pro Tyr Gly Ser Ala
        115                 120                 125

Ala Ala Ala Ala Gly Pro Gly Ser Gly Ile Tyr Gly Ile Gly Pro Tyr
    130                 135                 140

Gly Pro Gly Ala Ser Gly Pro Gly Ile Tyr Gly Pro Gly Val Phe Gly
145                 150                 155                 160

Pro Ser Ala Ser Ala Ala Ala Ala Ala Gly Ser Gly Val Phe Gly Pro
                165                 170                 175

Gly Ile Tyr Gly Pro Tyr Ala Ser Ala Ala Ala Ala Ala Gly Ile Tyr
            180                 185                 190

Gly Ser Gly Pro Gly Val Phe Gly Pro Tyr Gly Pro Gly Ile Ser Gly
        195                 200                 205

Ser Gly Val Phe Gly Pro Gly Val Phe Gly Pro Tyr Ala Ser Ala Ala
    210                 215                 220

Ala Ala Ala Gly Pro Gly Val Phe Gly Pro Tyr Gly Pro Gly Ser Ser
225                 230                 235                 240

Ala Ala Ala Ala Ala Gly Ile Tyr Gly Tyr Gly Pro Gly Val Phe Gly
                245                 250                 255

Pro Tyr Gly Pro Gly Ala Ser Gly Ile Asn Gly Pro Gly Ser Gly Ile
            260                 265                 270
```

```
Tyr Gly Pro Gly Val Phe Gly Pro Gly Ile Ser Ala Ala Ala Ala Ala
        275                 280                 285

Gly Pro Gly Val Phe Gly Pro Tyr Gly Pro Gly Ala Ser Ala Ala Ala
    290                 295                 300

Ala Ala Gly Ile Tyr Gly Pro Gly Val Phe Gly Pro Gly Ile Tyr Gly
305                 310                 315                 320

Pro Gly Ser Ser Gly Pro Gly Val Phe Gly Pro Tyr Gly Pro Gly Ser
                325                 330                 335

Ser Ala Ala Ala Ala Ala Gly Ile Tyr Gly Pro Gly Val Phe Gly Pro
            340                 345                 350

Tyr Gly Pro Gly Ile Ser Ala Ala Ala Ala Ala Gly Ile Tyr Val Phe
        355                 360                 365

Gly Pro Gly Val Phe Gly Pro Tyr Gly Pro Gly Ala Ser Gly Pro Gly
    370                 375                 380

Val Phe Gly Pro Tyr Gly Pro Gly Ala Ser Ala Ala Ala Ala Ala Gly
385                 390                 395                 400

Pro Gly Ile Tyr Gly Pro Gly Val Phe Gly Pro Ser Ala Ser Ala Ala
                405                 410                 415

Ala Ala Ala Gly Ile Tyr Gly Ser Gly Pro Gly Ile Tyr Gly Pro Tyr
            420                 425                 430

Gly Pro Gly Ile Ser Gly Pro Gly Ser Gly Val Phe Gly Ile Gly Pro
        435                 440                 445

Tyr Gly Pro Gly Ala Ser Ala Ala Ala Ala Ala Gly Ile Tyr Gly Pro
    450                 455                 460

Gly Val Phe Gly Pro Tyr Gly Pro Gly Ile Ser Ala Ala Ala Ala Ala
465                 470                 475                 480

Gly Pro Gly Ser Gly Ile Tyr Gly Pro Gly Ala Ser Gly Ile Asn Gly
                485                 490                 495

Pro Gly Ser Gly Ile Tyr Gly Pro Gly Val Phe Gly Pro Gly Ile Ser
            500                 505                 510

Ala Ala Ala Ala Ala Gly Ile Tyr Val Phe Gly Pro Gly Val Phe Gly
        515                 520                 525

Pro Tyr Gly Pro Gly Ala Ser Ala Ala Ala Ala Ala Gly Ile Tyr Gly
    530                 535                 540

Ser Gly Pro Gly Val Phe Gly Pro Tyr Gly Pro Gly Ile Ser Gly Ser
545                 550                 555                 560

Gly Val Phe Gly Pro Gly Val Phe Gly Pro Tyr Ala Ser Ala Ala Ala
                565                 570                 575

Ala Ala Gly Pro Gly Ser Gly Val Phe Gly Pro Gly Ala Ser
            580                 585                 590


<210> SEQ ID NO 30
<211> LENGTH: 565
<212> TYPE: PRT
<213> ORGANISM: Artificial Sequence
<220> FEATURE:
<223> OTHER INFORMATION: Met-PRT699

<400> SEQUENCE: 30

Met Gly Pro Gly Val Leu Gly Pro Tyr Gly Pro Gly Ala Ser Ala Ala
1               5                   10                  15

Ala Ala Ala Ala Ala Gly Ser Asn Gly Pro Gly Ser Gly Val Leu Gly
            20                  25                  30

Pro Gly Gln Ser Gly Gln Tyr Gly Pro Gly Val Leu Gly Pro Gly Val
        35                  40                  45
```

```
Leu Gly Pro Gly Ser Ser Ala Ala Ala Ala Ala Ala Ala Gly Pro Gly
    50                  55                  60

Gln Tyr Gly Pro Gly Val Leu Gly Pro Ser Ala Ser Ala Ala Ala Ala
65                  70                  75                  80

Ala Ala Ala Gly Pro Gly Ser Gly Val Leu Gly Pro Gly Ala Ser Gly
                85                  90                  95

Gln Tyr Gly Pro Gly Val Leu Gly Pro Gly Val Leu Gly Pro Gly Ser
            100                 105                 110

Ser Ala Ala Ala Ala Ala Ala Ala Gly Ser Tyr Gly Ser Gly Pro Gly
        115                 120                 125

Val Leu Gly Pro Tyr Gly Ser Ala Ala Ala Ala Ala Ala Ala Gly Pro
    130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Val Leu Gly Pro Ser Ala Ser Ala Ala
                165                 170                 175

Ala Ala Ala Ala Ala Gly Ser Gly Val Leu Gly Pro Gly Gln Tyr Gly
            180                 185                 190

Pro Tyr Ala Ser Ala Ala Ala Ala Ala Ala Ala Gly Ser Tyr Gly Ser
        195                 200                 205

Gly Pro Gly Val Leu Gly Pro Tyr Gly Pro Gly Gln Ser Gly Ser Gly
    210                 215                 220

Val Leu Gly Pro Gly Val Leu Gly Pro Tyr Ala Ser Ala Ala Ala Ala
225                 230                 235                 240

Ala Ala Ala Gly Pro Gly Val Leu Gly Pro Tyr Gly Pro Gly Ser Ser
                245                 250                 255

Ala Ala Ala Ala Ala Ala Ala Gly Ser Tyr Gly Tyr Gly Pro Gly Val
            260                 265                 270

Leu Gly Pro Tyr Gly Pro Gly Ala Ser Gly Gln Asn Gly Pro Gly Ser
        275                 280                 285

Gly Gln Tyr Gly Pro Gly Val Leu Gly Pro Gly Pro Ser Ala Ala Ala
    290                 295                 300

Ala Ala Ala Ala Gly Pro Gly Val Leu Gly Pro Tyr Gly Pro Gly Ala
305                 310                 315                 320

Ser Ala Ala Ala Ala Ala Ala Ala Gly Ser Tyr Gly Pro Gly Val Leu
                325                 330                 335

Gly Pro Gly Gln Tyr Gly Pro Gly Ser Ser Gly Pro Gly Val Leu Gly
            340                 345                 350

Pro Tyr Gly Pro Gly Ser Ser Ala Ala Ala Ala Ala Ala Ala Gly Ser
        355                 360                 365

Tyr Gly Pro Gly Val Leu Gly Pro Tyr Gly Pro Gly Pro Ser Ala Ala
    370                 375                 380

Ala Ala Ala Ala Ala Gly Ser Tyr Val Leu Gly Pro Gly Val Leu Gly
385                 390                 395                 400

Pro Tyr Gly Pro Gly Ala Ser Gly Pro Gly Val Leu Gly Pro Tyr Gly
                405                 410                 415

Pro Gly Ala Ser Ala Ala Ala Ala Ala Ala Ala Gly Pro Gly Gln Tyr
            420                 425                 430

Gly Pro Gly Val Leu Gly Pro Ser Ala Ser Ala Ala Ala Ala Ala Ala
        435                 440                 445

Ala Gly Ser Tyr Gly Ser Gly Pro Gly Gln Tyr Gly Pro Tyr Gly Pro
    450                 455                 460
```

```
Gly Gln Ser Gly Pro Gly Ser Gly Val Leu Gly Gln Gly Pro Tyr Gly
465                 470                 475                 480

Pro Gly Ala Ser Ala Ala Ala Ala Ala Ala Ala Gly Ser Tyr Gly Pro
                485                 490                 495

Gly Val Leu Gly Pro Tyr Gly Pro Gly Pro Ser Ala Ala Ala Ala Ala
            500                 505                 510

Ala Ala Gly Pro Gly Ser Gly Gln Tyr Gly Pro Gly Ala Ser Gly Gln
        515                 520                 525

Asn Gly Pro Gly Ser Gly Gln Tyr Gly Pro Gly Val Leu Gly Pro Gly
    530                 535                 540

Pro Ser Ala Ala Ala Ala Ala Ala Ala Gly Pro Gly Ser Gly Val Leu
545                 550                 555                 560

Gly Pro Gly Ala Ser
                565
```

<210> SEQ ID NO 31
<211> LENGTH: 565
<212> TYPE: PRT
<213> ORGANISM: Artificial Sequence
<220> FEATURE:
<223> OTHER INFORMATION: Met-PRT698

<400> SEQUENCE: 31

```
Met Gly Pro Gly Val Leu Gly Pro Tyr Gly Pro Gly Ala Ser Ala Ala
1               5                   10                  15

Ala Ala Ala Ala Ala Gly Ser Asn Gly Pro Gly Ser Gly Val Leu Gly
            20                  25                  30

Pro Gly Ile Ser Gly Ile Tyr Gly Pro Gly Val Leu Gly Pro Gly Val
        35                  40                  45

Leu Gly Pro Gly Ser Ser Ala Ala Ala Ala Ala Ala Ala Gly Pro Gly
    50                  55                  60

Ile Tyr Gly Pro Gly Val Leu Gly Pro Ser Ala Ser Ala Ala Ala Ala
65                  70                  75                  80

Ala Ala Ala Gly Pro Gly Ser Gly Val Leu Gly Pro Gly Ala Ser Gly
                85                  90                  95

Ile Tyr Gly Pro Gly Val Leu Gly Pro Gly Val Leu Gly Pro Gly Ser
            100                 105                 110

Ser Ala Ala Ala Ala Ala Ala Ala Gly Ser Tyr Gly Ser Gly Pro Gly
        115                 120                 125

Val Leu Gly Pro Tyr Gly Ser Ala Ala Ala Ala Ala Ala Ala Gly Pro
    130                 135                 140

Gly Ser Gly Ile Tyr Gly Ile Gly Pro Tyr Gly Pro Gly Ala Ser Gly
145                 150                 155                 160

Pro Gly Ile Tyr Gly Pro Gly Val Leu Gly Pro Ser Ala Ser Ala Ala
                165                 170                 175

Ala Ala Ala Ala Ala Gly Ser Gly Val Leu Gly Pro Gly Ile Tyr Gly
            180                 185                 190

Pro Tyr Ala Ser Ala Ala Ala Ala Ala Ala Ala Gly Ser Tyr Gly Ser
        195                 200                 205

Gly Pro Gly Val Leu Gly Pro Tyr Gly Pro Gly Ile Ser Gly Ser Gly
    210                 215                 220

Val Leu Gly Pro Gly Val Leu Gly Pro Tyr Ala Ser Ala Ala Ala Ala
225                 230                 235                 240

Ala Ala Ala Gly Pro Gly Val Leu Gly Pro Tyr Gly Pro Gly Ser Ser
                245                 250                 255
```

Ala Ala Ala Ala Ala Ala Ala Gly Ser Tyr Gly Tyr Gly Pro Gly Val
260 265 270

Leu Gly Pro Tyr Gly Pro Gly Ala Ser Gly Ile Asn Gly Pro Gly Ser
275 280 285

Gly Ile Tyr Gly Pro Gly Val Leu Gly Pro Gly Pro Ser Ala Ala Ala
290 295 300

Ala Ala Ala Ala Gly Pro Gly Val Leu Gly Pro Tyr Gly Pro Gly Ala
305 310 315 320

Ser Ala Ala Ala Ala Ala Ala Ala Gly Ser Tyr Gly Pro Gly Val Leu
325 330 335

Gly Pro Gly Ile Tyr Gly Pro Gly Ser Ser Gly Pro Gly Val Leu Gly
340 345 350

Pro Tyr Gly Pro Gly Ser Ser Ala Ala Ala Ala Ala Ala Ala Gly Ser
355 360 365

Tyr Gly Pro Gly Val Leu Gly Pro Tyr Gly Pro Gly Pro Ser Ala Ala
370 375 380

Ala Ala Ala Ala Ala Gly Ser Tyr Val Leu Gly Pro Gly Val Leu Gly
385 390 395 400

Pro Tyr Gly Pro Gly Ala Ser Gly Pro Gly Val Leu Gly Pro Tyr Gly
405 410 415

Pro Gly Ala Ser Ala Ala Ala Ala Ala Ala Ala Gly Pro Gly Ile Tyr
420 425 430

Gly Pro Gly Val Leu Gly Pro Ser Ala Ser Ala Ala Ala Ala Ala Ala
435 440 445

Ala Gly Ser Tyr Gly Ser Gly Pro Gly Ile Tyr Gly Pro Tyr Gly Pro
450 455 460

Gly Ile Ser Gly Pro Gly Ser Gly Val Leu Gly Ile Gly Pro Tyr Gly
465 470 475 480

Pro Gly Ala Ser Ala Ala Ala Ala Ala Ala Ala Gly Ser Tyr Gly Pro
485 490 495

Gly Val Leu Gly Pro Tyr Gly Pro Gly Pro Ser Ala Ala Ala Ala Ala
500 505 510

Ala Ala Gly Pro Gly Ser Gly Ile Tyr Gly Pro Gly Ala Ser Gly Ile
515 520 525

Asn Gly Pro Gly Ser Gly Ile Tyr Gly Pro Gly Val Leu Gly Pro Gly
530 535 540

Pro Ser Ala Ala Ala Ala Ala Ala Ala Gly Pro Gly Ser Gly Val Leu
545 550 555 560

Gly Pro Gly Ala Ser
565

<210> SEQ ID NO 32
<211> LENGTH: 1179
<212> TYPE: PRT
<213> ORGANISM: Artificial Sequence
<220> FEATURE:
<223> OTHER INFORMATION: Met-PRT966

<400> SEQUENCE: 32

Met Gly Pro Gly Val Phe Gly Pro Tyr Gly Pro Gly Ala Ser Ala Ala
1 5 10 15

Ala Ala Ala Gly Ile Asn Gly Pro Gly Ser Gly Val Phe Gly Pro Gly
20 25 30

Ile Ser Gly Ile Tyr Gly Pro Gly Val Phe Gly Pro Gly Val Phe Gly
35 40 45

```
Pro Gly Ser Ser Ala Ala Ala Ala Ala Gly Pro Gly Ile Tyr Gly Pro
    50                  55                  60

Gly Val Phe Gly Pro Ser Ala Ser Ala Ala Ala Ala Ala Gly Pro Gly
65                  70                  75                  80

Ser Gly Val Phe Gly Pro Gly Ala Ser Gly Ile Tyr Gly Pro Gly Val
                85                  90                  95

Phe Gly Pro Gly Val Phe Gly Pro Gly Ser Ser Ala Ala Ala Ala Ala
            100                 105                 110

Gly Ile Tyr Gly Ser Gly Pro Gly Val Phe Gly Pro Tyr Gly Ser Ala
        115                 120                 125

Ala Ala Ala Ala Gly Pro Gly Ser Gly Ile Tyr Gly Ile Gly Pro Tyr
    130                 135                 140

Gly Pro Gly Ala Ser Gly Pro Gly Ile Tyr Gly Pro Gly Val Phe Gly
145                 150                 155                 160

Pro Ser Ala Ser Ala Ala Ala Ala Ala Gly Ser Gly Val Phe Gly Pro
                165                 170                 175

Gly Ile Tyr Gly Pro Tyr Ala Ser Ala Ala Ala Ala Ala Gly Ile Tyr
            180                 185                 190

Gly Ser Gly Pro Gly Val Phe Gly Pro Tyr Gly Pro Gly Ile Ser Gly
        195                 200                 205

Ser Gly Val Phe Gly Pro Gly Val Phe Gly Pro Tyr Ala Ser Ala Ala
    210                 215                 220

Ala Ala Ala Gly Pro Gly Val Phe Gly Pro Tyr Gly Pro Gly Ser Ser
225                 230                 235                 240

Ala Ala Ala Ala Ala Gly Ile Tyr Gly Tyr Gly Pro Gly Val Phe Gly
                245                 250                 255

Pro Tyr Gly Pro Gly Ala Ser Gly Ile Asn Gly Pro Gly Ser Gly Ile
            260                 265                 270

Tyr Gly Pro Gly Val Phe Gly Pro Gly Ile Ser Ala Ala Ala Ala Ala
        275                 280                 285

Gly Pro Gly Val Phe Gly Pro Tyr Gly Pro Gly Ala Ser Ala Ala Ala
    290                 295                 300

Ala Ala Gly Ile Tyr Gly Pro Gly Val Phe Gly Pro Gly Ile Tyr Gly
305                 310                 315                 320

Pro Gly Ser Ser Gly Pro Gly Val Phe Gly Pro Tyr Gly Pro Gly Ser
                325                 330                 335

Ser Ala Ala Ala Ala Ala Gly Ile Tyr Gly Pro Gly Val Phe Gly Pro
            340                 345                 350

Tyr Gly Pro Gly Ile Ser Ala Ala Ala Ala Ala Gly Ile Tyr Val Phe
        355                 360                 365

Gly Pro Gly Val Phe Gly Pro Tyr Gly Pro Gly Ala Ser Gly Pro Gly
    370                 375                 380

Val Phe Gly Pro Tyr Gly Pro Gly Ala Ser Ala Ala Ala Ala Ala Gly
385                 390                 395                 400

Pro Gly Ile Tyr Gly Pro Gly Val Phe Gly Pro Ser Ala Ser Ala Ala
                405                 410                 415

Ala Ala Ala Gly Ile Tyr Gly Ser Gly Pro Gly Ile Tyr Gly Pro Tyr
            420                 425                 430

Gly Pro Gly Ile Ser Gly Pro Gly Ser Gly Val Phe Gly Ile Gly Pro
        435                 440                 445

Tyr Gly Pro Gly Ala Ser Ala Ala Ala Ala Ala Gly Ile Tyr Gly Pro
    450                 455                 460

Gly Val Phe Gly Pro Tyr Gly Pro Gly Ile Ser Ala Ala Ala Ala Ala
```

```
465                 470                 475                 480

Gly Pro Gly Ser Gly Ile Tyr Gly Pro Gly Ala Ser Gly Ile Asn Gly
                485                 490                 495

Pro Gly Ser Gly Ile Tyr Gly Pro Gly Val Phe Gly Pro Gly Ile Ser
            500                 505                 510

Ala Ala Ala Ala Ala Gly Ile Tyr Val Phe Gly Pro Gly Val Phe Gly
        515                 520                 525

Pro Tyr Gly Pro Gly Ala Ser Ala Ala Ala Ala Ala Gly Ile Tyr Gly
    530                 535                 540

Ser Gly Pro Gly Val Phe Gly Pro Tyr Gly Pro Gly Ile Ser Gly Ser
545                 550                 555                 560

Gly Val Phe Gly Pro Gly Val Phe Gly Pro Tyr Ala Ser Ala Ala Ala
                565                 570                 575

Ala Ala Gly Pro Gly Ser Gly Val Phe Gly Pro Gly Ala Ser Gly Pro
            580                 585                 590

Gly Val Phe Gly Pro Tyr Gly Pro Gly Ala Ser Ala Ala Ala Ala Ala
        595                 600                 605

Gly Ile Asn Gly Pro Gly Ser Gly Val Phe Gly Pro Gly Ile Ser Gly
    610                 615                 620

Ile Tyr Gly Pro Gly Val Phe Gly Pro Gly Val Phe Gly Pro Gly Ser
625                 630                 635                 640

Ser Ala Ala Ala Ala Ala Gly Pro Gly Ile Tyr Gly Pro Gly Val Phe
                645                 650                 655

Gly Pro Ser Ala Ser Ala Ala Ala Ala Ala Gly Pro Gly Ser Gly Val
            660                 665                 670

Phe Gly Pro Gly Ala Ser Gly Ile Tyr Gly Pro Gly Val Phe Gly Pro
        675                 680                 685

Gly Val Phe Gly Pro Gly Ser Ser Ala Ala Ala Ala Ala Gly Ile Tyr
    690                 695                 700

Gly Ser Gly Pro Gly Val Phe Gly Pro Tyr Gly Ser Ala Ala Ala Ala
705                 710                 715                 720

Ala Gly Pro Gly Ser Gly Ile Tyr Gly Ile Gly Pro Tyr Gly Pro Gly
                725                 730                 735

Ala Ser Gly Pro Gly Ile Tyr Gly Pro Gly Val Phe Gly Pro Ser Ala
            740                 745                 750

Ser Ala Ala Ala Ala Ala Gly Ser Gly Val Phe Gly Pro Gly Ile Tyr
        755                 760                 765

Gly Pro Tyr Ala Ser Ala Ala Ala Ala Ala Gly Ile Tyr Gly Ser Gly
    770                 775                 780

Pro Gly Val Phe Gly Pro Tyr Gly Pro Gly Ile Ser Gly Ser Gly Val
785                 790                 795                 800

Phe Gly Pro Gly Val Phe Gly Pro Tyr Ala Ser Ala Ala Ala Ala Ala
                805                 810                 815

Gly Pro Gly Val Phe Gly Pro Tyr Gly Pro Gly Ser Ser Ala Ala Ala
            820                 825                 830

Ala Ala Gly Ile Tyr Gly Tyr Gly Pro Gly Val Phe Gly Pro Tyr Gly
        835                 840                 845

Pro Gly Ala Ser Gly Ile Asn Gly Pro Gly Ser Gly Ile Tyr Gly Pro
    850                 855                 860

Gly Val Phe Gly Pro Gly Ile Ser Ala Ala Ala Ala Ala Gly Pro Gly
865                 870                 875                 880

Val Phe Gly Pro Tyr Gly Pro Gly Ala Ser Ala Ala Ala Ala Ala Gly
                885                 890                 895
```

```
Ile Tyr Gly Pro Gly Val Phe Gly Pro Gly Ile Tyr Gly Pro Gly Ser
            900                 905                 910

Ser Gly Pro Gly Val Phe Gly Pro Tyr Gly Pro Gly Ser Ser Ala Ala
        915                 920                 925

Ala Ala Ala Gly Ile Tyr Gly Pro Gly Val Phe Gly Pro Tyr Gly Pro
    930                 935                 940

Gly Ile Ser Ala Ala Ala Ala Ala Gly Ile Tyr Val Phe Gly Pro Gly
945                 950                 955                 960

Val Phe Gly Pro Tyr Gly Pro Gly Ala Ser Gly Pro Gly Val Phe Gly
                965                 970                 975

Pro Tyr Gly Pro Gly Ala Ser Ala Ala Ala Ala Ala Gly Pro Gly Ile
            980                 985                 990

Tyr Gly Pro Gly Val Phe Gly Pro  Ser Ala Ser Ala Ala  Ala Ala Ala
        995                 1000                 1005

Gly Ile  Tyr Gly Ser Gly Pro  Gly Ile Tyr Gly Pro  Tyr Gly Pro
    1010                 1015                 1020

Gly Ile  Ser Gly Pro Gly Ser  Gly Val Phe Gly Ile  Gly Pro Tyr
    1025                 1030                 1035

Gly Pro  Gly Ala Ser Ala Ala  Ala Ala Ala Gly Ile  Tyr Gly Pro
    1040                 1045                 1050

Gly Val  Phe Gly Pro Tyr Gly  Pro Gly Ile Ser Ala  Ala Ala Ala
    1055                 1060                 1065

Ala Gly  Pro Gly Ser Gly Ile  Tyr Gly Pro Gly Ala  Ser Gly Ile
    1070                 1075                 1080

Asn Gly  Pro Gly Ser Gly Ile  Tyr Gly Pro Gly Val  Phe Gly Pro
    1085                 1090                 1095

Gly Ile  Ser Ala Ala Ala Ala  Ala Gly Ile Tyr Val  Phe Gly Pro
    1100                 1105                 1110

Gly Val  Phe Gly Pro Tyr Gly  Pro Gly Ala Ser Ala  Ala Ala Ala
    1115                 1120                 1125

Ala Gly  Ile Tyr Gly Ser Gly  Pro Gly Val Phe Gly  Pro Tyr Gly
    1130                 1135                 1140

Pro Gly  Ile Ser Gly Ser Gly  Val Phe Gly Pro Gly  Val Phe Gly
    1145                 1150                 1155

Pro Tyr  Ala Ser Ala Ala Ala  Ala Ala Gly Pro Gly  Ser Gly Val
    1160                 1165                 1170

Phe Gly  Pro Gly Ala Ser
    1175


<210> SEQ ID NO 33
<211> LENGTH: 601
<212> TYPE: PRT
<213> ORGANISM: Artificial Sequence
<220> FEATURE:
<223> OTHER INFORMATION: PRT888

<400> SEQUENCE: 33

Met His His His His His His Ser Ser Gly Ser Ser Gly Pro Gly Val
1               5                   10                  15

Leu Gly Pro Tyr Gly Pro Gly Ala Ser Ala Ala Ala Ala Ala Gly Gln
            20                  25                  30

Asn Gly Pro Gly Ser Gly Val Leu Gly Pro Gly Gln Ser Gly Gln Tyr
        35                  40                  45

Gly Pro Gly Val Leu Gly Pro Gly Val Leu Gly Pro Gly Ser Ser Ala
    50                  55                  60
```

```
Ala Ala Ala Ala Gly Pro Gly Gln Tyr Gly Pro Gly Val Leu Gly Pro
65                  70                  75                  80

Ser Ala Ser Ala Ala Ala Ala Ala Gly Pro Gly Ser Gly Val Leu Gly
                85                  90                  95

Pro Gly Ala Ser Gly Gln Tyr Gly Pro Gly Val Leu Gly Pro Gly Val
            100                 105                 110

Leu Gly Pro Gly Ser Ser Ala Ala Ala Ala Ala Gly Gln Tyr Gly Ser
        115                 120                 125

Gly Pro Gly Val Leu Gly Pro Tyr Gly Ser Ala Ala Ala Ala Ala Gly
    130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Val Leu Gly Pro Ser Ala Ser Ala
                165                 170                 175

Ala Ala Ala Ala Gly Ser Gly Val Leu Gly Pro Gly Gln Tyr Gly Pro
            180                 185                 190

Tyr Ala Ser Ala Ala Ala Ala Ala Gly Gln Tyr Gly Ser Gly Pro Gly
        195                 200                 205

Val Leu Gly Pro Tyr Gly Pro Gly Gln Ser Gly Ser Gly Val Leu Gly
    210                 215                 220

Pro Gly Val Leu Gly Pro Tyr Ala Ser Ala Ala Ala Ala Ala Gly Pro
225                 230                 235                 240

Gly Val Leu Gly Pro Tyr Gly Pro Gly Ser Ser Ala Ala Ala Ala Ala
                245                 250                 255

Gly Gln Tyr Gly Tyr Gly Pro Gly Val Leu Gly Pro Tyr Gly Pro Gly
            260                 265                 270

Ala Ser Gly Gln Asn Gly Pro Gly Ser Gly Gln Tyr Gly Pro Gly Val
        275                 280                 285

Leu Gly Pro Gly Gln Ser Ala Ala Ala Ala Ala Gly Pro Gly Val Leu
    290                 295                 300

Gly Pro Tyr Gly Pro Gly Ala Ser Ala Ala Ala Ala Ala Gly Gln Tyr
305                 310                 315                 320

Gly Pro Gly Val Leu Gly Pro Gly Gln Tyr Gly Pro Gly Ser Ser Gly
                325                 330                 335

Pro Gly Val Leu Gly Pro Tyr Gly Pro Gly Ser Ser Ala Ala Ala Ala
            340                 345                 350

Ala Gly Gln Tyr Gly Pro Gly Val Leu Gly Pro Tyr Gly Pro Gly Gln
        355                 360                 365

Ser Ala Ala Ala Ala Ala Gly Gln Tyr Val Leu Gly Pro Gly Val Leu
    370                 375                 380

Gly Pro Tyr Gly Pro Gly Ala Ser Gly Pro Gly Val Leu Gly Pro Tyr
385                 390                 395                 400

Gly Pro Gly Ala Ser Ala Ala Ala Ala Ala Gly Pro Gly Gln Tyr Gly
                405                 410                 415

Pro Gly Val Leu Gly Pro Ser Ala Ser Ala Ala Ala Ala Ala Gly Gln
            420                 425                 430

Tyr Gly Ser Gly Pro Gly Gln Tyr Gly Pro Tyr Gly Pro Gly Gln Ser
        435                 440                 445

Gly Pro Gly Ser Gly Val Leu Gly Gln Gly Pro Tyr Gly Pro Gly Ala
    450                 455                 460

Ser Ala Ala Ala Ala Ala Gly Gln Tyr Gly Pro Gly Val Leu Gly Pro
465                 470                 475                 480
```

Tyr Gly Pro Gly Gln Ser Ala Ala Ala Ala Ala Gly Pro Gly Ser Gly
485 490 495

Gln Tyr Gly Pro Gly Ala Ser Gly Gln Asn Gly Pro Gly Ser Gly Gln
500 505 510

Tyr Gly Pro Gly Val Leu Gly Pro Gly Gln Ser Ala Ala Ala Ala Ala
515 520 525

Gly Gln Tyr Val Leu Gly Pro Gly Val Leu Gly Pro Tyr Gly Pro Gly
530 535 540

Ala Ser Ala Ala Ala Ala Ala Gly Gln Tyr Gly Ser Gly Pro Gly Val
545 550 555 560

Leu Gly Pro Tyr Gly Pro Gly Gln Ser Gly Ser Gly Val Leu Gly Pro
565 570 575

Gly Val Leu Gly Pro Tyr Ala Ser Ala Ala Ala Ala Ala Gly Pro Gly
580 585 590

Ser Gly Val Leu Gly Pro Gly Ala Ser
595 600

<210> SEQ ID NO 34
<211> LENGTH: 601
<212> TYPE: PRT
<213> ORGANISM: Artificial Sequence
<220> FEATURE:
<223> OTHER INFORMATION: PRT965

<400> SEQUENCE: 34

Met His His His His His His Ser Ser Gly Ser Ser Gly Pro Gly Thr
1 5 10 15

Ser Gly Pro Tyr Gly Pro Gly Ala Ser Ala Ala Ala Ala Ala Gly Ala
20 25 30

Asn Gly Pro Gly Ser Gly Thr Ser Gly Pro Gly Ala Ser Gly Ala Tyr
35 40 45

Gly Pro Gly Thr Ser Gly Pro Gly Thr Ser Gly Pro Gly Ser Ser Ala
50 55 60

Ala Ala Ala Ala Gly Pro Gly Ala Tyr Gly Pro Gly Thr Ser Gly Pro
65 70 75 80

Ser Ala Ser Ala Ala Ala Ala Ala Gly Pro Gly Ser Gly Thr Ser Gly
85 90 95

Pro Gly Ala Ser Gly Ala Tyr Gly Pro Gly Thr Ser Gly Pro Gly Thr
100 105 110

Ser Gly Pro Gly Ser Ser Ala Ala Ala Ala Ala Gly Ala Tyr Gly Ser
115 120 125

Gly Pro Gly Thr Ser Gly Pro Tyr Gly Ser Ala Ala Ala Ala Ala Gly
130 135 140

Pro Gly Ser Gly Ala Tyr Gly Ala Gly Pro Tyr Gly Pro Gly Ala Ser
145 150 155 160

Gly Pro Gly Ala Tyr Gly Pro Gly Thr Ser Gly Pro Ser Ala Ser Ala
165 170 175

Ala Ala Ala Ala Gly Ser Gly Thr Ser Gly Pro Gly Ala Tyr Gly Pro
180 185 190

Tyr Ala Ser Ala Ala Ala Ala Ala Gly Ala Tyr Gly Ser Gly Pro Gly
195 200 205

Thr Ser Gly Pro Tyr Gly Pro Gly Ala Ser Gly Ser Gly Thr Ser Gly
210 215 220

Pro Gly Thr Ser Gly Pro Tyr Ala Ser Ala Ala Ala Ala Ala Gly Pro
225 230 235 240

```
Gly Thr Ser Gly Pro Tyr Gly Pro Gly Ser Ser Ala Ala Ala Ala Ala
                245                 250                 255

Gly Ala Tyr Gly Tyr Gly Pro Gly Thr Ser Gly Pro Tyr Gly Pro Gly
            260                 265                 270

Ala Ser Gly Ala Asn Gly Pro Gly Ser Gly Ala Tyr Gly Pro Gly Thr
        275                 280                 285

Ser Gly Pro Gly Ala Ser Ala Ala Ala Ala Ala Gly Pro Gly Thr Ser
    290                 295                 300

Gly Pro Tyr Gly Pro Gly Ala Ser Ala Ala Ala Ala Ala Gly Ala Tyr
305                 310                 315                 320

Gly Pro Gly Thr Ser Gly Pro Gly Ala Tyr Gly Pro Gly Ser Ser Gly
                325                 330                 335

Pro Gly Thr Ser Gly Pro Tyr Gly Pro Gly Ser Ser Ala Ala Ala Ala
            340                 345                 350

Ala Gly Ala Tyr Gly Pro Gly Thr Ser Gly Pro Tyr Gly Pro Gly Ala
        355                 360                 365

Ser Ala Ala Ala Ala Ala Gly Ala Tyr Thr Ser Gly Pro Gly Thr Ser
    370                 375                 380

Gly Pro Tyr Gly Pro Gly Ala Ser Gly Pro Gly Thr Ser Gly Pro Tyr
385                 390                 395                 400

Gly Pro Gly Ala Ser Ala Ala Ala Ala Ala Gly Pro Gly Ala Tyr Gly
                405                 410                 415

Pro Gly Thr Ser Gly Pro Ser Ala Ser Ala Ala Ala Ala Ala Gly Ala
            420                 425                 430

Tyr Gly Ser Gly Pro Gly Ala Tyr Gly Pro Tyr Gly Pro Gly Ala Ser
        435                 440                 445

Gly Pro Gly Ser Gly Thr Ser Gly Ala Gly Pro Tyr Gly Pro Gly Ala
    450                 455                 460

Ser Ala Ala Ala Ala Ala Gly Ala Tyr Gly Pro Gly Thr Ser Gly Pro
465                 470                 475                 480

Tyr Gly Pro Gly Ala Ser Ala Ala Ala Ala Ala Gly Pro Gly Ser Gly
                485                 490                 495

Ala Tyr Gly Pro Gly Ala Ser Gly Ala Asn Gly Pro Gly Ser Gly Ala
            500                 505                 510

Tyr Gly Pro Gly Thr Ser Gly Pro Gly Ala Ser Ala Ala Ala Ala Ala
        515                 520                 525

Gly Ala Tyr Thr Ser Gly Pro Gly Thr Ser Gly Pro Tyr Gly Pro Gly
    530                 535                 540

Ala Ser Ala Ala Ala Ala Ala Gly Ala Tyr Gly Ser Gly Pro Gly Thr
545                 550                 555                 560

Ser Gly Pro Tyr Gly Pro Gly Ala Ser Gly Ser Gly Thr Ser Gly Pro
                565                 570                 575

Gly Thr Ser Gly Pro Tyr Ala Ser Ala Ala Ala Ala Ala Gly Pro Gly
            580                 585                 590

Ser Gly Thr Ser Gly Pro Gly Ala Ser
        595                 600
```

```
<210> SEQ ID NO 35
<211> LENGTH: 601
<212> TYPE: PRT
<213> ORGANISM: Artificial Sequence
<220> FEATURE:
<223> OTHER INFORMATION: PRT889

<400> SEQUENCE: 35
```

-continued

```
Met His His His His His His Ser Ser Gly Ser Ser Gly Pro Gly Val
1               5                   10                  15

Leu Gly Pro Tyr Gly Pro Gly Ala Ser Ala Ala Ala Ala Ala Gly Ile
            20                  25                  30

Asn Gly Pro Gly Ser Gly Val Leu Gly Pro Gly Ile Ser Gly Ile Tyr
        35                  40                  45

Gly Pro Gly Val Leu Gly Pro Gly Val Leu Gly Pro Gly Ser Ser Ala
    50                  55                  60

Ala Ala Ala Ala Gly Pro Gly Ile Tyr Gly Pro Gly Val Leu Gly Pro
65                  70                  75                  80

Ser Ala Ser Ala Ala Ala Ala Ala Gly Pro Gly Ser Gly Val Leu Gly
                85                  90                  95

Pro Gly Ala Ser Gly Ile Tyr Gly Pro Gly Val Leu Gly Pro Gly Val
            100                 105                 110

Leu Gly Pro Gly Ser Ser Ala Ala Ala Ala Ala Gly Ile Tyr Gly Ser
        115                 120                 125

Gly Pro Gly Val Leu Gly Pro Tyr Gly Ser Ala Ala Ala Ala Ala Gly
    130                 135                 140

Pro Gly Ser Gly Ile Tyr Gly Ile Gly Pro Tyr Gly Pro Gly Ala Ser
145                 150                 155                 160

Gly Pro Gly Ile Tyr Gly Pro Gly Val Leu Gly Pro Ser Ala Ser Ala
                165                 170                 175

Ala Ala Ala Ala Gly Ser Gly Val Leu Gly Pro Gly Ile Tyr Gly Pro
            180                 185                 190

Tyr Ala Ser Ala Ala Ala Ala Ala Gly Ile Tyr Gly Ser Gly Pro Gly
        195                 200                 205

Val Leu Gly Pro Tyr Gly Pro Gly Ile Ser Gly Ser Gly Val Leu Gly
    210                 215                 220

Pro Gly Val Leu Gly Pro Tyr Ala Ser Ala Ala Ala Ala Ala Gly Pro
225                 230                 235                 240

Gly Val Leu Gly Pro Tyr Gly Pro Gly Ser Ser Ala Ala Ala Ala Ala
                245                 250                 255

Gly Ile Tyr Gly Tyr Gly Pro Gly Val Leu Gly Pro Tyr Gly Pro Gly
            260                 265                 270

Ala Ser Gly Ile Asn Gly Pro Gly Ser Gly Ile Tyr Gly Pro Gly Val
        275                 280                 285

Leu Gly Pro Gly Ile Ser Ala Ala Ala Ala Ala Gly Pro Gly Val Leu
    290                 295                 300

Gly Pro Tyr Gly Pro Gly Ala Ser Ala Ala Ala Ala Ala Gly Ile Tyr
305                 310                 315                 320

Gly Pro Gly Val Leu Gly Pro Gly Ile Tyr Gly Pro Gly Ser Ser Gly
                325                 330                 335

Pro Gly Val Leu Gly Pro Tyr Gly Pro Gly Ser Ser Ala Ala Ala Ala
            340                 345                 350

Ala Gly Ile Tyr Gly Pro Gly Val Leu Gly Pro Tyr Gly Pro Gly Ile
        355                 360                 365

Ser Ala Ala Ala Ala Ala Gly Ile Tyr Val Leu Gly Pro Gly Val Leu
    370                 375                 380

Gly Pro Tyr Gly Pro Gly Ala Ser Gly Pro Gly Val Leu Gly Pro Tyr
385                 390                 395                 400

Gly Pro Gly Ala Ser Ala Ala Ala Ala Ala Gly Pro Gly Ile Tyr Gly
                405                 410                 415

Pro Gly Val Leu Gly Pro Ser Ala Ser Ala Ala Ala Ala Ala Gly Ile
```

```
            420                 425                 430

Tyr Gly Ser Gly Pro Gly Ile Tyr Gly Pro Tyr Gly Pro Gly Ile Ser
        435                 440                 445

Gly Pro Gly Ser Gly Val Leu Gly Ile Gly Pro Tyr Gly Pro Gly Ala
    450                 455                 460

Ser Ala Ala Ala Ala Ala Gly Ile Tyr Gly Pro Gly Val Leu Gly Pro
465                 470                 475                 480

Tyr Gly Pro Gly Ile Ser Ala Ala Ala Ala Ala Gly Pro Gly Ser Gly
                485                 490                 495

Ile Tyr Gly Pro Gly Ala Ser Gly Ile Asn Gly Pro Gly Ser Gly Ile
            500                 505                 510

Tyr Gly Pro Gly Val Leu Gly Pro Gly Ile Ser Ala Ala Ala Ala Ala
        515                 520                 525

Gly Ile Tyr Val Leu Gly Pro Gly Val Leu Gly Pro Tyr Gly Pro Gly
    530                 535                 540

Ala Ser Ala Ala Ala Ala Ala Gly Ile Tyr Gly Ser Gly Pro Gly Val
545                 550                 555                 560

Leu Gly Pro Tyr Gly Pro Gly Ile Ser Gly Ser Gly Val Leu Gly Pro
                565                 570                 575

Gly Val Leu Gly Pro Tyr Ala Ser Ala Ala Ala Ala Ala Gly Pro Gly
            580                 585                 590

Ser Gly Val Leu Gly Pro Gly Ala Ser
        595                 600


<210> SEQ ID NO 36
<211> LENGTH: 601
<212> TYPE: PRT
<213> ORGANISM: Artificial Sequence
<220> FEATURE:
<223> OTHER INFORMATION: PRT916

<400> SEQUENCE: 36

Met His His His His His His Ser Ser Gly Ser Ser Gly Pro Gly Val
1               5                   10                  15

Ile Gly Pro Tyr Gly Pro Gly Ala Ser Ala Ala Ala Ala Ala Gly Leu
            20                  25                  30

Asn Gly Pro Gly Ser Gly Val Ile Gly Pro Gly Leu Ser Gly Leu Tyr
        35                  40                  45

Gly Pro Gly Val Ile Gly Pro Gly Val Ile Gly Pro Gly Ser Ser Ala
    50                  55                  60

Ala Ala Ala Ala Gly Pro Gly Leu Tyr Gly Pro Gly Val Ile Gly Pro
65                  70                  75                  80

Ser Ala Ser Ala Ala Ala Ala Ala Gly Pro Gly Ser Gly Val Ile Gly
                85                  90                  95

Pro Gly Ala Ser Gly Leu Tyr Gly Pro Gly Val Ile Gly Pro Gly Val
            100                 105                 110

Ile Gly Pro Gly Ser Ser Ala Ala Ala Ala Ala Gly Leu Tyr Gly Ser
        115                 120                 125

Gly Pro Gly Val Ile Gly Pro Tyr Gly Ser Ala Ala Ala Ala Ala Gly
    130                 135                 140

Pro Gly Ser Gly Leu Tyr Gly Leu Gly Pro Tyr Gly Pro Gly Ala Ser
145                 150                 155                 160

Gly Pro Gly Leu Tyr Gly Pro Gly Val Ile Gly Pro Ser Ala Ser Ala
                165                 170                 175

Ala Ala Ala Ala Gly Ser Gly Val Ile Gly Pro Gly Leu Tyr Gly Pro
```

```
            180                 185                 190

Tyr Ala Ser Ala Ala Ala Ala Ala Gly Leu Tyr Gly Ser Gly Pro Gly
        195                 200                 205

Val Ile Gly Pro Tyr Gly Pro Gly Leu Ser Gly Ser Gly Val Ile Gly
    210                 215                 220

Pro Gly Val Ile Gly Pro Tyr Ala Ser Ala Ala Ala Ala Ala Gly Pro
225                 230                 235                 240

Gly Val Ile Gly Pro Tyr Gly Pro Gly Ser Ser Ala Ala Ala Ala Ala
                245                 250                 255

Gly Leu Tyr Gly Tyr Gly Pro Gly Val Ile Gly Pro Tyr Gly Pro Gly
            260                 265                 270

Ala Ser Gly Leu Asn Gly Pro Gly Ser Gly Leu Tyr Gly Pro Gly Val
        275                 280                 285

Ile Gly Pro Gly Leu Ser Ala Ala Ala Ala Ala Gly Pro Gly Val Ile
    290                 295                 300

Gly Pro Tyr Gly Pro Gly Ala Ser Ala Ala Ala Ala Ala Gly Leu Tyr
305                 310                 315                 320

Gly Pro Gly Val Ile Gly Pro Gly Leu Tyr Gly Pro Gly Ser Ser Gly
                325                 330                 335

Pro Gly Val Ile Gly Pro Tyr Gly Pro Gly Ser Ser Ala Ala Ala Ala
            340                 345                 350

Ala Gly Leu Tyr Gly Pro Gly Val Ile Gly Pro Tyr Gly Pro Gly Leu
        355                 360                 365

Ser Ala Ala Ala Ala Ala Gly Leu Tyr Val Ile Gly Pro Gly Val Ile
    370                 375                 380

Gly Pro Tyr Gly Pro Gly Ala Ser Gly Pro Gly Val Ile Gly Pro Tyr
385                 390                 395                 400

Gly Pro Gly Ala Ser Ala Ala Ala Ala Ala Gly Pro Gly Leu Tyr Gly
                405                 410                 415

Pro Gly Val Ile Gly Pro Ser Ala Ser Ala Ala Ala Ala Ala Gly Leu
            420                 425                 430

Tyr Gly Ser Gly Pro Gly Leu Tyr Gly Pro Tyr Gly Pro Gly Leu Ser
        435                 440                 445

Gly Pro Gly Ser Gly Val Ile Gly Leu Gly Pro Tyr Gly Pro Gly Ala
    450                 455                 460

Ser Ala Ala Ala Ala Ala Gly Leu Tyr Gly Pro Gly Val Ile Gly Pro
465                 470                 475                 480

Tyr Gly Pro Gly Leu Ser Ala Ala Ala Ala Ala Gly Pro Gly Ser Gly
                485                 490                 495

Leu Tyr Gly Pro Gly Ala Ser Gly Leu Asn Gly Pro Gly Ser Gly Leu
            500                 505                 510

Tyr Gly Pro Gly Val Ile Gly Pro Gly Leu Ser Ala Ala Ala Ala Ala
        515                 520                 525

Gly Leu Tyr Val Ile Gly Pro Gly Val Ile Gly Pro Tyr Gly Pro Gly
    530                 535                 540

Ala Ser Ala Ala Ala Ala Ala Gly Leu Tyr Gly Ser Gly Pro Gly Val
545                 550                 555                 560

Ile Gly Pro Tyr Gly Pro Gly Leu Ser Gly Ser Gly Val Ile Gly Pro
                565                 570                 575

Gly Val Ile Gly Pro Tyr Ala Ser Ala Ala Ala Ala Ala Gly Pro Gly
            580                 585                 590

Ser Gly Val Ile Gly Pro Gly Ala Ser
        595                 600
```

<210> SEQ ID NO 37
<211> LENGTH: 601
<212> TYPE: PRT
<213> ORGANISM: Artificial Sequence
<220> FEATURE:
<223> OTHER INFORMATION: PRT918

<400> SEQUENCE: 37

```
Met His His His His His His Ser Ser Gly Ser Ser Gly Pro Gly Val
1               5                   10                  15

Phe Gly Pro Tyr Gly Pro Gly Ala Ser Ala Ala Ala Ala Ala Gly Ile
            20                  25                  30

Asn Gly Pro Gly Ser Gly Val Phe Gly Pro Gly Ile Ser Gly Ile Tyr
        35                  40                  45

Gly Pro Gly Val Phe Gly Pro Gly Val Phe Gly Pro Gly Ser Ser Ala
    50                  55                  60

Ala Ala Ala Ala Gly Pro Gly Ile Tyr Gly Pro Gly Val Phe Gly Pro
65                  70                  75                  80

Ser Ala Ser Ala Ala Ala Ala Ala Gly Pro Gly Ser Gly Val Phe Gly
                85                  90                  95

Pro Gly Ala Ser Gly Ile Tyr Gly Pro Gly Val Phe Gly Pro Gly Val
            100                 105                 110

Phe Gly Pro Gly Ser Ser Ala Ala Ala Ala Ala Gly Ile Tyr Gly Ser
        115                 120                 125

Gly Pro Gly Val Phe Gly Pro Tyr Gly Ser Ala Ala Ala Ala Ala Gly
    130                 135                 140

Pro Gly Ser Gly Ile Tyr Gly Ile Gly Pro Tyr Gly Pro Gly Ala Ser
145                 150                 155                 160

Gly Pro Gly Ile Tyr Gly Pro Gly Val Phe Gly Pro Ser Ala Ser Ala
                165                 170                 175

Ala Ala Ala Ala Gly Ser Gly Val Phe Gly Pro Gly Ile Tyr Gly Pro
            180                 185                 190

Tyr Ala Ser Ala Ala Ala Ala Ala Gly Ile Tyr Gly Ser Gly Pro Gly
        195                 200                 205

Val Phe Gly Pro Tyr Gly Pro Gly Ile Ser Gly Ser Gly Val Phe Gly
    210                 215                 220

Pro Gly Val Phe Gly Pro Tyr Ala Ser Ala Ala Ala Ala Ala Gly Pro
225                 230                 235                 240

Gly Val Phe Gly Pro Tyr Gly Pro Gly Ser Ser Ala Ala Ala Ala Ala
                245                 250                 255

Gly Ile Tyr Gly Tyr Gly Pro Gly Val Phe Gly Pro Tyr Gly Pro Gly
            260                 265                 270

Ala Ser Gly Ile Asn Gly Pro Gly Ser Gly Ile Tyr Gly Pro Gly Val
        275                 280                 285

Phe Gly Pro Gly Ile Ser Ala Ala Ala Ala Ala Gly Pro Gly Val Phe
    290                 295                 300

Gly Pro Tyr Gly Pro Gly Ala Ser Ala Ala Ala Ala Ala Gly Ile Tyr
305                 310                 315                 320

Gly Pro Gly Val Phe Gly Pro Gly Ile Tyr Gly Pro Gly Ser Ser Gly
                325                 330                 335

Pro Gly Val Phe Gly Pro Tyr Gly Pro Gly Ser Ser Ala Ala Ala Ala
            340                 345                 350

Ala Gly Ile Tyr Gly Pro Gly Val Phe Gly Pro Tyr Gly Pro Gly Ile
        355                 360                 365
```

Ser Ala Ala Ala Ala Ala Gly Ile Tyr Val Phe Gly Pro Gly Val Phe
370 375 380

Gly Pro Tyr Gly Pro Gly Ala Ser Gly Pro Gly Val Phe Gly Pro Tyr
385 390 395 400

Gly Pro Gly Ala Ser Ala Ala Ala Ala Ala Gly Pro Gly Ile Tyr Gly
405 410 415

Pro Gly Val Phe Gly Pro Ser Ala Ser Ala Ala Ala Ala Ala Gly Ile
420 425 430

Tyr Gly Ser Gly Pro Gly Ile Tyr Gly Pro Tyr Gly Pro Gly Ile Ser
435 440 445

Gly Pro Gly Ser Gly Val Phe Gly Ile Gly Pro Tyr Gly Pro Gly Ala
450 455 460

Ser Ala Ala Ala Ala Ala Gly Ile Tyr Gly Pro Gly Val Phe Gly Pro
465 470 475 480

Tyr Gly Pro Gly Ile Ser Ala Ala Ala Ala Ala Gly Pro Gly Ser Gly
485 490 495

Ile Tyr Gly Pro Gly Ala Ser Gly Ile Asn Gly Pro Gly Ser Gly Ile
500 505 510

Tyr Gly Pro Gly Val Phe Gly Pro Gly Ile Ser Ala Ala Ala Ala Ala
515 520 525

Gly Ile Tyr Val Phe Gly Pro Gly Val Phe Gly Pro Tyr Gly Pro Gly
530 535 540

Ala Ser Ala Ala Ala Ala Ala Gly Ile Tyr Gly Ser Gly Pro Gly Val
545 550 555 560

Phe Gly Pro Tyr Gly Pro Gly Ile Ser Gly Ser Gly Val Phe Gly Pro
565 570 575

Gly Val Phe Gly Pro Tyr Ala Ser Ala Ala Ala Ala Ala Gly Pro Gly
580 585 590

Ser Gly Val Phe Gly Pro Gly Ala Ser
595 600

<210> SEQ ID NO 38
<211> LENGTH: 576
<212> TYPE: PRT
<213> ORGANISM: Artificial Sequence
<220> FEATURE:
<223> OTHER INFORMATION: PRT699

<400> SEQUENCE: 38

Met His His His His His His Ser Ser Gly Ser Ser Gly Pro Gly Val
1 5 10 15

Leu Gly Pro Tyr Gly Pro Gly Ala Ser Ala Ala Ala Ala Ala Ala Ala
20 25 30

Gly Ser Asn Gly Pro Gly Ser Gly Val Leu Gly Pro Gly Gln Ser Gly
35 40 45

Gln Tyr Gly Pro Gly Val Leu Gly Pro Gly Val Leu Gly Pro Gly Ser
50 55 60

Ser Ala Ala Ala Ala Ala Ala Ala Gly Pro Gly Gln Tyr Gly Pro Gly
65 70 75 80

Val Leu Gly Pro Ser Ala Ser Ala Ala Ala Ala Ala Ala Ala Gly Pro
85 90 95

Gly Ser Gly Val Leu Gly Pro Gly Ala Ser Gly Gln Tyr Gly Pro Gly
100 105 110

Val Leu Gly Pro Gly Val Leu Gly Pro Gly Ser Ser Ala Ala Ala Ala
115 120 125

```
Ala Ala Ala Gly Ser Tyr Gly Ser Gly Pro Gly Val Leu Gly Pro Tyr
    130                 135                 140

Gly Ser Ala Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Val Leu Gly Pro Ser Ala Ser Ala Ala Ala Ala Ala Ala Ala
            180                 185                 190

Gly Ser Gly Val Leu Gly Pro Gly Gln Tyr Gly Pro Tyr Ala Ser Ala
        195                 200                 205

Ala Ala Ala Ala Ala Ala Gly Ser Tyr Gly Ser Gly Pro Gly Val Leu
    210                 215                 220

Gly Pro Tyr Gly Pro Gly Gln Ser Gly Ser Gly Val Leu Gly Pro Gly
225                 230                 235                 240

Val Leu Gly Pro Tyr Ala Ser Ala Ala Ala Ala Ala Ala Ala Gly Pro
                245                 250                 255

Gly Val Leu Gly Pro Tyr Gly Pro Gly Ser Ser Ala Ala Ala Ala Ala
            260                 265                 270

Ala Ala Gly Ser Tyr Gly Tyr Gly Pro Gly Val Leu Gly Pro Tyr Gly
        275                 280                 285

Pro Gly Ala Ser Gly Gln Asn Gly Pro Gly Ser Gly Gln Tyr Gly Pro
    290                 295                 300

Gly Val Leu Gly Pro Gly Pro Ser Ala Ala Ala Ala Ala Ala Ala Gly
305                 310                 315                 320

Pro Gly Val Leu Gly Pro Tyr Gly Pro Gly Ala Ser Ala Ala Ala Ala
                325                 330                 335

Ala Ala Ala Gly Ser Tyr Gly Pro Gly Val Leu Gly Pro Gly Gln Tyr
            340                 345                 350

Gly Pro Gly Ser Ser Gly Pro Gly Val Leu Gly Pro Tyr Gly Pro Gly
        355                 360                 365

Ser Ser Ala Ala Ala Ala Ala Ala Ala Gly Ser Tyr Gly Pro Gly Val
    370                 375                 380

Leu Gly Pro Tyr Gly Pro Gly Pro Ser Ala Ala Ala Ala Ala Ala Ala
385                 390                 395                 400

Gly Ser Tyr Val Leu Gly Pro Gly Val Leu Gly Pro Tyr Gly Pro Gly
                405                 410                 415

Ala Ser Gly Pro Gly Val Leu Gly Pro Tyr Gly Pro Gly Ala Ser Ala
            420                 425                 430

Ala Ala Ala Ala Ala Ala Gly Pro Gly Gln Tyr Gly Pro Gly Val Leu
        435                 440                 445

Gly Pro Ser Ala Ser Ala Ala Ala Ala Ala Ala Ala Gly Ser Tyr Gly
    450                 455                 460

Ser Gly Pro Gly Gln Tyr Gly Pro Tyr Gly Pro Gly Gln Ser Gly Pro
465                 470                 475                 480

Gly Ser Gly Val Leu Gly Gln Gly Pro Tyr Gly Pro Gly Ala Ser Ala
                485                 490                 495

Ala Ala Ala Ala Ala Ala Gly Ser Tyr Gly Pro Gly Val Leu Gly Pro
            500                 505                 510

Tyr Gly Pro Gly Pro Ser Ala Ala Ala Ala Ala Ala Ala Gly Pro Gly
        515                 520                 525

Ser Gly Gln Tyr Gly Pro Gly Ala Ser Gly Gln Asn Gly Pro Gly Ser
    530                 535                 540
```

Gly Gln Tyr Gly Pro Gly Val Leu Gly Pro Gly Pro Ser Ala Ala Ala
545 550 555 560

Ala Ala Ala Ala Gly Pro Gly Ser Gly Val Leu Gly Pro Gly Ala Ser
565 570 575

<210> SEQ ID NO 39
<211> LENGTH: 576
<212> TYPE: PRT
<213> ORGANISM: Artificial Sequence
<220> FEATURE:
<223> OTHER INFORMATION: PRT698

<400> SEQUENCE: 39

Met His His His His His His Ser Ser Gly Ser Ser Gly Pro Gly Val
1 5 10 15

Leu Gly Pro Tyr Gly Pro Gly Ala Ser Ala Ala Ala Ala Ala Ala Ala
20 25 30

Gly Ser Asn Gly Pro Gly Ser Gly Val Leu Gly Pro Gly Ile Ser Gly
35 40 45

Ile Tyr Gly Pro Gly Val Leu Gly Pro Gly Val Leu Gly Pro Gly Ser
50 55 60

Ser Ala Ala Ala Ala Ala Ala Ala Gly Pro Gly Ile Tyr Gly Pro Gly
65 70 75 80

Val Leu Gly Pro Ser Ala Ser Ala Ala Ala Ala Ala Ala Ala Gly Pro
85 90 95

Gly Ser Gly Val Leu Gly Pro Gly Ala Ser Gly Ile Tyr Gly Pro Gly
100 105 110

Val Leu Gly Pro Gly Val Leu Gly Pro Gly Ser Ser Ala Ala Ala Ala
115 120 125

Ala Ala Ala Gly Ser Tyr Gly Ser Gly Pro Gly Val Leu Gly Pro Tyr
130 135 140

Gly Ser Ala Ala Ala Ala Ala Ala Ala Gly Pro Gly Ser Gly Ile Tyr
145 150 155 160

Gly Ile Gly Pro Tyr Gly Pro Gly Ala Ser Gly Pro Gly Ile Tyr Gly
165 170 175

Pro Gly Val Leu Gly Pro Ser Ala Ser Ala Ala Ala Ala Ala Ala Ala
180 185 190

Gly Ser Gly Val Leu Gly Pro Gly Ile Tyr Gly Pro Tyr Ala Ser Ala
195 200 205

Ala Ala Ala Ala Ala Ala Gly Ser Tyr Gly Ser Gly Pro Gly Val Leu
210 215 220

Gly Pro Tyr Gly Pro Gly Ile Ser Gly Ser Gly Val Leu Gly Pro Gly
225 230 235 240

Val Leu Gly Pro Tyr Ala Ser Ala Ala Ala Ala Ala Ala Ala Gly Pro
245 250 255

Gly Val Leu Gly Pro Tyr Gly Pro Gly Ser Ser Ala Ala Ala Ala Ala
260 265 270

Ala Ala Gly Ser Tyr Gly Tyr Gly Pro Gly Val Leu Gly Pro Tyr Gly
275 280 285

Pro Gly Ala Ser Gly Ile Asn Gly Pro Gly Ser Gly Ile Tyr Gly Pro
290 295 300

Gly Val Leu Gly Pro Gly Pro Ser Ala Ala Ala Ala Ala Ala Ala Gly
305 310 315 320

Pro Gly Val Leu Gly Pro Tyr Gly Pro Gly Ala Ser Ala Ala Ala Ala
325 330 335

```
Ala Ala Ala Gly Ser Tyr Gly Pro Gly Val Leu Gly Pro Gly Ile Tyr
            340                 345                 350

Gly Pro Gly Ser Ser Gly Pro Gly Val Leu Gly Pro Tyr Gly Pro Gly
        355                 360                 365

Ser Ser Ala Ala Ala Ala Ala Ala Ala Gly Ser Tyr Gly Pro Gly Val
    370                 375                 380

Leu Gly Pro Tyr Gly Pro Gly Pro Ser Ala Ala Ala Ala Ala Ala Ala
385                 390                 395                 400

Gly Ser Tyr Val Leu Gly Pro Gly Val Leu Gly Pro Tyr Gly Pro Gly
                405                 410                 415

Ala Ser Gly Pro Gly Val Leu Gly Pro Tyr Gly Pro Gly Ala Ser Ala
            420                 425                 430

Ala Ala Ala Ala Ala Ala Gly Pro Gly Ile Tyr Gly Pro Gly Val Leu
        435                 440                 445

Gly Pro Ser Ala Ser Ala Ala Ala Ala Ala Ala Ala Gly Ser Tyr Gly
    450                 455                 460

Ser Gly Pro Gly Ile Tyr Gly Pro Tyr Gly Pro Gly Ile Ser Gly Pro
465                 470                 475                 480

Gly Ser Gly Val Leu Gly Ile Gly Pro Tyr Gly Pro Gly Ala Ser Ala
                485                 490                 495

Ala Ala Ala Ala Ala Ala Gly Ser Tyr Gly Pro Gly Val Leu Gly Pro
            500                 505                 510

Tyr Gly Pro Gly Pro Ser Ala Ala Ala Ala Ala Ala Ala Gly Pro Gly
        515                 520                 525

Ser Gly Ile Tyr Gly Pro Gly Ala Ser Gly Ile Asn Gly Pro Gly Ser
    530                 535                 540

Gly Ile Tyr Gly Pro Gly Val Leu Gly Pro Gly Pro Ser Ala Ala Ala
545                 550                 555                 560

Ala Ala Ala Ala Gly Pro Gly Ser Gly Val Leu Gly Pro Gly Ala Ser
                565                 570                 575


<210> SEQ ID NO 40
<211> LENGTH: 1190
<212> TYPE: PRT
<213> ORGANISM: Artificial Sequence
<220> FEATURE:
<223> OTHER INFORMATION: PRT966

<400> SEQUENCE: 40

Met His His His His His His Ser Ser Gly Ser Ser Gly Pro Gly Val
1               5                   10                  15

Phe Gly Pro Tyr Gly Pro Gly Ala Ser Ala Ala Ala Ala Ala Gly Ile
            20                  25                  30

Asn Gly Pro Gly Ser Gly Val Phe Gly Pro Gly Ile Ser Gly Ile Tyr
        35                  40                  45

Gly Pro Gly Val Phe Gly Pro Gly Val Phe Gly Pro Gly Ser Ser Ala
    50                  55                  60

Ala Ala Ala Ala Gly Pro Gly Ile Tyr Gly Pro Gly Val Phe Gly Pro
65                  70                  75                  80

Ser Ala Ser Ala Ala Ala Ala Ala Gly Pro Gly Ser Gly Val Phe Gly
                85                  90                  95

Pro Gly Ala Ser Gly Ile Tyr Gly Pro Gly Val Phe Gly Pro Gly Val
            100                 105                 110

Phe Gly Pro Gly Ser Ser Ala Ala Ala Ala Ala Gly Ile Tyr Gly Ser
        115                 120                 125
```

```
Gly Pro Gly Val Phe Gly Pro Tyr Gly Ser Ala Ala Ala Ala Ala Gly
    130                 135                 140

Pro Gly Ser Gly Ile Tyr Gly Ile Gly Pro Tyr Gly Pro Gly Ala Ser
145                 150                 155                 160

Gly Pro Gly Ile Tyr Gly Pro Gly Val Phe Gly Pro Ser Ala Ser Ala
                165                 170                 175

Ala Ala Ala Ala Gly Ser Gly Val Phe Gly Pro Gly Ile Tyr Gly Pro
            180                 185                 190

Tyr Ala Ser Ala Ala Ala Ala Ala Gly Ile Tyr Gly Ser Gly Pro Gly
        195                 200                 205

Val Phe Gly Pro Tyr Gly Pro Gly Ile Ser Gly Ser Gly Val Phe Gly
    210                 215                 220

Pro Gly Val Phe Gly Pro Tyr Ala Ser Ala Ala Ala Ala Ala Gly Pro
225                 230                 235                 240

Gly Val Phe Gly Pro Tyr Gly Pro Gly Ser Ser Ala Ala Ala Ala Ala
                245                 250                 255

Gly Ile Tyr Gly Tyr Gly Pro Gly Val Phe Gly Pro Tyr Gly Pro Gly
            260                 265                 270

Ala Ser Gly Ile Asn Gly Pro Gly Ser Gly Ile Tyr Gly Pro Gly Val
        275                 280                 285

Phe Gly Pro Gly Ile Ser Ala Ala Ala Ala Ala Gly Pro Gly Val Phe
    290                 295                 300

Gly Pro Tyr Gly Pro Gly Ala Ser Ala Ala Ala Ala Ala Gly Ile Tyr
305                 310                 315                 320

Gly Pro Gly Val Phe Gly Pro Gly Ile Tyr Gly Pro Gly Ser Ser Gly
                325                 330                 335

Pro Gly Val Phe Gly Pro Tyr Gly Pro Gly Ser Ser Ala Ala Ala Ala
            340                 345                 350

Ala Gly Ile Tyr Gly Pro Gly Val Phe Gly Pro Tyr Gly Pro Gly Ile
        355                 360                 365

Ser Ala Ala Ala Ala Ala Gly Ile Tyr Val Phe Gly Pro Gly Val Phe
    370                 375                 380

Gly Pro Tyr Gly Pro Gly Ala Ser Gly Pro Gly Val Phe Gly Pro Tyr
385                 390                 395                 400

Gly Pro Gly Ala Ser Ala Ala Ala Ala Ala Gly Pro Gly Ile Tyr Gly
                405                 410                 415

Pro Gly Val Phe Gly Pro Ser Ala Ser Ala Ala Ala Ala Ala Gly Ile
            420                 425                 430

Tyr Gly Ser Gly Pro Gly Ile Tyr Gly Pro Tyr Gly Pro Gly Ile Ser
        435                 440                 445

Gly Pro Gly Ser Gly Val Phe Gly Ile Gly Pro Tyr Gly Pro Gly Ala
    450                 455                 460

Ser Ala Ala Ala Ala Ala Gly Ile Tyr Gly Pro Gly Val Phe Gly Pro
465                 470                 475                 480

Tyr Gly Pro Gly Ile Ser Ala Ala Ala Ala Ala Gly Pro Gly Ser Gly
                485                 490                 495

Ile Tyr Gly Pro Gly Ala Ser Gly Ile Asn Gly Pro Gly Ser Gly Ile
            500                 505                 510

Tyr Gly Pro Gly Val Phe Gly Pro Gly Ile Ser Ala Ala Ala Ala Ala
        515                 520                 525

Gly Ile Tyr Val Phe Gly Pro Gly Val Phe Gly Pro Tyr Gly Pro Gly
    530                 535                 540

Ala Ser Ala Ala Ala Ala Ala Gly Ile Tyr Gly Ser Gly Pro Gly Val
```

545 550 555 560

Phe Gly Pro Tyr Gly Pro Gly Ile Ser Gly Ser Gly Val Phe Gly Pro
565 570 575

Gly Val Phe Gly Pro Tyr Ala Ser Ala Ala Ala Ala Ala Gly Pro Gly
580 585 590

Ser Gly Val Phe Gly Pro Gly Ala Ser Gly Pro Gly Val Phe Gly Pro
595 600 605

Tyr Gly Pro Gly Ala Ser Ala Ala Ala Ala Ala Gly Ile Asn Gly Pro
610 615 620

Gly Ser Gly Val Phe Gly Pro Gly Ile Ser Gly Ile Tyr Gly Pro Gly
625 630 635 640

Val Phe Gly Pro Gly Val Phe Gly Pro Gly Ser Ser Ala Ala Ala Ala
645 650 655

Ala Gly Pro Gly Ile Tyr Gly Pro Gly Val Phe Gly Pro Ser Ala Ser
660 665 670

Ala Ala Ala Ala Ala Gly Pro Gly Ser Gly Val Phe Gly Pro Gly Ala
675 680 685

Ser Gly Ile Tyr Gly Pro Gly Val Phe Gly Pro Gly Val Phe Gly Pro
690 695 700

Gly Ser Ser Ala Ala Ala Ala Ala Gly Ile Tyr Gly Ser Gly Pro Gly
705 710 715 720

Val Phe Gly Pro Tyr Gly Ser Ala Ala Ala Ala Ala Gly Pro Gly Ser
725 730 735

Gly Ile Tyr Gly Ile Gly Pro Tyr Gly Pro Gly Ala Ser Gly Pro Gly
740 745 750

Ile Tyr Gly Pro Gly Val Phe Gly Pro Ser Ala Ser Ala Ala Ala Ala
755 760 765

Ala Gly Ser Gly Val Phe Gly Pro Gly Ile Tyr Gly Pro Tyr Ala Ser
770 775 780

Ala Ala Ala Ala Ala Gly Ile Tyr Gly Ser Gly Pro Gly Val Phe Gly
785 790 795 800

Pro Tyr Gly Pro Gly Ile Ser Gly Ser Gly Val Phe Gly Pro Gly Val
805 810 815

Phe Gly Pro Tyr Ala Ser Ala Ala Ala Ala Ala Gly Pro Gly Val Phe
820 825 830

Gly Pro Tyr Gly Pro Gly Ser Ser Ala Ala Ala Ala Ala Gly Ile Tyr
835 840 845

Gly Tyr Gly Pro Gly Val Phe Gly Pro Tyr Gly Pro Gly Ala Ser Gly
850 855 860

Ile Asn Gly Pro Gly Ser Gly Ile Tyr Gly Pro Gly Val Phe Gly Pro
865 870 875 880

Gly Ile Ser Ala Ala Ala Ala Ala Gly Pro Gly Val Phe Gly Pro Tyr
885 890 895

Gly Pro Gly Ala Ser Ala Ala Ala Ala Ala Gly Ile Tyr Gly Pro Gly
900 905 910

Val Phe Gly Pro Gly Ile Tyr Gly Pro Gly Ser Ser Gly Pro Gly Val
915 920 925

Phe Gly Pro Tyr Gly Pro Gly Ser Ser Ala Ala Ala Ala Ala Gly Ile
930 935 940

Tyr Gly Pro Gly Val Phe Gly Pro Tyr Gly Pro Gly Ile Ser Ala Ala
945 950 955 960

Ala Ala Ala Gly Ile Tyr Val Phe Gly Pro Gly Val Phe Gly Pro Tyr
965 970 975

Gly Pro Gly Ala Ser Gly Pro Gly Val Phe Gly Pro Tyr Gly Pro Gly
980 985 990

Ala Ser Ala Ala Ala Ala Ala Gly Pro Gly Ile Tyr Gly Pro Gly Val
995 1000 1005

Phe Gly Pro Ser Ala Ser Ala Ala Ala Ala Ala Gly Ile Tyr Gly
1010 1015 1020

Ser Gly Pro Gly Ile Tyr Gly Pro Tyr Gly Pro Gly Ile Ser Gly
1025 1030 1035

Pro Gly Ser Gly Val Phe Gly Ile Gly Pro Tyr Gly Pro Gly Ala
1040 1045 1050

Ser Ala Ala Ala Ala Ala Gly Ile Tyr Gly Pro Gly Val Phe Gly
1055 1060 1065

Pro Tyr Gly Pro Gly Ile Ser Ala Ala Ala Ala Ala Gly Pro Gly
1070 1075 1080

Ser Gly Ile Tyr Gly Pro Gly Ala Ser Gly Ile Asn Gly Pro Gly
1085 1090 1095

Ser Gly Ile Tyr Gly Pro Gly Val Phe Gly Pro Gly Ile Ser Ala
1100 1105 1110

Ala Ala Ala Ala Gly Ile Tyr Val Phe Gly Pro Gly Val Phe Gly
1115 1120 1125

Pro Tyr Gly Pro Gly Ala Ser Ala Ala Ala Ala Ala Gly Ile Tyr
1130 1135 1140

Gly Ser Gly Pro Gly Val Phe Gly Pro Tyr Gly Pro Gly Ile Ser
1145 1150 1155

Gly Ser Gly Val Phe Gly Pro Gly Val Phe Gly Pro Tyr Ala Ser
1160 1165 1170

Ala Ala Ala Ala Ala Gly Pro Gly Ser Gly Val Phe Gly Pro Gly
1175 1180 1185

Ala Ser
1190

<210> SEQ ID NO 41
<211> LENGTH: 590
<212> TYPE: PRT
<213> ORGANISM: Artificial Sequence
<220> FEATURE:
<223> OTHER INFORMATION: Met-PRT917

<400> SEQUENCE: 41

Met Gly Pro Gly Leu Ile Gly Pro Tyr Gly Pro Gly Ala Ser Ala Ala
1 5 10 15

Ala Ala Ala Gly Val Asn Gly Pro Gly Ser Gly Leu Ile Gly Pro Gly
20 25 30

Val Ser Gly Val Tyr Gly Pro Gly Leu Ile Gly Pro Gly Leu Ile Gly
35 40 45

Pro Gly Ser Ser Ala Ala Ala Ala Ala Gly Pro Gly Val Tyr Gly Pro
50 55 60

Gly Leu Ile Gly Pro Ser Ala Ser Ala Ala Ala Ala Ala Gly Pro Gly
65 70 75 80

Ser Gly Leu Ile Gly Pro Gly Ala Ser Gly Val Tyr Gly Pro Gly Leu
85 90 95

Ile Gly Pro Gly Leu Ile Gly Pro Gly Ser Ser Ala Ala Ala Ala Ala
100 105 110

Gly Val Tyr Gly Ser Gly Pro Gly Leu Ile Gly Pro Tyr Gly Ser Ala
115 120 125

```
Ala Ala Ala Ala Gly Pro Gly Ser Gly Val Tyr Gly Val Gly Pro Tyr
    130                 135                 140

Gly Pro Gly Ala Ser Gly Pro Gly Val Tyr Gly Pro Gly Leu Ile Gly
145                 150                 155                 160

Pro Ser Ala Ser Ala Ala Ala Ala Ala Gly Ser Gly Leu Ile Gly Pro
                165                 170                 175

Gly Val Tyr Gly Pro Tyr Ala Ser Ala Ala Ala Ala Ala Gly Val Tyr
            180                 185                 190

Gly Ser Gly Pro Gly Leu Ile Gly Pro Tyr Gly Pro Gly Val Ser Gly
        195                 200                 205

Ser Gly Leu Ile Gly Pro Gly Leu Ile Gly Pro Tyr Ala Ser Ala Ala
    210                 215                 220

Ala Ala Ala Gly Pro Gly Leu Ile Gly Pro Tyr Gly Pro Gly Ser Ser
225                 230                 235                 240

Ala Ala Ala Ala Ala Gly Val Tyr Gly Tyr Gly Pro Gly Leu Ile Gly
                245                 250                 255

Pro Tyr Gly Pro Gly Ala Ser Gly Val Asn Gly Pro Gly Ser Gly Val
            260                 265                 270

Tyr Gly Pro Gly Leu Ile Gly Pro Gly Val Ser Ala Ala Ala Ala Ala
        275                 280                 285

Gly Pro Gly Leu Ile Gly Pro Tyr Gly Pro Gly Ala Ser Ala Ala Ala
    290                 295                 300

Ala Ala Gly Val Tyr Gly Pro Gly Leu Ile Gly Pro Gly Val Tyr Gly
305                 310                 315                 320

Pro Gly Ser Ser Gly Pro Gly Leu Ile Gly Pro Tyr Gly Pro Gly Ser
                325                 330                 335

Ser Ala Ala Ala Ala Ala Gly Val Tyr Gly Pro Gly Leu Ile Gly Pro
            340                 345                 350

Tyr Gly Pro Gly Val Ser Ala Ala Ala Ala Ala Gly Val Tyr Leu Ile
        355                 360                 365

Gly Pro Gly Leu Ile Gly Pro Tyr Gly Pro Gly Ala Ser Gly Pro Gly
    370                 375                 380

Leu Ile Gly Pro Tyr Gly Pro Gly Ala Ser Ala Ala Ala Ala Ala Gly
385                 390                 395                 400

Pro Gly Val Tyr Gly Pro Gly Leu Ile Gly Pro Ser Ala Ser Ala Ala
                405                 410                 415

Ala Ala Ala Gly Val Tyr Gly Ser Gly Pro Gly Val Tyr Gly Pro Tyr
            420                 425                 430

Gly Pro Gly Val Ser Gly Pro Gly Ser Gly Leu Ile Gly Val Gly Pro
        435                 440                 445

Tyr Gly Pro Gly Ala Ser Ala Ala Ala Ala Ala Gly Val Tyr Gly Pro
    450                 455                 460

Gly Leu Ile Gly Pro Tyr Gly Pro Gly Val Ser Ala Ala Ala Ala Ala
465                 470                 475                 480

Gly Pro Gly Ser Gly Val Tyr Gly Pro Gly Ala Ser Gly Val Asn Gly
                485                 490                 495

Pro Gly Ser Gly Val Tyr Gly Pro Gly Leu Ile Gly Pro Gly Val Ser
            500                 505                 510

Ala Ala Ala Ala Ala Gly Val Tyr Leu Ile Gly Pro Gly Leu Ile Gly
        515                 520                 525

Pro Tyr Gly Pro Gly Ala Ser Ala Ala Ala Ala Ala Gly Val Tyr Gly
    530                 535                 540
```

Ser Gly Pro Gly Leu Ile Gly Pro Tyr Gly Pro Gly Val Ser Gly Ser
545 550 555 560

Gly Leu Ile Gly Pro Gly Leu Ile Gly Pro Tyr Ala Ser Ala Ala Ala
565 570 575

Ala Ala Gly Pro Gly Ser Gly Leu Ile Gly Pro Gly Ala Ser
580 585 590

<210> SEQ ID NO 42
<211> LENGTH: 587
<212> TYPE: PRT
<213> ORGANISM: Artificial Sequence
<220> FEATURE:
<223> OTHER INFORMATION: Met-PRT1028

<400> SEQUENCE: 42

Met Gly Pro Gly Ile Phe Gly Pro Tyr Gly Pro Gly Ala Ser Ala Ala
1 5 10 15

Ala Ala Ala Gly Thr Gly Pro Gly Ser Gly Ile Phe Gly Pro Gly Thr
20 25 30

Ser Gly Thr Tyr Gly Pro Gly Ile Phe Gly Pro Gly Ile Phe Gly Pro
35 40 45

Gly Ser Ser Ala Ala Ala Ala Ala Gly Pro Gly Thr Tyr Gly Pro Gly
50 55 60

Ile Phe Gly Pro Ser Ala Ser Ala Ala Ala Ala Ala Gly Pro Gly Ser
65 70 75 80

Gly Ile Phe Gly Pro Gly Ala Ser Gly Thr Tyr Gly Pro Gly Ile Phe
85 90 95

Gly Pro Gly Ile Phe Gly Pro Gly Ser Ser Ala Ala Ala Ala Ala Gly
100 105 110

Thr Tyr Gly Ser Gly Pro Gly Ile Phe Gly Pro Tyr Gly Ser Ala Ala
115 120 125

Ala Ala Ala Gly Pro Gly Ser Gly Thr Tyr Gly Thr Gly Pro Tyr Gly
130 135 140

Pro Gly Ala Ser Gly Pro Gly Thr Tyr Gly Pro Gly Ile Phe Gly Pro
145 150 155 160

Ser Ala Ser Ala Ala Ala Ala Ala Gly Ser Gly Ile Phe Gly Pro Gly
165 170 175

Thr Tyr Gly Pro Tyr Ala Ser Ala Ala Ala Ala Ala Gly Thr Tyr Gly
180 185 190

Ser Gly Pro Gly Ile Phe Gly Pro Tyr Gly Pro Gly Thr Ser Gly Ser
195 200 205

Gly Ile Phe Gly Pro Gly Ile Phe Gly Pro Tyr Ala Ser Ala Ala Ala
210 215 220

Ala Ala Gly Pro Gly Ile Phe Gly Pro Tyr Gly Pro Gly Ser Ser Ala
225 230 235 240

Ala Ala Ala Ala Gly Thr Tyr Gly Tyr Gly Pro Gly Ile Phe Gly Pro
245 250 255

Tyr Gly Pro Gly Ala Ser Gly Thr Gly Pro Gly Ser Gly Thr Tyr Gly
260 265 270

Pro Gly Ile Phe Gly Pro Gly Thr Ser Ala Ala Ala Ala Ala Gly Pro
275 280 285

Gly Ile Phe Gly Pro Tyr Gly Pro Gly Ala Ser Ala Ala Ala Ala Ala
290 295 300

Gly Thr Tyr Gly Pro Gly Ile Phe Gly Pro Gly Thr Tyr Gly Pro Gly
305 310 315 320

Ser Ser Gly Pro Gly Ile Phe Gly Pro Tyr Gly Pro Gly Ser Ser Ala
325 330 335

Ala Ala Ala Ala Gly Thr Tyr Gly Pro Gly Ile Phe Gly Pro Tyr Gly
340 345 350

Pro Gly Thr Ser Ala Ala Ala Ala Ala Gly Thr Tyr Ile Phe Gly Pro
355 360 365

Gly Ile Phe Gly Pro Tyr Gly Pro Gly Ala Ser Gly Pro Gly Ile Phe
370 375 380

Gly Pro Tyr Gly Pro Gly Ala Ser Ala Ala Ala Ala Ala Gly Pro Gly
385 390 395 400

Thr Tyr Gly Pro Gly Ile Phe Gly Pro Ser Ala Ser Ala Ala Ala Ala
405 410 415

Ala Gly Thr Tyr Gly Ser Gly Pro Gly Thr Tyr Gly Pro Tyr Gly Pro
420 425 430

Gly Thr Ser Gly Pro Gly Ser Gly Ile Phe Gly Thr Gly Pro Tyr Gly
435 440 445

Pro Gly Ala Ser Ala Ala Ala Ala Ala Gly Thr Tyr Gly Pro Gly Ile
450 455 460

Phe Gly Pro Tyr Gly Pro Gly Thr Ser Ala Ala Ala Ala Ala Gly Pro
465 470 475 480

Gly Ser Gly Thr Tyr Gly Pro Gly Ala Ser Gly Thr Gly Pro Gly Ser
485 490 495

Gly Thr Tyr Gly Pro Gly Ile Phe Gly Pro Gly Thr Ser Ala Ala Ala
500 505 510

Ala Ala Gly Thr Tyr Ile Phe Gly Pro Gly Ile Phe Gly Pro Tyr Gly
515 520 525

Pro Gly Ala Ser Ala Ala Ala Ala Ala Gly Thr Tyr Gly Ser Gly Pro
530 535 540

Gly Ile Phe Gly Pro Tyr Gly Pro Gly Thr Ser Gly Ser Gly Ile Phe
545 550 555 560

Gly Pro Gly Ile Phe Gly Pro Tyr Ala Ser Ala Ala Ala Ala Ala Gly
565 570 575

Pro Gly Ser Gly Ile Phe Gly Pro Gly Ala Ser
580 585

<210> SEQ ID NO 43
<211> LENGTH: 601
<212> TYPE: PRT
<213> ORGANISM: Artificial Sequence
<220> FEATURE:
<223> OTHER INFORMATION: PRT917

<400> SEQUENCE: 43

Met His His His His His His Ser Ser Gly Ser Ser Gly Pro Gly Leu
1 5 10 15

Ile Gly Pro Tyr Gly Pro Gly Ala Ser Ala Ala Ala Ala Ala Gly Val
20 25 30

Asn Gly Pro Gly Ser Gly Leu Ile Gly Pro Gly Val Ser Gly Val Tyr
35 40 45

Gly Pro Gly Leu Ile Gly Pro Gly Leu Ile Gly Pro Gly Ser Ser Ala
50 55 60

Ala Ala Ala Ala Gly Pro Gly Val Tyr Gly Pro Gly Leu Ile Gly Pro
65 70 75 80

Ser Ala Ser Ala Ala Ala Ala Ala Gly Pro Gly Ser Gly Leu Ile Gly
85 90 95

-continued

```
Pro Gly Ala Ser Gly Val Tyr Gly Pro Gly Leu Ile Gly Pro Gly Leu
            100                 105                 110

Ile Gly Pro Gly Ser Ser Ala Ala Ala Ala Ala Gly Val Tyr Gly Ser
        115                 120                 125

Gly Pro Gly Leu Ile Gly Pro Tyr Gly Ser Ala Ala Ala Ala Ala Gly
    130                 135                 140

Pro Gly Ser Gly Val Tyr Gly Val Gly Pro Tyr Gly Pro Gly Ala Ser
145                 150                 155                 160

Gly Pro Gly Val Tyr Gly Pro Gly Leu Ile Gly Pro Ser Ala Ser Ala
                165                 170                 175

Ala Ala Ala Ala Gly Ser Gly Leu Ile Gly Pro Gly Val Tyr Gly Pro
            180                 185                 190

Tyr Ala Ser Ala Ala Ala Ala Ala Gly Val Tyr Gly Ser Gly Pro Gly
        195                 200                 205

Leu Ile Gly Pro Tyr Gly Pro Gly Val Ser Gly Ser Gly Leu Ile Gly
    210                 215                 220

Pro Gly Leu Ile Gly Pro Tyr Ala Ser Ala Ala Ala Ala Ala Gly Pro
225                 230                 235                 240

Gly Leu Ile Gly Pro Tyr Gly Pro Gly Ser Ser Ala Ala Ala Ala Ala
                245                 250                 255

Gly Val Tyr Gly Tyr Gly Pro Gly Leu Ile Gly Pro Tyr Gly Pro Gly
            260                 265                 270

Ala Ser Gly Val Asn Gly Pro Gly Ser Gly Val Tyr Gly Pro Gly Leu
        275                 280                 285

Ile Gly Pro Gly Val Ser Ala Ala Ala Ala Ala Gly Pro Gly Leu Ile
    290                 295                 300

Gly Pro Tyr Gly Pro Gly Ala Ser Ala Ala Ala Ala Ala Gly Val Tyr
305                 310                 315                 320

Gly Pro Gly Leu Ile Gly Pro Gly Val Tyr Gly Pro Gly Ser Ser Gly
                325                 330                 335

Pro Gly Leu Ile Gly Pro Tyr Gly Pro Gly Ser Ser Ala Ala Ala Ala
            340                 345                 350

Ala Gly Val Tyr Gly Pro Gly Leu Ile Gly Pro Tyr Gly Pro Gly Val
        355                 360                 365

Ser Ala Ala Ala Ala Ala Gly Val Tyr Leu Ile Gly Pro Gly Leu Ile
    370                 375                 380

Gly Pro Tyr Gly Pro Gly Ala Ser Gly Pro Gly Leu Ile Gly Pro Tyr
385                 390                 395                 400

Gly Pro Gly Ala Ser Ala Ala Ala Ala Ala Gly Pro Gly Val Tyr Gly
                405                 410                 415

Pro Gly Leu Ile Gly Pro Ser Ala Ser Ala Ala Ala Ala Ala Gly Val
            420                 425                 430

Tyr Gly Ser Gly Pro Gly Val Tyr Gly Pro Tyr Gly Pro Gly Val Ser
        435                 440                 445

Gly Pro Gly Ser Gly Leu Ile Gly Val Gly Pro Tyr Gly Pro Gly Ala
    450                 455                 460

Ser Ala Ala Ala Ala Ala Gly Val Tyr Gly Pro Gly Leu Ile Gly Pro
465                 470                 475                 480

Tyr Gly Pro Gly Val Ser Ala Ala Ala Ala Ala Gly Pro Gly Ser Gly
                485                 490                 495

Val Tyr Gly Pro Gly Ala Ser Gly Val Asn Gly Pro Gly Ser Gly Val
            500                 505                 510

Tyr Gly Pro Gly Leu Ile Gly Pro Gly Val Ser Ala Ala Ala Ala Ala
```

515 520 525

Gly Val Tyr Leu Ile Gly Pro Gly Leu Ile Gly Pro Tyr Gly Pro Gly
530 535 540

Ala Ser Ala Ala Ala Ala Ala Gly Val Tyr Gly Ser Gly Pro Gly Leu
545 550 555 560

Ile Gly Pro Tyr Gly Pro Gly Val Ser Gly Ser Gly Leu Ile Gly Pro
565 570 575

Gly Leu Ile Gly Pro Tyr Ala Ser Ala Ala Ala Ala Ala Gly Pro Gly
580 585 590

Ser Gly Leu Ile Gly Pro Gly Ala Ser
595 600

<210> SEQ ID NO 44
<211> LENGTH: 598
<212> TYPE: PRT
<213> ORGANISM: Artificial Sequence
<220> FEATURE:
<223> OTHER INFORMATION: PRT1028

<400> SEQUENCE: 44

Met His His His His His His Ser Ser Gly Ser Ser Gly Pro Gly Ile
1 5 10 15

Phe Gly Pro Tyr Gly Pro Gly Ala Ser Ala Ala Ala Ala Ala Gly Thr
20 25 30

Gly Pro Gly Ser Gly Ile Phe Gly Pro Gly Thr Ser Gly Thr Tyr Gly
35 40 45

Pro Gly Ile Phe Gly Pro Gly Ile Phe Gly Pro Gly Ser Ser Ala Ala
50 55 60

Ala Ala Ala Gly Pro Gly Thr Tyr Gly Pro Gly Ile Phe Gly Pro Ser
65 70 75 80

Ala Ser Ala Ala Ala Ala Ala Gly Pro Gly Ser Gly Ile Phe Gly Pro
85 90 95

Gly Ala Ser Gly Thr Tyr Gly Pro Gly Ile Phe Gly Pro Gly Ile Phe
100 105 110

Gly Pro Gly Ser Ser Ala Ala Ala Ala Ala Gly Thr Tyr Gly Ser Gly
115 120 125

Pro Gly Ile Phe Gly Pro Tyr Gly Ser Ala Ala Ala Ala Ala Gly Pro
130 135 140

Gly Ser Gly Thr Tyr Gly Thr Gly Pro Tyr Gly Pro Gly Ala Ser Gly
145 150 155 160

Pro Gly Thr Tyr Gly Pro Gly Ile Phe Gly Pro Ser Ala Ser Ala Ala
165 170 175

Ala Ala Ala Gly Ser Gly Ile Phe Gly Pro Gly Thr Tyr Gly Pro Tyr
180 185 190

Ala Ser Ala Ala Ala Ala Ala Gly Thr Tyr Gly Ser Gly Pro Gly Ile
195 200 205

Phe Gly Pro Tyr Gly Pro Gly Thr Ser Gly Ser Gly Ile Phe Gly Pro
210 215 220

Gly Ile Phe Gly Pro Tyr Ala Ser Ala Ala Ala Ala Ala Gly Pro Gly
225 230 235 240

Ile Phe Gly Pro Tyr Gly Pro Gly Ser Ser Ala Ala Ala Ala Ala Gly
245 250 255

Thr Tyr Gly Tyr Gly Pro Gly Ile Phe Gly Pro Tyr Gly Pro Gly Ala
260 265 270

Ser Gly Thr Gly Pro Gly Ser Gly Thr Tyr Gly Pro Gly Ile Phe Gly

-continued

```
        275                 280                 285

Pro Gly Thr Ser Ala Ala Ala Ala Ala Gly Pro Gly Ile Phe Gly Pro
    290                 295                 300

Tyr Gly Pro Gly Ala Ser Ala Ala Ala Ala Ala Gly Thr Tyr Gly Pro
305                 310                 315                 320

Gly Ile Phe Gly Pro Gly Thr Tyr Gly Pro Gly Ser Ser Gly Pro Gly
                325                 330                 335

Ile Phe Gly Pro Tyr Gly Pro Gly Ser Ser Ala Ala Ala Ala Ala Gly
            340                 345                 350

Thr Tyr Gly Pro Gly Ile Phe Gly Pro Tyr Gly Pro Gly Thr Ser Ala
        355                 360                 365

Ala Ala Ala Ala Gly Thr Tyr Ile Phe Gly Pro Gly Ile Phe Gly Pro
    370                 375                 380

Tyr Gly Pro Gly Ala Ser Gly Pro Gly Ile Phe Gly Pro Tyr Gly Pro
385                 390                 395                 400

Gly Ala Ser Ala Ala Ala Ala Ala Gly Pro Gly Thr Tyr Gly Pro Gly
                405                 410                 415

Ile Phe Gly Pro Ser Ala Ser Ala Ala Ala Ala Ala Gly Thr Tyr Gly
            420                 425                 430

Ser Gly Pro Gly Thr Tyr Gly Pro Tyr Gly Pro Gly Thr Ser Gly Pro
        435                 440                 445

Gly Ser Gly Ile Phe Gly Thr Gly Pro Tyr Gly Pro Gly Ala Ser Ala
    450                 455                 460

Ala Ala Ala Ala Gly Thr Tyr Gly Pro Gly Ile Phe Gly Pro Tyr Gly
465                 470                 475                 480

Pro Gly Thr Ser Ala Ala Ala Ala Ala Gly Pro Gly Ser Gly Thr Tyr
                485                 490                 495

Gly Pro Gly Ala Ser Gly Thr Gly Pro Gly Ser Gly Thr Tyr Gly Pro
            500                 505                 510

Gly Ile Phe Gly Pro Gly Thr Ser Ala Ala Ala Ala Ala Gly Thr Tyr
        515                 520                 525

Ile Phe Gly Pro Gly Ile Phe Gly Pro Tyr Gly Pro Gly Ala Ser Ala
    530                 535                 540

Ala Ala Ala Ala Gly Thr Tyr Gly Ser Gly Pro Gly Ile Phe Gly Pro
545                 550                 555                 560

Tyr Gly Pro Gly Thr Ser Gly Ser Gly Ile Phe Gly Pro Gly Ile Phe
                565                 570                 575

Gly Pro Tyr Ala Ser Ala Ala Ala Ala Ala Gly Pro Gly Ser Gly Ile
            580                 585                 590

Phe Gly Pro Gly Ala Ser
        595
```

PROTEIN COMPOSITION PRODUCTION METHOD

SEQUENCE LISTING SUBMISSION VIA EFS-WEB

A computer readable text file, entitled "SequenceListing.txt," created on or about Mar. 24, 2021 with a file size of about 249,803 bytes contains the sequence listing for this application and is hereby incorporated by reference in its entirety.

TECHNICAL FIELD

The present invention relates to a production method of a protein composition.

BACKGROUND ART

A spinning method using an acid such as formic acid is widely used. For example, Patent Literature 1 discloses a method of treating a biological sample containing a structural polypeptide with an acid.

CITATION LIST

Patent Literature

Patent Literature 1: JP 2004-503204 A

SUMMARY OF INVENTION

Technical Problem

The present inventors found that in a protein fiber produced using a dope solution (spinning raw material solution) in which a carboxylic acid such as formic acid is used as a solvent, an ester group is formed by a dehydration condensation reaction between a hydroxyl group in a protein and the carboxylic acid during spinning. The present inventors further found that in the protein fiber obtained as described above, hydrolysis of the ester group added to the protein proceeds with a trace amount of the carboxylic acid, such as formic acid, remaining on a surface or inside of the protein as a catalyst, the carboxylic acid is thus isolated, and the isolated carboxylic acid causes an odor or the like. The present invention is provided to solve such problems newly found by the present inventors.

That is, an object of the present invention is to provide a protein composition in which an ester group included in a protein is removed or reduced, a production method of the same, and an ester group removal method.

Solution to Problem

The present invention relates to, for example, each of the following inventions.

[1]

A production method of a protein composition, the method including a step of hydrolyzing an ester group by bringing a raw material composition containing an esterified protein into contact with an acidic or basic medium.

[2]

The production method of a protein composition according to [1], wherein the medium is a medium containing water, and the medium containing water is 40 °C to 180 °C.

[3]

The production method of a protein composition according to [2], wherein the medium containing water is an aqueous solution or water vapor.

[4]

The production method of a protein composition according to [3], wherein the medium containing water is an aqueous solution, and a temperature of the aqueous solution is 40 °C or higher and a boiling point or lower.

[5]

The production method of a protein composition according to [4], wherein the aqueous solution is a basic aqueous solution having a pH of 12 or lower.

[6]

The production method of a protein composition according to any one of [1] to [5], wherein the protein is a structural protein.

[7]

The production method of a protein composition according to [6], wherein the structural protein is fibroin.

[8]

The production method of a protein composition according to [7], wherein the fibroin is spider silk fibroin.

[9]

The production method of a protein composition according to any one of [1] to [8], wherein the esterified protein contains formic acid ester.

[10]

The production method of a protein composition according to any one of [1] to [9], wherein the raw material composition is at least one selected from the group consisting of a fiber, a film, a molded article, a gel, a porous body, and a particle.

[11]

The production method of a protein composition according to [10], wherein the raw material composition is a fiber, the medium containing water is an aqueous solution, and the production method further includes a crimping step of crimping the fiber by bringing the fiber into contact with the aqueous solution.

[12]

The production method of a protein composition according to [10], wherein the raw material composition is a fiber, the medium containing water is an aqueous solution, and the production method further includes a shrink-proof step of shrink-proofing the fiber by bringing the fiber into contact with the aqueous solution.

[13]

The production method of a protein composition according to any one of [10] to [12], wherein the raw material composition is a fiber, and the fiber is a hank state.

[14]

The production method of a protein composition according to any one of [10] to [12], wherein the raw material composition is a fiber, and the fiber is a cloth state.

[15]

A production method of a protein composition, the method including a step of hydrolyzing an ester group by bringing a raw material composition containing an esterified protein and an acid or a base into contact with water vapor.

[16]

A protein composition containing a protein, wherein the protein composition has a hydrolysis history of an ester group.

[17]

The protein composition according to [16], wherein the hydrolysis history is a history of hydrolysis of the ester group performed by bringing the protein composition into contact with an acidic or basic medium containing water, and the medium containing water is 40 °C to 180 °C.

[18]

The protein composition according to [16] or [17], wherein the ester group is included in formic acid ester.

[19]

The protein composition according to any one of [16] to [18], wherein the protein composition further has a shrinkage history of being irreversibly shrunk.

[20]

The protein composition according to any one of [16] to [19], wherein the protein is a structural protein.

[21]

The protein composition according to [20], wherein the structural protein is at least one selected from the group consisting of spider silk fibroin, silk fibroin, keratin, collagen, and elastin.

[22]

The protein composition according to [21], wherein the structural protein is spider silk fibroin.

[23]

The protein composition according to any one of [16] to [22], wherein the protein composition is a protein fiber.

[24]

The protein composition according to [23], wherein the protein composition is a protein fiber, and a shrinkage rate is −5% to +5%, the shrinkage rate being defined by the following Equation (1):

Shrinkage rate={1−(length of protein fiber when dried from wet state/length of protein fiber before in wet state)}×100[%].

[25]

An ester group removal method including a step of bringing a raw material composition containing an esterified protein into contact with an acidic or basic medium containing water.

[26]

The ester group removal method according to [25], wherein the raw material composition is at least one selected from the group consisting of a fiber, a film, a molded article, a gel, a porous body, and a particle.

[27]

The ester group removal method according to [25] or [26], wherein the protein is a structural protein.

Advantageous Effects of Invention

According to the present invention, a production method of a protein composition in which an ester group included in a protein is removed or reduced, and an ester group removal method are provided. By performing a hydrolysis treatment on the ester group in the protein composition, a shrink-proof treatment effect of the protein composition is also exhibited at the same time. That is, in the protein composition according to the present invention, the ester group is removed or reduced, and the shrinkage when being brought into contact with water is also reduced.

DESCRIPTION OF EMBODIMENTS

Figure 1:
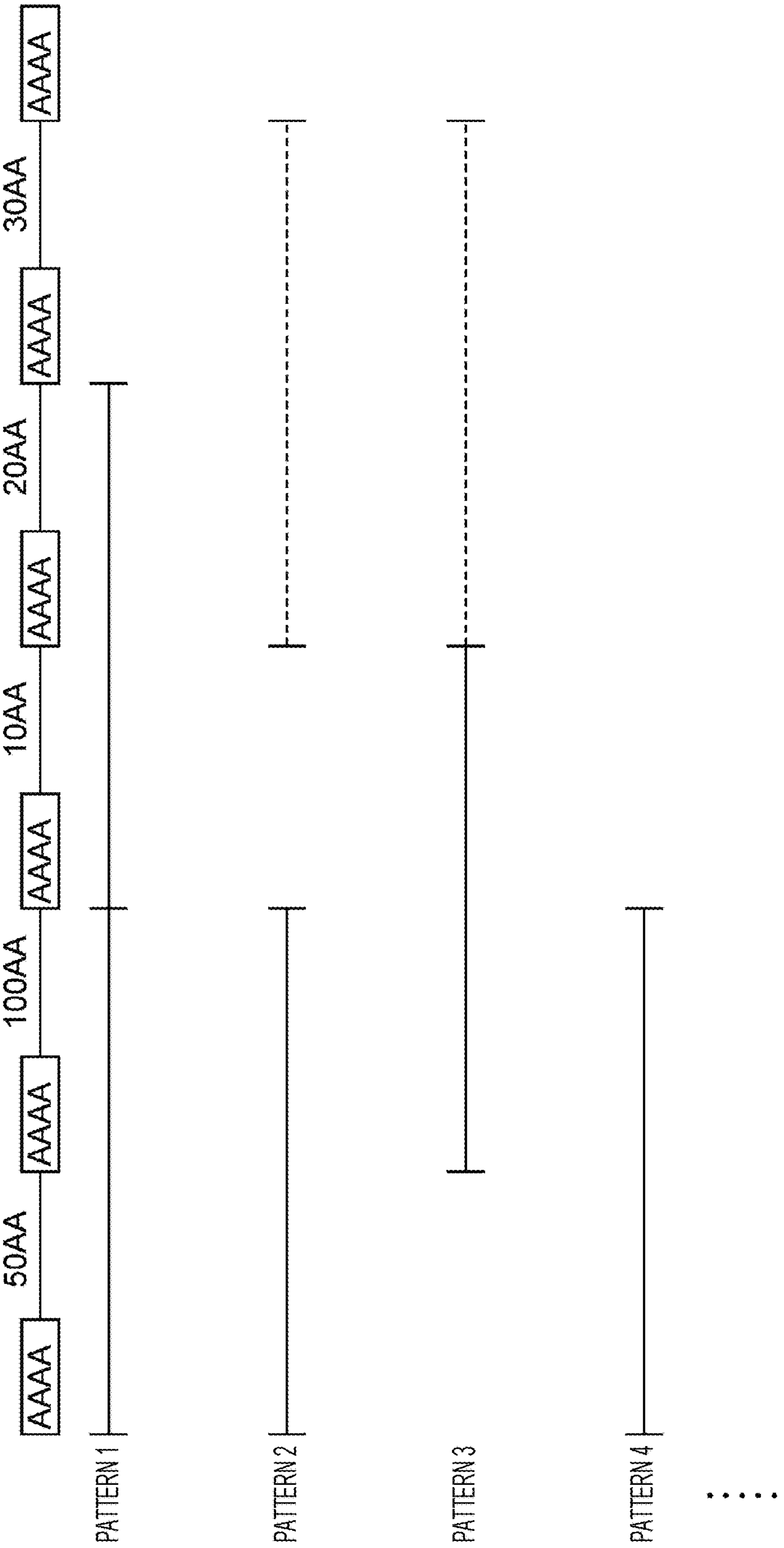
FIG. 1 is a schematic diagram illustrating an example of a domain sequence of modified fibroin.

Hereinafter, embodiments of the present invention will be described in detail. However, the present invention is not limited to the following embodiments.

[Production Method of Protein Composition]

A production method of a protein composition according to the present embodiment includes a step of hydrolyzing an ester group by bringing a raw material composition containing an esterified protein (a protein having an ester group) into contact with an acidic or basic (alkaline) medium.

In the present embodiment, the raw material composition may be at least one selected from the group consisting of a fiber (raw material fiber), a film (a raw material film), a molded article (a raw material molded article), a gel (raw material gel), a porous body (a raw material porous body), and a particle (raw material particle).

In the present embodiment, the raw material composition contains an esterified protein. In the present specification, the “esterified protein” refers to a protein having an ester group formed by ester-bonding a hydroxyl group of the protein and a carboxylic acid. The esterified protein may contain formic acid ester, acetic acid ester, propionic acid ester, and the like, and the esterified protein preferably contains formic acid ester.

(Protein)

Examples of the protein according to the present embodiment (hereinafter, also referred to as a “protein to be targeted”) can include a natural protein and a recombinant protein (artificial protein). In addition, an example of the recombinant protein can include any protein that can be produced in an industrial scale, and examples thereof can include a protein that can be used for industrial purposes, a protein that can be used for medical purposes, and a structural protein. Specific examples of the protein that can be used for industrial purposes or medical purposes can include an enzyme, a regulatory protein, a receptor, a peptide hormone, a cytokine, a membrane or transport protein, an antigen used for vaccination, a vaccine, an antigen-binding protein, an immunostimulatory protein, an allergen, and a full length antibody or an antibody fragment or a derivative thereof. The structural protein refers to a protein forming or maintaining a structure, morphology, or the like in a living body. The structural protein may be fibroin. Specific examples of the structural protein can include spider silk fibroin, silk fibroin, keratin, collagen, elastin, resilin, and proteins derived from them. The structural protein may be, for example, modified fibroin described below, and modified spider silk fibroin is preferred, from the viewpoint of obtaining heat retaining properties, hygroscopic and exothermic properties, and/or flame retardancy.

The modified fibroin is a protein containing a domain sequence represented by Formula 1: $[(A)_n$ motif-REP$]_m$ or Formula 2: $[(A)_n$ motif-REP$]_m$-$(A)_n$ motif. An amino acid sequence (N-terminal sequence and C-terminal sequence) may be further added to either or both of the N-terminus and the C-terminus of the domain sequence of the modified fibroin. The N-terminal sequence and the C-terminal sequence, although not limited thereto, are typically regions that do not have repetitions of amino acid motifs characteristic of fibroin and consist of amino acids of about 100 residues.

The term "modified fibroin" in the present specification refers to artificially produced fibroin (artificial fibroin). The modified fibroin may be fibroin in which a domain sequence is different from an amino acid sequence of naturally derived fibroin or may be fibroin in which a domain sequence is the same as an amino acid sequence of naturally derived fibroin. The "naturally derived fibroin" referred to in the present specification is also a protein containing a domain sequence represented by Formula 1: $[(A)_n$ motif-REP$]_m$ or Formula 2: $[(A)_n$ motif-REP$]_m$-$(A)_n$ motif.

The "modified fibroin" may be fibroin obtained by using an amino acid sequence of naturally derived fibroin as it is, fibroin in which an amino acid sequence is modified based on an amino acid sequence of naturally derived fibroin (for example, fibroin in which an amino acid sequence is modified by modifying a cloned gene sequence of naturally derived fibroin), or fibroin artificially designed and synthesized independently of naturally derived fibroin (for example, fibroin having a desired amino acid sequence by chemically synthesizing a nucleic acid encoding a designed amino acid sequence).

In the present specification, the term "domain sequence" refers to an amino acid sequence which produces a crystalline region (typically, corresponding to an $(A)_n$ motif of an amino acid sequence) and an amorphous region (typically, corresponding to REP of an amino acid sequence) specific to fibroin, and refers to an amino acid sequence represented by Formula 1: $[(A)_n$ motif-REP$]_m$ or Formula 2: $[(A)_n$ motif-REP$]_m$-$(A)_n$ motif. Here, the $(A)_n$ motif represents an amino acid sequence mainly consisting of alanine residues, and the number of amino acid residues in the $(A)_n$ motif is 2 to 27. The number of amino acid residues in the $(A)_n$ motif may be an integer of 2 to 20, 4 to 27, 4 to 20, 8 to 20, 10 to 20, 4 to 16, 8 to 16, or 10 to 16. In addition, a proportion of the number of alanine residues to a total number of amino acid residues in the $(A)_n$ motif may be 40% or more, and may also be 60% or more, 70% or more, 80% or more, 83% or more, 85% or more, 86% or more, 90% or more, 95% or more, or 100% (which means that the $(A)_n$ motif consists of only alanine residues). At least a plurality of seven $(A)_n$ motifs present in the domain sequence may consist of only alanine residues. The REP represents an amino acid sequence consisting of 2 to 200 amino acid residues. The REP may be an amino acid sequence consisting of 10 to 200 amino acid residues or may be an amino acid sequence consisting of 10 to 40, 10 to 60, 10 to 80, 10 to 100, 10 to 120, 10 to 140, 10 to 160, or 10 to 180 amino acid residues. m represents an integer of 2 to 300, and may be an integer of 8 to 300, 10 to 300, 20 to 300, 40 to 300, 60 to 300, 80 to 300, 10 to 200, 20 to 200, 20 to 180, 20 to 160, 20 to 140, or 20 to 120. The plurality of $(A)_n$ motifs may be the same amino acid sequences or different amino acid sequences. A plurality of REP's may be the same amino acid sequences or different amino acid sequences.

The modified fibroin according to the present embodiment can be obtained by, for example, performing modification of an amino acid sequence corresponding to substitution, deletion, insertion, and/or addition of one or a plurality of amino acid residues with respect to a cloned gene sequence of naturally derived fibroin. Substitution, deletion, insertion, and/or addition of the amino acid residues can be performed by methods well known to those skilled in the art, such as site-directed mutagenesis. Specifically, it can be performed according to a method described in literatures such as Nucleic Acid Res. 10, 6487 (1982) and Methods in Enzymology, 100, 448 (1983).

The naturally derived fibroin is a protein containing a domain sequence represented by Formula 1: $[(A)_n$ motif-REP$]_m$ or Formula 2: $[(A)_n$ motif-REP$]_m$-$(A)_n$ motif, and a specific example thereof can include fibroin produced by insects or spiders.

Examples of the fibroin produced by insects can include silk proteins produced by silkworms such as *Bombyx mori, Bombyx mandarina, Antheraea yamamai, Anteraea pernyi, Eriogyna pyretorum, Pilosamia Cynthia ricini, Samia cynthia, Caligura japonica, Antheraea mylitta*, and *Antheraea assama*, and hornet silk proteins discharged from larvae of *Vespa simillima xanthoptera.*

A more specific example of the fibroin produced by insects can include a silkworm fibroin L chain (GenBank Accession No. M76430 (base sequence) and AAA27840.1 (amino acid sequence)).

Examples of the fibroin produced by spiders can include spider silk proteins produced by spiders belonging to the genus *Araneus* such as *Araneus ventricosus, Araneus diadematus, Araneus quadratus, Araneus pentagrammicus*, and *Araneus nojimai*, spiders belonging to the genus *Neoscona* such as *Neoscona scylla, Neoscona nautica, Neoscona adianta*, and *Neoscona scylloides*, spiders belonging to the genus *Pronus* such as Pronouns minutes, spiders belonging to the genus *Cyrtarachne* such as *Cyrtarachne bufo* and *Cyrtarachne inaequalis*, spiders belonging to the genus *Gasteracantha* such as *Gasteracantha kuhli* and *Gasteracantha mammosa*, spiders belonging to the genus *Ordgarius* such as *Ordgarius hobsoni* and *Ordgarius sexspinosus*, spiders belonging to the genus *Argiope* such as *Argiope amoena, Argiope minuta*, and *Argiope bruennichi*, spiders belonging to the genus *Arachnura* such as *Arachnura logio*, spiders belonging to the genus *Acusilas* such as *Acusilas coccineus*, spiders belonging to the genus *Cytophora* such as *Cyrtophora moluccensis, Cyrtophora exanthematica*, and *Cyrtophora* unicolor, spiders belonging to the genus *Poltys* such as *Poltys illepidus*, spiders belonging to the genus *Cyclosa* such as *Cyclosa octotuberculata, Cyclosa sedeculata, Cyclosa vallata*, and *Cyclosa atrata*, and spiders belonging to the genus *Chorizopes* such as *Chorizopes*

*nipponicus*, and spider silk proteins produced by spiders belonging to the genus *Tetragnatha* such as *Tetragnatha praedonia, Tetragnatha maxillosa, Tetragnatha extensa*, and *Tetragnatha squamata*, spiders belonging to the genus *Leucauge* such as *Leucauge magnifica, Leucauge blanda*, and *Leucauge subblanda*, spiders belonging to the genus *Nephila* such as *Nephila clavata* and *Nephila pilipes*, spiders belonging to the genus *Menosira* such as *Menosira ornata*, spiders belonging to the genus *Dyschiriognatha* such as *Dyschiriognatha tenera*, spiders belonging to the genus *Latrodectus* such as *Latrodectus mactans, Latrodectus hasseltii, Latrodectus geometricus*, and *Latrodectus tredecimguttatus*, and spiders belonging to the family Tetragnathidae such as spiders belonging to the genus *Euprosthenops*. Examples of the spider silk protein can include traction fiber proteins such as MaSp (MaSp1 and MaSp2) and ADF (ADF3 and ADF4), and MiSp (MiSp1 and MiSp2).

More specific examples of the spider silk protein produced by spiders can include fibroin-3 (adf-3) [derived from *Araneus diadematus*] (GenBank Accession No. AAC47010 (amino acid sequence), U47855 (base sequence)), fibroin-4 (adf-4) [derived from *Araneus diadematus*] (GenBank Accession No. AAC47011 (amino acid sequence), U47856 (base sequence)), dragline silk protein spidroin 1 [derived from *Nephila clavipes*] (GenBank Accession No. AAC04504 (amino acid sequence), U37520 (base sequence)), major ampullate spidroin 1 [derived from *Latrodectus hesperus*] (GenBank Accession No. ABR68856 (amino acid sequence), EF595246 (base sequence)), dragline silk protein spidroin 2 [derived from *Nephila clavata*] (GenBank Accession No. AAL32472 (amino acid sequence), AF441245 (base sequence)), major ampullate spidroin 1 [derived from *Euprosthenops australis*](GenBank Accession No. CAJ00428 (amino acid sequence), AJ973155 (base sequence)), major ampullate spidroin 2 [*Euprosthenops australis*] (GenBank Accession No. CAM32249.1 (amino acid sequence), AM490169 (base sequence)), minor ampullate silk protein 1 [*Nephila clavipes*] (GenBank Accession No. AAC14589.1 (amino acid sequence)), minor ampullate silk protein 2 [*Nephila clavipes*] (GenBank Accession No. AAC14591.1 (amino acid sequence)), and minor ampullate spidroin-like protein [*Nephilengys cruentata*] (GenBank Accession No. ABR37278.1 (amino acid sequence)).

A still more specific example of the naturally derived fibroin can include fibroin with sequence information registered in NCBI GenBank. For example, it can be confirmed by extracting sequences in which spidroin, ampullate, fibroin, "silk and polypeptide", or "silk and protein" is described as a keyword in DEFINITION among sequences containing INV as DIVISION among sequence information registered in NCBI GenBank, sequences in which a specific character string of products is described from CDS, or sequences in which a specific character string is described from SOURCE to TISSUE TYPE.

The modified fibroin according to the present embodiment may be modified silk fibroin (in which an amino acid sequence of silk protein produced by silkworm is modified), may be modified spider silk fibroin (in which an amino acid sequence of a spider silk protein produced by spiders is modified), or may be sericin-removed silk fibroin (so-called regenerated silk fibroin). The sericin-removed silk fibroin is purified by removing sericin covering silk fibroin and other fat contents. Modified spider silk fibroin is preferred as the modified fibroin.

Specific examples of the modified fibroin can include modified fibroin derived from a major dragline silk protein produced in a major ampullate gland of a spider (first modified fibroin), modified fibroin containing a domain sequence in which a content of glycine residues is reduced (second modified fibroin), modified fibroin containing a domain sequence in which a content of an $(A)_n$ motif is reduced (third modified fibroin), modified fibroin containing a domain sequence in which a content of glycine residues and a content of an $(A)_n$ motif are reduced (fourth modified fibroin), modified fibroin containing a domain sequence including a region locally having a high hydropathy index (fifth modified fibroin), and modified fibroin containing a domain sequence in which a content of glutamine residues is reduced (sixth modified fibroin).

An example of the first modified fibroin can include a protein containing a domain sequence represented by Formula 1: $[(A)_n \text{ motif-REP}]_m$. In the first modified fibroin, the number of amino acid residues in the $(A)_n$ motif is preferably an integer of 3 to 20, more preferably an integer of 4 to 20, still more preferably an integer of 8 to 20, still more preferably an integer of 10 to 20, still more preferably an integer of 4 to 16, particularly preferably an integer of 8 to 16, and most preferably an integer of 10 to 16. In the first modified fibroin, the number of amino acid residues constituting REP in Formula 1 is preferably 10 to 200 residues, more preferably 10 to 150 residues, and still more preferably 20 to 100 residues, and still more preferably 20 to 75 residues. In the first modified fibroin, a total number of glycine residues, serine residues, and alanine residues contained in the amino acid sequence represented by Formula 1: $[(A)_n \text{ motif-REP}]_m$ is preferably 40% or more, more preferably 60% or more, and still more preferably 70% or more, with respect to a total number of amino acid residues.

The first modified fibroin may be a polypeptide having an amino acid sequence unit represented by Formula 1: $[(A)_n \text{ motif-REP}]_m$, and having a C-terminal sequence which is an amino acid sequence set forth in any one of SEQ ID NOs: 1 to 3 or a C-terminal sequence which is an amino acid sequence having 90% or more homology with the amino acid sequence set forth in any one of SEQ ID NOs: 1 to 3.

The amino acid sequence set forth in SEQ ID NO: 1 is identical to an amino acid sequence consisting of 50 amino acid residues at the C-terminus of an amino acid sequence of ADF3 (GI:1263287, NCBI), the amino acid sequence set forth in SEQ ID NO: 2 is identical to an amino acid sequence obtained by removing 20 residues from the C-terminus of the amino acid sequence set forth in SEQ ID NO: 1, and the amino acid sequence set forth in SEQ ID NO: 3 is identical to an amino acid sequence obtained by removing 29 residues from the C-terminus of the amino acid sequence set forth in SEQ ID NO: 1.

A more specific example of the first modified fibroin can include modified fibroin having an amino acid sequence set forth in (1-i) SEQ ID NO: 4 (recombinant spider silk protein ADF3KaiLargeNRSH1), or (1-ii) an amino acid sequence having 90% or more sequence identity with the amino acid sequence set forth in (1-i) SEQ ID NO: 4. The sequence identity is preferably 95% or more.

The amino acid sequence set forth in SEQ ID NO: 4 is an amino acid sequence obtained by approximately doubling first to thirteenth repeating regions and performing mutation so that translation is terminated at the $1154^{th}$ amino acid residue in an amino acid sequence obtained by adding the amino acid sequence (SEQ ID NO: 5) of ADF3 consisting of a start codon, a His10 tag, and a recognition site for HRV3C protease (human rhinovirus 3C protease) to the N-terminus thereof. The C-terminal amino acid sequence of the amino acid sequence set forth in SEQ ID NO: 4 is identical to the amino acid sequence set forth in SEQ ID NO: 3.

The modified fibroin of (1-i) may consist of the amino acid sequence set forth in SEQ ID NO: 4.

The domain sequence of the second modified fibroin has an amino acid sequence in which a content of glycine residues is reduced, as compared with the naturally derived fibroin. It can be said that the second modified fibroin has an amino acid sequence corresponding to an amino acid sequence in which at least one or a plurality of glycine residues in REP are substituted with another amino acid residue, as compared with the naturally derived fibroin.

The domain sequence of the second modified fibroin may have an amino acid sequence corresponding to an amino acid sequence in which one glycine residue in at least one or the plurality of motif sequences is substituted with another amino acid residue, in at least one motif sequence selected from GGX and GPGXX (where G represents a glycine residue, P represents a proline residue, and X represents an amino acid residue other than glycine) in REP, as compared with the naturally derived fibroin.

In the second modified fibroin, a proportion of the motif sequences in which the above-described glycine residue is substituted with another amino acid residue may be 10% or more with respect to the entire motif sequences.

The second modified fibroin may contain a domain sequence represented by Formula 1: $[(A)_n$ motif-REP$]_m$ and may have an amino acid sequence in which z/w is 30% or more, 40% or more, 50% or more, or 50.9% or more, in which a total number of amino acid residues in an amino acid sequence consisting of XGX (where X represents an amino acid residue other than glycine) contained in all REP's in a sequence excluding the sequence from the $(A)_n$ motif located at the most C-terminal side to the C-terminus of the domain sequence from the domain sequence is z, and a total number of amino acid residues in a sequence excluding the sequence from the $(A)_n$ motif located at the most C-terminal side to the C-terminus of the domain sequence from the domain sequence is w. The number of alanine residues with respect to the total number of amino acid residues in the $(A)_n$ motif is 83% or more, preferably 86% or more, more preferably 90% or more, still more preferably 95% or more, and still more preferably 100% (which means that the $(A)_n$ motif consists of only alanine residues).

In the second modified fibroin, a content ratio of the amino acid sequence consisting of XGX is preferably increased by substituting one glycine residue in a GGX motif with another amino acid residue. In the second modified fibroin, a content ratio of an amino acid sequence consisting of GGX in the domain sequence is preferably 30% or less, more preferably 20% or less, still more preferably 10% or less, still more preferably 6% or less, still more preferably 4% or less, and particularly preferably 2% or less. The content ratio of the amino acid sequence consisting of GGX in the domain sequence can be calculated by the same method as the following calculation method of a content ratio (z/w) of the amino acid sequence consisting of XGX.

The calculation method of z/w will be described in more detail. First, the amino acid sequence consisting of XGX is extracted from all the REP's contained in the sequence excluding the sequence from the $(A)_n$ motif located at the most C-terminal side to the C-terminus of the domain sequence from the domain sequence in the fibroin containing the domain sequence represented by Formula 1: $[(A)_n$ motif-REP$]_m$ (modified fibroin or naturally derived fibroin). A total number of amino acid residues consisting of XGX is z. For example, in a case where 50 amino acid sequences consisting of XGX are extracted (there is no overlap), z is 50×3=150. In addition, for example, in a case where two Xs (central X) contained in XGX are present as in a case of an amino acid sequence consisting of XGXGX, it is calculated by subtracting the overlapping portion (in the case of XGXGX, z is 5 amino acid residues). w is a total number of amino acid residues contained in the sequence excluding the sequence from the $(A)_n$ motif located at the most C-terminal side to the C-terminus of the domain sequence from the domain sequence. For example, in the case of the domain sequence illustrated in FIG. 1, w is 4+50+4+100+4+10+4+20+4+30=230 (excluding the $(A)_n$ motif located at the most C-terminal side). Next, z/w (%) can be calculated by dividing z by w.

Here, z/w in the naturally derived fibroin will be described. First, as described above, 663 types of fibroins (415 types of fibroins derived from spiders among them) were extracted by confirming fibroins with amino acid sequence information registered in NCBI GenBank by an exemplified method. z/w was calculated by the above-described calculation method from the amino acid sequences of the naturally derived fibroins which contain a domain sequence represented by Formula 1: $[(A)_n$ motif-REP$]_m$ and in which the content ratio of the amino acid sequence consisting of GGX in the fibroin is 6% or less, among all the extracted fibroins. As a result, z/w in each of the naturally derived fibroins is less than 50.9% (highest, 50.86%).

In the second modified fibroin, z/w is preferably 50.9% or more, more preferably 56.1% or more, still more preferably 58.7% or more, still more preferably 70% or more, and still more preferably 80% or more. An upper limit of z/w is not particularly limited, but may be, for example, 95% or less.

The second modified fibroin can be obtained by, for example, substituting and modifying at least a part of a base sequence encoding a glycine residue from a cloned gene sequence of naturally derived fibroin so as to encode another amino acid residue. In this case, one glycine residue in a GGX motif or a GPGXX motif may be selected as the glycine residue to be modified, and substitution may be performed so that z/w is 50.9% or more. In addition, the second modified fibroin can also be obtained by, for example, designing an amino acid sequence satisfying each of the above aspects from the amino acid sequence of the naturally derived fibroin, and chemically synthesizing a nucleic acid encoding the designed amino acid sequence. In any case, in addition to the modification corresponding to substitution of a glycine residue in the REP with another amino acid residue from the amino acid sequence of the naturally derived fibroin, modification of the amino acid sequence corresponding to substitution, deletion, insertion, and/or addition of one or a plurality of amino acid residues may be performed.

The above-described another amino acid residue is not particularly limited as long as it is an amino acid residue other than a glycine residue, but it is preferably a hydrophobic amino acid residue such as a valine (V) residue, a leucine (L) residue, an isoleucine (I) residue, a methionine (M) residue, a proline (P) residue, a phenylalanine (F) residue, or a tryptophan (W) residue, or a hydrophilic amino acid residue such as a glutamine (Q) residue, an asparagine (N) residue, a serine (S) residue, a lysine (K) residue, or a glutamic acid (E) residue, more preferably a valine (V) residue, a leucine (L) residue, an isoleucine (I) residue, a phenylalanine (F) residue, or a glutamine (Q) residue, and still more preferably a glutamine (Q) residue.

A more specific example of the second modified fibroin can include a modified fibroin having (2-i) an amino acid sequence set forth in SEQ ID NO: 6 (Met-PRT380), SEQ ID NO: 7 (Met-PRT410), SEQ ID NO: 8 (Met-PRT525), or SEQ ID NO: 9 (Met-PRT799), or (2-ii) an amino acid sequence having 90% or more sequence identity with the amino acid sequence set forth in SEQ ID NO: 6, SEQ ID NO: 7, SEQ ID NO: 8, or SEQ ID NO: 9.

The modified fibroin of (2-i) will be described. The amino acid sequence set forth in SEQ ID NO: 6 is obtained by substituting GQX for all GGXs in REP of the amino acid sequence set forth in SEQ ID NO: 10 (Met-PRT313) corresponding to the naturally derived fibroin. The amino acid sequence set forth in SEQ ID NO: 7 is obtained by deleting every other two $(A)_n$ motifs from the N-terminus to the C-terminus from the amino acid sequence set forth in SEQ ID NO: 6 and further inserting one $[(A)_n$ motif-REP]before the C-terminal sequence. The amino acid sequence set forth in SEQ ID NO: 8 is obtained by inserting two alanine residues at the C-terminus of each $(A)_n$ motif of the amino acid sequence set forth in SEQ ID NO: 7 and further substituting a part of glutamine (Q) residues with a serine (S) residue to delete a part of amino acids at the C-terminus so as to be almost the same as a molecular weight of SEQ ID NO: 7. The amino acid sequence set forth in SEQ ID NO: 9 is an amino acid sequence obtained by adding a predetermined hinge sequence and a His tag sequence to the C-terminus of a sequence obtained by repeating a region of 20 domain sequences (where several amino acid residues on the C-terminal side of the region are substituted) present in the amino acid sequence set forth in SEQ ID NO: 7 four times.

A value of z/w in the amino acid sequence set forth in SEQ ID NO: 10 (corresponding to naturally derived fibroin) is 46.8%. The values of z/w in the amino acid sequence set forth in SEQ ID NO: 6, the amino acid sequence set forth in SEQ ID NO: 7, the amino acid sequence set forth in SEQ ID NO: 8, and the amino acid sequence set forth in SEQ ID NO: 9 are 58.7%, 70.1%, 66.1%, and 70.0%, respectively. In addition, the values of x/y in the amino acid sequences set forth in SEQ ID NO: 10, SEQ ID NO: 6, SEQ ID NO: 7, SEQ ID NO: 8, and SEQ ID NO: 9 at a Giza ratio (described below) of 1:1.8 to 11.3 are 15.0%, 15.0%, 93.4%, 92.7%, and 89.8%, respectively.

The modified fibroin of (2-i) may consist of the amino acid sequence set forth in SEQ ID NO: 6, SEQ ID NO: 7, SEQ ID NO: 8, or SEQ ID NO: 9.

The modified fibroin of (2-ii) may consist of an amino acid sequence having 90% or more sequence identity with the amino acid sequence set forth in SEQ ID NO: 6, SEQ ID NO: 7, SEQ ID NO: 8, or SEQ ID NO: 9. The modified fibroin of (2-ii) is also a protein containing the domain sequence represented by Formula 1: $[(A)_n$ motif-REP$]_m$. The sequence identity is preferably 95% or more.

The modified fibroin of (2-ii) preferably has 90% or more sequence identity with the amino acid sequence set forth in SEQ ID NO: 6, SEQ ID NO: 7, SEQ ID NO: 8, or SEQ ID NO: 9, and z/w is preferably 50.9% or more, in which the total number of amino acid residues in the amino acid sequence consisting of XGX (where X represents the amino acid residue other than glycine) in the REP is z, and the total number of amino acid residues in the REP in the domain sequence is w.

The second modified fibroin may have a tag sequence at either or both of the N-terminus and the C-terminus. Therefore, it is possible to isolate, immobilize, detect, or visualize the modified fibroin.

An example of the tag sequence can include an affinity tag using specific affinity (binding property and affinity) with another molecule. A specific example of the affinity tag can include a histidine tag (His tag). The His tag is a short peptide in which about 4 to 10 histidine residues are arranged and has a property of specifically binding to a metal ion such as nickel. Thus, the His tag can be used for isolation of modified fibroin by chelating metal chromatography. A specific example of the tag sequence can include an amino acid sequence set forth in SEQ ID NO: 11 (amino acid sequence having a His tag sequence and a hinge sequence).

In addition, a tag sequence such as glutathione-S-transferase (GST) that specifically binds to glutathione or a maltose binding protein (MBP) that specifically binds to maltose can also be used.

Further, an "epitope tag" using an antigen-antibody reaction can also be used. By adding a peptide (epitope) showing antigenicity as a tag sequence, an antibody can be bound to the epitope. Examples of the epitope tag can include an HA (peptide sequence of hemagglutinin of influenza virus) tag, a myc tag, and a FLAG tag. The modified fibroin can be easily purified with high specificity by using the epitope tag.

Further, a tag sequence which can be cleaved with a specific protease can be used. By treating a protein adsorbed through the tag sequence with protease, it is also possible to recover the modified fibroin from which the tag sequence is cleaved.

A more specific example of the modified fibroin having a tag sequence can include modified fibroin having (2-iii) an amino acid sequence set forth in SEQ ID NO: 12 (PRT380), SEQ ID NO: 13 (PRT410), SEQ ID NO: 14 (PRT525), or SEQ ID NO: 15 (PRT799), or (2-iv) an amino acid sequence having 90% or more sequence identity with the amino acid sequence set forth in SEQ ID NO: 12, SEQ ID NO: 13, SEQ ID NO: 14, or SEQ ID NO: 15.

Each of amino acid sequences set forth in SEQ ID NO: 16 (PRT313), SEQ ID NO: 12, SEQ ID NO: 13, SEQ ID NO: 14, and SEQ ID NO: 15 is obtained by adding the amino acid sequence set forth in SEQ ID NO: 11 (having a His tag sequence and a hinge sequence) to the N-terminus of each of the amino acid sequences set forth in SEQ ID NO: 10, SEQ ID NO: 6, SEQ ID NO: 7, SEQ ID NO: 8, and SEQ ID NO: 9.

The modified fibroin of (2-iii) may consist of the amino acid sequence set forth in SEQ ID NO: 12, SEQ ID NO: 13, SEQ ID NO: 14, or SEQ ID NO: 15.

The modified fibroin of (2-iv) may consist of an amino acid sequence having 90% or more sequence identity with the amino acid sequence set forth in SEQ ID NO: 12, SEQ ID NO: 13, SEQ ID NO: 14, or SEQ ID NO: 15. The modified fibroin of (2-iv) is also a protein containing the domain sequence represented by Formula 1: $[(A)_n$ motif-REP$]_m$. The sequence identity is preferably 95% or more.

The modified fibroin of (2-iv) preferably has 90% or more sequence identity with the amino acid sequence set forth in SEQ ID NO: 12, SEQ ID NO: 13, SEQ ID NO: 14, or SEQ ID NO: 15, and z/w is preferably 50.9% or more, in which the total number of amino acid residues in the amino acid sequence consisting of XGX (where X represents the amino acid residue other than glycine) in the REP is z, and the total number of amino acid residues in the REP in the domain sequence is w.

The second modified fibroin may include a secretory signal for releasing the protein produced in a recombinant protein production system to the outside of a host. A sequence of the secretory signal can be appropriately set depending on a type of the host.

The domain sequence of the third modified fibroin has an amino acid sequence in which a content of an $(A)_n$ motif is reduced, as compared with the naturally derived fibroin. It can be said that the domain sequence of the third modified fibroin has an amino acid sequence corresponding to an amino acid sequence in which at least one or a plurality of $(A)_n$ motifs are deleted, as compared with the naturally derived fibroin.

The third modified fibroin may have an amino acid sequence corresponding to an amino acid sequence in which 10 to 40% of the $(A)_n$ motifs are deleted from the naturally derived fibroin.

The third modified fibroin may have an amino acid sequence corresponding to an amino acid sequence obtained by deleting one $(A)_n$ motif of every one to three $(A)_n$ motifs at least from the N-terminus to the C-terminus, as compared with the naturally derived fibroin.

The third modified fibroin may have an amino acid sequence corresponding to an amino acid sequence obtained by repeating deletion of at least two consecutive $(A)_n$ motifs and deletion of one $(A)_n$ motif in this order from the N-terminus to the C-terminus, as compared with the naturally derived fibroin.

The domain sequence of the third modified fibroin may have an amino acid sequence corresponding to an amino acid sequence obtained by deleting every other two $(A)_n$ motifs at least from the N-terminus to the C-terminus.

The third modified fibroin may contain a domain sequence represented by Formula 1: $[(A)_n$ motif-REP$]_m$, and may have an amino acid sequence in which x/y may be 20% or more, 30% or more, 40% or more, or 50% or more, in which when the number of amino acid residues in REP's in two $[(A)_n$ motif-REP] units adjacent to each other are sequentially compared from the N-terminus to the C-terminus, and then the number of amino acid residues in REP having a small number of amino acid residues is set as 1, a maximum value of the total value obtained by summing up the number of amino acid residues in the two adjacent $[(A)_n$ motif-REP] units where the ratio of the number of amino acid residues in the other REP is 1.8 to 11.3 is x, and the total number of amino acid residues in the domain sequence is y. The number of alanine residues with respect to the total number of amino acid residues in the $(A)_n$ motif is 83% or more, preferably 86% or more, more preferably 90% or more, still more preferably 95% or more, and still more preferably 100% (which means that the $(A)_n$ motif consists of only alanine residues).

The calculation method of x/y will be described in more detail with reference to FIG. 1. FIG. 1 illustrates a domain sequence excluding the N-terminal sequence and the C-terminal sequence from the modified fibroin. This domain sequence has a sequence of $(A)_n$ motif-first REP (50 amino acid residues)-$(A)_n$ motif-second REP (100 amino acid residues)-$(A)_n$ motif-third REP (10 amino acid residues)-$(A)_n$ motif-fourth REP (20 amino acid residues)-$(A)_n$ motif-fifth REP (30 amino acid residues)-$(A)_n$ motif from the N-terminal side (left side).

The two adjacent $[(A)_n$ motif-REP] units are sequentially selected from the N-terminus to the C-terminus so as not to overlap. In this case, an unselected $[(A)_n$ motif-REP] unit may exist. FIG. 1 illustrates a pattern 1 (a comparison between first REP and second REP and a comparison between third REP and fourth REP), a pattern 2 (a comparison between first REP and second REP and a comparison between fourth REP and fifth REP), a pattern 3 (a comparison between second REP and third REP and a comparison between fourth REP and fifth REP), and a pattern 4 (a comparison between first REP and second REP). There are selection methods other than this.

Next, for each pattern, the number of amino acid residues in each REP in the selected two adjacent $[(A)_n$ motif-REP] units is compared. The comparison is performed by determining a ratio of the number of amino acid residues in the other REP when one REP having a smaller number of amino acid residues is 1. For example, in the case of comparing the first REP (50 amino acid residues) with the second REP (100 amino acid residues), a ratio of the number of amino acid residues in the second REP when the first REP having a smaller number of amino acid residues is 1 is 100/50=2. Similarly, in the case of comparing the fourth REP (20 amino acid residues) with the fifth REP (30 amino acid residues), a ratio of the number of amino acid residues in the fifth REP when the fourth REP having a smaller number of amino acid residues is 1 is 30/20=1.5.

In FIG. 1, a set of $[(A)_n$ motif-REP] units in which the ratio of the number of amino acid residues in the other REP when one REP having a smaller number of amino acid residues is 1 is 1.8 to 11.3 is indicated by a solid line. In the present specification, the ratio is referred to as a Giza ratio. A set of $[(A)_n$ motif-REP] units in which the ratio of the number of amino acid residues in the other REP when one REP having a smaller number of amino acid residues is 1 is less than 1.8 or more than 11.3 is indicated by a broken line.

In each pattern, the number of all amino acid residues in two adjacent $[(A)_n$ motif-REP] units indicated by solid lines (including not only the number of amino acid residues in REP but also the number of amino acid residues in $(A)_n$ motif) are summed up. Then, the total values thus summed up are compared and the total value in the patterns at which the total value is maximized (the maximum value of the total value) is x. In the example illustrated in FIG. 1, the total value in the pattern 1 is the maximum.

Next, x/y (%) can be calculated by dividing x by the total amino acid residue number y of the domain sequence.

In the third modified fibroin, x/y is preferably 50% or more, more preferably 60% or more, still more preferably 65% or more, still more preferably 70% or more, still more preferably 75% or more, and particularly preferably 80% or more. An upper limit of x/y is not particularly limited, but may be, for example, 100% or less. In the case where the Giza ratio is 1:1.9 to 11.3, x/y is preferably 89.6% or more. In the case where the Giza ratio is 1:1.8 to 3.4, x/y is preferably 77.1% or more. In the case where the Giza ratio is 1:1.9 to 8.4, x/y is preferably 75.9% or more. In the case where the Giza ratio is 1:1.9 to 4.1, x/y is preferably 64.2% or more.

In the case where the third modified fibroin is modified fibroin in which at least a plurality of seven $(A)_n$ motifs present in the domain sequence consist of only alanine residues, x/y is preferably 46.4% or more, more preferably 50% or more, still more preferably 55% or more, still more preferably 60% or more, still more preferably 70% or more, and particularly preferably 80% or more. The upper limit of x/y is not particularly limited, but may be 100% or less.

Here, x/y in the naturally derived fibroin will be described. First, as described above, 663 types of fibroins (415 types of fibroins derived from spiders among them) were extracted by confirming fibroins with amino acid sequence information registered in NCBI GenBank by an exemplified method. x/y was calculated by the above-described calculation method from the amino acid sequences of naturally derived fibroins consisting of a domain sequence represented by Formula 1: $[(A)_n$ motif-REP$]_m$, among all the extracted fibroins. As a result, x/y in each of the naturally derived fibroins is less than 64.2% (highest, 64.14%).

The third modified fibroin can be obtained from, for example, a cloned gene sequence of naturally derived fibroin, by deleting one or a plurality of sequences encoding an $(A)_n$ motif so that x/y is 64.2% or more. In addition, for example, the third modified fibroin can also be obtained, from the amino acid sequence of naturally derived fibroin, by designing an amino acid sequence corresponding to deletion of one or a plurality of $(A)_n$ motifs so that x/y is 64.2% or more, and chemically synthesizing a nucleic acid encoding the designed amino acid sequence. In any case, in addition to the modification corresponding to deletion of the $(A)_n$ motif from the amino acid sequence of the naturally derived fibroin, modification of the amino acid sequence corresponding to substitution, deletion, insertion, and/or addition of one or a plurality of amino acid residues may be performed.

A more specific example of the third modified fibroin can include a modified fibroin having (3-i) an amino acid sequence set forth in SEQ ID NO: 17 (Met-PRT399), SEQ ID NO: 7 (Met-PRT410), SEQ ID NO: 8 (Met-PRT525), or SEQ ID NO: 9 (Met-PRT799), or (3-ii) an amino acid sequence having 90% or more sequence identity with the amino acid sequence set forth in SEQ ID NO: 17, SEQ ID NO: 7, SEQ ID NO: 8, or SEQ ID NO: 9.

The modified fibroin of (3-i) will be described. The amino acid sequence set forth in SEQ ID NO: 17 is obtained by deleting every other two $(A)_n$ motifs from the N-terminus to the C-terminus from the amino acid sequence set forth in SEQ ID NO: 10 (Met-PRT313) corresponding to the naturally derived fibroin and further inserting one $[(A)_n$ motif-REP$]$ before the C-terminal sequence. The amino acid sequence set forth in SEQ ID NO: 7, SEQ ID NO: 8, or SEQ ID NO: 9 is as described in the second modified fibroin.

The value of x/y in the amino acid sequence set forth in SEQ ID NO: 10 (corresponding to naturally derived fibroin) at a Giza ratio of 1:1.8 to 11.3 is 15.0%. Both the value of x/y in the amino acid sequence set forth in SEQ ID NO: 17 and the value of x/y in the amino acid sequence set forth in SEQ ID NO: 7 are 93.4%. The value of x/y in the amino acid sequence set forth in SEQ ID NO: 8 is 92.7%. The value of x/y in the amino acid sequence set forth in SEQ ID NO: 9 is 89.8%. The values of z/w in the amino acid sequences set forth in SEQ ID NO: 10, SEQ ID NO: 17, SEQ ID NO: 7, SEQ ID NO: 8, and SEQ ID NO: 9 are 46.8%, 56.2%, 70.1%, 66.1%, and 70.0%, respectively.

The modified fibroin of (3-i) may consist of the amino acid sequence set forth in SEQ ID NO: 17, SEQ ID NO: 7, SEQ ID NO: 8, or SEQ ID NO: 9.

The modified fibroin of (3-ii) may consist of an amino acid sequence having 90% or more sequence identity with the amino acid sequence set forth in SEQ ID NO: 17, SEQ ID NO: 7, SEQ ID NO: 8, or SEQ ID NO: 9. The modified fibroin of (3-ii) is also a protein containing the domain sequence represented by Formula 1: $[(A)_n$ motif-REP$]_m$. The sequence identity is preferably 95% or more.

The modified fibroin of (3-ii) preferably has 90% or more sequence identity with the amino acid sequence set forth in SEQ ID NO: 17, SEQ ID NO: 7, SEQ ID NO: 8, or SEQ ID NO: 9, and x/y is preferably 64.2% or more, in which when the number of amino acid residues in REP's in two $[(A)_n$ motif-REP$]$ units adjacent to each other are sequentially compared from the N-terminus to the C-terminus, and then the number of amino acid residues in REP having a small number of amino acid residues is set as 1, a maximum value of the total value obtained by summing up the number of amino acid residues in the two adjacent $[(A)_n$ motif-REP$]$ units where the ratio of the number of amino acid residues in the other REP is 1.8 to 11.3 (the Giza ratio is 1:1.8 to 11.3) is x, and the total number of amino acid residues in the domain sequence is y.

The third modified fibroin may have the above-described tag sequence at either or both of the N-terminus and the C-terminus.

A more specific example of the modified fibroin having a tag sequence can include modified fibroin having (3-iii) an amino acid sequence set forth in SEQ ID NO: 18 (PRT399), SEQ ID NO: 13 (PRT410), SEQ ID NO: 14 (PRT525), or SEQ ID NO: 15 (PRT799), or (3-iv) an amino acid sequence having 90% or more sequence identity with the amino acid sequence set forth in SEQ ID NO: 18, SEQ ID NO: 13, SEQ ID NO: 14, or SEQ ID NO: 15.

Each of the amino acid sequences set forth in SEQ ID NO: 18, SEQ ID NO: 13, SEQ ID NO: 14, and SEQ ID NO: 15 is obtained by adding the amino acid sequence set forth in SEQ ID NO: 11 (having a His tag sequence and a hinge sequence) to the N-terminus of each of the amino acid sequences set forth in SEQ ID NO: 17, SEQ ID NO: 7, SEQ ID NO: 8, and SEQ ID NO: 9.

The modified fibroin of (3-iii) may consist of the amino acid sequence set forth in SEQ ID NO: 18, SEQ ID NO: 13, SEQ ID NO: 14, or SEQ ID NO: 15.

The modified fibroin of (3-iv) may consist of an amino acid sequence having 90% or more sequence identity with the amino acid sequence set forth in SEQ ID NO: 18, SEQ ID NO: 13, SEQ ID NO: 14, or SEQ ID NO: 15. The modified fibroin of (3-iv) is also a protein containing the domain sequence represented by Formula 1: $[(A)_n$ motif-REP$]_m$. The sequence identity is preferably 95% or more.

The modified fibroin of (3-iv) preferably has 90% or more sequence identity with the amino acid sequence set forth in SEQ ID NO: 18, SEQ ID NO: 13, SEQ ID NO: 14, or SEQ ID NO: 15, and x/y is preferably 64.2% or more, in which when the number of amino acid residues in REP's in two $[(A)_n$ motif-REP$]$ units adjacent to each other are sequentially compared from the N-terminus to the C-terminus, and then the number of amino acid residues in REP having a small number of amino acid residues is set as 1, a maximum value of the total value obtained by summing up the number of amino acid residues in the two adjacent $[(A)_n$ motif-REP$]$ units where the ratio of the number of amino acid residues in the other REP is 1.8 to 11.3 is x, and the total number of amino acid residues in the domain sequence is y.

The third modified fibroin may include a secretory signal for releasing the protein produced in a recombinant protein production system to the outside of a host. A sequence of the secretory signal can be appropriately set depending on a type of the host.

The domain sequence of the fourth modified fibroin has an amino acid sequence in which a content of an $(A)_n$ motif and a content of glycine residues are reduced, as compared with the naturally derived fibroin. It can be said that the domain sequence of the fourth modified fibroin has an amino acid sequence corresponding to an amino acid sequence in which at least one or a plurality of $(A)_n$ motifs are deleted and at least one or a plurality of glycine residues in REP are substituted with another amino acid residue, as compared with the naturally derived fibroin. That is, the fourth modified fibroin is modified fibroin having the characteristics of the above-described second modified fibroin and third modified fibroin. Specific aspects and the like of the fourth modified fibroin are as described in the second modified fibroin and the third modified fibroin.

A more specific example of the fourth modified fibroin can include modified fibroin having (4-i) an amino acid sequence set forth in SEQ ID NO: 7 (Met-PRT410), SEQ ID NO: 8 (Met-PRT525), SEQ ID NO: 9 (Met-PRT799), SEQ ID NO: 13 (PRT410), SEQ ID NO: 14 (PRT525), or SEQ ID NO: 15 (PRT799), or (4-ii) an amino acid sequence having 90% or more sequence identity with the amino acid sequence set forth in SEQ ID NO: 7, SEQ ID NO: 8, SEQ ID NO: 9, SEQ ID NO: 13, SEQ ID NO: 14, or SEQ ID NO: 15. Specific aspects of the modified fibroin having the amino acid sequence set forth in SEQ ID NO: 7, SEQ ID NO: 8, SEQ ID NO: 9, SEQ ID NO: 13, SEQ ID NO: 14, or SEQ ID NO: 15 are as described above.

The domain sequence of the fifth modified fibroin may have an amino acid sequence including a region locally having a high hydropathy index corresponding to an amino acid sequence in which one or a plurality of amino acid residues in REP are substituted with amino acid residues having a high hydropathy index and/or one or a plurality of amino acid residues having a high hydropathy index are inserted into REP, as compared with the naturally derived fibroin.

It is preferable that the region locally having a high hydropathy index consists of two to four consecutive amino acid residues.

It is more preferable that the above-described amino acid residue having a high hydropathy index is an amino acid residue selected from isoleucine (I), valine (V), leucine (L), phenylalanine (F), cysteine (C), methionine (M), and alanine (A).

The fifth modified fibroin may be further subjected to modification of an amino acid sequence corresponding to substitution, deletion, insertion, and/or addition of one or a plurality of amino acid residues as compared with the naturally derived fibroin, in addition to modification corresponding to substitution of one or a plurality of amino acid residues in REP with amino acid residues having a high hydropathy index and/or insertion of one or a plurality of amino acid residues having a high hydropathy index into REP, as compared with the naturally derived fibroin.

The fifth modified fibroin can be obtained by, for example, substituting one or a plurality of hydrophilic amino acid residues in REP (for example, amino acid residues having a negative hydropathy index) with hydrophobic amino acid residues (for example, amino acid residues having a positive hydropathy index) from a cloned gene sequence of naturally derived fibroin, and/or inserting one or a plurality of hydrophobic amino acid residues into REP. In addition, the fifth modified fibroin can be obtained by, for example, designing an amino acid sequence corresponding to substitution of one or a plurality of hydrophilic amino acid residues in REP with hydrophobic amino acid residues from an amino acid sequence of naturally derived fibroin, and/or insertion of one or a plurality of hydrophobic amino acid residues into REP, and chemically synthesizing a nucleic acid encoding the designed amino acid sequence. In any case, in addition to modification corresponding to substitution of one or a plurality of hydrophilic amino acid residues in REP with hydrophobic amino acid residues from amino acid sequences of naturally derived fibroin, and/or insertion of one or a plurality of hydrophobic amino acid residues into REP, modification of an amino acid sequence corresponding to substitution, deletion, insertion, and/or addition of one or a plurality of amino acid residues may be further performed.

The fifth modified fibroin may contain a domain sequence represented by Formula 1: $[(A)_n\ \text{motif-REP}]_m$, and may have an amino acid sequence in which p/q is 6.2% or more, in which in all REP's contained in a sequence excluding a sequence from a $(A)_n$ motif located the most C-terminal side to the C-terminus of the domain sequence from the domain sequence, a total number of amino acid residues contained in a region where an average value of hydropathy indices of four consecutive amino acid residues is 2.6 or more is p, and a total number of amino acid residues contained in the sequence excluding the sequence from the $(A)_n$ motif located the most C-terminal side to the C-terminus of the domain sequence from the domain sequence is q.

A known index (Hydropathy index: Kyte J, & Doolittle R (1982), "A simple method for displaying the hydropathic character of a protein", J. Mol. Biol., 157, pp. 105-132) is used as the hydropathy index of the amino acid residue. Specifically, the hydropathy index (hereinafter, also referred to as "HI") of each amino acid is as shown in Table 1.

TABLE 1

| Amino acid | HI | Amino acid | HI |
|---|---|---|---|
| Isoleucine (Ile) | 4.5 | Tryptophan (Trp) | −0.9 |
| Valine (Val) | 4.2 | Tyrosine (Tyr) | −1.3 |
| Leucine (Leu) | 3.8 | Proline (Pro) | −1.6 |
| Phenylalanine (Phe) | 2.8 | Histidine (His) | −3.2 |
| Cysteine (Cys) | 2.5 | Asparagine (Asn) | −3.5 |
| Methionine (Met) | 1.9 | Asparaginic acid (Asp) | −3.5 |
| Alanine (Ala) | 1.8 | Glutamine (Gln) | −3.5 |
| Glycine (Gly) | −0.4 | Glutamic acid (Glu) | −3.5 |
| Threonine (Thr) | −0.7 | Lysine (Lys) | −3.9 |
| Serine (Ser) | −0.8 | Arginine (Arg) | −4.5 |

The calculation method of p/q will be described in more detail. In the calculation, the sequence excluding the sequence from the $(A)_n$ motif located at the most C-terminal side to the C-terminus of the domain sequence from the domain sequence represented by Formula 1: $[(A)_n\ \text{motif-REP}]_m$ (hereinafter, referred to as "sequence A") is used. First, in all REP's contained in the sequence A, an average value of hydropathy indices of four consecutive amino acid residues is calculated. The average value of the hydropathy indices is determined by dividing the sum of HI of each of the amino acid residues contained in the four consecutive amino acid residues by 4 (the number of amino acid residues). The average value of the hydropathy indices is determined for all of the four consecutive amino acid residues (each of the amino acid residues is used for calculating the average value 1 to 4 times). Next, a region where the average value of the hydropathy indices of the four consecutive amino acid residues is 2.6 or more is specified. Even in a case where certain amino acid residues correspond to a plurality of "four consecutive amino acid residues having an average value of hydropathy indices of 2.6 or more", the amino acid residue is counted as one amino acid residue in the region. Then, the total number of amino acid residues contained in the region is p. In addition, the total number of amino acid residues contained in the sequence A is q.

Figure 2:
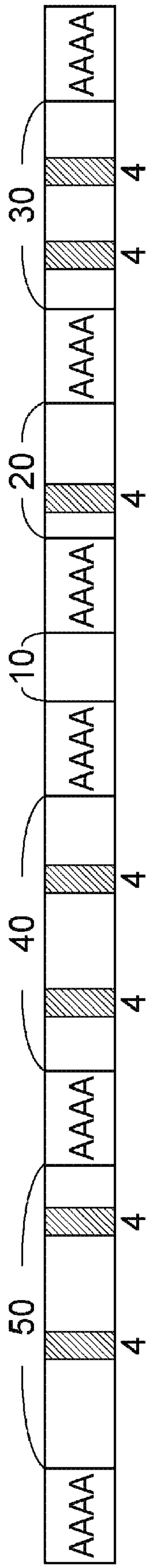
FIG. 2 is a schematic diagram illustrating an example of a domain sequence of modified fibroin.

For example, in a case where the "four consecutive amino acid residues having an average value of the hydropathy indices of 2.6 or more" are extracted from 20 places (no overlap), in the region where the average value of the hydropathy indices of four consecutive amino acid residues is 2.6 or more, the number of the four consecutive amino acid residues (no overlap) is 20, and thus p is 20×4=80. In addition, for example, in a case where two of the "four consecutive amino acid residues having an average value of the hydropathy indices of 2.6 or more" overlap by only one amino acid residue, in the region where the average value of the hydropathy indices of four consecutive amino acid residues is 2.6 or more, the number of amino acid residues is 7 (p=2×4−1=7, "−1" is the deduction of overlap). For example, in the case of the domain sequence illustrated in FIG. 2, since the number of the "four consecutive amino acid residues having an average value of the hydropathy indices of 2.6 or more", which do not overlap, is 7, p is 7×4=28. In addition, for example, in the case of the domain sequence illustrated in FIG. 2, q is 4+50+4+40+4+10+4+20+4+30=170 (excluding the $(A)_n$ motif located at the most C-terminal side). Next, p/q (%) can be calculated by dividing p by q. In the case of FIG. 2, 28/170=16.47%.

In the fifth modified fibroin, p/q is preferably 6.2% or more, more preferably 7% or more, still more preferably 10% or more, still more preferably 20% or more, and still more preferably 30% or more. An upper limit of p/q is not particularly limited, but may be, for example, 45% or less.

The fifth modified fibroin can be obtained by, for example, substituting one or a plurality of hydrophilic amino acid residues in REP (for example, amino acid residues having a negative hydropathy index) with hydrophobic amino acid residues (for example, amino acid residues having a positive hydropathy index) so that a cloned amino acid sequence of naturally derived fibroin satisfies the condition of p/q, and/or modifying the cloned amino acid sequence of naturally derived fibroin with an amino acid sequence including a region locally having a high hydropathy index by inserting one or a plurality of hydrophobic amino acid residues into REP. In addition, the fifth modified fibroin can also be obtained by, for example, designing an amino acid sequence satisfying the condition of p/q from the amino acid sequence of the naturally derived fibroin, and chemically synthesizing a nucleic acid encoding the designed amino acid sequence. In any case, modification corresponding to substitution, deletion, insertion, and/or addition of one or a plurality of amino acid residues may also be performed, in addition to modification corresponding to substitution of one or a plurality of amino acid residues in REP with amino acid residues having a high hydropathy index, and/or insertion of one or a plurality of amino acid residues having a high hydropathy index into REP, as compared with the naturally derived fibroin.

The amino acid residue having a high hydropathy index is not particularly limited, but is preferably isoleucine (I), valine (V), leucine (L), phenylalanine (F), cysteine (C), methionine (M), and alanine (A), and more preferably valine (V), leucine (L), and isoleucine (I).

A more specific example of the fifth modified fibroin can include modified fibroin having (5-i) an amino acid sequence set forth in SEQ ID NO: 19 (Met-PRT720), SEQ ID NO: 20 (Met-PRT665), or SEQ ID NO: 21 (Met-PRT666), or (5-ii) an amino acid sequence having 90% or more sequence identity with the amino acid sequence set forth in SEQ ID NO: 19, SEQ ID NO: 20, or SEQ ID NO: 21.

The modified fibroin of (5-i) will be described. The amino acid sequence set forth in SEQ ID NO: 19 is obtained by inserting an amino acid sequence consisting of three amino acid residues (VLI) at two sites for each REP into the amino acid sequence set forth in SEQ ID NO: 7 (Met-PRT410), except for the domain sequence at the end on the C-terminal side, and further substituting a part of glutamine (Q) residues with serine (S) residues and deleting a part of amino acids on the C-terminal side. The amino acid sequence set forth in SEQ ID NO: 20 is obtained by inserting the amino acid sequence consisting of three amino acid residues (VLI) at one site for each REP into the amino acid sequence set forth in SEQ ID NO: 8 (Met-PRT525). The amino acid sequence set forth in SEQ ID NO: 21 is obtained by inserting the amino acid sequence consisting of three amino acid residues (VLI) at two sites for each REP into the amino acid sequence set forth in SEQ ID NO: 8.

The modified fibroin of (5-i) may consist of the amino acid sequence set forth in SEQ ID NO: 19, SEQ ID NO: 20, or SEQ ID NO: 21.

The modified fibroin of (5-ii) may consist of an amino acid sequence having 90% or more sequence identity with the amino acid sequence set forth in SEQ ID NO: 19, SEQ ID NO: 20, or SEQ ID NO: 21. The modified fibroin of (5-ii) is also a protein containing the domain sequence represented by Formula 1: $[(A)_n \text{ motif-REP}]_m$. The sequence identity is preferably 95% or more.

The modified fibroin of (5-ii) preferably has 90% or more sequence identity with the amino acid sequence set forth in SEQ ID NO: 19, SEQ ID NO: 20, or SEQ ID NO: 21, and p/q is preferably 6.2% or more, in which in all REP's contained in a sequence excluding a sequence from a $(A)_n$ motif located the most C-terminal side to the C-terminus of the domain sequence from the domain sequence, a total number of amino acid residues contained in a region where an average value of hydropathy indices of four consecutive amino acid residues is 2.6 or more is p, and a total number of amino acid residues contained in the sequence excluding the sequence from the $(A)_n$ motif located the most C-terminal side to the C-terminus of the domain sequence from the domain sequence is q.

The fifth modified fibroin may have a tag sequence at either or both of the N-terminus and the C-terminus.

A more specific example of the modified fibroin having a tag sequence can include modified fibroin having (5-iii) an amino acid sequence set forth in SEQ ID NO: 22 (PRT720), SEQ ID NO: 23 (PRT665), or SEQ ID NO: 24 (PRT666), or (5-iv) an amino acid sequence having 90% or more sequence identity with the amino acid sequence set forth in SEQ ID NO: 22, SEQ ID NO: 23, or SEQ ID NO: 24.

Each of the amino acid sequences set forth in SEQ ID NO: 22, SEQ ID NO: 23, and SEQ ID NO: 24 is obtained by adding the amino acid sequence set forth in SEQ ID NO: 11 (having a His tag sequence and a hinge sequence) to the N-terminus of each of the amino acid sequences set forth in SEQ ID NO: 19, SEQ ID NO: 20, and SEQ ID NO: 21.

The modified fibroin of (5-iii) may consist of the amino acid sequence set forth in SEQ ID NO: 22, SEQ ID NO: 23, or SEQ ID NO: 24.

The modified fibroin of (5-iv) may consist of an amino acid sequence having 90% or more sequence identity with the amino acid sequence set forth in SEQ ID NO: 22, SEQ ID NO: 23, or SEQ ID NO: 24. The modified fibroin of (5-iv) is also a protein containing the domain sequence represented by Formula 1: $[(A)_n \text{ motif-REP}]_m$. The sequence identity is preferably 95% or more.

The modified fibroin of (5-iv) preferably has 90% or more sequence identity with the amino acid sequence set forth in SEQ ID NO: 22, SEQ ID NO: 23, or SEQ ID NO: 24, and p/q is preferably 6.2% or more, in which in all REP's contained in a sequence excluding a sequence from a $(A)_n$ motif located the most C-terminal side to the C-terminus of the domain sequence from the domain sequence, a total number of amino acid residues contained in a region where an average value of hydropathy indices of four consecutive amino acid residues is 2.6 or more is p, and a total number of amino acid residues contained in the sequence excluding the sequence from the $(A)_n$ motif located the most C-terminal side to the C-terminus of the domain sequence from the domain sequence is q.

The fifth modified fibroin may include a secretory signal for releasing the protein produced in a recombinant protein production system to the outside of a host. A sequence of the secretory signal can be appropriately set depending on a type of the host.

The sixth modified fibroin has an amino acid sequence in which a content of glutamine residues is reduced, as compared with the naturally derived fibroin.

The sixth modified fibroin preferably contains at least one motif selected from a GGX motif and a GPGXX motif in the amino acid sequence of REP.

In a case where the sixth modified fibroin contains the GPGXX motif in REP, a content rate of the GPGXX motif is generally 1% or more, may be 5% or more, and is preferably 10% or more. An upper limit of the content rate of the GPGXX motif is not particularly limited, but may be 50% or less or 30% or less.

In the present specification, the "content rate of the GPGXX motif" is a value calculated by the following method.

In fibroin (modified fibroin or naturally derived fibroin) containing a domain sequence represented by Formula 1: $[(A)_n$ motif-REP$]_m$ or Formula 2: $[(A)_n$ motif-REP$]_m$-$(A)_n$ motif, the content rate of the GPGXX motif is calculated as s/t, in which the number obtained by tripling the total number of GPGXX motifs in the regions of all REP's contained in a sequence excluding the sequence from the $(A)_n$ motif located at the most C-terminal side to the C-terminus of the domain sequence from the domain sequence (that is, corresponding to the total number of G and P in the GPGXX motifs) is s, and the total number of amino acid residues in all REP's excluding the sequence from the $(A)_n$ motif located at the most C-terminal side to the C-terminus of the domain sequence from the domain sequence and further excluding the $(A)_n$ motifs is t.

For the calculation of the content rate of the GPGXX motif, the "sequence excluding a sequence from the $(A)_n$ motif located at the most C-terminal side to the C-terminus of the domain sequence from the domain sequence" is used to exclude the effect occurring due to the fact that the "sequence from the $(A)_n$ motif located at the most C-terminal side to the C-terminus of the domain sequence" (sequence corresponding to REP) may have a sequence having a low correlation with the sequence characteristic of fibroin, which influences the calculation result of the content rate of the GPGXX motif in a case where m is small (that is, in a case where the domain sequence is short). In a case where the "GPGXX motif" is located at the C-terminus of REP, it is regarded as the "GPGXX motif" even in a case where "XX" is, for example, "AA".

Figure 3:
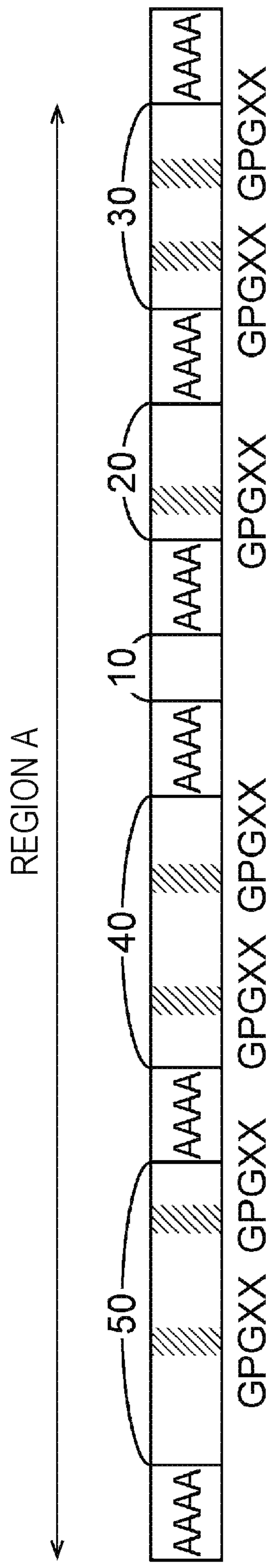
FIG. 3 is a schematic diagram illustrating an example of a domain sequence of modified fibroin.

FIG. 3 is a schematic diagram illustrating a domain sequence of modified fibroin. The calculation method of the content rate of the GPGXX motif will be specifically described with reference to FIG. 3. First, in the domain sequence of the modified fibroin ("$[(A)_n$ motif-REP$]_m$-$(A)_n$ motif" type) illustrated in FIG. 3, since all REP's are contained in the "sequence excluding the sequence from the $(A)_n$ motif located at the most C-terminal side to the C-terminus of the domain sequence from the domain sequence" (the sequence indicated by the "region A" in FIG. 3), the number of GPGXX motifs for calculating s is 7, and s is 7×3=21. Similarly, since all REP's are contained in the "sequence excluding the sequence from the $(A)_n$ motif located at the most C-terminal side to the C-terminus of the domain sequence from the domain sequence" (the sequence indicated by the "region A" in FIG. 3), a total number t of amino acid residues in all REP's further excluding $(A)_n$ motifs from the sequence is 50+40+10+20+30=150. Next, s/t (%) can be calculated by dividing s by t, and in the case of the modified fibroin of FIG. 3, s/t (%) is 21/150=14.0%.

In the sixth modified fibroin, a content rate of glutamine residues is preferably 9% or less, more preferably 7% or less, still more preferably 4% or less, and particularly preferably 0%.

In the present specification, the "content rate of the glutamine residues" is a value calculated by the following method.

In fibroin (modified fibroin or naturally derived fibroin) containing a domain sequence represented by Formula 1: $[(A)_n$ motif-REP$]_m$ or Formula 2: $[(A)_n$ motif-REP$]_m$-$(A)_n$ motif, the content rate of the glutamine residues is calculated as u/t, in which a total number of glutamine residues in regions of all REP's contained in a sequence excluding the sequence from the $(A)_n$ motif located at the most C-terminal side to the C-terminus of the domain sequence from the domain sequence (sequence corresponding to the "region A" in FIG. 3) is u, and a total number of amino acid residues in all REP's excluding the sequence from the $(A)_n$ motif located at the most C-terminal side to the C-terminus of the domain sequence from the domain sequence and further excluding $(A)_n$ motifs is t. For the calculation of the content rate of the glutamine residues, the "sequence excluding the sequence from the $(A)_n$ motif located at the most C-terminal side to the C-terminus of the domain sequence from the domain sequence" is used for the same reason described above.

The domain sequence of the sixth modified fibroin may have an amino acid sequence corresponding to deletion of one or a plurality of glutamine residues in REP, or substitution of one or a plurality of glutamine residues with another amino acid residue, as compared with the naturally derived fibroin.

"Another amino acid residue" may be an amino acid residue other than a glutamine residue, but is preferably an amino acid residue having a higher hydropathy index than that of a glutamine residue. The hydropathy index of the amino acid residue is shown in Table 1.

As shown in Table 1, examples of the amino acid residue having a higher hydropathy index than that of a glutamine residue can include an amino acid residue selected from isoleucine (I), valine (V), leucine (L), phenylalanine (F), cysteine (C), methionine (M) alanine (A), glycine (G), threonine (T), serine (S), tryptophan (W), tyrosine (Y), proline (P), and histidine (H). Among them, an amino acid residue selected from isoleucine (I), valine (V), leucine (L), phenylalanine (F), cysteine (C), methionine (M), and alanine (A) is more preferred, and an amino acid residue selected from isoleucine (I), valine (V), leucine (L), and phenylalanine (F) is still more preferred.

In the sixth modified fibroin, hydrophobicity of REP is preferably −0.8 or more, more preferably −0.7 or more, still more preferably 0 or more, still more preferably 0.3 or more, and still more preferably 0.4 or more. An upper limit of the hydrophobicity of REP is not particularly limited, but may be 1.0 or less or 0.7 or less.

In the present specification, the "hydrophobicity of REP" is a value calculated by the following method.

In fibroin (modified fibroin or naturally derived fibroin) containing a domain sequence represented by Formula 1: $[(A)_n$ motif-REP$]_m$ or Formula 2: $[(A)_n$ motif-REP$]_m$-$(A)_n$ motif, the hydrophobicity of REP is calculated as v/t, in which the sum of hydropathy indices of the amino acid residues in the regions of all REP's contained in the sequence excluding the sequence from the $(A)_n$ motif located at the most C-terminal side to the C-terminus of the domain sequence from the domain sequence (sequence corresponding to the "region A" in FIG. 3) is v, and the total number of amino acid residues in all REP's excluding the sequence from the $(A)_n$ motif located at the most C-terminal side to the C-terminus of the domain sequence from the domain sequence and further excluding $(A)_n$ motifs is t. For the calculation of the hydrophobicity of REP, the "sequence excluding the sequence from the $(A)_n$ motif located at the most C-terminal side to the C-terminus of the domain sequence from the domain sequence" is used for the same reason described above.

The sixth modified fibroin may be further subjected to modification of an amino acid sequence corresponding to substitution, deletion, insertion, and/or addition of one or a plurality of amino acid residues, in addition to modification corresponding to deletion of one or a plurality of glutamine residues in REP, and/or substitution of one or a plurality of glutamine residues in REP with another amino acid residue, as compared to naturally derived fibroin.

The sixth modified fibroin can be obtained by, for example, deleting one or a plurality of glutamine residues in REP from a cloned gene sequence of naturally derived fibroin, and/or substituting one or a plurality of glutamine residues in REP with another amino acid residue. In addition, the sixth modified fibroin can be obtained by, for example, designing an amino acid sequence corresponding to deletion of one or a plurality of glutamine residues in REP from an amino acid sequence of naturally derived fibroin, and/or substitution of one or a plurality of glutamine residues in REP with another amino acid residue, and chemically synthesizing a nucleic acid encoding the designed amino acid sequence.

More specific examples of the sixth modified fibroin can include modified fibroin having (6-i) an amino acid sequence set forth in SEQ ID NO: 25 (Met-PRT888), SEQ ID NO: 26 (Met-PRT965), SEQ ID NO: 27 (Met-PRT889), SEQ ID NO: 28 (Met-PRT916), SEQ ID NO: 29 (Met-PRT918), SEQ ID NO: 30 (Met-PRT699), SEQ ID NO: 31 (Met-PRT698), SEQ ID NO: 32 (Met-PRT966), SEQ ID NO: 41 (Met-PRT917), or SEQ ID NO: 42 (Met-PRT1028), and modified fibroin having (6-ii) an amino acid sequence having 90% or more sequence identity with the amino acid sequence set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, or SEQ ID NO: 42.

The modified fibroin of (6-i) will be described. The amino acid sequence set forth in SEQ ID NO: 25 is obtained by substituting all QQs in the amino acid sequence set forth in SEQ ID NO: 7 (Met-PRT410) with VL. The amino acid sequence set forth in SEQ ID NO: 26 is obtained by substituting all QQs in the amino acid sequence set forth in SEQ ID NO: 7 with TS and substituting the remaining Q with A. The amino acid sequence set forth in SEQ ID NO: 27 is obtained by substituting all QQs in the amino acid sequence set forth in SEQ ID NO: 7 with VL and substituting the remaining Q with I. The amino acid sequence set forth in SEQ ID NO: 28 is obtained by substituting all QQs in the amino acid sequence set forth in SEQ ID NO: 7 with VI and substituting the remaining Q with L. The amino acid sequence set forth in SEQ ID NO: 29 is obtained by substituting all QQs in the amino acid sequence set forth in SEQ ID NO: 7 with VF and substituting the remaining Q with I.

The amino acid sequence set forth in SEQ ID NO: 30 is obtained by substituting all QQs in the amino acid sequence set forth in SEQ ID NO: 8 (Met-PRT525) with VL. The amino acid sequence set forth in SEQ ID NO: 31 is obtained by substituting all QQs in the amino acid sequence set forth in SEQ ID NO: 8 with VL and substituting the remaining Q with I.

The amino acid sequence set forth in SEQ ID NO: 32 is obtained by substituting, with VF, all QQs in a sequence obtained by repeating a region of 20 domain sequences present in the amino acid sequence set forth in SEQ ID NO: 7 (Met-PRT410) two times and substituting the remaining Q with I.

The amino acid sequence set forth in SEQ ID NO: 41 (Met-PRT917) is obtained by substituting all QQs in the amino acid sequence set forth in SEQ ID NO: 7 with LI and substituting the remaining Q with V. The amino acid sequence set forth in SEQ ID NO: 42 (Met-PRT1028) is obtained by substituting all QQs in the amino acid sequence set forth in SEQ ID NO: 7 with IF and substituting the remaining Q with T.

The content rate of the glutamine residues in each of the amino acid sequences set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, and SEQ ID NO: 42 is 9% or less (Table 2).

TABLE 2

| Modified fibroin | Content of glutamine residue | Content of GPGXX motif | Hydro-phobicity of REP |
|---|---|---|---|
| Met-PRT410 (SEQ ID NO: 7) | 17.7% | 27.9% | −1.52 |
| Met-PRT888 (SEQ ID NO: 25) | 6.3% | 27.9% | −0.07 |
| Met-PRT965 (SEQ ID NO: 26) | 0.0% | 27.9% | −0.65 |
| Met-PRT889 (SEQ ID NO: 27) | 0.0% | 27.9% | 0.35 |
| Met-PRT916 (SEQ ID NO: 28) | 0.0% | 27.9% | 0.47 |
| Met-PRT918 (SEQ ID NO: 29) | 0.0% | 27.9% | 0.45 |
| Met-PRT699 (SEQ ID NO: 30) | 3.6% | 26.4% | −0.78 |
| Met-PRT698 (SEQ ID NO: 31) | 0.0% | 26.4% | −0.03 |
| Met-PRT966 (SEQ ID NO: 32) | 0.0% | 28.0% | 0.35 |
| Met-PRT917 (SEQ ID NO: 41) | 0.0% | 27.9% | 0.46 |
| Met-PRT1028 (SEQ ID NO: 42) | 0.0% | 28.1% | 0.05 |

The modified fibroin of (6-i) may consist of the amino acid sequence set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, or SEQ ID NO: 42.

The modified fibroin of (6-ii) may consist of the amino acid sequence having 90% or more sequence identity with the amino acid sequence set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, or SEQ ID NO: 42. The modified fibroin of (6-ii) is also a protein containing a domain sequence represented by Formula 1: $[(A)_n \text{ motif-REP}]_m$ or Formula 2: $[(A)_n \text{ motif-REP}]_m\text{-}(A)_n$ motif. The sequence identity is preferably 95% or more.

It is preferable that a content rate of glutamine residues in the modified fibroin of (6-ii) is preferably 9% or less. In addition, it is preferable that a content rate of a GPGXX motif in the modified fibroin of (6-ii) is preferably 10% or more.

The sixth modified fibroin may have a tag sequence at either or both of the N-terminus and the C-terminus. Therefore, it is possible to isolate, immobilize, detect, or visualize the modified fibroin.

More specific examples of the modified fibroin having a tag sequence can include modified fibroin having (6-iii) an amino acid sequence set forth in SEQ ID NO: 33 (PRT888), SEQ ID NO: 34 (PRT965), SEQ ID NO: 35 (PRT889), SEQ ID NO: 36 (PRT916), SEQ ID NO: 37 (PRT918), SEQ ID NO: 38 (PRT699), SEQ ID NO: 39 (PRT698), SEQ ID NO: 40 (PRT966), SEQ ID NO: 43 (PRT917), or SEQ ID NO: 44 (PRT1028), or modified fibroin having (6-iv) an amino acid sequence having 90% or more sequence identity with the amino acid sequence set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44.

Each of the amino acid sequences set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, and SEQ ID NO: 44 is obtained by adding the amino acid sequence set forth in SEQ ID NO: 11 (having a His tag sequence and a hinge sequence) to the N-terminus of each of the amino acid sequences set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, and SEQ ID NO: 42. Since only the tag sequence is added to the N-terminus, the content rate of the glutamine residues is not changed, and the content rate of the glutamine residues in each of the amino acid sequences set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44 is 9% or less (Table 3).

TABLE 3

| Modified fibroin | Content of glutamine residue | Content of GPGXX motif | Hydro-phobicity of REP |
|---|---|---|---|
| PRT888 (SEQ ID NO: 33) | 6.3% | 27.9% | −0.07 |
| PRT965 (SEQ ID NO: 34) | 0.0% | 27.9% | −0.65 |
| PRT889 (SEQ ID NO: 35) | 0.0% | 27.9% | 0.35 |
| PRT916 (SEQ ID NO: 36) | 0.0% | 27.9% | 0.47 |
| PRT918 (SEQ ID NO: 37) | 0.0% | 27.9% | 0.45 |
| PRT699 (SEQ ID NO: 38) | 3.6% | 26.4% | −0.78 |
| PRT698 (SEQ ID NO: 39) | 0.0% | 26.4% | −0.03 |
| PRT966 (SEQ ID NO: 40) | 0.0% | 28.0% | 0.35 |
| PRT917 (SEQ ID NO: 43) | 0.0% | 27.9% | 0.46 |
| PRT1028 (SEQ ID NO: 44) | 0.0% | 28.1% | 0.05 |

The modified fibroin of (6-iii) may consist of the amino acid sequence set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44.

The modified fibroin of (6-iv) may consist of the amino acid sequence having 90% or more sequence identity with the amino acid sequence set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44. The modified fibroin of (6-iv) is also a protein containing a domain sequence represented by Formula 1: $[(A)_n \text{ motif-REP}]_m$ or Formula 2: $[(A)_n \text{ motif-REP}]_m\text{-}(A)_n$ motif. The sequence identity is preferably 95% or more.

It is preferable that a content rate of glutamine residues in the modified fibroin of (6-iv) is preferably 9% or less. In addition, it is preferable that a content rate of a GPGXX motif in the modified fibroin of (6-iv) is preferably 10% or more.

The sixth modified fibroin may include a secretory signal for releasing the protein produced in a recombinant protein production system to the outside of a host. A sequence of the secretory signal can be appropriately set depending on a type of the host.

The modified fibroin may be modified fibroin having at least two or more characteristics of the characteristics of the first modified fibroin, the second modified fibroin, the third modified fibroin, the fourth modified fibroin, the fifth modified fibroin, and the sixth modified fibroin.

The modified fibroin may be hydrophilic modified fibroin or hydrophobic modified fibroin. The hydrophobic modified fibroin is modified fibroin in which a value obtained by determining the sum of hydropathy indices (HI) of all amino acid residues constituting the modified fibroin and then dividing the sum by the number of all amino acid residues (average HI) is 0 or more. The hydropathy index is as shown in Table 1. In addition, the hydrophilic modified fibroin is modified fibroin in which the average HI is less than 0.

An example of the hydrophobic modified fibroin can include the above-described sixth modified fibroin. A more specific example of the hydrophobic modified fibroin can include modified fibroin having an amino acid sequence set forth in SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 43, or an amino acid sequence set forth in SEQ ID NO: 35, SEQ ID NO: 37, SEQ ID NO: 38, SEQ ID NO: 39, SEQ ID NO: 40, SEQ ID NO: 41, or SEQ ID NO: 44.

Examples of the hydrophilic modified fibroin can include the above-described first modified fibroin, second modified fibroin, third modified fibroin, fourth modified fibroin, and fifth modified fibroin. A more specific example of the hydrophilic modified fibroin can include fibroin having an amino acid sequence set forth in SEQ ID NO: 4, an amino acid sequence set forth in SEQ ID NO: 6, SEQ ID NO: 7, SEQ ID NO: 8, or SEQ ID NO: 9, an amino acid sequence set forth in SEQ ID NO: 13, SEQ ID NO: 11, SEQ ID NO: 14, or SEQ ID NO: 15, an amino acid sequence set forth in SEQ ID NO: 18, SEQ ID NO: 7, SEQ ID NO: 8, or SEQ ID NO: 9, an amino acid sequence set forth in SEQ ID NO: 17, SEQ ID NO: 11, SEQ ID NO: 14, or SEQ ID NO: 15, or an amino acid sequence set forth in SEQ ID NO: 19, SEQ ID NO: 20, or SEQ ID NO: 21.

(Production Method of Protein)

The protein can be produced by, for example, expressing a nucleic acid by a nucleic acid sequence encoding the protein and a host transformed with an expression vector having one or a plurality of regulatory sequences operably linked to the nucleic acid sequence.

A production method of a gene encoding the protein is not particularly limited. For example, the gene can be produced by a method in which a gene encoding a natural structural protein is amplified and cloned by a polymerase chain reaction (PCR) or the like, or a method of chemically synthesizing a gene. A method for chemically synthesizing a gene is not particularly limited. For example, genes can be chemically synthesized by a method of linking, by PCR or the like, oligonucleotides that are automatically synthesized by AKTA oligopilot plus 10/100 (GE Healthcare Japan Ltd.) or the like, based on the amino acid sequence information of the structural protein obtained from the web database of NCBI and the like. In this case, in order to facilitate purification or confirmation of the protein, a gene encoding a protein consisting of an amino acid sequence obtained by adding an amino acid sequence consisting of a start codon and a His10 tag to the N-terminus of the above amino acid sequence may be synthesized.

The regulatory sequence is a sequence that controls the expression of a protein in a host (for example, a promoter, an enhancer, a ribosome binding sequence, a transcription termination sequence, or the like), and can be appropriately selected depending on the type of the host. As a promoter, an inducible promoter which functions in host cells and is capable of inducing expression of a protein may be used. An inducible promoter is a promoter that can control transcription due to the presence of an inducer (expression inducer), the absence of a repressor molecule, or a physical factor such as an increase or decrease in temperature, osmotic pressure, or pH value.

The type of the expression vector such as a plasmid vector, a viral vector, a cosmid vector, a fosmid vector, or an artificial chromosome vector can be appropriately selected depending on the type of the host. As the expression vector, an expression vector which can automatically replicate in a host cell or can be incorporated into a chromosome of a host and which contains a promoter at a position capable of transcribing the nucleic acid encoding the protein is suitably used.

Both a prokaryote and a eukaryote such as yeast, filamentous fungi, insect cells, animal cells, and plant cells can be suitably used as hosts.

Preferred examples of the prokaryote can include bacteria belonging to the genus *Escherichia*, the genus *Brevibacillus*, the genus *Serratia*, the genus *Bacillus*, the genus *Microbacterium*, the genus *Brevibacterium*, the genus *Corynebacterium*, and the genus *Pseudomonas*. An example of microorganisms belonging to the genus *Escherichia* can include *E. coli*. An example of microorganisms belonging to the genus *Brevibacillus* can include *Brevibacillus agri*. An example of microorganisms belonging to the genus *Serratia* can include *Serratia liquefaciens*. An example of microorganisms belonging to the genus *Bacillus* can include *Bacillus subtilis*. An example of microorganisms belonging to the genus *Microbacterium* can include *Microbacterium ammoniaphilum*. An example of microorganisms belonging to the genus *Brevibacterium* can include *Brevibacterium divaricatum*. An example of microorganisms belonging to the genus *Corynebacterium* can include *Corynebacterium ammoniagenes*. An example of microorganisms belonging to the genus *Pseudomonas* can include *Pseudomonas putida*.

In a case where a prokaryote is used as a host, examples of a vector into which a nucleic acid encoding the recombinant protein is introduced can include pBTrp2 (manufactured by Boehringer Mannheim GmbH), pGEX (manufactured by Pharmacia Corporation), and pUC18, pBluescriptII, pSupex, pET22b, pCold, pUB110, and pNCO2 (JP 2002-238569 A).

Examples of the eukaryotic host can include yeast and filamentous fungi (mold or the like). An example of the yeast can include yeast which belongs to the genus *Saccharomyces*, the genus *Pichia*, or the genus *Schizosaccharomyces*. An example of filamentous fungi can include filamentous fungi belonging to the genus *Aspergillus*, the genus *Penicillium*, or the genus *Trichoderma*.

In a case where a eukaryote is used as a host, examples of a vector into which a nucleic acid encoding the protein is introduced can include YEP13 (ATCC37115) and YEp24 (ATCC37051). As a method of introducing an expression vector into the host cell, any method can be used as long as a DNA is introduced into the host cell. Examples thereof can include a method using calcium ions [Proc. Natl. Acad. Sci. USA, 69, 2110 (1972)], an electroporation method, a spheroplast method, a protoplast method, a lithium acetate method, and a competent method.

As a method of expressing a nucleic acid by a host transformed with an expression vector, secretory production, fusion protein expression, or the like, can be performed according to the method described in Molecular Cloning, 2nd edition, in addition to direct expression.

The protein can be produced by, for example, culturing a host transformed with the expression vector in a culture medium, producing and accumulating the protein in the culture medium, and then collecting the protein from the culture medium. A method of culturing the host in the culture medium can be performed according to a method commonly used for culturing a host.

In the case where the host is a prokaryote such as *E. coli* or a eukaryote such as yeast, any of a natural medium and a synthetic medium may be used as a culture medium as long as it contains a carbon source, a nitrogen source, inorganic salts, and the like which can be assimilated by the host and it is a culture medium capable of efficiently culturing the host.

As the carbon source, any carbon source that can be assimilated by the transformed microorganisms may be used, and it is possible to use, for example, carbohydrate such as glucose, fructose, sucrose, or molasses, starch, or starch hydrolyzates containing the carbohydrate, organic acid such as acetic acid or propionic acid, and alcohol such as ethanol or propanol. As the nitrogen source, for example, it is possible to use an ammonium salt of inorganic or organic acid such as ammonia, ammonium chloride, ammonium sulfate, ammonium acetate, or ammonium phosphate, other nitrogen-containing compounds, peptone, meat extract, yeast extract, corn steep liquor, casein hydrolyzate, soybean cake, soybean cake hydrolyzate, and various fermentative bacteria and digested products thereof. As the inorganic salts, for example, it is possible to use monopotassium phosphate, dipotassium phosphate, magnesium phosphate, magnesium sulfate, sodium chloride, ferrous sulfate, manganese sulfate, copper sulfate, and calcium carbonate.

A prokaryote such as *E. coli* or a eukaryote such as yeast can be cultured under aerobic conditions such as shaking culture or deep aeration stirring culture. A culture temperature is, for example, 15 to 40 °C. A culture time is generally 16 hours to 7 days. It is preferable to maintain a pH of the culture medium during the culture at 3.0 to 9.0. The pH of the culture medium can be adjusted using inorganic acid, organic acid, an alkali solution, urea, calcium carbonate, ammonia, or the like.

In addition, antibiotics such as ampicillin and tetracycline may be added to the culture medium during the culture, if necessary. When culturing microorganisms transformed with an expression vector using an inducible promoter as a promoter, an inducer may be added to the medium, if necessary. For example, when culturing microorganisms transformed with an expression vector using a lac promoter, isopropyl-β-D-thiogalactopyranoside or the like may be added to the medium, and when culturing microorganisms transformed with an expression vector using a trp promoter, indole acrylic acid or the like may be added to the medium.

Isolation and purification of the expressed protein can be performed by a commonly used method. For example, in the case where the protein is expressed in a dissolved state in cells, the host cells are collected by centrifugation after completion of the culture, the collected cells are suspended in an aqueous buffer, and then the host cells are disrupted using an ultrasonicator, a French press, a Manton-Gaulin homogenizer, a Dyno-Mill, or the like to obtain a cell-free extract. From the supernatant obtained by centrifuging the cell-free extract, a purified preparation can be obtained by a method commonly used for isolation and purification of a protein, that is, a solvent extraction method, a salting-out method using ammonium sulfate or the like, a desalting method, a precipitation method using an organic solvent, an anion exchange chromatography method using a resin such as diethylaminoethyl (DEAE)-Sepharose or DIAION HPA-75 (manufactured by Mitsubishi Kasei Kogyo Kabushiki Kaisha), a cation exchange chromatography method using a resin such as S-Sepharose FF (Pharmacia Corporation), a hydrophobic chromatography method using a resin such as butyl sepharose or phenyl sepharose, a gel filtration method using a molecular sieve, an affinity chromatography method, a chromatofocusing method, an electrophoresis method such as isoelectric focusing or the like, alone or in combination thereof.

In addition, in the case where the protein is expressed by formation of an insoluble matter in cells, similarly, the host cells are collected, disrupted, and then centrifuged to recover the insoluble matter of the protein as a precipitated fraction. The recovered insoluble matter of the protein can be solubilized with a protein denaturing agent. After this operation, a purified preparation of the protein can be obtained by the same isolation and purification method as described above. In the case where the protein is secreted extracellularly, the protein can be recovered from the culture supernatant. That is, a culture supernatant can be obtained by treating the culture by a method such as centrifugation, and a purified preparation can be obtained from the culture supernatant using the same isolation and purification method as described above.

(Production Method of Raw Material Composition)

In the present embodiment, the production method of the raw material composition is not particularly limited, and an example thereof may be a method including the following respective steps.

[Dissolution Step]

A dissolution step is a step of dissolving a protein in a solvent (for example, a carboxylic acid such as formic acid) to obtain a protein solution.

In the dissolution step, as a protein to be dissolved (hereinafter, referred to as "hereinafter, a protein to be targeted"), a purified protein may be used, or a protein in host cells in which the protein is expressed (recombinant protein) may be used. The purified protein may be a protein purified from host cells in which the protein is expressed. In a case where the protein in the host cells is dissolved as the target protein, the host cells are brought into contact with a solvent to dissolve the protein in the host cells in the solvent. Any host cell is used as long as it is a cell in which the target protein is expressed, and may be, for example, an intact cell or a cell subjected to a treatment such as a disruption treatment. Alternatively, the cell may be a cell subjected to a simple purification treatment in advance.

A method of purifying a protein from host cells in which the protein is expressed is not particularly limited, and, for example, the methods disclosed in JP 6077570 B2 and JP 6077569 B2 can be used.

In the dissolution step, in a case where a carboxylic acid such as formic acid is used as a solvent, an esterified protein is produced by a dehydration condensation reaction between a hydroxyl group in the protein and the carboxylic acid. As the carboxylic acid, it is possible to use, for example, a monocarboxylic acid such as formic acid, acetic acid, dichloroacetic acid, trifluoroacetic acid, propionic acid, butanoic acid, isobutyric acid, pentanoic acid, caproic acid, caprylic acid, capric acid, or benzoic acid, a saturated aliphatic carboxylic acid such as capric acid, lauric acid, myristic acid, palmitic acid, stearic acid, arachidic acid, behenic acid, lignoceric acid, cerotic acid, montanic acid, melissic acid, or ceroplastic acid, an unsaturated aliphatic carboxylic acid such as undecylenic acid, oleic acid, elaidic acid, cetoleic acid, erucic acid, brassidic acid, sorbic acid, linoleic acid, linolenic acid, arachidonic acid, propiolic acid, or stearolic acid, and a dicarboxylic acid such as oxalic acid, malonic acid, succinic acid, glutaric acid, adipic acid, pimelic acid, suberic acid, azelaic acid, sebacic acid, undecanoic acid, brassylic acid, maleic acid, fumaric acid, or glutaconic acid. The carboxylic acid may be in a form of acid anhydride or acid chloride.

The dissolution step may be performed at room temperature, or may be performed to dissolve the protein in the solvent while holding the temperature at various heating temperatures. A holding time for the heating temperature is not particularly limited, but may be 10 minutes or longer, and in consideration of industrial production, 10 to 120 minutes is preferred, 10 to 60 minutes is more preferred, and 10 to 30 minutes is still more preferred. The holding time for the heating temperature may be appropriately set under a condition in which the protein is sufficiently dissolved and impurities (other than the protein to be targeted) are less dissolved.

An addition amount of the solvent added to dissolve the protein is not particularly limited as long as it is the amount in which the protein can be dissolved.

In a case where a purified protein is dissolved, the addition amount of the solvent may be 1 to 100 times, 1 to 50 times, 1 to 25 times, 1 to 10 times, or 1 to 5 times, in terms of a ratio (volume (mL)/weight (g)) of a volume (mL) of the solvent to a weight (g) of the protein (dry powder containing the protein).

In a case where a protein in host cells in which the protein is expressed is dissolved, the addition amount of the solvent may be 1 to 100 times, 1 to 50 times, 1 to 25 times, 1 to 10 times, or 1 to 5 times, in terms of a ratio (volume (mL)/weight (g)) of a volume (mL) of the solvent to a weight (g) of the host cells.

The solvent may contain an inorganic salt. Solubility of the protein can be increased by adding the inorganic salt to the solvent.

Examples of the inorganic salt that can be added to the solvent can include an alkali metal halide, an alkaline earth metal halide, an alkaline earth metal nitrate, a thiocyanate, and a perchlorate.

Examples of the alkali metal halide can include potassium bromide, sodium bromide, lithium bromide, potassium chloride, sodium chloride, lithium chloride, sodium fluoride, potassium fluoride, cesium fluoride, potassium iodide, sodium iodide, and lithium iodide.

Examples of the alkaline earth metal halide can include calcium chloride, magnesium chloride, magnesium bromide, calcium bromide, magnesium iodide, and calcium iodide.

Examples of the alkaline earth metal nitrate can include calcium nitrate, magnesium nitrate, strontium nitrate, and barium nitrate.

Examples of the thiocyanate can include sodium thiocyanate, ammonium thiocyanate, and guanidinium thiocyanate.

Examples of the perchlorate can include ammonium perchlorate, potassium perchlorate, calcium perchlorate, silver perchlorate, sodium perchlorate, and magnesium perchlorate.

These inorganic salts may be used alone or in a combination of two or more thereof.

Examples of a preferred inorganic salt can include an alkali metal halide and an alkaline earth metal halide. Specific examples of the preferred inorganic salt can include lithium chloride and calcium chloride.

An addition amount (content) of the inorganic salt may be 0.5% by mass to 10% by mass or 0.5% by mass to 5% by mass, with respect to a total mass of the solvent.

An insoluble matter may be removed from the protein solution, if necessary. That is, the production method of the raw material composition may include a step of removing an insoluble matter from the protein solution after the dissolution step, if necessary. Examples of a method of removing the insoluble matter from the protein solution can include general methods such as centrifugation and filter filtration with a drum filter, a press filter, or the like. In the case of filter filtration, the insoluble matter can be more efficiently removed from the protein solution using a filter aid such as celite or diatomaceous earth and a pre-coating agent in combination.

The protein solution contains a protein and a solvent (solvent for dissolution) that dissolves the protein. The protein solution may contain impurities included together with the protein in the dissolution step. The protein solution may be a solution for molding the raw material composition.

A content of the protein in the protein solution may be 5% by mass to 35% by mass, 5% by mass to 50% by mass, 10% by mass to 40% by mass, or 15% by mass to 35% by mass, with respect to a total amount of the protein solution.

A method of producing the protein to which the ester group is added is not particularly limited, but a production method using a carboxylic acid such as formic acid as a solvent in the above-described dissolution step may be used, or other production methods performed in the above-described dissolution step may be used. Such a method may be, for example, a production method performed in a step of reacting at least one selected from the group consisting of a carboxylic acid, acid anhydride, and acid chloride with a protein having a hydroxyl group such as serine, tyrosine, or threonine.

[Molding Step]

A molding step is a step of molding a raw material composition using a protein solution. A shape of the raw material composition is not particularly limited, and examples of the raw material composition can include a fiber, a film, a molded article, a gel, a porous body, and a particle.

In the protein solution, it is preferable to adjust a concentration and viscosity of the protein depending on use of the raw material composition to be molded.

A method of adjusting the concentration of the protein in the protein solution is not particularly limited, and examples thereof can include a method of increasing the concentration of the protein by evaporating a solvent by distillation, a method using a solution having a high concentration of a protein in the dissolution step, and a method of reducing an addition amount of a solvent with respect to the amount of protein.

A viscosity suitable for spinning is generally 1,000 to 50,000 cP (centipoise) at 40 °C, and the viscosity can be measured using, for example, an “EMS viscometer” (trade name) manufactured by Kyoto Electronics Manufacturing Co., Ltd. When the viscosity of the protein solution is not within the above range, the viscosity of the protein solution may be adjusted to a viscosity at which spinning can be performed. The viscosity can be adjusted using the above-described method and the like. The solvent may contain an appropriate inorganic salt as exemplified above.

In a case where the raw material composition to be molded is a raw material (raw material fiber), a content (concentration) of a protein in the protein solution may be adjusted to have a concentration and viscosity at which spinning can be performed, if necessary. A method of adjusting the concentration and viscosity of the protein is not particularly limited. In addition, an example of a spinning method can include wet spinning. When the protein solution having the adjusted concentration and viscosity suitable for spinning is added to a coagulation liquid as a dope solution, the protein coagulates. In this case, since the protein solution is added to the coagulation liquid as a yarn-shaped liquid, the protein coagulates in a yarn state, and thus, a yarn (undrawn yarn) can be formed. The undrawn yarn can be formed, for example, according to a method disclosed in JP 5584932 B2.

Hereinafter, an example of the wet spinning will be described, but a spinning method is not limited, and may be dry wet spinning.

Wet Spinning and Drawing (a) Wet Spinning

The coagulation liquid may be any solution that can be desolventized. As the coagulation liquid, it is preferable to use a lower alcohol having 1 to 5 carbon atoms, such as methanol, ethanol, or 2-propanol, or acetone. The coagulation liquid may also contain water. A temperature of the coagulation liquid is preferably 5 to 30 °C from the viewpoint of stability of spinning.

A method of adding the protein solution as a yarn-shaped liquid is not particularly limited, and an example thereof can include a method of extruding (discharging) the protein solution from a spinneret to a coagulation liquid in a desolvation bath. An undrawn yarn is obtained by coagulating the protein. An extrusion (discharging) speed in a case where the protein solution is extruded (discharged) to the coagulation liquid can be appropriately set according to a diameter of the spinneret, a viscosity of the protein solution, or the like. For example, in a case of a syringe pump having a nozzle having a diameter of 0.1 to 0.6 mm, an extrusion (discharging) speed may be 0.2 to 6.0 mL/h per hole, or may be 1.4 to 4.0 mL/h per hole, from the viewpoint of stability of spinning. A length of the desolvation bath (coagulation liquid bath) into which the coagulation liquid is introduced is not particularly limited, but may be, for example, 200 to 500 mm. A withdrawing speed of the undrawn yarn formed by coagulation of the protein may be, for example, 1 to 14 m/min, and a retention time may be, for example, 0.01 to 0.15 min. The withdrawing speed of the undrawn yarn may be 1 to 3 m/min from the viewpoint of efficiency of desolvation. The undrawn yarn formed by coagulation of the protein may be further drawn (pre-drawn) in a coagulation liquid, but it is preferable that the coagulation liquid is kept at a low temperature and the undrawn yarn is drawn from the coagulation liquid in a form of an undrawn yarn, from the viewpoint of suppressing vaporization of the lower alcohol used in the coagulation liquid.

(b) Drawing

A step of further drawing the undrawn yarn obtained by the above-described method can be included. The drawing may be one-stage drawing or multi-stage drawing including two or more stages. When the drawing is performed in multi stages, molecules can be aligned in multiple stages and a total draw ratio can be increased, which is suitable for producing a fiber having high toughness.

In a case where the raw material composition is a film (raw material film), the protein solution may be adjusted to have a concentration and viscosity at which the protein solution can be formed into a film, if necessary. A method of forming the raw material composition into a film is not particularly limited, and an example thereof can include a method of obtaining a film having a predetermined thickness by applying a protein solution to a flat plate having a resistance to a solvent in a predetermined thickness to form a coating film, and removing the solvent from the coating film.

As a method of forming a film having a predetermined thickness can include a casting method. In a case where a film is formed by a casting method, a raw material film (a polypeptide film) can be obtained by casting, on a flat plate, the protein solution to a thickness of several microns or more using a tool such as a doctor coat or a knife coater to form a cast film, and then removing the solvent by reduced pressure drying or immersion in a desolvation bath. The raw material film can be formed, for example, according to a method disclosed in JP 5678283 B2.

In a case where the raw material composition is a molded article (raw material molded article), a method of forming the raw material molded article is not particularly limited. For example, dried protein powder is introduced into a pressure molding machine, and pressurization and heating are performed using a hand press machine or the like, such that the dried protein power reaches a required temperature, and thus, a raw material molded article can be obtained. In addition, the raw material molded article can be formed according to a method described in the patent literature (JP 2017-539869 A, PCT/JP2016/076500).

In a case where the raw material composition is a gel (raw material gel), a method of forming the raw material gel is not particularly limited. For example, the raw material gel can be obtained by a solution production step of dissolving a dry protein in a solvent for dissolution to obtain a solution of a polypeptide and a step of substituting the solution produced in the solution generation step with a water-soluble solvent. In this case, a step of pouring the solution into a mold to mold the raw material gel into a predetermined shape is performed between the solution production step and the step of substituting the solvent for dissolution with the water-soluble solvent, or cutting of the raw material gel into a predetermined shape can be performed after the step of substituting the solvent for dissolution with the water-soluble solvent. In addition, the raw material gel can be formed, for example, according to a method disclosed in JP 05782580 B2.

In a case where the raw material composition is a porous body (raw material porous body), the protein solution may be adjusted to have the concentration and viscosity at which the protein solution can be formed into a porous body. A method of forming the raw material porous body is not particularly limited. Examples thereof can include a method of obtaining a raw material porous body by adding an appropriate amount of a foaming agent to the protein solution adjusted to have a concentration and viscosity suitable for forming the protein solution into a porous body and removing the solvent, and a method described in JP 5796147 B2.

In a case where the raw material composition is a particle (raw material particle), a method of forming the particle is not particularly limited. The raw material particle can be obtained by, for example, a method including a step of obtaining an aqueous solution of a protein by substituting a solvent in a dope solution with a water-soluble solvent using the above-described dope solution, and a step of drying the aqueous solution of the protein. The water-soluble solvent is a solvent containing water, and examples thereof can include water, a water-soluble buffer, and a physiological salt solution. The step of substituting the solvent with the water-soluble solvent is preferably performed by a method in which a dope solution is placed in a dialysis membrane, the dialysis membrane is immersed in a water-soluble solvent, and the water-soluble solvent is replaced at least once. Specifically, it is more preferable that the dope solution is placed in the dialysis membrane, the dialysis membrane is left to stand in the water-soluble solvent in an amount of 100 times or more the amount of the dope solution (dose) for 3 hours, and the replacement of the water-soluble solvent is performed three times or more in total. Any dialysis membrane may be used as long as it does not allow the protein to permeate, and for example, the dialysis membrane may be a cellulose dialysis membrane or the like. The amount of the solvent in the dope solution can be adjusted to approach zero by repeating the substitution with the water-soluble solvent. The dialysis membrane may not be used in the latter half of the step of substituting the solvent with the water-soluble solvent. In the step of drying the aqueous solution of the protein, vacuum freeze-drying is preferable used. A degree of vacuum during the vacuum freeze-drying is preferably 200 pascal (Pa) or less, more preferably 150 Pa or less, and still more preferably 100 Pa or less. A moisture content in the freeze-dried particles is preferably 5.0% or less and more preferably 3.0% or less.

In a case where the raw material composition is a fiber (raw material fiber), the raw material fiber may be a hank state or a cloth state.

A lower limit of a fiber diameter of the raw material fiber may be, for example, 10 μm or more, 15 μm or more, 20 μm or more, more than 25 μm, 28 μm or more, 30 μm or more, 32 μm or more, 34 μm or more, 35 μm or more, 36 μm or more, 38 μm or more, or 40 μm or more. An upper limit of the fiber diameter of the raw material fiber is preferably 120 μm or less.

The fiber diameter of the raw material fiber may be 10 μm to 120 μm, 10 μm to 40 μm, 10 μm to 30 μm, 10 μm to 20 μm, 10 μm to 25 μm, 15 μm to 25 μm, more than 25 μm to 120 μm, 30 μm to 120 μm, 35 μm to 120 μm, 40 μm to 120 μm, 45 μm to 120 μm, 48 μm to 120 μm, 50 μm to 120 μm, 55 μm to 120 μm, 60 μm to 120 μm, 65 μm to 120 μm, 55 μm to 100 μm, 55 μm to 80 μm, or 60 μm to 80 μm. When the fiber diameter is 10 μm or more, it is possible to reduce the shrinkage by contact with water. When the fiber diameter is 120 μm or less, desolvation when forming the fiber can be further efficiently performed, and a hydrolysis reaction rate of the ester group can be further increased.

(Production Method of Protein Composition)

A production method according to the present embodiment includes a step of hydrolyzing an ester group by bringing a raw material composition containing an esterified protein (a protein having an ester group) into contact with an acidic or basic medium (hereinafter, also referred to as a "hydrolysis step"). By performing the hydrolysis step for the ester group, it is possible to perform a shrinkage treatment on the raw material composition at the same time, thereby obtaining a shrink-proof effect.

[Hydrolysis Step]

In the present embodiment, the medium may be a medium containing water. The medium containing water may be an aqueous solution or water vapor. The medium containing water may be an acidic or basic medium. The acidic medium may have acidity. For example, the acidic medium may be an acidic aqueous solution or acidic water vapor having a pH of lower than 7, and the acidic medium is preferably an acidic aqueous solution or acidic water vapor having a pH of 1 or higher, from the viewpoint of controlling hydrolysis and side reaction of a molecule chain. The basic medium may have alkalinity. For example, the basic medium may be a basic aqueous solution or basic water vapor having a pH of higher than 7, and the basic medium is preferably a basic aqueous solution or basic water vapor having a pH of 12 or lower, from the viewpoint of controlling hydrolysis and side reaction of a molecule chain.

In the present embodiment, a temperature of the medium containing water is 40 °C to 180 °C. The temperature of the medium containing water may be, for example, 50 °C or higher, 60 °C or higher, 70 °C or higher, 80 °C or higher, 85 °C or higher, 90 °C or higher, or 95 °C or higher. The temperature of the medium containing water is preferably a boiling point or lower.

In the present embodiment, an example of a method for performing hydrolysis can include a method of bringing a raw material composition (for example, a raw material fiber) into contact with an acidic or basic aqueous solution. In this case, the amount of acidic or basic substances is preferably 0.1% by mass or more, and more preferably 1.0% by mass or more, with respect to the total amount of the protein solution.

The acidic substances that can be used in hydrolysis may be, but not particularly limited to, an inorganic acid or organic acid. Examples of the inorganic acid can include hydrochloric acid, sulfuric acid, nitric acid, phosphoric acid, and boric acid. Examples of the organic acid can include carboxylic acid and sulfonic acid. Examples of the carboxylic acid can include a monocarboxylic acid such as formic acid, acetic acid, dichloroacetic acid, trifluoroacetic acid, propionic acid, butanoic acid, isobutyric acid, pentanoic acid, caproic acid, caprylic acid, capric acid, or benzoic acid, a saturated aliphatic carboxylic acid such as capric acid, lauric acid, myristic acid, palmitic acid, stearic acid, arachidic acid, behenic acid, lignoceric acid, cerotic acid, montanic acid, melissic acid, or ceroplastic acid, an unsaturated aliphatic carboxylic acid such as undecylenic acid, oleic acid, elaidic acid, cetoleic acid, erucic acid, brassidic acid, sorbic acid, linoleic acid, linolenic acid, arachidonic acid, propiolic acid, or stearolic acid, and a dicarboxylic acid such as oxalic acid, malonic acid, succinic acid, glutaric acid, adipic acid, pimelic acid, suberic acid, azelaic acid, sebacic acid, undecanoic acid, brassylic acid, maleic acid, fumaric acid, or glutaconic acid. The carboxylic acid may be in a form of acid anhydride or acid chloride. Examples of the sulfonic acid can include methanesulfonic acid, trifluoromethanesulfonic acid, benzenesulfonic acid, and p-toluenesulfonic acid.

The basic substances that can be used in hydrolysis may be, but not particularly limited to, an inorganic base or organic base. The inorganic base is not particularly limited as long as it is soluble in water. Examples of the inorganic base can include potassium hydroxide, sodium hydroxide, sodium bicarbonate, and sodium carbonate. Examples of the organic base can include alkylamine such as ammonia, methylamine, dimethylamine, trimethylamine, ethylamine, diethylamine, and triethylamine, and primary to tertiary amines such as aminoethanol, methylaminoethanol, dimethylaminoethanol, ethylaminoethanol, diethylaminoethanol, and diethanolamine.

The hydrolysis of the ester group is an equilibrium reaction. An acid similar to the acid produced when the ester group is dissociated can be used as an acid required for hydrolysis, but it is preferable not to use such an acid.

In the present embodiment, the hydrolysis proceeds under an acidic condition or basic condition. An acidic condition in which a pH is 1 to 6 or a basic condition in which a pH is 8 to 14 is preferred, and the pH can be adjusted by acidic substances or basic substances to be used.

In the present embodiment, in a case where a basic aqueous solution is used, the pH is preferably higher than 8, and preferably 12 or lower, from the viewpoint of the above-described reasons.

In a case where the basic aqueous solution is used, after the carboxylic acid is dissociated by hydrolysis, a carboxylic acid anion is formed. In this case, the electrophilicity is lost, and thus, a reverse reaction is less likely to occur. The pH of the basic aqueous solution is preferably 8 to 14, from the viewpoint of implementing high reactivity without heating, and the pH of the basic aqueous solution is more preferably higher than 8, from the viewpoint of the hydrolysis reaction rate.

Since the hydrolysis of the ester group proceeds rapidly in the acidic or basic aqueous solution, a reaction time is not limited, but is preferably longer than 1 minute, from the viewpoint of sufficiently removing the ester group.

In the present embodiment, a temperature at which the hydrolysis is performed may be, for example, 40 °C or higher, 50 °C or higher, 60 °C or higher, 70 °C or higher, 80 °C or higher, 85 °C or higher, 90 °C or higher, or 95 °C or higher. The temperature at which the hydrolysis is performed may be, for example, 180 °C or lower, and is preferably a boiling point or lower.

In the present embodiment, a contact time with the medium containing water may be, for example, 5 minutes or longer, 10 minutes or longer, 20 minutes or longer, or 30 minutes or longer. The contact time with the medium containing water may be 90 minutes or shorter, 60 minutes or shorter, or 40 minutes or shorter.

In the present embodiment, the acidic substances or basic substances may remain in the protein composition (for example, the protein fiber) taken out from the aqueous solution used for the hydrolysis, and the acidic substances or basic substances may cause breakage of the molecular chains. In order to prevent the breakage of the molecular chains, the production method of the protein composition (for example, the protein fiber) may further include a step of removing the remaining acid substances or basic substances. Examples of the step of removing the remaining acid substances or basic substances can include a step of washing the protein composition (for example, the protein fiber) with water and a step of neutralizing the protein composition (for example, the protein fiber).

In the present embodiment, in a case where the protein composition is a protein fiber, the protein fiber obtained in the hydrolysis step may have a shrinkage rate of −5% to +5%, the shrinkage rate being defined by the following Equation (1). Details of the shrinkage rate will be described below, the shrinkage rate defined by the following Equation (1):

$$\text{Shrinkage rate}=\{1-(\text{length of protein fiber when dried from wet state}/\text{length of protein fiber before in wet state})\}\times 100[\%]$$

[Shrinking Step]

The production method according to the present embodiment may further include a step of irreversibly shrinking the raw material composition (for example, the raw material fiber) before and/or after the hydrolysis step (hereinafter, also referred to as a "shrinking step"). By performing the hydrolysis step, the raw material composition (for example, the raw material fiber) can be simultaneously subjected to a shrinkage (shrink-proof) treatment, and thus, one or both of the shrinking steps can be omitted. In the shrinking step, the raw material composition may be irreversibly shrunk by bringing the raw material composition (for example, the raw material fiber) into contact with water, or the raw material composition may be irreversibly shrunk by heating and relaxing the raw material composition (for example, the raw material fiber). In the case where the raw material composition (for example, the raw material fiber) is irreversibly shrunk by bringing the raw material fiber into contact with water, the irreversibly shrunk composition may be dried and further shrunk.

(Shrinking Step by Contact with Water (Contact Step))

The raw material fiber (the fiber containing a protein) according to the present embodiment has the property of shrinking when being in contact (being wetted) with water below the boiling point. Therefore, in the shrinking step, the raw material fiber is brought into contact with water, such that a protein fiber having a shrinkage history of being irreversibly shrunk can be obtained. A step of irreversibly shrinking the raw material fiber by bringing the raw material fiber into contact with water is hereinafter referred to as a "contact step".

It is considered that the irreversible shrinkage of the raw material fiber (the fiber containing the protein) in the contact step occurs, for example, for the following reasons. That is, one reason is considered to be due to a primary structure of the raw material fiber (the fiber containing the protein). Another reason is considered to be that, for example, in the raw material fiber (the fiber containing the protein) having a residual stress due to drawing or the like in the production process, the residual stress is relieved by water entering between fibers or into the fiber.

In the contact step, the raw material fiber before being brought into contact with water after spinning is brought into contact with water to bring the raw material fiber into a wet state. The wet state refers to a state in which at least a part of the raw material fiber is wetted with water. Therefore, the raw material fiber can be shrunk regardless of an external force. This shrinkage is irreversible.

A temperature of the water coming into contact with the raw material fiber in the contact step may be lower than a boiling point. Therefore, handleability, workability in the shrinking step, and the like are improved. In addition, a lower limit of the temperature of the water is preferably 10 °C or higher, more preferably 40 °C or higher, still more preferably 70 °C or higher, still more preferably 80 °C or higher, and particularly preferably 90 °C or higher, from the viewpoint of sufficiently shortening the shrinkage time. An upper limit of the temperature of the water is preferably the boiling point or lower.

In the contact step, a method of bringing the raw material fiber into contact with water is not particularly limited. Examples of the method can include a method of immersing the raw material fiber in water, a method of spraying water onto the raw material fiber at room temperature or in a heated steam state, and a method of exposing the raw material fiber to a high humidity environment filled with water vapor. Among these methods, the method of immersing the raw material fiber in water is preferred in the contact step, since the shrinkage time can be effectively shortened and the processing equipment can be simplified.

In the contact step, when the raw material fiber is brought into contact with water in a relaxed state, the raw material fiber may be not only shrunk but also be curled to be wavy. In order to prevent the occurrence of curling, for example, the contact step may be performed in a state where the raw material fiber is not relaxed, for example, in a state where the raw material fiber is brought into contact with water while being tensioned in an axial direction of the fiber to the extent that a tension is not applied.

(Drying Step)

The production method according to the present embodiment may further include a drying step. The drying step is a step of drying the raw material fiber subjected to the contact step (or the protein fiber obtained through the contact step). Drying may be, for example, natural drying, or forced drying using drying equipment. As the drying equipment, any known drying equipment of contact type or non-contact type can be used. In addition, a drying temperature is not limited as long as it is lower than a temperature at which the protein contained in the raw material fiber is degraded or the raw material fiber is thermally damaged. In general, the drying temperature is a temperature in a range of 20 to 150 °C, and is preferably a temperature in a range of 50 to 100 °C. When the temperature is in this range, the fiber is more quickly and efficiently dried without thermal damage to the fiber or degradation of the protein contained in the fiber. A drying time is appropriately set depending on the drying temperature or the like, and for example, a time during which the influence on the quality and physical properties of the protein fiber due to overdrying can be eliminated as much as possible is employed.

Figure 5:
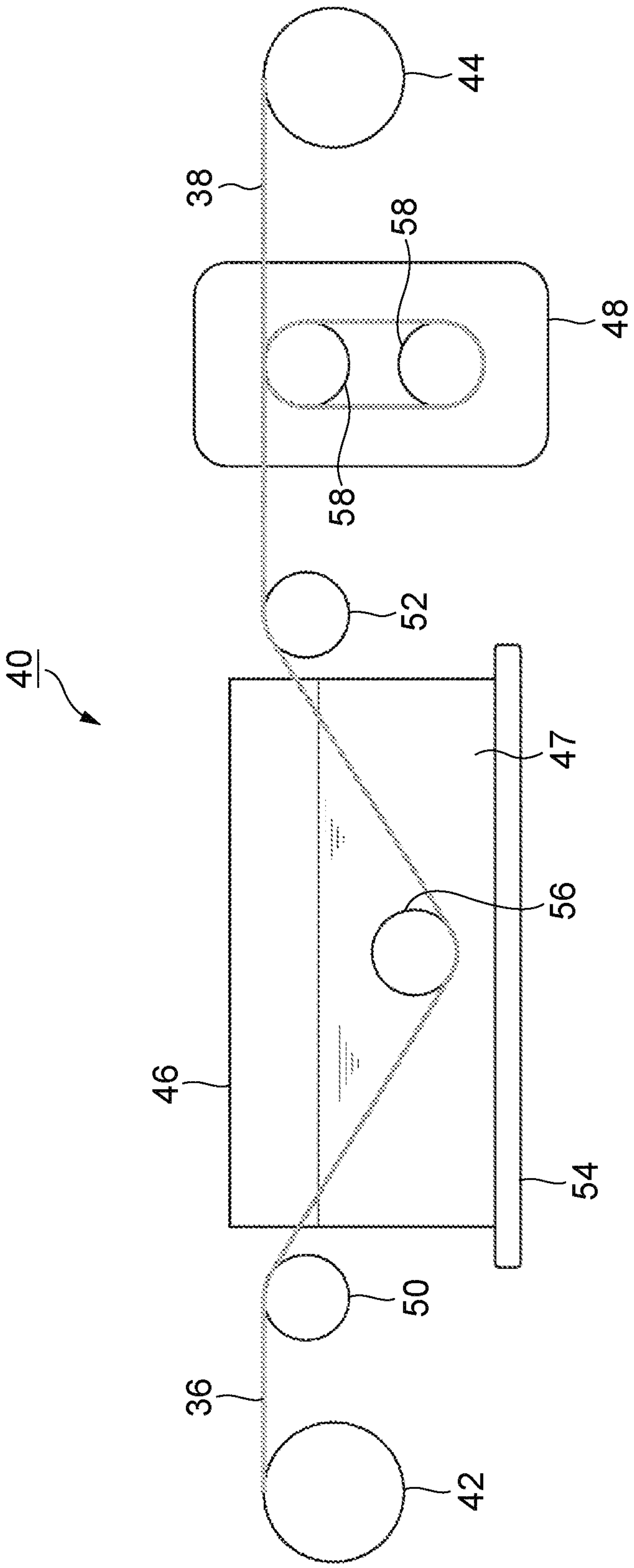
FIG. 5 is an explanation diagram schematically illustrating an example of a production apparatus for producing a protein fiber.

FIG. 5 is an explanation diagram schematically illustrating an example of a production apparatus for producing a protein fiber. A production apparatus 40 illustrated in FIG. 5 includes a feed roller 42 for feeding the raw material fiber, a winder 44 for winding a protein fiber 38, a water bath 46 for performing the contact step, and a dryer 48 for performing the drying step.

More specifically, the feed roller 42 can be loaded with a wound product of a raw material fiber 36, and the raw material fiber 36 can be continuously and automatically fed from the wound product of the raw material fiber 36 by rotation of an electric motor or the like (not illustrated). The winder 44 can continuously and automatically wind the protein fiber 38 produced through the contact step and the drying step after being fed out from the feed roller 42 by the rotation of the electric motor (not illustrated). Here, a feed speed of the raw material fiber 36 by the feed roller 42 and a winding speed of the protein fiber 38 by the winder 44 can be controlled independently of each other.

The water bath 46 and the dryer 48 are arranged between the feed roller 42 and the winder 44 on the upstream side and the downstream side in a feed direction of the raw material fiber 36, respectively. The production apparatus 40 illustrated in FIG. 5 includes relay rollers 50 and 52 relaying the raw material fiber 36 before and after the contact step which moves from the feed roller 42 toward the winder 44.

The water bath 46 includes a heater 54, and water 47 heated by the heater 54 is accommodated in the water bath 46. In addition, in the water bath 46, a tension roller 56 is installed in a state of being immersed in the water 47. Accordingly, the raw material fiber 36 fed from the feed roller 42 moves toward the winder 44 while being immersed in the water 47 in a state of being wound around the tension roller 56 in the water bath 46. An immersion time of the raw material fiber 36 in the water 47 is appropriately controlled according to a moving speed of the raw material fiber 36.

The dryer 48 has a pair of hot rollers 58. The pair of hot rollers 58 can be wound with the raw material fiber 36 which is released from the water bath 46 and moves toward the winder 44. Accordingly, the raw material fiber 36 immersed in the water 47 in the water bath 46 is heated by the pair of hot rollers 58 in the dryer 48, dried, and then further fed toward the winder 44.

Figure 4:
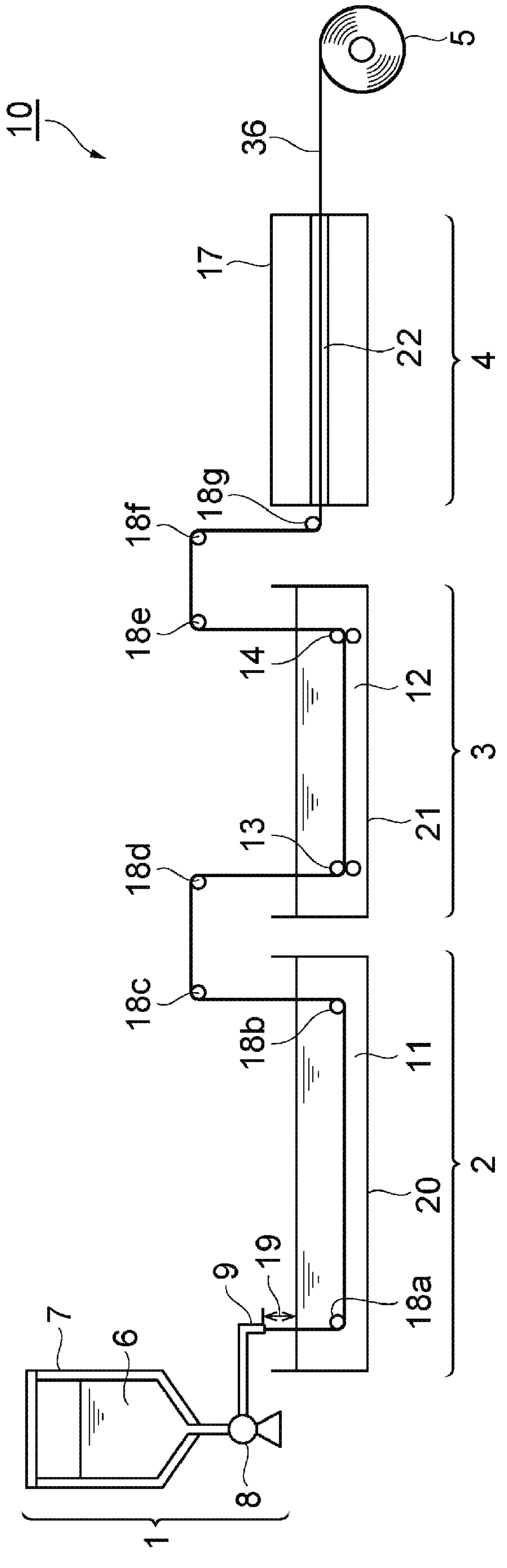
FIG. 4 is an explanation diagram schematically illustrating an example of a spinning apparatus for producing a raw material fiber.

When the protein fiber 38 is produced using the production apparatus 40 having such a structure, first, for example, the wound product of the raw material fiber 36 spun using the spinning apparatus 10 illustrated in FIG. 4 is mounted on the feed roller 42. Next, the raw material fiber 36 is continuously fed from the feed roller 42 and immersed in the water 47 in the water bath 46. In this case, for example, the winding speed of the winder 44 is slower than the feed speed of the feed roller 42. Accordingly, since the raw material fiber 36 is shrunk due to contact with the water 47 in a state of not being relaxed between the feed roller 42 and the winder 44, the occurrence of curling can be prevented. The raw material fiber 36 is irreversibly shrunk due to contact with the water 47.

Next, the raw material fiber 36 after being brought into contact with the water 47 (or the protein fiber 38 produced through contact with the water 47) is heated by the pair of hot rollers 58 of the dryer 48. Accordingly, the raw material fiber 36 after being brought into contact with the water 47 (or the protein fiber 38 produced through contact with the water 47) can be dried and further shrunk. In this case, a ratio of the feed speed of the feed roller 42 and the winding speed of the winder 44 can be controlled so that the length of the protein fiber 38 is not changed. Then, the obtained protein fiber 38 is wound around the winder 44 to obtain the wound product of the protein fiber 38.

Figure 6:
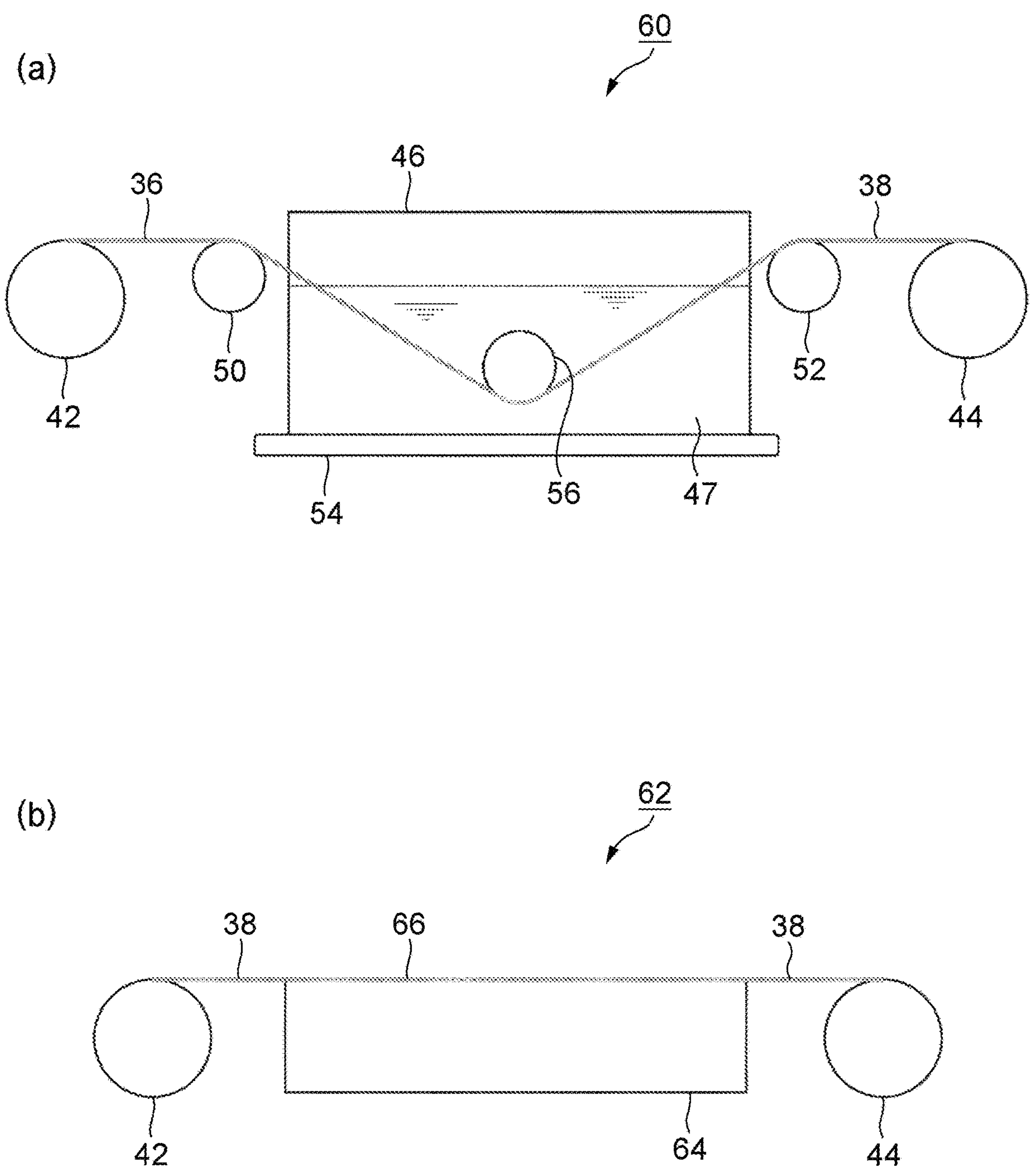
FIG. 6 is an explanation diagram schematically illustrating an example of a production apparatus for producing a protein fiber.

Instead of the pair of hot rollers 58, the raw material fiber 36 obtained after being brought into contact with the water 47 may be dried using drying equipment having only a heat source, such as a dry heat plate 64 as illustrated in FIG. 6(*b*). Also, in this case, by adjusting a relative speed between the feed speed of the feed roller 42 and the winding speed of the winder 44 in the same manner as in the case of using the pair of hot rollers 58 as the drying equipment, the length of the protein fiber cannot be changed. Here, the drying means includes the dry heat plate 64. In addition, the dryer 48 is optional.

As described above, the protein fiber 38 to be targeted can be automatically, continuously, and extremely easily produced using the production apparatus 40.

Figure 7:
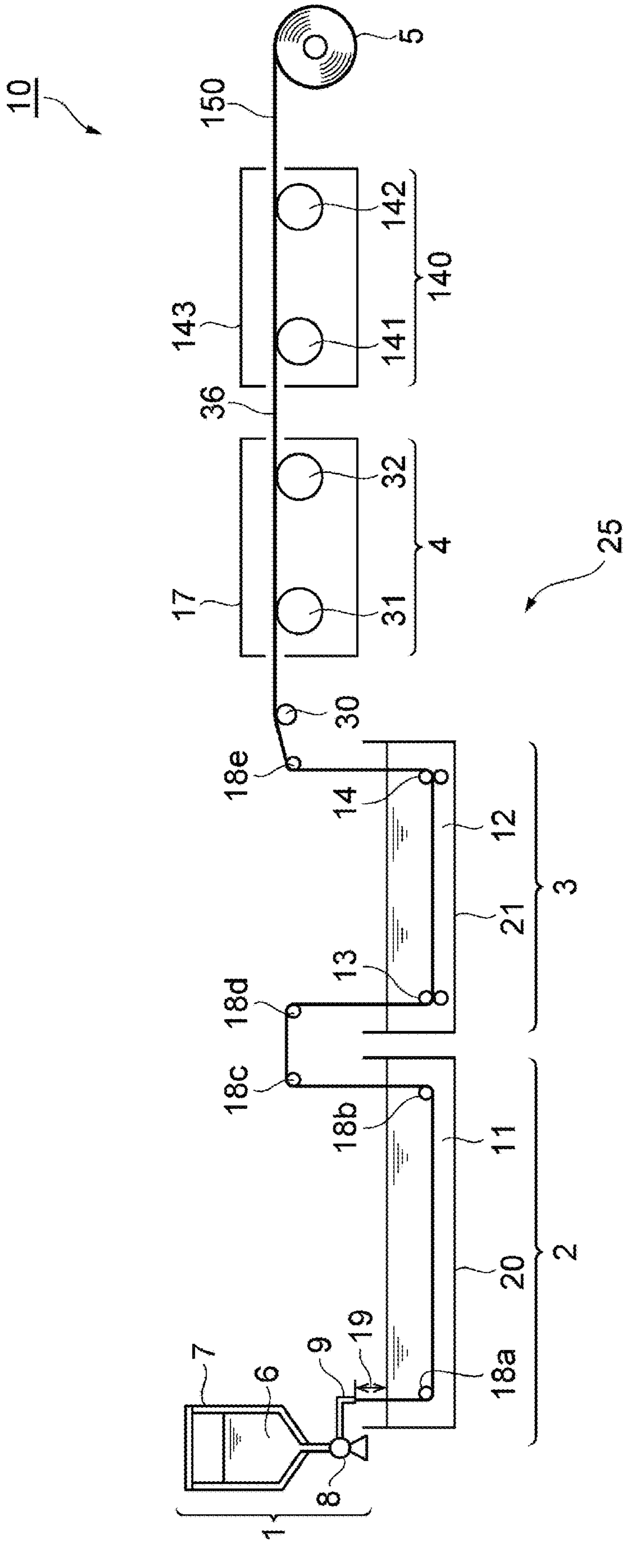
FIG. 7 is an explanation diagram schematically illustrating an example of a production apparatus for producing a protein fiber.

FIG. 6 is an explanation diagram schematically illustrating another example of a production apparatus for producing a protein fiber. FIG. 6(*a*) illustrates a processing device that is included in the production apparatus and that performs the contact step. FIG. 6(*b*) illustrates a drying device that is included in the production apparatus and that performs the drying step. The production apparatus illustrated in FIG. 7 includes a processing device 60 for performing the contact step on the raw material fiber 36, and a drying device 62 for drying the raw material fiber 36 after the contact step (or the protein fiber 38 produced through the contact step), and the production apparatus has a structure in which these devices are installed independently of each other.

More specifically, the processing device 60 illustrated in FIG. 6(*a*) has a structure in which the feed roller 42, the water bath 46, and the winder 44 are arranged in order from the upstream side to the downstream side in a moving direction of the raw material fiber 36. Such a processing device 60 is designed to allow the raw material fiber 36 fed from the feed roller 42 to be immersed in the water 47 in the water bath 46 and to be shrunk. In addition, the obtained protein fiber 38 is wound around the winder 44. In this case, for example, the winding speed of the winder 44 is slower than the feed speed of the feed roller 42. Accordingly, since the raw material fiber 36 is shrunk due to contact with the water 47 in a state of being relaxed between the feed roller 42 and the winder 44, it is possible to prevent the fiber from being tensioned. The raw material fiber 36 is irreversibly shrunk due to contact with the water 47.

The drying device 62 illustrated in FIG. 6(*b*) includes a feed roller 42, a winder 44, and a dry heat plate 64. The dry heat plate 64 is arranged between the feed roller 42 and the winder 44 so that a dry heat surface 66 comes into contact with the protein fiber 38 and extends along in the moving direction thereof. In the drying device 62, as described above, the length of the protein fiber 38 cannot be changed by, for example, controlling a ratio of a feed speed of the feed roller 42 and a winding speed of the winder 44.

By using the production apparatus having such a structure, the protein fiber 38 is obtained by shrinking the raw material fiber 36 by the processing device 60, and then, the protein fiber 38 can be dried by the drying device 62.

The feed roller 42 and the winder 44 may be omitted from the processing device 60 illustrated in FIG. 6(*a*), and the processing device may include only the water bath 46. In a case where the production apparatus including such a processing device is used, for example, the protein fiber is produced in a so-called batch system. In addition, the drying device 62 illustrated in FIG. 6(*b*) is optional.

(Shrinking Step by Heating and Relaxation)

Figure 8:
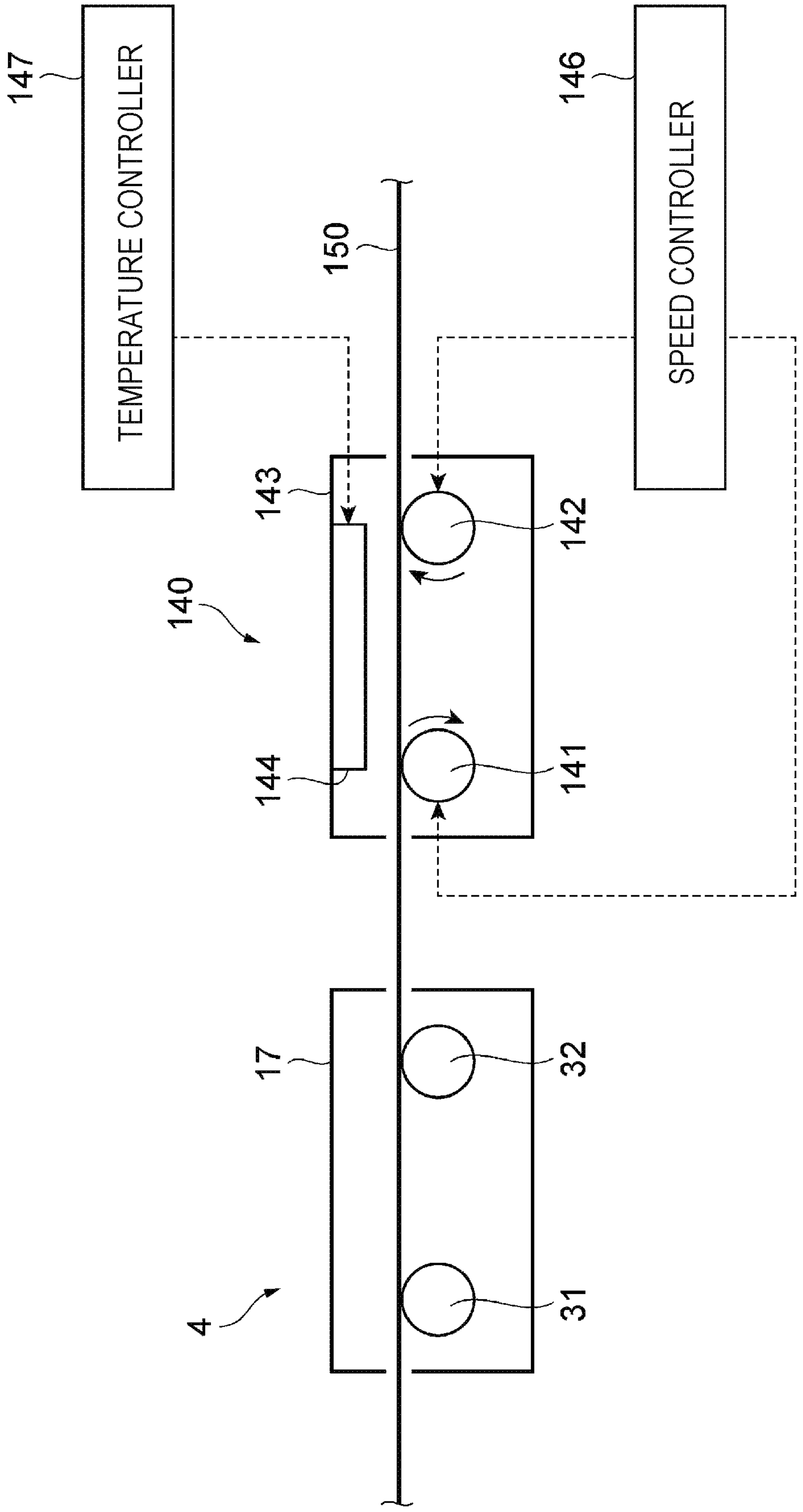
FIG. 8 is an explanation diagram schematically illustrating speed control means and temperature control means which can be provided in a high temperature heating furnace of FIG. 7.

The shrinking step of irreversibly shrinking the raw material fiber may be performed by heating and relaxing the raw material fiber. The heating and relaxation of the raw material fiber can be performed by heating the raw material fiber and relaxing and shrinking the heated raw material fiber. Hereinafter, in the shrinkage performed by the heating and relaxation of the raw material fiber, the step of heating the raw material fiber is referred to as a "heating step", and the step of relaxing and shrinking the heated raw material fiber is referred to as a "relaxation and shrinking step". The heating step and the relaxation and shrinking step can be performed by, for example, a high temperature heating relaxation device 140 illustrated in FIG. 7 or FIG. 8.

(Heating Step)

In the heating step, the heating temperature of the raw material fiber 36 is preferably equal to or higher than a softening temperature of the protein used in the raw material fiber 36. In the specification, the softening temperature of the protein is a temperature at which shrinkage is initiated due to stress relaxation of the raw material fiber 36. In the heating and relaxation shrinking at the temperature equal to or higher than the softening temperature of the protein, the fiber is shrunk to the extent that it cannot be obtained simply by removing moisture in the fiber. As a result, a residual stress in the fiber generated by drawing in the spinning process can be removed.

An example of a temperature corresponding to the softening temperature can include 180 °C. In a case where the heating and relaxation shrinking is performed in a high temperature range of 180 °C or higher, as a relaxation ratio becomes large or the temperature becomes high, the residual stress in the raw material fiber can be more efficiently removed. Accordingly, the heating temperature of the raw material fiber 36 is preferably 180 °C or higher, more preferably 180 °C to 280 °C, still more preferably 200 °C to 240 °C, and particularly preferably 220 °C to 240 °C.

A heating time in the heating step, that is, a retention time in a high temperature heating furnace 143 is preferably 60 seconds or shorter, more preferably 30 seconds or shorter, and still more preferably 5 seconds or shorter, from the viewpoint that stretching of the fiber obtained after the heat treatment is not impaired. It is considered that the length of the heating time does not significantly affect the stress. When the heating time at the heating temperature of 200 °C is 5 seconds or shorter, a deterioration of stretching of the fiber obtained by the heat treatment can be prevented.

(Relaxation and Shrinking Step)

In the relaxation and shrinking step, the relaxation ratio preferably exceeds 1 time, more preferably 1.4 times or more, still more preferably 1.7 times or more, and particularly preferably 2 times or more. The relaxation ratio is a ratio of the feed speed to the winding speed of the raw material fiber 36, and more specifically, a ratio of a feed speed by a feed roller 141 to a winding speed by a winding roller 142.

In the heating and relaxation method performed using the high temperature heating relaxation device 140, the heating step and the relaxation and shrinking step may be separately performed as long as the raw material fiber 36 can be relaxed in a heated state. That is, the heating device may be a device separated from and independent of a relaxation device. In this case, the relaxation device is provided at a subsequence stage of the heating device (the downstream side in the moving direction of the raw material fiber 36) so that the relaxation and shrinking step is performed after the heating step.

The heating and relaxation step may be performed on the raw material fiber separately from the production process of the raw material fiber. That is, the same device as the high temperature heating relaxation device 140 may be provided as an independent device separated from a spinning apparatus 25. A method in which the separately produced raw material fiber 36 is set to the feed roller and the raw material fiber is fed from the feed roller may be adopted. The heating and relaxation step may be performed on one raw material fiber or a plurality of bundled fibers.

(Crosslinking Step)

A crosslinking step of performing chemical crosslinking between polypeptide molecules in the protein fiber having a shrinkage history of being irreversibly shrunk, which is obtained as described above, or in the raw material fiber before being irreversibly shrunk may be further performed. Examples of a functional group which can be crosslinked can include an amino group, a carboxyl group, a thiol group, and a hydroxyl group. For example, an amino group of a lysine side chain contained in a polypeptide can be crosslinked through an amide bond by dehydration condensation with a carboxyl group of a glutamic acid or asparaginic acid side chain. The crosslinking may be performed by a dehydration condensation reaction under vacuum heating or may be performed using a dehydration condensation agent such as carbodiimide.

The crosslinking between polypeptide molecules may be performed using a crosslinking agent such as carbodiimide or glutaraldehyde or may be performed using an enzyme such as transglutaminase. The carbodiimide is a compound represented by General Formula: $R_1N{=}C{=}NR_2$ (where $R_1$ and $R_2$ each independently represent an organic group having an alkyl group or cycloalkyl group having 1 to 6 carbon atoms). Specific examples of the carbodiimide can include 1-ethyl-3-(3-dimethylaminopropyl)carbodiimide hydrochloride (EDC), N,N'-dicyclohexylcarbodiimide (DCC), 1-cyclohexyl-3-(2-morpholinoethyl)carbodiimide, and diisopropyl carbodiimide (DIC). Among them, EDC and DIC are preferred since they have a high ability to form an amide bond between polypeptide molecules and facilitate a crosslinking reaction.

A crosslinking treatment is preferably performed by applying a crosslinking agent to the fiber and performing crosslinking by vacuum heating drying. As the crosslinking agent, a pure product may be applied to the fiber. Alternatively, the crosslinking agent may be applied to the fiber by diluting a pure product with a lower alcohol having 1 to 5 carbon atoms and a buffer or the like to a concentration of 0.005 to 10% by mass. The crosslinking treatment is preferably performed at a temperature of 20 to 45 °C for 3 to 42 hours. By the crosslinking treatment, a higher stress (strength) can be imparted to the fiber.

In the present embodiment, the raw material composition is a fiber, the medium is an aqueous solution, and the production method of the protein composition may further include a crimping step of crimping the fiber by bringing the fiber into contact with the aqueous solution. When the production method includes the crimping step, the removal of the ester group and the shrinkage of the fiber can be simultaneously performed by contact of the fiber with water.

In the present embodiment, the raw material composition is a fiber, the medium is an aqueous solution, and the production method of the protein composition may further include a shrink-proof step of shrink-proofing the fiber by bringing the fiber into contact with the aqueous solution. In the case of the fiber shrunk by contact with water first, a degree of shrinkage when being in contact with water is suppressed than a fiber which is not brought into contact with water. That is, when the production method includes the shrink-proof step, the removal of the ester group and the shrink-proof of the fiber can be simultaneously performed by contact of the fiber with water.

A production method of a protein composition according to another embodiment includes a step of hydrolyzing an ester group by bringing a raw material composition containing an esterified protein and an acid or a base into contact with water vapor.

[Protein Composition]

A protein composition according to the present embodiment contains a protein and has a hydrolysis history of an ester group. The protein is preferably a structural protein. The protein composition may be a fiber (protein fiber), a film (protein film), a molded article (protein molded article), a gel (protein gel), a porous body (protein porous body), and a particle (protein particle).

The hydrolysis history is preferably a history in which the ester group is hydrolyzed by bringing the protein composition into contact with an acidic or basic medium containing water.

In the present embodiment, a temperature of the medium containing water may be, for example, 40 °C or higher, 50 °C or higher, 60 °C or higher, 70 °C or higher, 80 °C or higher, 85 °C or higher, 90 °C or higher, or 95 °C or higher. The temperature of the medium containing water may be, for example, 180 °C or lower, and is preferably a boiling point or lower.

In the present embodiment, the ester group may be included in formic acid ester, acetic acid ester, propionic acid ester, or the like, and the ester group is preferably included in formic acid ester.

The protein composition may further have a shrinkage history of being irreversibly shrunk. The "irreversible shrinkage" of the protein composition (for example, the protein fiber) refers to shrinkage when first being brought into contact with water after spinning, and corresponds to shrinkage (shrink-proof) by contact with water during the hydrolysis treatment of the ester group.

<Shrinkage Rate>

In a case where the protein composition is a protein fiber, a shrinkage rate of the protein fiber is preferably −5% to +5%, the shrinkage rate being defined by the following Equation (1):

Shrinkage rate [%]={1−(length of protein fiber when dried from wet state/length of protein fiber before in wet state)}×100.

Shrinkability by contact of the fiber with water can be evaluated using, for example, the shrinkage rate determined by Equation (1) as an index. "Length of protein fiber before in wet state" and "length of protein fiber when dried from wet state" can be measured by, for example, the following method.

A plurality of protein fibers having a length of about 30 cm are bundled to obtain a fiber bundle having a fineness of 150 denier. The length can be used as "length of protein fiber before in wet state". The fiber bundle is immersed (wetted) in water at 40 °C for 15 minutes, and the immersed fiber bundle is dried at room temperature for 2 hours. After drying, a length of the fiber bundle is measured. The length when dried can be used as "length of protein fiber when dried from wet state".

In the protein fiber, it is preferable that such shrinkage is small, and it is particularly preferable that shrinkage of a product such as a fabric formed of a protein fiber is small.

The shrinkage rate defined by Equation (1) may be, for example, −4.5% to +4.5%, −4% to +4%, −3.5% to +3.5%, −3% to +3%, −2% to +2%, −1% to +1%, 0% to +5%, 0% to +4%, 0% to +3%, 0% to +2%, or 0% to +1%.

The protein fiber may have various sectional shapes depending on the shape of the spinneret, but the sectional shape of the protein fiber may be a circular shape or an elliptical shape.

The protein fiber may have a matte-toned appearance or a glossy appearance. A desolvation speed and/or coagulation speed in the spinning process are appropriately adjusted, such that the glossy of the appearance of the fiber can be adjusted. In the present specification, the "matte-toned appearance" means that an appearance is low-gloss.

In addition, a lower limit of a fiber diameter of the protein fiber is not particularly limited, but may be 10 μm or more, 15 μm or more, 20 μm or more, 25 μm or more, 28 μm or more, 30 μm or more, 32 μm or more, 33 μm or more, more than 33 μm, 34 μm or more, 35 μm or more, 36 μm or more, 38 μm or more, or 40 μm or more. When the fiber diameter is 10 μm or more, it is possible to further increase productivity.

An upper limit of the fiber diameter of the protein fiber is not particularly limited, but may be 120 μm or less. The fiber diameter of the protein fiber may be 10 μm to 120 μm, 12 μm to 40 μm, 10 μm to 40 μm, 12 μm to 30 μm, 10 μm to 30 μm, 10 μm to 20 μm, 12 μm to 20 μm, 20 μm to 30 μm, more than 25 μm to 120 μm, 30 μm to 120 μm, more than 33 μm to 120 μm, 34 μm to 120 μm, 35 μm to 120 μm, 40 μm to 120 μm, 45 μm to 120 μm, 48 μm to 120 μm, 50 μm to 120 μm, 55 μm to 120 μm, 60 μm to 120 μm, 65 μm to 120 μm, 55 μm to 100 μm, 55 μm to 80 μm, or 60 μm to 80 μm. When the fiber diameter is 10 μm or more, it is possible to further increase productivity. When the fiber diameter is 120 μm or less, it is possible to further increase the hydrolysis reaction rate of the ester group.

It is preferable that the protein fiber according to the present embodiment has a small change in fiber diameter before and after the shrinking step of irreversibly shrinking the raw material fiber. Specifically, it is preferable that the protein fiber has a fiber diameter of less than ±20% of the fiber diameter of the raw material fiber before being irreversibly shrunk. The fiber diameter of the protein fiber with respect to the fiber diameter of the raw material fiber is preferably less than ±20%, and may be ±19% or less, ±18% or less, ±17% or less, ±16% or less, ±15% or less, less than ±15%, ±12% or less, ±10% or less, less than ±10%, ±5% or less, less than ±5%, ±4% or less, less than ±4%, ±3% or less, less than ±3%, ±2% or less, less than ±2%, ±1% or less, less than ±1%, ±0.9% or less, ±0.8% or less, ±0.7% or less, ±0.7% or less, ±0.6% or less, ±0.5% or less, less than ±0.5%, or ±0.45% or less. The value can be determined by a calculation formula of (fiber diameter of protein fiber−fiber diameter of raw material fiber)/fiber diameter of raw material fiber×100%.

[Ester Group Removal Method]

An ester group removal method according to the present embodiment includes a step of bringing a raw material composition containing an esterified protein (a protein having an ester group) into contact with an acidic or basic medium containing water.

In the present embodiment, the same aspects as those described in the above-described production method of the protein composition can be applied to the protein and the raw material composition.

In the present embodiment, the protein composition (for example, the protein fiber) obtained in the above step may have a shrinkage rate of −5% to +5%, the shrinkage rate being defined by the following Equation (1). The same aspects as those described in the above-described protein composition can be applied to the shrinkage rate defined by the following Equation (1):

Shrinkage rate={1−(length of protein fiber when dried from wet state/length of protein fiber before in wet state)}×100[%].

In the present embodiment, the same aspects as those described in the above-described production method of the protein composition can be applied to the temperature and properties of the medium containing water and the contact time with the medium containing water.

[Product]

The protein composition (for example, the protein fiber) according to the present embodiment can be applied to various products. Examples of the product can include a fiber, a yarn, a fabric, a knitted fabric, a braided fabric, a non-woven fabric, a paper, cotton, and a clothing product. Examples of the fiber can include a long fiber, a short fiber, a monofilament, and a multifilament. Examples of the yarn can include a spun yarn, a twisted yarn, a false twisted yarn, a processed yarn, a blended yarn, and a blended spun yarn. Furthermore, it is possible to produce, from these fibers or yarns, a fabric such as a woven fabric, a knitted fabric, a braided fabric, or a non-woven fabric, a paper, cotton, and the like. These products can be produced by a known method. In addition, the protein composition according to the present embodiment, which can also be applied to high strength applications such as a rope, a surgical suture, a flexible stop for electrical components, and further, a physiologically active material for implantation (for example, artificial ligament and aortic band) can be applied to a yarn (a spun yarn, a twisted yarn, a false twisted yarn, a processed yarn, a blended yarn, a blended spun yarn, or the like), a woven fabric (fabric), a knitted fabric, a braided fabric, a non-woven fabric, a paper, cotton, and the like. In addition, the modified fibroin fiber can also be applied to high strength applications such as a rope, a surgical suture, a flexible stop for electrical components, and a physiologically active material for implantation (for example, artificial ligament and aortic band). These fibers can be produced based on a known method.

EXAMPLES

Hereinafter, although the present invention will be described in more detail by Examples, the present invention is not limited to these Examples.

Experimental Example 1

(1) Preparation of Protein Expression Strain (Recombinant Cell) to be Targeted

A nucleic acid encoding modified spider silk fibroin (PRT799) having an amino acid sequence set forth in ■ SEQ ID NO: 15 was synthesized. In the nucleic acids, an NdeI site was added to the 5'-terminus and an EcoRI site was added to a termination codon downstream.

Each of the nucleic acids was cloned with a cloning vector (pUC118). Thereafter, the same nucleic acids were cleaved by restriction enzyme treatment with NdeI and EcoRI, and then recombined into a protein expression vector pET-22b (+) to obtain an expression vector. Transformed *E. coli* (recombinant cell) expressing a protein was to be targeted obtained by transforming *E. coli* BLR (DE3) with each pET-22b (+) expression vector in which each of the nucleic acids was recombined.

(2) Expression of Protein to be Targeted

The transformed *E. coli* was cultured in a 2 mL LB medium containing ampicillin for 15 hours. The culture solution was added to a 100 mL seed culture medium containing ampicillin (Table 4) so that $OD_{600}$ was 0.005. The culture solution temperature was maintained at 30 °C, and flask culture was performed until $OD_{600}$ reached 5 (for about 15 hours) to obtain a seed culture solution.

TABLE 4

| Seed culture medium (at the start of culturing, per 1 L) | |
|---|---|
| Glucose | 5 g |
| $KH_2PO_4$ | 4 g |
| $K_2HPO_4$ | 10 g |
| Yeast Extract | 6 g |

Ampicillin was added so that the final concentration was 100 mg/L to be used as a seed culture medium.

The seed culture solution was added to a jar fermenter to which a 500 mL production medium (Table 5) was added so that $OD_{600}$ was 0.05. The culture was performed while maintaining the culture solution temperature at 37 °C and constantly controlling the pH to 6.9. In addition, a dissolved oxygen concentration in the culture solution was set to be maintained at 20% of a dissolved oxygen saturation concentration.

TABLE 5

| Production medium (at the start of culturing, per 1 L) | |
|---|---|
| Glucose | 12 g |
| $KH_2PO_4$ | 9 g |
| $MgSO_4 \cdot 7H_2O$ | 2.4 g |
| Yeast Extract | 15 g |
| $FeSO_4 \cdot 7H_2O$ | 40 mg |
| $MnSO_4 \cdot 5H_2O$ | 40 mg |
| $CaCl_2 \cdot 2H_2O$ | 40 mg |
| GD-113 (Antifoaming agent) | 0.1 mL |

Immediately after glucose in the production medium was completely consumed, a feed solution (glucose 455 g/1 L, yeast extract 120 g/1 L) was added at a rate of 1 mL/min. The culture was performed while maintaining the culture solution temperature at 37 °C and constantly controlling the pH to 6.9. In addition, the culture was performed for 20 hours while maintaining a dissolved oxygen concentration in the culture solution at 20% of a dissolved oxygen saturation concentration. Thereafter, 1 M isopropyl-β-thiogalactopyranoside (IPTG) was added to the culture solution so that the final concentration was 1 mM to induce expression of the target protein. 20 hours after the addition of IPTG, the culture solution was centrifuged to collect fungus bodies. SDS-PAGE was performed by using fungus bodies prepared from the culture solution before the addition of IPTG and the culture solution after the addition of IPTG, and expression of the protein to be targeted as an insoluble matter was confirmed by appearance of a band with a size of the protein to be targeted depending on the addition of IPTG.

(3) Purification of Protein 2 hours after the addition of IPTG, the collected fungus bodies were washed with a 20 mM Tris-HCl buffer (pH 7.4). The washed fungus bodies were suspended in a 20 mM Tris-HCl buffer (pH 7.4) containing approximately 1 mM PMSF, and cells were disrupted in a high-pressure homogenizer (manufactured by GEA Niro Soavi Technologies). The disrupted cells were centrifuged to obtain a precipitate. The obtained precipitate was washed with a 20 mM Tris-HCl buffer (pH 7.4) until the purity was high. The washed precipitate was suspended in an 8 M guanidine buffer (8 M guanidine hydrochloride, 10 mM sodium dihydrogen phosphate, 20 mM NaCl, and 1 mM Tris-HCl, pH 7.0) so that a concentration thereof was 100 mg/mL, and the suspended precipitate was dissolved by performing stirring using a stirrer at 60 °C for 30 minutes. After dissolution, the resultant product was dialyzed with water by using a dialysis tube (cellulose tube 36/32 manufactured by Sanko Junyaku Co., Ltd.). A white coagulation protein obtained after dialysis was collected by centrifugation, and water was removed in a freeze dryer to recover freeze-dried powdered protein.

(4) Molding of Protein Fiber

The dry power of modified spider silk fibroin was dissolved in formic acid to obtain a dope solution (a protein concentration in the dope solution: 25% by mass). The dope solution was discharged to a coagulation liquid (methanol) by a gear pump using a known spinning apparatus. Spinning conditions were as below. As a result, a protein fiber (fibroin fiber) was obtained.

(Spinning Conditions)

Dope solution temperature: 25 °C.

Hot roller temperature: 60 °C.

(5) Hydrolysis Treatment

A hydrolysis treatment was performed by the following steps i to iv.

i. The protein fiber was immersed and stirred in an acidic or basic aqueous solution for various times.

ii. The protein fiber was immersed and stirred in an excess amount of pure water for 2 minutes.

iii. The pure water was replaced, and the operation of ii was further performed twice more.

iv. The protein fiber was air-dried at room temperature.

A pH and reaction time of the acidic or basic aqueous solution used in each of Examples and Comparative Examples are shown in Table 6.

(6) Confirmation of Reduction Behavior of Formic Acid Ester Group by FT-IR

A reduction behavior of a formic acid ester group was confirmed by measuring each fiber dried through the hydrolysis treatment by FT-IR transmission microscopy. As for each sample treated under each of the pH conditions, a peak height ratio P1/P2 was determined and recorded. In this case, (P1/P2)≤0.01 was used as a determination criterion for completion of removal. The results are shown in Table 6. P1 and P2 are peak heights corresponding to subsequent wave numbers. The smaller the value of the absorbance ratio P1/P2, the smaller the number of the structural ester groups.

P1: a peak height of 1,725 $cm^{-1}$ (peak based on C═O of ester)

P2: a peak height of 1,445 $cm^{-1}$ (peak based on amide III of protein)

(7) Retention Rate of Elongation

Each fiber dried through the hydrolysis treatment was fixed with an adhesive to a piece of a test paper having a distance between gripping tools of 20 mm, and a stress (strength) and elongation were measured under conditions of a temperature of 20 °C and a relative humidity of 65% at a tensile speed of 10 cm/min using a tensile tester 3342 manufactured by Instron Co., Ltd. The load cell capacity was 10 N and the gripping tool was a clip type. The elongation of the protein fiber treated with the acidic or basic aqueous solution and the elongation of the protein fiber treated with water having a pH of 7 were measured to calculate a retention rate of the elongation according to the following equation. The results are shown in Table 6.

[Retention rate of elongation]=[elongation of protein fiber treated with acidic or basic aqueous solution]/[elongation of protein fiber treated with water having pH of 7]×100

TABLE 6

| | pH | Immersion time [min] | Absorbance ratio (P1/P2) of formic acid ester | Retention rate [%] of elongation |
|---|---|---|---|---|
| Example 1-1 | 1 | 180 (70 deg) | 0.00 | 99 |
| Example 1-2 | 8 | 2400 (r.t.) | 0.00 | 94 |
| Example 1-3 | 10 | 80 (r.t.) | 0.00 | 101 |
| Example 1-4 | 11 | 20 (r.t.) | 0.00 | 99 |
| Example 1-5 | 12 | 10 (r.t.) | 0.00 | 55 |
| Comparative Example 1-1 | 7 | 90 (r.t.) | 0.09 | 100 |

The absorbance ratio of formic acid ester was reduced in the protein fiber treated with the acidic or basic aqueous solution. From the results, it was shown that the ester group included in the protein fiber was hydrolyzed by the treatment with the acidic or basic aqueous solution, and the ester group was thus removed. In addition, when the pH of the acidic or basic aqueous solution is 11 or lower (lower than 12), the elongation of the treated protein fiber was also maintained.

(8) Evaluation of Crimp Property

Figure 9:
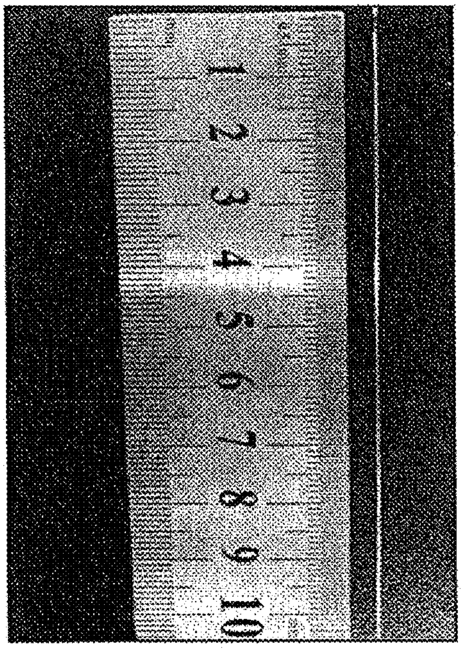
FIG. 9 illustrates photographs obtained by observing a crimp state immediately after a hydrolysis treatment of the protein fiber.
Figure 9:
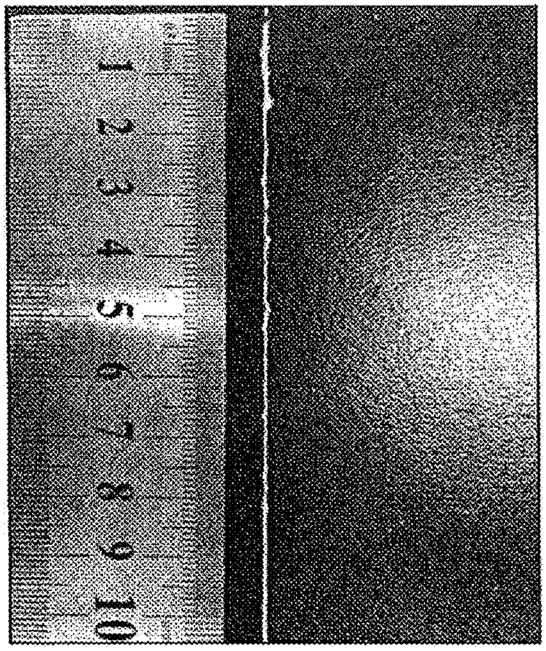
Figure 9:
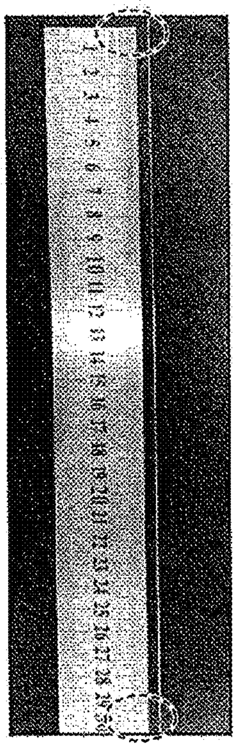
Figure 9:
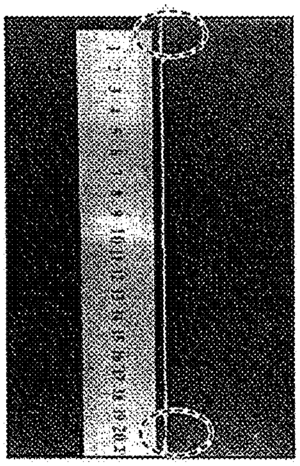

The hydrolysis treatment was performed on the protein fiber under the conditions (pH and immersion time) of Example 1-2, and the crimped states of the protein fiber before the hydrolysis treatment and the protein fiber after the hydrolysis treatment were compared. The crimped states were further compared by measuring each of the protein fibers with a ruler. The results are illustrated in FIG. 9.

FIGS. 9(A) and (C) illustrate photographs of the protein fibers before the hydrolysis treatment (before crimping). FIGS. 9(B) and (D) illustrate photographs of the protein fibers after the hydrolysis treatment (after crimping). The 300 mm protein fiber before the hydrolysis treatment became 200 mm (FIGS. 9(C) and (D)). In addition, coupled with FIGS. 9(A) and (B), it could be seen that the protein fiber after the hydrolysis treatment was crimped as compared to the protein fiber before the hydrolysis treatment.

(9) Evaluation of Shrink-Proof Property

The protein fiber (200 mm) after the hydrolysis treatment was not shrunk any further even in a case where the protein fiber was immersed in water.

On the other hand, when the protein (300 nm) before the hydrolysis treatment was immersed in water as Comparative Example 1-1, the protein became 200 mm. Therefore, it could be seen that the protein fiber after the hydrolysis treatment was shrink-proofed as compared with the protein fiber before the hydrolysis treatment.

(10) Hydrolysis by Water Vapor

The protein fiber was allowed to stand under conditions of humidity of 80% and 60°, and a daily absorbance ratio P1/P2 was measured using FT-IR (manufactured by NICOLET Co., Ltd., FT-IR iS50). The results are shown in Table 7.

TABLE 7

| Treatment time [day] (60° C., 80%) | P1: 1,725 $cm^{-1}$ Ester C═O stretch | P2: 1,445 $cm^{-1}$ Artificial protein amide III | Absorbance ratio (P1/P2) |
|---|---|---|---|
| 0 | 0.0017 | 0.0230 | 0.074 |
| 1 | 0.0020 | 0.0320 | 0.063 |
| 2 | 0.0015 | 0.0280 | 0.054 |
| 3 | 0.0017 | 0.0380 | 0.045 |
| 4 | 0.0015 | 0.0280 | 0.054 |
| 5 | 0.0016 | 0.0310 | 0.052 |
| 6 | 0.0012 | 0.0330 | 0.036 |

Figure 10:
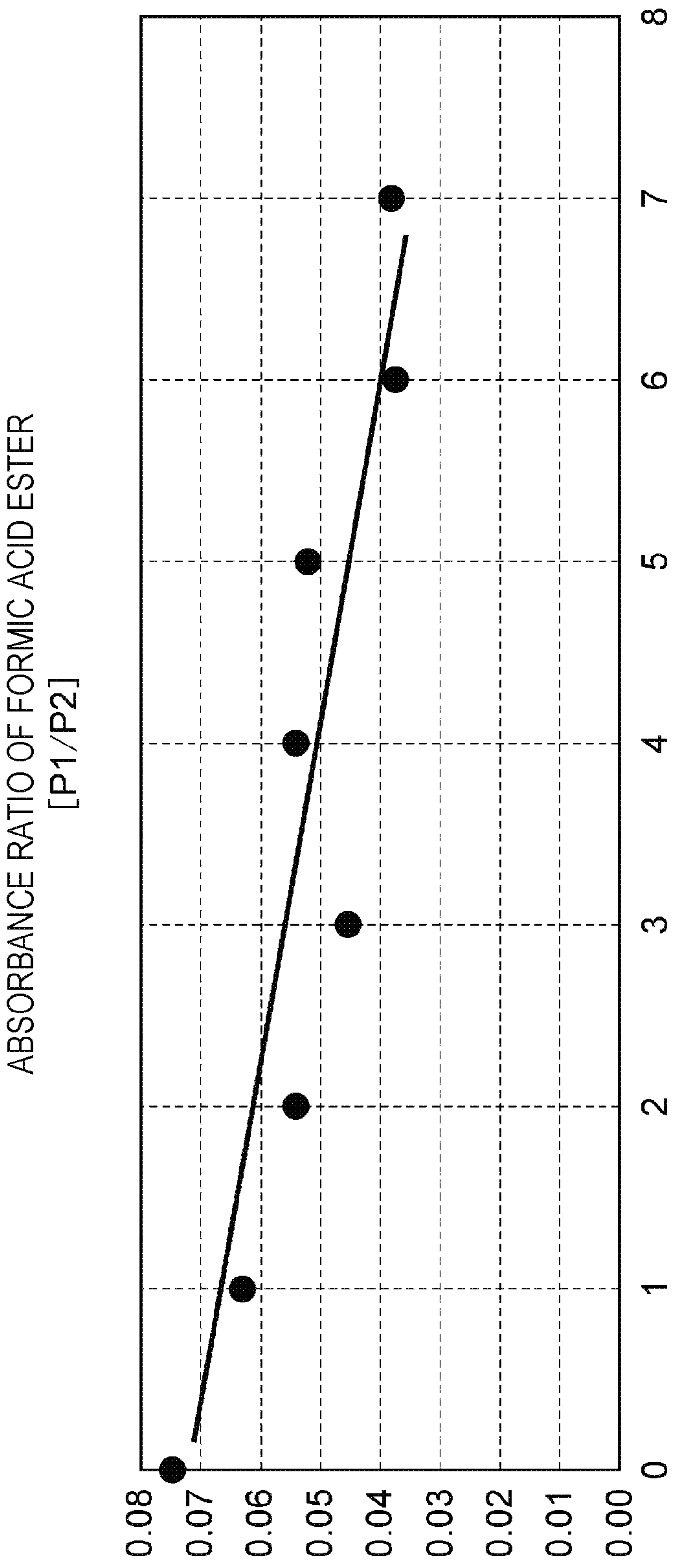
FIG. 10 is a graph obtained by plotting an absorbance ratio (P1/P2) in which a residual amount of the ester group is reflected against the number of contact days between the protein fiber and water vapor, in which P1: a peak height of 1,725 $cm^{-1}$ (peak based on C═O of ester), and P2: a peak height of 1,445 $cm^{-1}$ (peak based on amide III of protein).

FIG. 10 is a diagram obtained by plotting data of Table 7 with the absorbance ratio P1/P2 on the vertical axis and the treatment time (unit: day) on the horizontal axis.

As shown in Table 7 and illustrated in FIG. 10, when the protein fiber was brought into contact with water, the absorbance ratio P1/P2 was reduced. From the results, it was shown that the ester hydrolysis reaction proceeded by contact with water using the remaining formic acid as a catalyst, and the ester group added to the protein fiber was reduced.

Experimental Example 2

(1) Preparation of Expression Vector

Spider silk fibroin having ■ SEQ ID NO: 40 (hereinafter, also referred to as "PRT966") was designed based on a base sequence and an amino acid sequence of fibroin derived from *Nephila clavipes* (GenBank Accession No.: P46804.1, GI: 1174415). The amino acid sequence set forth in SEQ ID NO: 40 has a sequence obtained by substituting, with VF, all QQs in a sequence obtained by repeating a region of 20 domain sequences present in an amino acid sequence set forth in SEQ ID NO: 7 two times and substituting the remaining Q with I, for the purpose of improving hydrophobicity, and is obtained by adding an amino acid sequence (tag sequence and hinge sequence) set forth in SEQ ID NO: 11 to the N-terminus.

Subsequently, a nucleic acid encoding the designed protein (spider silk fibroin) was synthesized to obtain transformed *E. coli* (recombinant cell) expressing a protein to be targeted in the same manner as that of Experimental Example 1.

(2) Expression of Protein

The transformed *E. coli* was cultured in a 2 mL LB medium containing ampicillin for 15 hours. The culture solution was added to a 100 mL seed culture medium containing ampicillin (Table 8) so that $OD_{600}$ was 0.005. The culture solution temperature was maintained at 30 °C, and flask culture was performed until $OD_{600}$ reached 5 (for about 15 hours) to obtain a seed culture solution.

TABLE 8

| Seed culture medium | |
|---|---|
| Reagent | Concentration (g/L) |
| Glucose | 5.0 |
| $KH_2PO_4$ | 4.0 |
| $K_2HPO_4$ | 9.3 |
| Yeast Extract | 6.0 |
| Ampicillin | 0.1 |

The seed culture solution was added to a jar fermenter to which a 500 ml production medium (Table 5 of Experimental Example 1) was added so that $OD_{600}$ was 0.05. The culture was performed while maintaining the culture solution temperature at 37 °C and constantly controlling the pH to 6.9. In addition, a dissolved oxygen concentration in the culture solution was set to be maintained at 20% of a dissolved oxygen saturation concentration.

Immediately after glucose in the production medium was completely consumed, a feed solution (glucose 455 g/1 L, Yeast Extract 120 g/1 L) was added at a rate of 1 mL/min. The culture was performed while maintaining the culture solution temperature at 37 °C and constantly controlling the pH to 6.9. In addition, the culture was performed for 20 hours so that a dissolved oxygen concentration in the culture solution was set to be maintained at 20% of a dissolved oxygen saturation concentration. Thereafter, 1 M isopropyl-β-thiogalactopyranoside (IPTG) was added to the culture solution so that the final concentration was 1 mM to induce expression of the modified fibroin. 20 hours after the addition of IPTG, the culture solution was centrifuged to collect fungus bodies. SDS-PAGE was performed by using fungus bodies prepared from the culture solution before the addition of IPTG and the culture solution after the addition of IPTG, and expression of the protein (spider silk fibroin) to be targeted was confirmed by appearance of a band of the recombinant protein to be targeted depending on the addition of IPTG.

(3) Purification of Protein

The protein was purified by the same method as in Experimental Example 1 to recover freeze-dried powdered protein (dry powder of spider silk fibroin).

(4) Production of Raw Material Fiber

The dry powder of spider silk fibroin was dissolved in formic acid, filtration was performed with a metal filter having a mesh size of 1 μm, thereby obtaining a dope solution (a concentration of the protein in the dope solution: 30% by mass). The dope solution was discharged to a coagulation liquid by a gear pump using a known spinning apparatus. Spinning conditions were as below. Therefore, a raw material fiber (raw material spider silk fibroin fiber) was obtained.

(Spinning Conditions)

Nozzle hole diameter: 0.1 mm
Coagulation liquid: methanol
Temperature of coagulant liquid: 25 °C.
Temperature of water washing bath: 25 °C.
Hot roller temperature: 60 °C.

(5) Ester Hydrolysis Treatment of Raw Material Fiber (Production of Protein Fiber)

200 g of the raw material fiber obtained in (4) was formed into a hank state and a hydrolysis treatment was performed by the following steps [i] to [x] using a known hank treatment machine. The treatment time, treatment temperature, and treatment medium in the step [iii] are shown in Table 9. The step [v] is a neutralization treatment step performed when a basic medium is used as the treatment medium. The steps [vii] and [viii] may be appropriately performed, if necessary. In addition, an agent for removing an oil agent in the treatment medium shown in Table 9 is added for removing the oil agent added to a surface of the fiber, and the agent may be appropriately used, if necessary.

[i] A hank was set to the hank treatment machine.
[ii] The hank was washed with tap water.
[iii] The hank was impregnated with the treatment medium shown in Table 9 and stirring was performed. The treatment time is as shown in Table 9.
[iv] The hank was washed by replacing the tap water.
[v] The hank was subjected to a neutralization treatment in a 1% aqueous acetic acid solution.
[vi] The hank was washed by replacing the tap water.
[vii] The hank was impregnated with an aqueous softener and stirring was performed.
[viii] The hank was washed by replacing the tap water.
[ix] The hank was dehydrated.
[x] The hank was air-dried at 50 to 60 °C for 2 hours.

TABLE 9

| | Treatment conditions of hydrolysis treatment | | | | | | Relative |
|---|---|---|---|---|---|---|---|
| | Temperature [°C] | Treatment time [min] | Treatment medium | Formic acid ester $V_{C=O}$ 1,730 $cm^{-1}$) | Elongation [%] | Standard deviation [σ] | value [%] of elongation |
| Example 2-1 | 40 | 60 | Aqueous solution of $Na_2CO_3$ with pH 11 | Undetectable | 82.3 | 3.25 | 127 |
| Example 2-2 | 90 | 15 | Aqueous solution of $Na_2CO_3$ with pH 11 Agent for removing oil agent | Undetectable | 88.2 | 1 | 136 |
| Example 2-3 | 98 | 15 | Aqueous solution of $Na_2CO_3$ with pH 11 | Undetectable | 89.1 | 3.44 | 138 |

TABLE 9-continued

| | Treatment conditions of hydrolysis treatment | | | | | | Relative |
|---|---|---|---|---|---|---|---|
| | Temperature [°C] | Treatment time [min] | Treatment medium | Formic acid ester $V_{C=O}$ 1,730 $cm^{-1}$) | Elongation [%] | Standard deviation [σ] | value [%] of elongation |
| | | | Agent for removing oil agent | | | | |
| Comparative example 2-1 | — | 0 | None (untreated) | Detect | 64.8 | 11.4 | 100 |
| Comparative example 2-2 | 90 | 15 | Aqueous solution of agent for removing oil agent | Detect | 81.3 | 3.54 | 125 |
| Comparative example 2-3 | 98 | 15 | Aqueous solution of agent for removing oil agent | Detect | 81.5 | 2.13 | 126 |

(6) Evaluation of Removal of Ester Group by FT-IR

Figure 11:
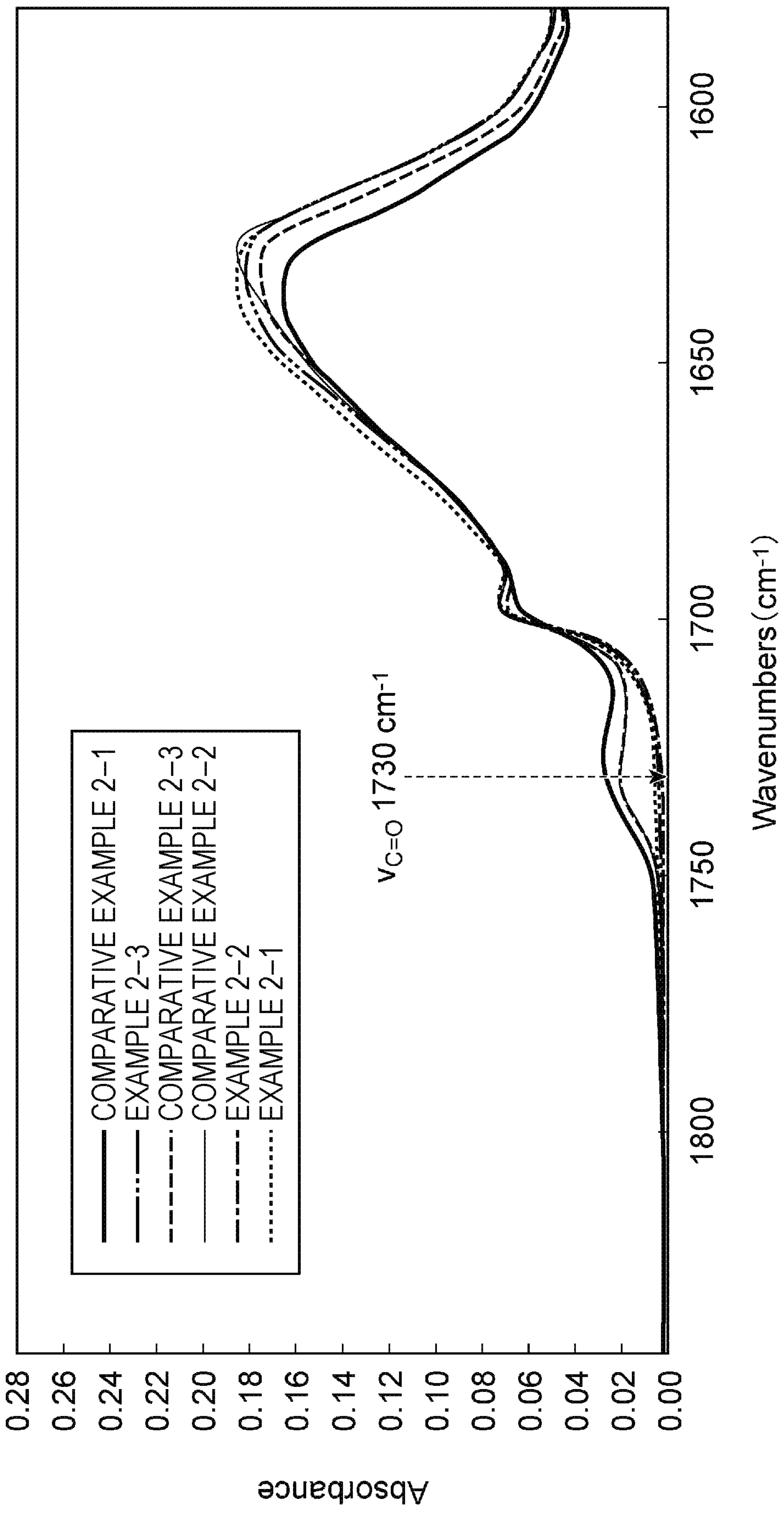
FIG. 11 is a spectrum diagram of FT-IR of the protein fiber immediately after the hydrolysis treatment of the ester group (1,730 $cm^{-1}$: peak based on C═O of ester)

Each fiber obtained in (5) was measured by an ATR method (total reflection method) using a Fourier-transform infrared spectrophotometer to evaluate the removal of the formic acid ester group. In each of fibers (Examples 2-1 to 2-3 and Comparative Examples 2-1 to 2-3), a height of a peak (peak assigned to C═O of the ester group) with a wave number of 1,730 $cm^{-1}$ was confirmed from an IR spectrum to evaluate whether or not the peak was detected (FIG. 11). A case where the peak was not detected was determined that the formic acid ester group was removed.

(7) Evaluation of Elongation

Each fiber obtained in (5) was fixed with an adhesive to a piece of a test paper having a distance between gripping tools of 20 mm, and elongation was measured under conditions of a temperature of 20 °C and a relative humidity of 65% at a tensile speed of 10 cm/min using a tensile tester 3342 manufactured by Instron Co., Ltd (Table 9). The load cell capacity was 10 N and the gripping tool was a clip type.

As shown in Table 9, it was confirmed that the hydrolysis reaction of the formic acid ester group proceeded and the formic acid ester group in the fiber was removed only in a case where the raw material fiber was treated with the medium (basic aqueous solution) containing basic water (Examples 2-1 to 2-3). Furthermore, it was shown that the formic acid ester group was hydrolyzed and removed in a shorter time by setting the treatment temperature to a high temperature (90 °C to 98 °C, Examples 2-2 and 2-3). Productivity in the hydrolysis step was significantly improved by performing the hydrolysis treatment to form the fiber into a hank state. In addition, it was confirmed that the elongation was not reduced by the hydrolysis treatment.

(8) Evaluation of Shrinkability to Water

Shrinkability (dimensional stability) of the protein fiber after the ester hydrolysis treatment obtained in (5) to water was evaluated by the following procedure. The shrinkability to water was calculated and evaluated according to the following Equation (1) as a shrinkage rate. The calculation values are shown in Table 10. The shrinkability was evaluated using a fiber which was not subjected to the ester hydrolysis treatment (Comparative Example 2-1) for comparison in the same manner as above.

A plurality of fibers obtained in (5) were bundled to a length of about 30 cm to obtain a fiber bundle having a fineness of 150 denier. The length of the fiber bundle was used as "length of protein fiber before in wet state". The fiber bundle was immersed (wetted) in water at 90 °C for 15 minutes, and the immersed fiber bundle was dried at room temperature for 2 hours to measure a length thereof. The length was used as "length of protein fiber when dried from wet state" to calculate a shrinkage rate according to the following Equation (1). A measured value was an average value of the number of samples (n=3).

Shrinkage rate={1−(length of protein fiber when dried from wet state/length of protein fiber before in wet state)}×100[%]

TABLE 10

| | Treatment conditions of hydrolysis treatment | | | |
|---|---|---|---|---|
| | Temperature [°C] | Treatment time [min] | Treatment medium | Shrinkage rate [%] |
| Example 2-2 | 90 | 15 | Aqueous solution of $Na_2CO_3$ with pH 11 | 3 |
| | | | Agent for removing oil agent | |
| Comparative example 2-1 | — | — | None (untreated) | 40 |

As shown in Table 10, it was confirmed that in the case of the protein fiber which was subjected to the ester hydrolysis treatment (Example 2-2), the shrinkage rate was reduced as compared to that of the protein fiber which was not subjected to the ester hydrolysis treatment (Comparative Example 2-1), and the shrinkability to water was reduced. It was shown that the shrink-proof effect was obtained by simultaneously performing the shrink-proof (shrink) treatment through the ester hydrolysis treatment.

REFERENCE SIGNS LIST

1 Extrusion device
2 Undrawn yarn production apparatus
3 Wet heat drawing device
4 Drying device
6 Dope solution
10 Spinning apparatus
20 Coagulation bath
21 Drawing bath
25 Spinning apparatus
36 Raw material fiber
38 Protein fiber
40 Production apparatus
42 Feed roller

44 Winder
46 Water bath
48 Dryer
54 Heater
56 Tension roller
58 Hot roller
60 Processing device
62 Drying device
64 Dry heat plate
140 Relaxation shrinking means (heating means)
141 Feed means
142 Winding means
146 Speed control means
147 Temperature control means

The invention claimed is:

1. A production method of a protein composition, the method comprising shrinking a raw material composition containing an esterified protein by bringing the raw material composition into contact with a basic medium and hydrolyzing an ester group of the raw material composition, wherein the esterified protein contains:

a formic acid ester formed by a reaction of formic acid with a hydroxyl group in the esterified protein, or an acetic acid ester formed by a reaction of acetic acid with a hydroxyl group in the esterified protein, and wherein the basic medium contains water, and the basic medium containing water is from 40 °C to 180 °C.

2. The production method of a protein composition according to claim 1, wherein the basic medium containing water is a basic aqueous solution.

3. The production method of a protein composition according to claim 2, wherein a temperature of the basic aqueous solution is from 40 °C to a boiling point of the basic aqueous solution.

4. The production method of a protein composition according to claim 3, wherein the basic aqueous solution has a pH of 8 to 12.

5. The production method of a protein composition according to claim 1, wherein the protein comprises a structural protein.

6. The production method of a protein composition according to claim 5, wherein the structural protein comprises fibroin.

7. The production method of a protein composition according to claim 6, wherein the fibroin comprises spider silk fibroin.

8. The production method of a protein composition according to claim 1, wherein the esterified protein contains the formic acid ester.

9. The production method of a protein composition according to claim 1, wherein the raw material composition comprises at least one selected from the group consisting of a fiber, a film, a molded article, a gel, a porous body, and a particle.

10. The production method of a protein composition according to claim 1, wherein the raw material composition comprises a fiber, the basic medium containing water is a basic aqueous solution, and the production method further comprises a crimping step of crimping the fiber by bringing the fiber into contact with the basic aqueous solution.

11. The production method of a protein composition according to claim 9, wherein the raw material composition comprises a fiber, and the fiber is in a hank state.

12. The production method of a protein composition according to claim 9, wherein the raw material composition comprises a fiber, and the fiber is in a cloth state.

13. A production method of a protein composition, the method comprising shrinking a raw material composition containing an esterified protein by bringing the raw material composition and a base into contact with water vapor and hydrolyzing an ester group of the raw material composition, wherein the esterified protein contains:

a formic acid ester formed by a reaction of formic acid with a hydroxyl group in the esterified protein, or an acetic acid ester formed by a reaction of acetic acid with a hydroxyl group in the esterified protein, and wherein the water vapor is from 40 °C to 180 °C.

14. The production method of a protein composition according to claim 1, wherein the basic medium containing water is water vapor.

15. The production method of a protein composition according to claim 1, wherein the protein composition is a protein fiber having a shrinkage rate of −5% to +5%, wherein the shrinkage rate is defined by Equation (1):

shrinkage rate={1−(length of protein fiber when dried from wet state/length of protein fiber before in wet state)}×100(%).

16. The production method of a protein composition according to claim 1, wherein the raw material composition is at least one selected from the group consisting of a film, a molded article, a gel, a porous body, and a particle.

17. A production method of a protein composition comprising a spider silk fibroin, the method comprising shrinking a raw material composition containing an esterified protein by bringing the raw material composition into contact with a basic medium and hydrolyzing an ester group of the raw material composition, wherein the basic medium contains water, and the basic medium containing water is from 40 °C to 180 °C.

18. The production method of a protein composition according to claim 1, wherein the protein composition excludes esterified collagen.

19. The production method of a protein composition comprising the spider silk fibroin according to claim 17, wherein the protein composition is a spider silk fibroin fiber having a shrinkage rate of −5% to +5%, wherein the shrinkage rate is defined by Equation (1):

shrinkage rate={1−(length of spider silk fibroin fiber when dried from wet state/length of spider silk fibroin fiber before in wet state)}×100(%).

* * * * *